(12) United States Patent
Barry et al.

(10) Patent No.: US 12,297,442 B2
(45) Date of Patent: May 13, 2025

(54) INSECTICIDAL PROTEINS FROM PLANTS AND METHODS FOR THEIR USE

(71) Applicant: PIONEER HI-BRED INTERNATIONAL, INC, Johnston, IA (US)

(72) Inventors: Jennifer Kara Barry, Ames, IA (US); Catherine J Clark, Altoona, IA (US); Ryan Michael Gerber, Apex, NC (US); Amy Lum, Redwood City, CA (US); John P Mathis, Johnston, IA (US); Azalea S Ong, Castro Valley, CA (US); Brooke Peterson-Burch, Ankeny, IA (US); Thomas Chad Wolfe, Des Moines, IA (US); Weiping Xie, East Palo Alto, CA (US); Nasser Yalpani, Kelowna (CA); Xiaohong Zhong, San Leandro, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 18/488,274

(22) Filed: Oct. 17, 2023

(65) Prior Publication Data
US 2024/0076688 A1    Mar. 7, 2024

Related U.S. Application Data

(63) Continuation of application No. 17/483,364, filed on Sep. 23, 2021, now abandoned, which is a continuation of application No. 16/311,765, filed as application No. PCT/US2017/039376 on Jun. 27, 2017, now Pat. No. 11,155,829.

(60) Provisional application No. 62/357,501, filed on Jul. 1, 2016.

(51) Int. Cl.
| | | |
|---|---|---|
| *C12N 15/82* | (2006.01) |
| *A01N 37/46* | (2006.01) |
| *A01N 63/50* | (2020.01) |
| *C07K 14/415* | (2006.01) |

(52) U.S. Cl.
CPC ......... *C12N 15/8286* (2013.01); *A01N 37/46* (2013.01); *A01N 63/50* (2020.01); *C07K 14/415* (2013.01); *Y02A 40/146* (2018.01)

(58) Field of Classification Search
None
See application file for complete search history.

(56) References Cited

U.S. PATENT DOCUMENTS

| 5,024,837 | A | | 6/1991 | Donovan et al. |
| 11,155,829 | B2 | * | 10/2021 | Barry ............... A01N 63/50 |
| 12,071,630 | B2 | * | 8/2024 | Barry ............... C07K 14/415 |
| 2007/0044179 | A1 | | 2/2007 | Stewart, Jr. et al. |
| 2011/0277180 | A1 | | 11/2011 | Romano |
| 2015/0139976 | A1 | | 5/2015 | Singh et al. |
| 2016/0040184 | A1 | | 2/2016 | Cong et al. |
| 2022/0002747 | A1 | | 1/2022 | Barry et al. |
| 2022/0010329 | A1 | | 1/2022 | Barry et al. |

FOREIGN PATENT DOCUMENTS

| WO | 2010085289 A1 | 7/2010 |
| WO | 2012006271 A1 | 1/2012 |
| WO | 2016060948 A1 | 4/2016 |
| WO | 2016060949 A1 | 4/2016 |

OTHER PUBLICATIONS

Extended European Search Report for European Application No. 17821042.3, mailed Nov. 4, 2019, 7 Pages.
Extended European Search Report for European Application No. 21186172.9, mailed Jan. 18, 2022, 7 Pages.
International Preliminary Report on Patentability for International Application No. PCT/US2017/039376, mailed Jan. 10, 2019, 6 Pages.
International Search Report and Written Opinion for International Application No. PCT/US2017/039376, mailed Sep. 22, 2017, 9 Pages.
Williamson V.M., et al., "Nematode Resistance in Plants: The Battle Underground," Trends in Genetics, Elsevier Science Publishers B.V. Amsterdam, NL, Jul. 1, 2006, vol. 22, No. 7, pp. 396-403, DOI: 10.1016/J.TIG.2006.05.003, ISSN 0168-9525, XP028054939.
Williamson V.M., "Plant Nematode Resistance Genes," Current Opinion in Plant Biology, Jul. 1, 1997, pp. 327-331, DOI:10.1016/S1369-5266(99)80057-0, XP055061995, Retrieved on [May 6, 2013] Retrieved from URL: http://www.ufv.br/dbv/pgfvg/bve684/htms/pdfs_revisao/estresse/nematoderesist.pdf.

* cited by examiner

*Primary Examiner* — Medina A Ibrahim

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

12 Claims, 5 Drawing Sheets

Specification includes a Sequence Listing.

Fig. 1A

```
                    1            ▼        •              50
IPD103Aa   (1)  -----------MADKAAAAAREAEEEVEITMDETEAVGTHLDFLGADVKL
IPD103Ab   (1)  -----------MADQAAAAREAEEEVEITMDETEAVGTHLDFLGADVKL
IPD103Ac   (1)  -----------MAEPAAAAREAEEEVEITMDETEAVGTHLDFLGADVKL
IPD103Ad   (1)  -----------MADQGAAAAREAEEEVEITMDETEAVGTHLDFL-ADVKV
IPD103Ae   (1)  -----------MADQ-AAAAREAEEEVEITMDETEAVGTHLDFL-ADVKV
IPD103Bd   (1)  -----------MADQVAAARGAEEEVEITMDETEAVGTHLDFL-ADVKV
IPD103Ba   (1)  MREREREREREMAEPAAAAAKKAEEEVEIIMDDTEAVGTHLDFL-AGLKV
IPD103Bb   (1)  -----------MAEPAAAAAKKAEEEVEIIMDDTEAVGTHLDFL-AGLKV
IPD103Ca   (1)  MREREREREREMAEPAAAAAKKAEEEVEIIMDDTEAVGTHLDFL-AGLKV
IPD103Be   (1)  -----------MADPATAAREAEEEVQEIIMDETEAVGTHLDFV-AGLEV
IPD103Bf   (1)  ----MQREREREMADQAAAAAREAEEEEVEVFMDETEAVGTHLDFL-AGLNV
IPD103Bk   (1)  -----------MADQAAAAAREAEEEEVEVMDETEAVGTHLDFL-AGLNV
IPD103Db   (1)  --------------------------------------------------
IPD103Bi   (1)  ----------MADKVAAASRAQGAEEEVEDLMDETEAVGTHLDCMGGDVKV
IPD103Da   (1)  ----------MADEVAGHHGPACEEEEEMLMDETEAVGVHAIDG---LPV
IPD103Bc   (1)  ----------MADKAPPPAREAEEEVEETMDETEAVGTHLDLIAHLSVQ
IPD103Bj   (1)  ----------MADKAPPPAREAEEEVEETMDETEAVGTHLDLIAHLSVQ
IPD103Bg   (1)  --------MADKVAAAPPPAREAEEEVEETMDETEAVGTHLDLIATL---
IPD103Bh   (1)  --------MADKVAAAPPPAREAEEEVEETMDETEAVGTHLDLIATL---

51▼                                           100
IPD103Aa  (40)  QPRNIITVEVDAAAVIQQIREIFQTMARHFNSTRVVRDEAIKGIRDHFRA
IPD103Ab  (39)  QPRNIITVEVDAAAVIQQIREIFQTMARHFNSTRVVRDEAIKGIRDHFRA
IPD103Ac  (39)  QPRNIITVEVDAAAVIQQIREIFQTMARHFNSTRVVRDEAIKGIRDHFRA
IPD103Ad  (38)  QPRNIITVEVDAAAVIQQIREIFQTMARHFNSTRVVRDEAIKGIRDHFRA
IPD103Ae  (37)  QPRNIITVEVDAAAVIQQIREIFQTMARHFNSTRVVRDEAIKGIRDHFRA
IPD103Bd  (38)  QPRSIITVEVDAAAVIQQIREIFQTMARHFNSTRVVRDEAIKGIRDHFRA
IPD103Ba  (50)  QPRKIITVEVDPAAVIQQIREIFQTMARHFNSTVVRDEAIKGIRDHFRA
IPD103Bb  (39)  QPRKIITVEVDPAAVIQQIREIFQTLARHFNSTVVRDEAIKGIRDHFRA
IPD103Ca  (50)  QPRKIITVEVDPAAVIQQIREIFQTLARHFNSTVVRDEAIKGIRDHFRA
IPD103Be  (39)  QPRKVITVEVDAAAVIQQIREIFRTMASHFNSTRVVRDEAIKGIRDHFRA
IPD103Bf  (47)  QPRKVITVEVDAAAVIQQIREIFQTMARHFNSTRVVRDEAIKGIRDHFRA
IPD103Bk  (39)  QPRKVITVEVDAAAVIQQIREIFQTMARHFNSTRVVRDEAIKGIRDHFRA
IPD103Db   (1)  --------MDAAAVIQQIREIFQSMADDFSSTKVVRDEAIKGIRDHFRA
IPD103Bi  (41)  QARGIITVEVDPAAVIQQIREIFQTLARHYNSTRVVRDAAIKAIRDHFRA
IPD103Da  (39)  QNRSIITVEVDAAAVIQQIREIFASMIKHYNSTRVVRDEAIKSIRDHFRL
IPD103Bc  (40)  -PRGIITVEVDPAAVIQQIREIFQTMARHFNSTRVVRDEAIKGIRDHFRA
IPD103Bj  (40)  -PRGIITVEVDPAAVIQQIREIFQTMARHFNSTRVVRDEAIKGIRDHFRA
IPD103Bg  (40)  -PRGIITVEVDSAAVIQQIREIFQTMARHFNSTRVVRDEAIKGIRDHFRA
IPD103Bh  (40)  -PRGIITVEVDGAAVIQQIREIFQTMARHFNSTRVVRDEAIKGIRDHFRA
```

Fig. 1B

```
              101                                                150
IPD103Aa  (90)  AVPTRNVVVIHTQHVHT-LVGLEHTHLVLQTGIFKKVPVDIYVFKSGVFT
IPD103Ab  (89)  AVPTRNVVVIHTQHVHT-LVGLEHTHLVLQTGIFKKVPVDIYVFKSGVFT
IPD103Ac  (89)  AVPTRNVVVIHTQHVHT-LVGLEHTHLVLQTGIFKKVPVDIYVFKSGVFT
IPD103Ad  (88)  AVPTRNVVVIHTQHVQT-LVAVEHSIVLQTGIFKKVPVDIYVFKSGVFT
IPD103Ae  (87)  AVPTRNVVVIHTQHVQT-LVAVEHSIVLQTGIFKKVPVDIYVFKSGVFT
IPD103Bd  (88)  AVPTRNVVVVHTQHVHT-LVGLEHTNIVLQTGLFKKVPVDIYVFKSGVFT
IPD103Ba (100)  AVPTRNVVVVHTQHIHT-LEGLEHTNLVLQTGLFRKVPVDIYVFKSGVFT
IPD103Bb  (89)  AVPTRNVVVVHTQHIHT-LEGLEHTNLVLQTGRFRKVPVDIYVFKSGVFT
IPD103Ca (100)  AVPTRNVVVVHTQHIHT-LEGLEHTNLVLQTGRFRKVPVDIYVFKSGVFT
IPD103Be  (89)  AVPTRNVVVVHTQHIHT-LEGLEHTNLVLQTGLFKKVPVDIYVFKSGVFT
IPD103Bf  (97)  AVPTRNVVVVHTQHIHT-LVDVEHTNLVLQTGIFKKVPVDIYVFKSGVFT
IPD103Bk  (89)  AVPTRNVVVVHTQHIHT-LVDVEHTNLVLQTGIFKKVPVDIYVFKSGVFT
IPD103Db  (42)  AVPTRNVVVVHTPHIHTQLVDVEHTKLVLKTGIFEKVPVDIYVFKSGVFT
IPD103Bi  (91)  AVPTRNVVVIHTQHVHT-LADVEHSHLVLQTGLFKKVPVDIYVFKSGVFT
IPD103Da  (89)  AVPTRNVVVIHTQHVHT-LDAVESSHLVLRTGLFKKVPVDIFVFKSGVFT
IPD103Bc  (89)  AVPTRNVVVIHTQHVHT-LVGLEHTHLVLQTGIFRTVPVDIYVFKSGVFT
IPD103Bj  (89)  AVPTRNVVVIHTQHVHT-LVGLEHTHLVLQTGIFRTVPVDIYVFKSGVLT
IPD103Bg  (89)  AIPTRNVVVIHTQHVHT-LVGLEHTHLVLQTGIFKKVPVDVYVFKSGVLT
IPD103Bh  (89)  AIPTRNVVVIHTQHVHT-LVGLEHTHLVLQTGIFKKVPVDVYVFKSGVLT 151                184
IPD103Aa (139)  NLGDGGFINWAWGGFVDQVVGKRIHFRLPPGALP
IPD103Ab (138)  NLGDGGFINWAWGGFVDQVVGKRIHFRLPPGALP
IPD103Ac (138)  NLGDGGFINWAWGGFVDQVVGKRIHFRLPPGALP
IPD103Ad (137)  NLGDGGYINWAWGGFVDQVVGKRIHFRLPPGALP
IPD103Ae (136)  NLGDGGYINWAWGGFVDQVVGKRIHFRLPPGALP
IPD103Bd (137)  ILGDGGFINWAWGGFVDQVVGKRIHFRLPPGALP
IPD103Ba (149)  ILGDGGFINWAWGGFVEQVVGKRIHFRLPPGALP
IPD103Bb (138)  ILGDGGFINWAWGGFVEQVVGKRIHFRLPPGALP
IPD103Ca (149)  ILGDGGFINWAWGGFVEQVVGKRIHFRLPPGALP
IPD103Be (138)  ILGDGGFINWAWGGFVQEVAGKRIXFRLPPGALP
IPD103Bf (146)  ILGDGGFINWAWGGFVDQVDGKRIHFRLPPGALP
IPD103Bk (138)  ILGDGGFINWAWGGFVDQVDGKRIHFRLPPGALP
IPD103Db  (92)  ILGDGGYNNWAWGGFVDQVVGKRIHFRLPPGALP
IPD103Bi (140)  NLGDGGFINWAWGYVIEVVGKRIHFRLPPGALP
IPD103Da (138)  NLGDGGFINWAWGGYGVNHTAKRVVFSRPPGALP
IPD103Bc (138)  NLGDGGFINWAWGGFVIEVVGKRVHFRLPPGALP
IPD103Bj (138)  NLGDGGFINWAWGGFVIEVVGKRVHFRLPPGALP
IPD103Bg (138)  NLGDGGFINWAWGGFVIEVVGKRVHFRLPPGALP
IPD103Bh (138)  NLGDGGFINWAWGGFVIEVVGKRVHFRLPPGALP
```

INSECTICIDAL PROTEINS FROM PLANTS AND METHODS FOR THEIR USE

CROSS-REFERENCE TO RELATED APPLICATIONS

This application is a continuation of U.S. patent application Ser. No. 17/483,364 filed Sep. 23, 2021, which is a continuation of U.S. patent application Ser. No. 16/311,765 filed Dec. 20, 2018, which is a 371 of PCT Patent Application Number PCT/US2017/039376 filed Jun. 27, 2017, which claims priority to U.S. provisional patent application Ser. No. 62/357,501 filed Jul. 1, 2016, herein incorporated by reference in its entirety.

REFERENCE TO SEQUENCE LISTING SUBMITTED ELECTRONICALLY

The official copy of the sequence listing is submitted electronically via EFS-Web as an XML formatted sequence listing with a file named "105982-US-CON-3 Sequence Listing" created on Oct. 17, 2023, and having a size of 772,000 bytes and is filed concurrently with the specification. The sequence listing contained in this XML formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD103 polypeptides including amino acid substitutions, deletions, insertions, and fragments thereof. Provided are isolated or recombinant nucleic acid molecules capable of encoding IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD103 polypeptides are encompassed. Also provided are isolated or recombinant IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, as well as amino acid substitutions, deletions, insertions, fragments thereof and combinations thereof.

In another aspect methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of an IPD103 polypeptide or detecting the presence of a polynucleotide encoding an IPD103 polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD103 polypeptides.

BRIEF DESCRIPTION OF THE FIGURES

FIG. 1A-1B shows an amino acid sequence alignment, using the ALIGNX® module of the Vector NTI® suite, of the IPD103Aa polypeptide (SEQ ID NO: 2), IPD103Ab polypeptide (SEQ ID NO: 4), IPD103Ac polypeptide (SEQ ID NO: 6), IPD103Ad polypeptide (SEQ ID NO: 8), IPD103Ae polypeptide (SEQ ID NO: 10), IPD103Ba polypeptide (SEQ ID NO: 12), IPD103Bb polypeptide (SEQ ID NO: 14), IPD103Bc polypeptide (SEQ ID NO: 16), IPD103Bd polypeptide (SEQ ID NO: 18), IPD103Be polypeptide (SEQ ID NO: 20), IPD103Bf polypeptide (SEQ ID NO: 22), IPD103Bg polypeptide (SEQ ID NO: 24), IPD103Bh polypeptide (SEQ ID NO: 26), IPD103Ca polypeptide (SEQ ID NO: 34), IPD103 Da polypeptide (SEQ ID NO: 38), and IPD103db polypeptide (SEQ ID NO: 40). The amino acid sequence diversity between the amino acid sequences is highlighted. Conservative amino acid differences are indicated by (▨) shading and non-conservative amino acid difference by (▨) shading. The start site of the truncation variant M20 IPD103Aa polypeptide (SEQ ID NO: 417) of Example 6, is indicated above the IPD103Aa sequence (SEQ ID NO: 2) by a "●" above residue 20. The position of residues R10 and R42 where amino acid substitutions were made Example 16 are indicated above the IPD103Aa sequence (SEQ ID NO: 2) by a "◇" above the residue.

DETAILED DESCRIPTION

Figure 2:
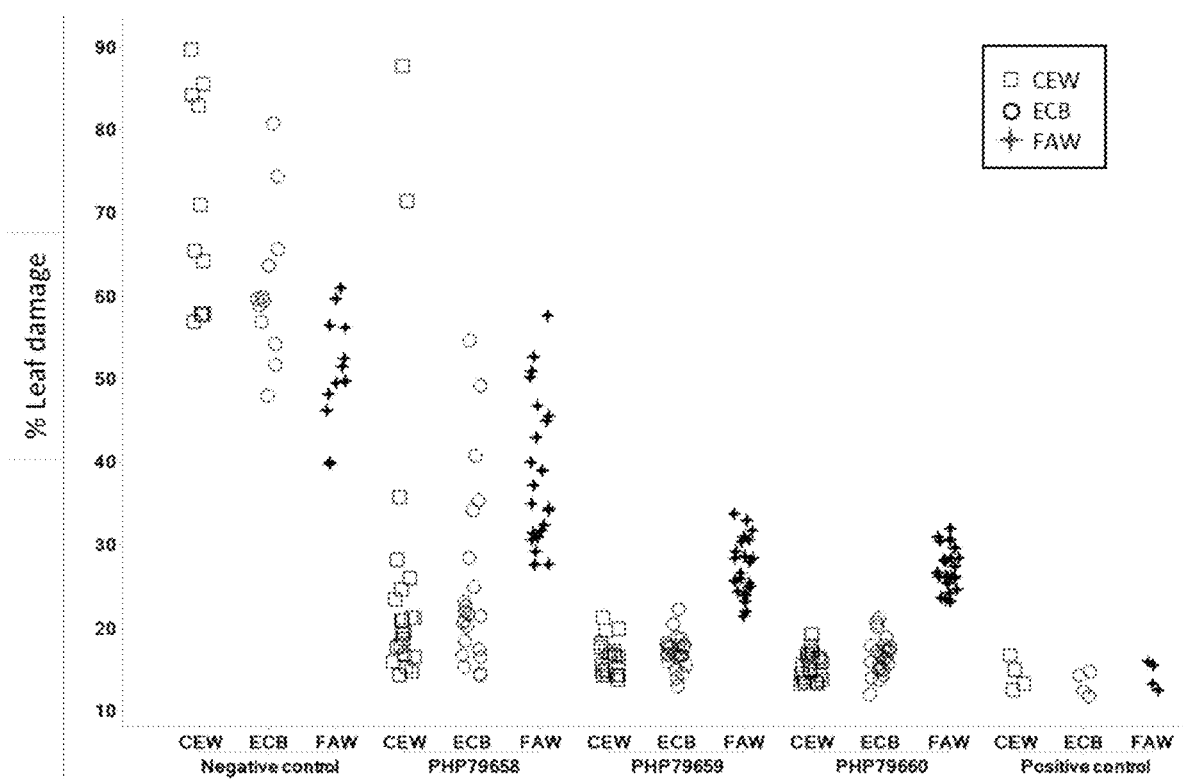
FIG. 2 shows the % leaf damage by CEW, ECB and FAW of individual transgenic T0 maize events from constructs PHP79658, PHP79559 and PHP79660 expressing the IPD103Aa polypeptide (SEQ ID NO: 2).
Figure 3:
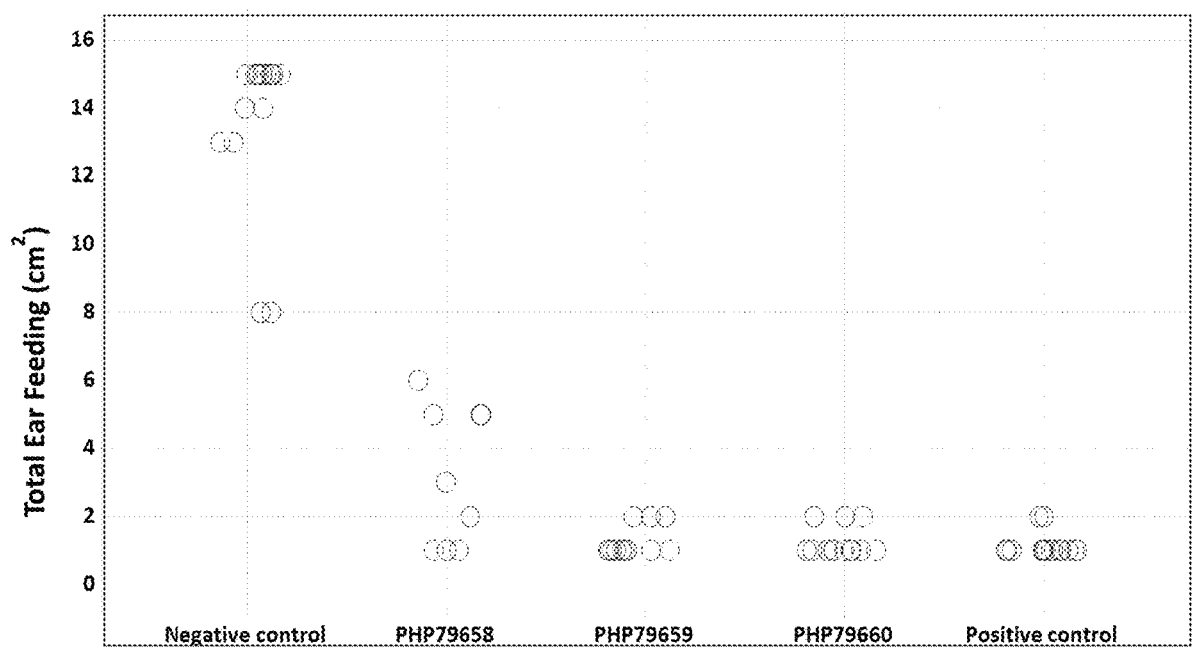
FIG. 3 shows the Total Corn Ear Feeding ($cm^2$) by CEW of individual transgenic T0 maize events from constructs PHP79658, PHP79559 and PHP79660 expressing the IPD103Aa polypeptide (SEQ ID NO: 2).

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding IPD103 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD103 polypeptides by methods known in the art, such as site directed mutagenesis, domain swapping or DNA shuffling. The IPD103 polypeptides find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica* undecimpunctata howardi)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., Xenorhabdus sp., *Clostridium bifermentans* and *Paenibacillus popilliae*. Pesticidal proteins include but are not limited to: insecticidal proteins from *Pseudomonas* sp. such as PSEEN3174 (Monalysin; (2011) PLoS Pathogens 7:1-13); from *Pseudomonas protegens* strain CHAO and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.*, 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and 5-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of 5-endotoxin genes and the *B. thuringiensis* cytolytic cyt1 and cyt2 genes. Members of these classes of *B. thuringiensis* insecticidal proteins well known to one skilled in the art (see, Crickmore, et al., "*Bacillus thuringiensis* toxin nomenclature" (2011), at life-sci.sussex.ac.uk/home/Neil_Crickmore/Bt/ which can be accessed on the world-wide web using the "www" prefix).

Examples of 5-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology*, 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923, 602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal*

9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1E (US2012/0324605); Cry34Ab/35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

In some embodiments the IPD103 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of IPD103 polypeptides. The protein resulting from translation of these IPD103 genes allows cells to control or kill pests that ingest it.

IPD103 Proteins and Variants and Fragments Thereof

IPD103 polypeptides are encompassed by the disclosure. "IPD103 polypeptide" and "IPD103 protein" as used herein interchangeably refers to a polypeptide having insecticidal activity including but not limited to insecticidal activity against one or more insect pests of the Lepidoptera and/or Coleoptera orders, and is sufficiently homologous to the IPD103Aa polypeptide of SEQ ID NO: 2. A variety of IPD103 polypeptides are contemplated. Sources of IPD103 polypeptides or related proteins include fern or other primitive plant species selected from but not limited to *Athyrium* species, *Platycerium* species, *Pteris* species, *Colysis* species, *Nephrolepis* species, *Polystichium* species, *Thelypteris* species, *Tectaria* species, and *Davallia* species. Alignment of the amino acid sequences of IPD103 polypeptide homologs (for example—FIG. 1), allows for the identification of residues that are highly conserved amongst the natural homologs of this family.

In some embodiments the IPD103 polypeptide is derived from a fern species in the Order Athyriales.

In some embodiments the IPD103 polypeptide is derived from a fern species in the Order Athyriales, Family Athyriaceae.

In some embodiments the IPD103 polypeptide is derived from a fern species in the Order Athyriales, Family Athyriaceae, Genus *Athyrium* selected from but not limited to *Athyrium arisanense, Athyrium atkinsonii, Athyrium biserrulatum, Athyrium brevifrons, Athyrium chingianum, Athyrium clarkei, Athyrium clivicola, Athyrium cryptogrammoides, Athyrium cumingianum, Athyrium cuspidatum, Athyrium deltoidofrons, Athyrium distentifolium, Athyrium epirachis, Athyrium eremicola, Athyrium fangii, Athyrium filix-femina, Athyrium frangulum, Athyrium giraldii, Athyrium iseanum, Athyrium kirisimaense, Athyrium kuratae, Athyrium masamunei, Athyrium melanolepis, Athyrium monomachi, Athyrium multidentatum, Athyrium nakanoi, Athyrium neglectum, Athyrium nigripes, Athyrium nikkoense, Athyrium niponicum, Athyrium nyalamense, Athyrium oblitescens, Athyrium otophorum, Athyrium palustre, Athyrium pinetorum, Athyrium pubicostatum, Athyrium reflexipinnum, Athyrium rhachidosorum, Athyrium rupestre, Athyrium scandicinum, Athyrium setuligerum, Athyrium sheareri, Athyrium silvicola, Athyrium sinense, Athyrium skinneri, Athyrium spinulosum, Athyrium strigillosum, Athyrium subrigescens, Athyrium subtriangulare, Athyrium supraspinescens, Athyrium tashiroi, Athyrium tozanense, Athyrium vidalii, Athyrium viridescentipes, Athyrium wardii, Athyrium×akiense, Athyrium×hisatsuanum, Athyrium×tokashikii, Athyrium yokoscense,* and *Athyrium yui.*

In some embodiments the IPD103 polypeptide is derived from a fern species in the Order Polypodiales.

In some embodiments the IPD103 polypeptide is derived from a fern species in the Order Polypodiales, Family Nephrolepidaceae.

n some embodiments the IPD103 polypeptide is derived from a fern species in the Order Polypodiales, Family Nephrolepidaceae, Genus *Nephrolepis* selected from but not limited to *Nephrolepis abrupta, Nephrolepis acutifolia, Nephrolepis averyi, Nephrolepis biserrata, Nephrolepis brownii, Nephrolepis copelandi, Nephrolepis cordifolia, Nephrolepis davalliae, Nephrolepis davallioides, Nephrolepis dicksonioides, Nephrolepis exaltata, Nephrolepis falcata, Nephrolepis falciformis, Nephrolepis hippocrepicis, Nephrolepis laurifolia, Nephrolepis lauterbachii, Nephrolepis medlerae, Nephrolepis obliterata, Nephrolepis pectinata, Nephrolepis pendula, Nephrolepis pseudobiserrata, Nephrolepis radicans, Nephrolepis rivularis,* and *Nephrolepis undulata.*

In some embodiments the IPD103 polypeptide is derived from a fern species in the Order Polypodiales, Family Polypodiaceae.

In some embodiments the IPD103 polypeptide is derived from a fern species in the order Polypodiales, Family Polypodiaceae, Genus *Platycerium* selected from but not limited to *Platycerium alcicorne, Platycerium andinum, Platycerium angolense, Platycerium bifurcatum, Platycerium coronarium, Platycerium elephantotis, Platycerium ellisii, Platycerium grande, Platycerium hillii, Platycerium holttumii, Platycerium madagascariense, Platycerium quadridichotomum, Platycerium ridleyi, Platycerium stemaria, Platycerium superbum, Platycerium veitchii, Platycerium wallichii, Platycerium wandae, Platycerium wilhelminae-reginae*, and *Platycerium willinkii*.

In some embodiments the IPD103 polypeptide is derived from a fern species in the order Polypodiales, Family Polypodiaceae, Genus *Colysis* selected from but not limited to *Colysis ampla, Colysis digitata, Colysis diversifolia, Colysis elegans Colysis elliptica, Colysis flexiloba, Colysis hemionitidea, Colysis hemitoma, Colysis henryi, Colysis insignis, Colysis intermedia, Colysis leveillei, Colysis longipes, Colysis pedunculata, Colysis pentaphylla, Colysis pothifolia, Colysis pteropus, Colysis shintenensis, Colysis simplicifrons, Colysis triphylla, Colysis wrightii*, and *Colysis×shintenensis*.

In some embodiments the IPD103 polypeptide is derived from a fern species in the Order Polypodiales, Family Pteridaceae.

In some embodiments the IPD103 polypeptide is derived from a fern species in the Order Polypodiales, Family Pteridaceae, Genus *Pteris* selected from but not limited to *Pteris actiniopteroides, Pteris amoena, Pteris angustipinna, Pteris angustipinnula, Pteris aspericaulis, Pteris austrosinica, Pteris baksaensis, Pteris bella, Pteris biaurita, Pteris bomiensis, Pteris cadieri, Pteris changjiangensis, Pteris confertinervia, Pteris crassiuscula, Pteris cretica, Pteris cryptogrammoides, Pteris dactylina, Pteris dangiana, Pteris decrescens, Pteris deltodon, Pteris dispar, Pteris dissitifolia, Pteris ensiformis, Pteris esquirolii, Pteris excelsa, Pteris fauriei, Pteris finotii, Pteris formosana, Pteris gallinopes, Pteris gracillima, Pteris grevilleana, Pteris guangdongensis, Pteris guizhouensis, Pteris henryi, Pteris heteromorpha, Pteris hui, Pteris insignis, Pteris kidoi, Pteris kiuschinensis, Pteris kiuschiuensis, Pteris laurisilvicola, Pteris libonsis, Pteris linearis, Pteris longipes, Pteris longipinna, Pteris longipinnula, Pteris maclurei, Pteris maclurioides, Pteris medogensis, Pteris morii, Pteris multifida, Pteris nipponica, Pteris obtusiloba, Pteris occidentali-sinica, Pteris oshimensis, Pteris paucipinnula, Pteris plumbea, Pteris pseudodactylina, Pteris pseudopellucida, Pteris puberula, Pteris quadristipitis, Pteris quinquefoliata, Pteris rufopilosa, Pteris ryukyuensis, Pteris sanduensis, Pteris scabristipes, Pteris semipinnata, Pteris setulosocostulata, Pteris shimianensis, Pteris sichuanensis, Pteris sinensis, Pteris splendida, Pteris stenophylla, Pteris subquinata, Pteris taiwanensis, Pteris tibetica, Pteris tripartita, Pteris undulatipinna, Pteris venusta, Pteris viridissima, Pteris vittata, Pteris wallichiana, Pteris wangiana, Pteris xiaoyingiae, Pteris xichouensis*, and *Pteris wulaiensis*.

In some embodiments the IPD103 polypeptide is derived from a fern species in the Order Polypodiales, Family Tectariaceae.

In some embodiments the IPD103 polypeptide is derived from a fern species in the Order Polypodiales, Family Tectariaceae, Genus *Tectaria* selected from but not limited to *Tectaria acerifolia, Tectaria acrocarpa, Tectaria adenophora, Tectaria aequatoriensis, Tectaria amblyotis, Tectaria amphiblestra, Tectaria andersonii, Tectaria angelicifolia, Tectaria angulata, Tectaria antioquiana, Tectaria athyrioides, Tectaria athyriosora, Tectaria aurita, Tectaria balansae, Tectaria barberi, Tectaria barteri, Tectaria beccariana, Tectaria blumeana, Tectaria brachiata, Tectaria brauniana, Tectaria brevilobata, Tectaria brooksii, Tectaria buchtienii, Tectaria calcarea, Tectaria camerooniana, Tectaria chattagramica, Tectaria cherasica, Tectaria chimborazensis, Tectaria chinensis, Tectaria christii, Tectaria christovalensis, Tectaria cicutaria, Tectaria coadunata, Tectaria confluens, Tectaria consimilis, Tectaria cordulata, Tectaria coriandrifolia, Tectaria craspedocarpa, Tectaria crenata, Tectaria crinigera, Tectaria croftii, Tectaria curtisii, Tectaria danfuensis, Tectaria decaryana, Tectaria decastroi, Tectaria decurrens, Tectaria degeneri, Tectaria dolichosora, Tectaria draconoptera, Tectaria dubia, Tectaria durvillei, Tectaria ebenina, Tectaria estremerana, Tectaria exauriculata, Tectaria fauriei, Tectaria fengii, Tectaria fernandensis, Tectaria ferruginea, Tectaria filisquamata, Tectaria fimbriata, Tectaria fissa, Tectaria gaudichaudii, Tectaria gemmifera, Tectaria godeffroyi, Tectaria grandidentata, Tectaria griffithii* var. *singaporeana, Tectaria grossedentata, Tectaria hederifolia, Tectaria hekouensis, Tectaria heracleifolia, Tectaria herpetocaulos, Tectaria heterocarpa, Tectaria hilocarpa, Tectaria holttumii, Tectaria hookeri, Tectaria humbertiana, Tectaria hymenodes, Tectaria hymenophylla, Tectaria impressa, Tectaria incisa, Tectaria inopinata, Tectaria isomorpha, Tectaria jacobsii, Tectaria jardini, Tectaria johannis-winkleri, Tectaria keckii, Tectaria kehdingiana, Tectaria kingii, Tectaria kouniensis, Tectaria kweichowensis, Tectaria labrusca, Tectaria lacei, Tectaria laotica, Tectaria latifolia, Tectaria lawrenceana, Tectaria laxa, Tectaria leptophylla, Tectaria lifuensis, Tectaria lizarzaburui, Tectaria lobbii, Tectaria lombokensis, Tectaria macrosora, Tectaria macrota, Tectaria madagascarica, Tectaria magnifica, Tectaria manilensis, Tectaria marchionica, Tectaria media, Tectaria melanocaulis, Tectaria melanocauloides, Tectaria melanorachis, Tectaria menyanthidis, Tectaria mesodon, Tectaria mexicana, Tectaria microchlamys, Tectaria microlepis, Tectaria minuta, Tectaria moorei, Tectaria morlae, Tectaria moussetii, Tectaria murrayi, Tectaria nabirensis, Tectaria nausoriensis, Tectaria nebulosa, Tectaria nesiotica, Tectaria nicaraguensis, Tectaria nicotianifolia, Tectaria nitens, Tectaria novoguineensis, Tectaria organensis, Tectaria palmate, Tectaria pandurifolia, Tectaria pedata, Tectaria pentagonalis, Tectaria perdimorpha, Tectaria phaeocaulis, Tectaria pica, Tectaria pilosa, Tectaria plantaginea, Tectaria pleiosora, Tectaria pleiotoma, Tectaria poilanei, Tectaria polymorpha, Tectaria prolifera, Tectaria pseudosinuata, Tectaria×pteropus-minor, Tectaria pubens, Tectaria puberula, Tectaria pubescens, Tectaria quinquefida, Tectaria quitensis, Tectaria ramosii, Tectaria rara, Tectaria remotipinna, Tectaria repanda, Tectaria rheophytica, Tectaria rigida, Tectaria rivalis, Tectaria rockii, Tectaria rufescens, Tectaria rufovillosa, Tectaria sagenioides, Tectaria schmutzii, Tectaria schultzei, Tectaria seemannii, Tectaria semibipinnata, Tectaria semipinnata, Tectaria seramensis, Tectaria siifolia, Tectaria simaoensis, Tectaria simonsii, Tectaria simulans, Tectaria singaporeana, Tectaria sinuata, Tectaria squamipes, Tectaria stalactica, Tectaria stearnsii, Tectaria stenosemioides, Tectaria subcaudata, Tectaria subconfluens, Tectaria subcordata, Tectaria subdigitata, Tectaria subebenea, Tectaria subrepanda, Tectaria subsageniacea, Tectaria subtriloba, Tectaria subtriphylla, Tectaria sulitii, Tectaria suluensis, Tectaria sumatrana, Tectaria tabonensis, Tectaria taccifolia, Tectaria tahitensis, Tectaria tenerifrons, Tectaria tenuifolia, Tectaria teratocarpa, Tectaria ternata, Tectaria transiens, Tectaria translucens, Tectaria tricuspis, Tectaria trifida, Tectaria trifoliata, Tectaria triglossa, Tectaria triloba, Tectaria trimenii, Tectaria trinitensis, Tectaria tripartita, Tectaria variabilis, Tectaria vasta, Tectaria vieillardii, Tectaria villosa,*

*Tectaria vitiensis, Tectaria vivipara, Tectaria waterlotii, Tectaria weberi, Tectaria wightii, Tectaria×amesiana, Tectaria×cynthiae, Tectaria yunnanensis, Tectaria zeylanica,* and *Tectaria zollingeri.*

In some embodiments the IPD103 polypeptide is derived from a fern species in the Order Polypodiales, Family Davalliaceae.

In some embodiments the IPD103 polypeptide is derived from a fern species in the Order Polypodiales, Family Davalliaceae Genus *Davallia* selected from but not limited to *Davallia adiantoides, Davallia amabilis, Davallia assamica, Davallia austrosinica, Davallia biflora, Davallia boryana, Davallia brachypoda, Davallia brevisora, Davallia bullata, Davallia bullata, Davallia calvescens, Davallia calvescens, Davallia canariensis, Davallia chaerophylla, Davallia chaerophylloide, Davallia chrysanthemifolia, Davallia clarkei, Davallia cumingii, Davallia cylindrica, Davallia divaricata, Davallia divaricata, Davallia divaricata* var. *orientale, Davallia domingensis, Davallia dubia, Davallia elmeri, Davallia falcata, Davallia falcinella, Davallia ferulacea, Davallia flaccida, Davallia formosana, Davallia fumarioides, Davallia goudotiana, Davallia gracilis, Davallia griffithiana, Davallia griffithiana, Davallia henryana, Davallia heterophylla, Davallia hookeriana, Davallia hymenophylloides, Davallia immersa, Davallia inaequalis* var. *minor, Davallia jamaicensis, Davallia khasiyana, Davallia kurzii, Davallia lepida, Davallia lepida, Davallia macraeana, Davallia magellanica, Davallia mariesii, Davallia membranulosa, Davallia membranulosa, Davallia millefolium, Davallia moorei, Davallia multidentata, Davallia nodosa, Davallia novae-guineae, Davallia orientalis, Davallia parallela, Davallia parkeri, Davallia parvipinnula, Davallia patens, Davallia pectinata, Davallia perdurans, Davallia pilosula, Davallia platylepis, Davallia polypodioides, Davallia polypodioides* var. *hispida, Davallia polypodioides* var. *pilosula, Davallia pseudocystopteris, Davallia puberula, Davallia pyramidata, Davallia pyxidata, Davallia repens, Davallia rhomboidea, Davallia rhomboidea, Davallia rhomboidea, Davallia sinensis, Davallia sloanei, Davallia solida, Davallia solida, Davallia stipellata, Davallia strigosa, Davallia strigosa, Davallia strigosa* var. *rhomboidea, Davallia subalpina, Davallia subsolida, Davallia teyermannii, Davallia triangularis, Davallia tripinnata, Davallia truncata, Davallia tyermanni, Davallia tyermannii, Davallia uncinella, Davallia urophylla, Davallia vestita, Davallia wilfordii* var. *contracta,* and *Davallia yunnanensis.*

In some embodiments the IPD103 polypeptide is derived from a fern species in the Order Polypodiales, Family Dryopteridaceae.

In some embodiments the IPD103 polypeptide is derived from a fern species in the Order Polypodiales, Family Dryopteridaceae, Genus *Polystichum* selected from but not limited to *Polystichum acanthophyllum, Polystichum aculeatum, Polystichum acutidens, Polystichum acutipinnulum, Polystichum adungense, Polystichum alcicorne, Polystichum altum, Polystichum anomalum, Polystichum ariticulatipilosum, Polystichum assurgentipinnum, Polystichum atkinsonii, Polystichum attenuatum, Polystichum auriculum, Polystichum bakerianum, Polystichum baoxingense, Polystichum biaristatum, Polystichum bifidum, Polystichum bigemmatum, Polystichum bissectum, Polystichum bomiense, Polystichum brachypterum, Polystichum braunii, Polystichum capillipes, Polystichum castaneum, Polystichum chingiae, Polystichum christii, Polystichum chunii, Polystichum consimile, Polystichum costularisorum, Polystichum craspedosorum, Polystichum crassinervium, Polystichum cringerum, Polystichum cuneatiforme, Polystichum cyclolobum, Polystichum daguanense, Polystichum dangii, Polystichum delavayi, Polystichum deltodon, Polystichum dielsii, Polystichum diffundens, Polystichum discretum, Polystichum disjunctum, Polystichum duthiei, Polystichum elevatovenusum, Polystichum erosum, Polystichum exauriforme, Polystichum excellens, Polystichum excelsius, Polystichum fimbriatum, Polystichum formosanum, Polystichum frigidicola, Polystichum fugongense, Polystichum gongboense, Polystichum grandifrons, Polystichum guangxiense, Polystichum gymnocarpium, Polystichum habaense, Polystichum hancockii, Polystichum hecatopteron, Polystichum herbaceum, Polystichum houchangense, Polystichum huae, Polystichum ichangense, Polystichum inaense, Polystichum incisopinnulum, Polystichum integrilimbum, Polystichum integrilobum, Polystichum jinfoshaense, Polystichum jiulaodongense, Polystichum jizhushanense, Polystichum kangdingense, Polystichum kungianum, Polystichum kwangtungense, Polystichum lachenense, Polystichum lanceolatum, Polystichum langchungense, Polystichum latilepis, Polystichum lentum, Polystichum leveillei, Polystichum liui, Polystichum lonchitis, Polystichum longiaristatum, Polystichum longidens, Polystichum longipaleatum, Polystichum longipes, Polystichum longipinnulum, Polystichum longispinosum, Polystichum longissimum, Polystichum macrochlaenum, Polystichum makinoi, Polystichum manmeiense, Polystichum martinii, Polystichum mayebarae, Polystichum medogense, Polystichum mehrae, Polystichum meiguense, Polystichum melanostipes, Polystichum mollissimum, Polystichum morii, Polystichum moupinense, Polystichum muscicola, Polystichum nayongense, Polystichum neoliuii, Polystichum neolobatum, Polystichum nepalense, Polystichum nigrum, Polystichum ningshenense, Polystichum nudisorum, Polystichum obliquum, Polystichum oblongum, Polystichum oligocarpum, Polystichum omeiense, Polystichum oreodoxa, Polystichum orientalitibeticum, Polystichum otophorum, Polystichum ovato-paleaceum, Polystichum paramoupinense, Polystichum parvifoliolatum, Polystichum parvipinnulum, Polystichum pianmaense, Polystichum piceo-paleaceum, Polystichum polyblepharum, Polystichum prescottianum, Polystichum prionolepis, Polystichum pseudocastaneum, Polystichum pseudolanceolatum, Polystichum pseudomakinoi, Polystichum pseudorhomboideum, Polystichum pseudosetosum, Polystichum pseudoxiphophyllum, Polystichum punctiferum, Polystichum puteicola, Polystichum pycnopterum, Polystichum qamdoense, Polystichum retrosopaleaceum, Polystichum revolutum, Polystichum rhombiforme, Polystichum rigens, Polystichum robustum, Polystichum rufopaleaceum, Polystichum saxicola, Polystichum semifertile, Polystichum setillosum, Polystichum shandongense, Polystichum shensiense, Polystichum shimurae, Polystichum simplicipinnum, Polystichum sinense, Polystichum sinotsussimense, Polystichum sozanense, Polystichum speluncicola, Polystichum squarrosum, Polystichum stenophyllum, Polystichum stimulans, Polystichum subacutidens, Polystichum subdeltodon, Polystichum subfimbriatum, Polystichum submarginale, Polystichum submite, Polystichum subulatum, Polystichum tacticopterum, Polystichum taizhongense, Polystichum tangmaiense, Polystichum thomsonii, Polystichum tibeticum, Polystichum tonkinense, Polystichum tripteron, Polystichum tsingkanshanense, Polystichum tsussimense, Polystichum wattii, Polystichum xiphophyllum, Polystichum yadongense, Polystichum yuanum, Polystichum yunnanense,*and *Polystichum zayuense.*

In some embodiments the IPD103 polypeptide is derived from a fern species in the Order Polypodiales, Family Thelypteridaceae.

In some embodiments the IPD103 polypeptide is derived from a fern species in the Order Polypodiales, Family Thelypteridaceae, Genus *Thelypteris* selected from but not limited to *Thelypteris abrupta, Thelypteris acuminata, Thelypteris affinis, Thelypteris angulariloba, Thelypteris angustifrons, Thelypteris aurita, Thelypteris beddomei, Thelypteris boninensis, Thelypteris bukoensis, Thelypteris castanea, Thelypteris clypeolutata, Thelypteris consanguinea, Thelypteris cystopteroides, Thelypteris dayi, Thelypteris erubescens, Thelypteris esquirolii, Thelypteris flexilis, Thelypteris gemmulifera, Thelypteris glandulosa, Thelypteris globulifera, Thelypteris gracilescens, Thelypteris gracilis, Thelypteris interrupta, Thelypteris jaculosa, Thelypteris japonica, Thelypteris laxa, Thelypteris linkiana, Thelypteris liukiuensis, Thelypteris longissima, Thelypteris meniscioides, Thelypteris miyagii, Thelypteris musashiensis, Thelypteris navarrensis, Thelypteris nevadensis, Thelypteris nipponica, Thelypteris ogasawarensis, Thelypteris oligocarpa, Thelypteris omeiensis, Thelypteris opulenta, Thelypteris ovata, Thelypteris palustris, Thelypteris parasitica, Thelypteris poiteana, Thelypteris reticulata, Thelypteris rustica, Thelypteris seemannii, Thelypteris sp. b1-007, Thelypteris sp. Janssen 2679, Thelypteris subaurita, Thelypteris taiwanensis, Thelypteris truncata, Thelypteris tylodes, Thelypteris uraiensis*, and *Thelypteris viridifrons*.

"Sufficiently homologous" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments the sequence homology is against the full length sequence of an IPD103 polypeptide. In some embodiments the IPD103 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. The term "about" when used herein in context with percent sequence identity means+/−0.5%. One of skill in the art will recognize that these values can be appropriately adjusted to determine corresponding homology of proteins taking into account amino acid similarity and the like. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX® module of the Vector NTI® Program Suite (Invitrogen Corporation, Carlsbad, Calif.) with all default parameters.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. An IPD103 polypeptide that is substantially free of cellular material includes preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to an IPD103 polypeptide and that exhibit insecticidal activity. "Fragments" or "biologically active portions" of IPD103 polypeptides includes fragments comprising amino acid sequences sufficiently identical to the amino acid sequence set forth in IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38 wherein the IPD103 polypeptide has insecticidal activity. Such biologically active portions can be prepared by recombinant techniques and evaluated for insecticidal activity. In some embodiments, the IPD103 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, e.g., by proteolysis, by insertion of a start codon, by deletion of the codons encoding the deleted amino acids and concomitant insertion of a start codon, and/or insertion of a stop codon. In some embodiments, the IPD103 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments, the IPD103 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments the truncated variant is the polypeptide of SEQ ID NO: 445.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD103 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, wherein the IPD103 polypeptide has insecticidal activity.

In some embodiments an IPD103 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of the IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments the sequence identity is across the entire length of the polypeptide calculated using ClustalW algorithm in the ALIGNX® module of the Vector NTI® Program Suite (Invitrogen Corporation, Carlsbad, Calif.) with all default parameters.

In some embodiments the IPD103 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

In some embodiments an IPD103 polypeptide comprises an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38, having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the native amino acid at the corresponding position of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38.

In some embodiments an IPD103 polypeptide variant comprises any one or more active amino acid substitutions of Table 5 and/or 7.

Methods for such manipulations are generally known in the art. For example, amino acid sequence variants of an IPD103 polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of an IPD103 polypeptide to confer pesticidal activity may be improved by the use of such techniques upon the compositions of this disclosure.

For example, conservative amino acid substitutions may be made at one or more predicted nonessential amino acid residues. A "nonessential" amino acid residue is a residue that can be altered from the wild-type sequence of an IPD103 polypeptide without altering the biological activity. Nonessential amino acid residues can be identified by aligning related IPD103 homologs such as is shown in FIG. 1. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different IPD103 polypeptide coding regions can be used to create a new IPD103 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered IPD103 polypeptides. Domains may be swapped between IPD103 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Phylogenetic, sequence motif, and structural analyses of insecticidal protein families. A sequence and structure analysis method can be employed, which is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences can be subjected to ClustalW version 2 analysis (Larkin M. A et al (2007) Bioinformatics 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, California, 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100.

The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the IPD103 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD103 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

One skilled in the art understands that the polynucleotide coding sequence can be modified to add a codon at the penultimate position following the methionine start codon to create a restriction enzyme site for recombinant cloning purposes and/or for expression purposes. In some embodiments the IPD103 polypeptide further comprises an alanine residue at the penultimate position after the translation initiator methionine.

In some embodiments the translation initiator methionine of the IPD103 polypeptide is cleaved off post translationally. One skilled in the art understands that the N-terminal translation initiator methionine can be removed by methionine aminopeptidase in many cellular expression systems.

In some embodiments the IPD103 polypeptide comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments the IPD103 polypeptide comprises the amino acid sequence of SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO:

386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471 or SEQ ID NO: 472.

In some embodiments, chimeric polypeptides are provided comprising regions of at least two different IPD103 polypeptides of the disclosure.

In some embodiments, chimeric polypeptides are provided comprising regions of at least two different IPD103 polypeptides selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments, chimeric IPD103 polypeptide are provided comprising an N-terminal Region of a first IPD103 polypeptide of the disclosure operably fused to a C-terminal Region of a second IPD103 polypeptide of the disclosure.

In some embodiments, chimeric IPD103 polypeptide are provided comprising an N-terminal Region of a first IPD103 polypeptide operably fused to a C-terminal Region of a second IPD103 polypeptide, where the first and second IPD103 polypeptide is selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In other embodiments the IPD103 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.*, 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another embodiment the IPD103 polypeptide may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the IPD103 polypeptide and the 3' intein coding sequence is linked to the 5' end of the second fragment coding for the C-terminal part of the IPD103 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In some embodiments the IPD103 polypeptide is a circular permuted variant. In certain embodiments the IPD103 polypeptide is a circular permuted variant of the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472, or variant thereof having an amino acid substitution, deletion, addition or combinations thereof. The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) Critical Rev. Biotech. 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) Proteins: Struct., Funct. & Genetics 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted IPD103 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted IPD103 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another embodiment fusion proteins are provided that include within its amino acid sequence an amino acid sequence comprising an IPD103 polypeptide or chimeric IPD103 polypeptide of the disclosure. Methods for design and construction of fusion proteins (and polynucleotides encoding same) are known to those of skill in the art. Polynucleotides encoding an IPD103 polypeptide may be fused to signal sequences which will direct the localization of the IPD103 polypeptide to particular compartments of a prokaryotic or eukaryotic cell and/or direct the secretion of the IPD103 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD103 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD103 polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the IPD103 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29): 15104-9. In some embodiments the IPD103 polypeptide is fused to a heterologous signal peptide or heterologous transit peptide.

In some embodiments fusion proteins are provide comprising an IPD103 polypeptide or chimeric IPD103 polypeptide of the disclosure represented by a formula selected from the group consisting of:

$$R^1\text{-}L\text{-}R^2, R^2\text{-}L\text{-}R^1, R^1\text{-}R^2 \text{ or } R^2\text{-}R^1$$

wherein $R^1$ is an IPD103 polypeptide or chimeric IPD103 polypeptide of the disclosure and $R^2$ is a protein of interest. In some embodiments $R^1$ and $R^2$ are an IPD103 polypeptide or chimeric IPD103 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO: 508) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD103 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD103 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD103 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD103 polypeptide is a non-genomic sequence.

A variety of polynucleotides that encode IPD103 polypeptides or related proteins are contemplated. Such polynucleotides are useful for production of IPD103 polypeptides in host cells when operably linked to a suitable promoter, transcription termination and/or polyadenylation sequences. Such polynucleotides are also useful as probes for isolating homologous or substantially homologous polynucleotides that encode IPD103 polypeptides or related proteins.

Polynucleotides Encoding IPD103 Polypeptides

One source of polynucleotides that encode IPD103 polypeptides or related proteins is a fern or other primitive plant species selected from but not limited to Athyrium species, Platycerium species, Pteris species, Colysis species, Nephrolepis species, Polystichium species, Thelypteris species, Tectaria species, and Davallia species, which contains an IPD103 polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, respectively. The polynucleotides of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 can be used to express IPD103 polypeptides in recombinant bacterial hosts that include but are not limited to Agrobacterium, Bacillus, Escherichia, Salmonella, Pseudomonas and *Rhizobium* bacterial host cells. The polynucleotides are also useful as probes for isolating homologous or substantially homologous polynucleotides that encode IPD103 polypeptides or related proteins. Such probes can be used to identify homologous or substantially homologous polynucleotides derived from fern or other primitive plant species selected from but not limited to *Athyrium* species, *Platycerium* species, *Pteris* species, *Colysis* species, *Nephrolepis* species, *Polystichium* species, *Thelypteris* species, *Tectaria* species, and *Davallia* species.

In some embodiments the nucleic acid molecule encoding the IPD103 polypeptide is derived from a fern species in the Order Athyriales.

In some embodiments the nucleic acid molecule encoding the IPD103 polypeptide is derived from a fern species in the Order Athyriales, Family Athyriaceae.

In some embodiments the nucleic acid molecule encoding the IPD103 polypeptide is derived from a fern species in the Order Athyriales, Family Athyriaceae, Genus *Athyrium* selected from but not limited to *Athyrium arisanense, Athyrium atkinsonii, Athyrium biserrulatum, Athyrium brevifrons, Athyrium chingianum, Athyrium clarkei, Athyrium clivicola, Athyrium cryptogrammoides, Athyrium cumingianum, Athyrium cuspidatum, Athyrium deltoidofrons, Athyrium distentifolium, Athyrium epirachis, Athyrium eremicola, Athyrium fangii, Athyrium fiix-femina, Athyrium frangulum, Athyrium giraldii, Athyrium iseanum, Athyrium kirisimaense, Athyrium kuratae, Athyrium masamunei, Athyrium melanolepis, Athyrium monomachi, Athyrium multidentatum, Athyrium nakanoi, Athyrium neglectum, Athyrium nigripes, Athyrium nikkoense, Athyrium niponicum, Athyrium nyalamense, Athyrium oblitescens, Athyrium otophorum, Athyrium palustre, Athyrium pinetorum, Athyrium pubicostatum, Athyrium reflexipinnum, Athyrium rhachidosorum, Athyrium rupestre, Athyrium scandicinum, Athyrium setuligerum, Athyrium sheareri, Athyrium silvicola, Athyrium sinense, Athyrium skinneri, Athyrium spinulosum, Athyrium strigillosum, Athyrium subrigescens, Athyrium subtriangulare, Athyrium supraspinescens, Athyrium tashiroi, Athyrium tozanense, Athyrium vidalii, Athyrium viridescentipes, Athyrium wardii, Athyrium×akiense, Athyrium×hisatsuanum, Athyrium×tokashikii, Athyrium yokoscense*, and *Athyrium yui*.

In some embodiments the nucleic acid molecule encoding the IPD103 polypeptide is derived from a fern species in the Order Polypodiales.

In some embodiments the nucleic acid molecule encoding the IPD103 polypeptide is derived from a fern species in the Order Polypodiales, Family Nephrolepidaceae.

In some embodiments the nucleic acid molecule encoding the IPD103 polypeptide is derived from a fern species in the Order Polypodiales, Family Nephrolepidaceae, Genus *Nephrolepis* selected from but not limited to *Nephrolepis abrupta, Nephrolepis acutifolia, Nephrolepis averyi, Nephrolepis biserrata, Nephrolepis brownii, Nephrolepis copelandi, Nephrolepis cordifolia, Nephrolepis davalliae, Nephrolepis davallioides, Nephrolepis dicksonioides, Nephrolepis exaltata, Nephrolepis falcata, Nephrolepis falciformis, Nephrolepis hippocrepicis, Nephrolepis laurifolia, Nephrolepis lauterbachii, Nephrolepis medlerae, Nephrolepis obliterata, Nephrolepis pectinata, Nephrolepis pendula, Nephrolepis pseudobiserrata, Nephrolepis radicans, Nephrolepis rivularis*, and *Nephrolepis undulata*.

In some embodiments the nucleic acid molecule encoding the IPD103 polypeptide is derived from a fern species in the Order Polypodiales, Family Polypodiaceae.

In some embodiments the nucleic acid molecule encoding the IPD103 polypeptide is derived from a fern species in the order Polypodiales, Family Polypodiaceae, Genus *Platycerium* selected from but not limited to *Platycerium alcicorne, Platycerium andinum, Platycerium angolense, Platycerium bifurcatum, Platycerium coronarium, Platycerium elephantotis, Platycerium ellisii, Platycerium grande, Platycerium hillii, Platycerium holttumii, Platycerium madagascariense, Platycerium quadridichotomum, Platycerium ridleyi, Platycerium stemaria, Platycerium superbum, Platycerium veitchii, Platycerium wallichii, Platycerium wandae, Platycerium wilhelminae-reginae*, and *Platycerium willinkii*.

In some embodiments the nucleic acid molecule encoding the IPD103 polypeptide is derived from a fern species in the order Polypodiales, Family Polypodiaceae, Genus *Colysis* selected from but not limited to *Colysis ampla, Colysis digitata, Colysis diversifolia, Colysis elegans Colysis elliptica, Colysis flexiloba, Colysis hemionitidea, Colysis hemitoma, Colysis henryi, Colysis insignis, Colysis intermedia, Colysis leveillei, Colysis longipes, Colysis pedunculata, Colysis pentaphylla, Colysis pothifolia, Colysis pteropus, Colysis shintenensis, Colysis simplicifrons, Colysis triphylla, Colysis wrightii*, and *Colysis×shintenensis*.

In some embodiments the nucleic acid molecule encoding the IPD103 polypeptide is derived from a fern species in the Order Polypodiales, Family Pteridaceae.

In some embodiments the nucleic acid molecule encoding the IPD103 polypeptide is derived from a fern species in the Order Polypodiales, Family Pteridaceae, Genus *Pteris* selected from but not limited to *Pteris actiniopteroides, Pteris amoena, Pteris angustipinna, Pteris angustipinnula, Pteris aspericaulis, Pteris austrosinica, Pteris baksaensis, Pteris bella, Pteris biaurita, Pteris bomiensis, Pteris cadieri, Pteris changjiangensis, Pteris confertinervia, Pteris crassiuscula, Pteris cretica, Pteris cryptogrammoides, Pteris dactylina, Pteris dangiana, Pteris decrescens, Pteris deltodon, Pteris dispar, Pteris dissitifolia, Pteris ensiformis, Pteris esquirolii, Pteris excelsa, Pteris fauriei, Pteris finotii, Pteris formosana, Pteris gallinopes, Pteris gracillima, Pteris grevilleana, Pteris guangdongensis, Pteris guizhouensis, Pteris henryi, Pteris heteromorpha, Pteris hui, Pteris insignis, Pteris kidoi, Pteris kiuschinensis, Pteris kiuschiuensis, Pteris laurisilvicola, Pteris libonsis, Pteris linearis, Pteris longipes, Pteris longipinna, Pteris longipinnula, Pteris maclurei, Pteris maclurioides, Pteris medogensis, Pteris morii, Pteris multifida, Pteris nipponica, Pteris obtusiloba, Pteris occidentali-sinica, Pteris oshimensis, Pteris paucipinnula, Pteris plumbea, Pteris pseudodactylina, Pteris pseudopellucida, Pteris puberula, Pteris quadristipitis, Pteris quinquefoliata, Pteris rufopilosa, Pteris ryukyuensis, Pteris sanduensis, Pteris scabristipes, Pteris semipinnata, Pteris setulosocostulata, Pteris shimianensis, Pteris sichuanensis, Pteris sinensis, Pteris splendida, Pteris stenophylla, Pteris subquinata, Pteris taiwanensis, Pteris tibetica, Pteris tripartita, Pteris undulatipinna, Pteris venusta, Pteris viridissima, Pteris vittata, Pteris wallichiana, Pteris wangiana, Pteris xiaoyingiae, Pteris xichouensis*, and *Pteris×wulaiensis*.

In some embodiments the nucleic acid molecule encoding the IPD103 polypeptide is derived from a fern species in the Order Polypodiales, Family Tectariaceae.

In some embodiments the nucleic acid molecule encoding the IPD103 polypeptide is derived from a fern species in the Order Polypodiales, Family Tectariaceae, Genus *Tectaria* selected from but not limited to *Tectaria acerifolia, Tectaria acrocarpa, Tectaria adenophora, Tectaria aequatoriensis,*

*Tectaria amblyotis, Tectaria amphiblestra, Tectaria andersonii, Tectaria angelicifolia, Tectaria angulata, Tectaria antioquiana, Tectaria athyrioides, Tectaria athyriosora, Tectaria aurita, Tectaria balansae, Tectaria barberi, Tectaria barteri, Tectaria beccariana, Tectaria blumeana, Tectaria brachiata, Tectaria brauniana, Tectaria brevilobata, Tectaria brooksii, Tectaria buchtienii, Tectaria calcarea, Tectaria camerooniana, Tectaria chattagramica, Tectaria cherasica, Tectaria chimborazensis, Tectaria chinensis, Tectaria christii, Tectaria christovalensis, Tectaria cicutaria, Tectaria coadunata, Tectaria confluens, Tectaria consimilis, Tectaria cordulata, Tectaria coriandrifolia, Tectaria craspedocarpa, Tectaria crenata, Tectaria crinigera, Tectaria croftii, Tectaria curtisii, Tectaria danfuensis, Tectaria decaryana, Tectaria decastroi, Tectaria decurrens, Tectaria degeneri, Tectaria dolichosora, Tectaria draconoptera, Tectaria dubia, Tectaria durvillei, Tectaria ebenina, Tectaria estremerana, Tectaria exauriculata, Tectaria fauriei, Tectaria fengii, Tectaria fernandensis, Tectaria ferruginea, Tectaria filisquamata, Tectaria fimbriata, Tectaria fissa, Tectaria gaudichaudii, Tectaria gemmifera, Tectaria godeffroyi, Tectaria grandidentata, Tectaria griffithii var. singaporeana, Tectaria grossedentata, Tectaria hederifolia, Tectaria hekouensis, Tectaria heracleifolia, Tectaria herpetocaulos, Tectaria heterocarpa, Tectaria hilocarpa, Tectaria holttumii, Tectaria hookeri, Tectaria humbertiana, Tectaria hymenodes, Tectaria hymenophylla, Tectaria impressa, Tectaria incisa, Tectaria inopinata, Tectaria isomorpha, Tectaria jacobsii, Tectaria jardini, Tectaria johannis-winkleri, Tectaria keckii, Tectaria kehdingiana, Tectaria kingii, Tectaria kouniensis, Tectaria kweichowensis, Tectaria labrusca, Tectaria lacei, Tectaria laotica, Tectaria latifolia, Tectaria lawrenceana, Tectaria laxa, Tectaria leptophylla, Tectaria lifuensis, Tectaria lizarzaburui, Tectaria lobbii, Tectaria lombokensis, Tectaria macrosora, Tectaria macrota, Tectaria madagascarica, Tectaria magnifica, Tectaria manilensis, Tectaria marchionica, Tectaria media, Tectaria melanocaulis, Tectaria melanocauloides, Tectaria melanorachis, Tectaria menyanthidis, Tectaria mesodon, Tectaria mexicana, Tectaria microchlamys, Tectaria microlepis, Tectaria minuta, Tectaria moorei, Tectaria morlae, Tectaria moussetii, Tectaria murrayi, Tectaria nabirensis, Tectaria nausoriensis, Tectaria nebulosa, Tectaria nesiotica, Tectaria nicaraguensis, Tectaria nicotianifolia, Tectaria nitens, Tectaria novoguineensis, Tectaria organensis, Tectaria palmate, Tectaria pandurifolia, Tectaria pedata, Tectaria pentagonalis, Tectaria perdimorpha, Tectaria phaeocaulis, Tectaria pica, Tectaria pilosa, Tectaria plantaginea, Tectaria pleiosora, Tectaria pleiotoma, Tectaria poilanei, Tectaria polymorpha, Tectaria prolifera, Tectaria pseudosinuata, Tectaria×pteropus-minor, Tectaria pubens, Tectaria puberula, Tectaria pubescens, Tectaria quinquefida, Tectaria quitensis, Tectaria ramosii, Tectaria rara, Tectaria remotipinna, Tectaria repanda, Tectaria rheophytica, Tectaria rigida, Tectaria rivalis, Tectaria rockii, Tectaria rufescens, Tectaria rufovillosa, Tectaria sagenioides, Tectaria schmutzii, Tectaria schultzei, Tectaria seemannii, Tectaria semibipinnata, Tectaria semipinnata, Tectaria seramensis, Tectaria siifolia, Tectaria simaoensis, Tectaria simonsii, Tectaria simulans, Tectaria singaporeana, Tectaria sinuata, Tectaria squamipes, Tectaria stalactica, Tectaria stearnsii, Tectaria stenosemioides, Tectaria subcaudata, Tectaria subconfluens, Tectaria subcordata, Tectaria subdigitata, Tectaria subebenea, Tectaria subrepanda, Tectaria subsageniacea, Tectaria subtriloba, Tectaria subtriphylla, Tectaria sulitii, Tectaria suluensis, Tectaria sumatrana, Tectaria tabonensis, Tectaria taccifolia, Tectaria tahitensis, Tectaria tenerifrons, Tectaria tenuifolia, Tectaria teratocarpa, Tectaria ternata, Tectaria transiens, Tectaria translucens, Tectaria tricuspis, Tectaria trifida, Tectaria trifoliata, Tectaria triglossa, Tectaria triloba, Tectaria trimenii, Tectaria trinitensis, Tectaria tripartita, Tectaria variabilis, Tectaria vasta, Tectaria vieillardii, Tectaria villosa, Tectaria vitiensis, Tectaria vivipara, Tectaria waterlotii, Tectaria weberi, Tectaria wightii, Tectaria× amesiana, Tectaria×cynthiae, Tectaria yunnanensis, Tectaria zeylanica,* and *Tectaria zollingeri.*

In some embodiments the nucleic acid molecule encoding the IPD103 polypeptide is derived from a fern species in the Order Polypodiales, Family Davalliaceae.

In some embodiments the nucleic acid molecule encoding the IPD103 polypeptide is derived from a fern species in the Order Polypodiales, Family Davalliaceae Genus *Davallia* selected from but not limited to *Davallia adiantoides, Davallia amabilis, Davallia assamica, Davallia austrosinica, Davallia biflora, Davallia boryana, Davallia brachypoda, Davallia brevisora, Davallia bullata, Davallia bullata, Davallia calvescens, Davallia calvescens, Davallia canariensis, Davallia chaerophylla, Davallia chaerophylloide, Davallia chrysanthemifolia, Davallia clarkei, Davallia cumingii, Davallia cylindrica, Davallia divaricata, Davallia divaricata, Davallia divaricata* var. *orientale, Davallia domingensis, Davallia dubia, Davallia elmeri, Davallia falcata, Davallia falcinella, Davallia ferulacea, Davallia flaccida, Davallia formosana, Davallia fumarioides, Davallia goudotiana, Davallia gracilis, Davallia griffithiana, Davallia griffithiana, Davallia henryana, Davallia heterophylla, Davallia hookeriana, Davallia hymenophylloides, Davallia immersa, Davallia inaequalis* var. *minor, Davallia jamaicensis, Davallia khasiyana, Davallia kurzii, Davallia lepida, Davallia lepida, Davallia macraeana, Davallia magellanica, Davallia mariesii, Davallia membranulosa, Davallia membranulosa, Davallia millefolium, Davallia moorei, Davallia multidentata, Davallia nodosa, Davallia novae-guineae, Davallia orientalis, Davallia parallela, Davallia parkeri, Davallia parvipinnula, Davallia patens, Davallia pectinata, Davallia perdurans, Davallia pilosula, Davallia platylepis, Davallia polypodioides, Davallia polypodioides* var. *hispida, Davallia polypodioides* var. *pilosula, Davallia pseudocystopteris, Davallia puberula, Davallia pyramidata, Davallia pyxidata, Davallia repens, Davallia rhomboidea, Davallia rhomboidea, Davallia rhomboidea, Davallia sinensis, Davallia sloanei, Davallia solida, Davallia solida, Davallia stipellata, Davallia strigosa, Davallia strigosa, Davallia strigosa* var. *rhomboidea, Davallia subalpina, Davallia subsolida, Davallia teyermannii, Davallia triangularis, Davallia tripinnata, Davallia truncata, Davallia tyermanni, Davallia tyermannii, Davallia uncinella, Davallia urophylla, Davallia vestita, Davallia wilfordii* var. *contracta*, and *Davallia yunnanensis*.

In some embodiments the nucleic acid molecule encoding the IPD103 polypeptide is derived from a fern species in the Order Polypodiales, Family Dryopteridaceae.

In some embodiments the nucleic acid molecule encoding the IPD103 polypeptide is derived from a fern species in the Order Polypodiales, Family Dryopteridaceae, Genus *Polystichum* selected from but not limited to *Polystichum acanthophyllum, Polystichum aculeatum, Polystichum acutidens, Polystichum acutipinnulum, Polystichum adungense, Polystichum alcicorne, Polystichum altum, Polystichum anomalum, Polystichum ariticulatipilosum, Polystichum assurgentipinnum, Polystichum atkinsonii, Polystichum attenuatum, Polystichum auriculum, Polystichum bakerianum, Polystichum baoxingense, Polystichum biaristatum, Polystichum bifidum, Polystichum bigemmatum, Polystichum bissectum,*

*Polystichum bomiense, Polystichum brachypterum, Polystichum braunii, Polystichum capillipes, Polystichum castaneum, Polystichum chingiae, Polystichum christii, Polystichum chunii, Polystichum consimile, Polystichum costularisorum, Polystichum craspedosorum, Polystichum crassinervium, Polystichum cringerum, Polystichum cuneatiforme, Polystichum cyclolobum, Polystichum daguanense, Polystichum dangii, Polystichum delavayi, Polystichum deltodon, Polystichum dielsii, Polystichum diffundens, Polystichum discretum, Polystichum disjunctum, Polystichum duthiei, Polystichum elevatovenusum, Polystichum erosum, Polystichum exauriforme, Polystichum excellens, Polystichum excelsius, Polystichum fimbriatum, Polystichum formosanum, Polystichum frigidicola, Polystichum fugongense, Polystichum gongboense, Polystichum grandifrons, Polystichum guangxiense, Polystichum gymnocarpium, Polystichum habaense, Polystichum hancockii, Polystichum hecatopteron, Polystichum herbaceum, Polystichum houchangense, Polystichum huae, Polystichum ichangense, Polystichum inaense, Polystichum incisopinnulum, Polystichum integrilimbum, Polystichum integrilobum, Polystichum jinfoshaense, Polystichum jiulaodongense, Polystichum jizhushanense, Polystichum kangdingense, Polystichum kungianum, Polystichum kwangtungense, Polystichum lachenense, Polystichum lanceolatum, Polystichum langchungense, Polystichum latilepis, Polystichum lentum, Polystichum leveillei, Polystichum liui, Polystichum lonchitis, Polystichum longiaristatum, Polystichum longidens, Polystichum longipaleatum, Polystichum longipes, Polystichum longipinnulum, Polystichum longispinosum, Polystichum longissimum, Polystichum macrochlaenum, Polystichum makinoi, Polystichum manmeiense, Polystichum martinii, Polystichum mayebarae, Polystichum medogense, Polystichum mehrae, Polystichum meiguense, Polystichum melanostipes, Polystichum mollissimum, Polystichum morii, Polystichum moupinense, Polystichum muscicola, Polystichum nayongense, Polystichum neoliuii, Polystichum neolobatum, Polystichum nepalense, Polystichum nigrum, Polystichum ningshenense, Polystichum nudisorum, Polystichum obliquum, Polystichum oblongum, Polystichum oligocarpum, Polystichum omeiense, Polystichum oreodoxa, Polystichum orientalitibeticum, Polystichum otophorum, Polystichum ovato-paleaceum, Polystichum paramoupinense, Polystichum parvifoliolatum, Polystichum parvipinnulum, Polystichum pianmaense, Polystichum piceo-paleaceum, Polystichum polyblepharum, Polystichum prescottianum, Polystichum prionolepis, Polystichum pseudocastaneum, Polystichum pseudolanceolatum, Polystichum pseudomakinoi, Polystichum pseudorhomboideum, Polystichum pseudosetosum, Polystichum pseudoxiphophyllum, Polystichum punctiferum, Polystichum puteicola, Polystichum pycnopterum, Polystichum qamdoense, Polystichum retrosopaleaceum, Polystichum revolutum, Polystichum rhombiforme, Polystichum rigens, Polystichum robustum, Polystichum rufopaleaceum, Polystichum saxicola, Polystichum semifertile, Polystichum setillosum, Polystichum shandongense, Polystichum shensiense, Polystichum shimurae, Polystichum simplicipinnum, Polystichum sinense, Polystichum sinotsus-simense, Polystichum sozanense, Polystichum speluncicola, Polystichum squarrosum, Polystichum stenophyllum, Polystichum stimulans, Polystichum subacutidens, Polystichum subdeltodon, Polystichum subfimbriatum, Polystichum submarginale, Polystichum submite, Polystichum subulatum, Polystichum tacticopterum, Polystichum taizhongense, Polystichum tangmaiense, Polystichum thomsonii, Polystichum tibeticum, Polystichum tonkinense, Polystichum tripteron, Polystichum tsingkanshanense, Polystichum tsus-simense, Polystichum wattii, Polystichum xiphophyllum, Polystichum yadongense, Polystichum yuanum, Polystichum yunnanense,* and *Polystichum zayuense.*

In some embodiments the nucleic acid molecule encoding the IPD103 polypeptide is derived from a fern species in the Order Polypodiales, Family Thelypteridaceae.

In some embodiments the nucleic acid molecule encoding the IPD103 polypeptide is derived from a fern species in the Order Polypodiales, Family Thelypteridaceae, Genus *Thelypteris* selected from but not limited to *Thelypteris abrupta, Thelypteris acuminata, Thelypteris affinis, Thelypteris angulariloba, Thelypteris angustifrons, Thelypteris aurita, Thelypteris beddomei, Thelypteris boninensis, Thelypteris bukoensis, Thelypteris castanea, Thelypteris clypeolutata, Thelypteris consanguinea, Thelypteris cystopteroides, Thelypteris dayi, Thelypteris erubescens, Thelypteris esquirolii, Thelypteris flexilis, Thelypteris gemmulifera, Thelypteris glandulosa, Thelypteris globulifera, Thelypteris gracilescens, Thelypteris gracilis, Thelypteris interrupta, Thelypteris jaculosa, Thelypteris japonica, Thelypteris laxa, Thelypteris linkiana, Thelypteris liukiuensis, Thelypteris longissima, Thelypteris meniscioides, Thelypteris miyagii, Thelypteris musashiensis, Thelypteris navarrensis, Thelypteris nevadensis, Thelypteris nipponica, Thelypteris ogasawarensis, Thelypteris oligocarpa, Thelypteris omeiensis, Thelypteris opulenta, Thelypteris ovata, Thelypteris palustris, Thelypteris parasitica, Thelypteris poiteana, Thelypteris reticulata, Thelypteris rustica, Thelypteris seemannii, Thelypteris* sp. *b*1-007, *Thelypteris* sp. *Janssen* 2679, *Thelypteris subaurita, Thelypteris taiwanensis, Thelypteris truncata, Thelypteris tylodes, Thelypteris uraiensis,* and *Thelypteris viridifrons.*

Polynucleotides that encode IPD103 polypeptides can also be synthesized de novo from an IPD103 polypeptide sequence. The sequence of the polynucleotide gene can be deduced from an IPD103 polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide. Examples of IPD103 polypeptide sequences that can be used to obtain corresponding nucleotide encoding sequences include, but are not limited to the IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38. Furthermore, synthetic IPD103 polynucleotide sequences of the disclosure can be designed so that they will be expressed in plants.

In some embodiments the nucleic acid molecule encoding an IPD103 polypeptide is a polynucleotide having the sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD103 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an IPD103 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, wherein the IPD103 polypeptide has insecticidal activity.

In some embodiments the nucleic acid molecule encodes an IPD103 polypeptide comprising an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the native amino acid at the corresponding position of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38.

In some embodiments the nucleic acid molecule encodes an IPD103 polypeptide variant comprising any one or more amino acid substitutions of Table 5 or 7.

Also provided are nucleic acid molecules that encode transcription and/or translation products that are subsequently spliced to ultimately produce functional IPD103 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD103 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365, 377 and 6,531,316). Thus, in some embodiments the polynucleotides do not directly encode a full-length IPD103 polypeptide, but rather encode a fragment or fragments of an IPD103 polypeptide. These polynucleotides can be used to express a functional IPD103 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD103 polypeptides are also encompassed by the embodiments. "Fragment" as used herein refers to a portion of the nucleic acid sequence encoding an IPD103 polypeptide. A fragment of a nucleic acid sequence may encode a biologically active portion of an IPD103 polypeptide or it may be a fragment that can be used as a hybridization probe or PCR primer using methods disclosed below. Nucleic acid molecules that are fragments of a nucleic acid sequence encoding an IPD103 polypeptide comprise at least about 150, 180, 210, 240, 270, 300, 330 or 360, contiguous nucleotides or up to the number of nucleotides present in a full-length nucleic acid sequence encoding an IPD103 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD103 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD103Aa polypeptide (SEQ ID NO: 2). In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*; Southern corn rootworm or spotted cucumber beetle; *Diabrotica* undecimpunctata howardi, and the Mexican corn rootworm, *D. virgifera zeae*. In one embodiment, the insecticidal activity is against a *Diabrotica* species.

In some embodiments the IPD103 polypeptide is encoded by a nucleic acid sequence sufficiently homologous to the nucleic acid sequence of SEQ ID NO: 1, SEQ ID NO: 3, SEQ ID NO: 5, SEQ ID NO: 7, SEQ ID NO: 9, SEQ ID NO:

11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments the sequence homology is against the full length sequence of the polynucleotide encoding an IPD103 polypeptide or against the full length sequence of an IPD103 polypeptide.

In some embodiments the nucleic acid encodes an IPD103 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two amino acid sequences or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of SEQ ID NO: 1). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments the IPD103 polynucleotide encodes an IPD103 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

In some embodiments polynucleotides are provided encoding chimeric polypeptides comprising regions of at least two different IPD103 polypeptides of the disclosure.

In some embodiments polynucleotides are provided encoding chimeric polypeptides comprising regions of at least two different IPD103 polypeptides selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO:

380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments polynucleotides are provided encoding chimeric polypeptides comprising an N-terminal Region of a first IPD103 polypeptide of the disclosure operably fused to a C-terminal Region of a second IPD103 polypeptide of the disclosure.

In some embodiments polynucleotides are provided encoding chimeric polypeptides comprising an N-terminal Region of a first IPD103 polypeptide operably fused to a C-terminal Region of a second IPD103 polypeptide, where the IPD103 polypeptide is selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

In some embodiments an IPD103 polynucleotide encodes the IPD103 polypeptide comprising an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO:

308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, SEQ ID NO: 364, SEQ ID NO: 365, SEQ ID NO: 366, SEQ ID NO: 367, SEQ ID NO: 368, SEQ ID NO: 369, SEQ ID NO: 370, SEQ ID NO: 371, SEQ ID NO: 372, SEQ ID NO: 373, SEQ ID NO: 374, SEQ ID NO: 375, SEQ ID NO: 376, SEQ ID NO: 377, SEQ ID NO: 378, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, SEQ ID NO: 411, SEQ ID NO: 412, SEQ ID NO: 413, SEQ ID NO: 414, SEQ ID NO: 415, SEQ ID NO: 416, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, SEQ ID NO: 453, SEQ ID NO: 454, SEQ ID NO: 455, SEQ ID NO: 456, SEQ ID NO: 457, SEQ ID NO: 458, SEQ ID NO: 459, SEQ ID NO: 460, SEQ ID NO: 461, SEQ ID NO: 462, SEQ ID NO: 463, SEQ ID NO: 464, SEQ ID NO: 465, SEQ ID NO: 466, SEQ ID NO: 467, SEQ ID NO: 468, SEQ ID NO: 469, SEQ ID NO: 470, SEQ ID NO: 471, and SEQ ID NO: 472.

The embodiments also encompass nucleic acid molecules encoding IPD103 polypeptide variants. "Variants" of the IPD103 polypeptide encoding nucleic acid sequences include those sequences that encode the IPD103 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD103 polypeptides disclosed as discussed below.

The present disclosure provides isolated or recombinant polynucleotides that encode any of the IPD103 polypeptides disclosed herein. Those having ordinary skill in the art will readily appreciate that due to the degeneracy of the genetic code, a multitude of nucleotide sequences encoding IPD103 polypeptides of the present disclosure exist.

The skilled artisan will further appreciate that changes can be introduced by mutation of the nucleic acid sequences thereby leading to changes in the amino acid sequence of the encoded IPD103 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a bacterial source, including but not limited to a *Pseudomonas* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD103 polypeptides from fern or other primitive plants, the fern or other primitive plant cell lysates can be screened with antibodies generated against an IPD103 polypeptides and/or IPD103 polypeptides using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD103 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD103 polypeptides) with sequence information of IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28 and their homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known IPD103 polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an IPD103 polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding an IPD103 polypeptide, disclosed herein or one or more portions thereof may be used as a probe capable of specifically hybridizing to corresponding nucleic acid sequences encoding IPD103 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Compositions Compositions comprising at least one IPD103 polypeptide or IPD103 chimeric polypeptide of the disclosure are also embraced.

Antibodies

Antibodies to an IPD103 polypeptide of the embodiments or to variants or fragments thereof are also encompassed. The antibodies of the disclosure include polyclonal and monoclonal antibodies as well as fragments thereof which retain their ability to bind to an IPD103 polypeptide found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD103 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD103 polypeptide as antigens.

A kit for detecting the presence of an IPD103 polypeptide or detecting the presence of a nucleotide sequence encoding an IPD103 polypeptide in a sample is provided. In one embodiment, the kit provides antibody-based reagents for detecting the presence of an IPD103 polypeptide in a tissue sample. In another embodiment, the kit provides labeled nucleic acid probes useful for detecting the presence of one or more polynucleotides encoding an IPD103 polypeptide.

The kit is provided along with appropriate reagents and controls for carrying out a detection method, as well as instructions for use of the kit.

Receptor Identification and Isolation

Receptors to the IPD103 polypeptide of the embodiments or to variants or fragments thereof are also encompassed. Methods for identifying receptors are well known in the art (see, Hofmann, et. al., (1988) Eur. J. Biochem. 173:85-91; Gill, et al., (1995) J. Biol. Chem. 27277-27282) can be employed to identify and isolate the receptor that recognizes the IPD103 polypeptide using the brush-border membrane vesicles from susceptible insects. In addition to the radioactive labeling method listed in the cited literatures, an IPD103 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled IPD103 polypeptide can be incubated with blotted membrane of BBMV and labeled IPD103 polypeptide can be identified with the labeled reporters. Identification of protein band(s) that interact with the IPD103 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD103 polypeptide. Receptor function for insecticidal activity by the IPD103 polypeptide can be verified by accomplished by RNAi type of gene knock out method (Rajagopal, et al., (2002) J. Biol. Chem. 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD103 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD103 polypeptide of the embodiments.

In some embodiments the DNA construct comprises a polynucleotide encoding a chimeric IPD103 polypeptide of the embodiments.

In some embodiments the DNA construct comprises a polynucleotide encoding a fusion protein comprising an IPD103 polypeptide of the embodiments.

In some embodiments the DNA construct comprises a polynucleotide comprising a first coding sequence encoding the N-terminal Region of a first IPD103 polypeptide of the disclosure and a second coding sequence encoding the C-terminal Region of a second IPD103 polypeptide of the disclosure.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix.

A *Glycine max* usage table can be found at kazusa.or.jp//cgi-bin/show.cgi?species=3847&aa=1&style=N, which can be accessed using the www prefix.

In some embodiments the recombinant nucleic acid molecule encoding an IPD103 polypeptide has *maize* optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a *maize* host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and *maize* chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The IPD103 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the *maize* PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced an IPD103 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3): 337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5): 773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20): 9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265;

Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2 gene is root specific in the intact plant and stimulated by wounding in leaf tissue, an especially desirable combination of characteristics for use with an insecticidal or larvicidal gene (see, EMBO J. 8(2):343-350). The TR1 gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to, seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about $\frac{1}{1000}$ transcripts to about $\frac{1}{100,000}$ transcripts to about $\frac{1}{500,000}$ transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.*

10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in Plant Cell, Tissue, and Organ Culture: Fundamental Methods, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the IPD103 polynucleotide or variants and fragments thereof directly into the plant or the introduction of the IPD103 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784, all of which are herein incorporated by reference. Alternatively, the IPD103 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) Plant Cell Reports 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD103 polypeptide. It is also recognized that such a viral polyprotein, comprising at least a portion of the amino acid sequence of an IPD103 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastidborne transgene by tissue-preferred expression of a nuclear-encoded and plastid-directed RNA polymerase. Such a system has been reported in McBride, et al., (1994) Proc. Natl. Acad. Sci. USA 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD103 polypeptide.

Methods to Introduce Genome Editing Technologies into Plants

In some embodiments, the disclosed IPD103 polynucleotide compositions can be introduced into the genome of a plant using genome editing technologies, or previously introduced IPD103 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD103 polynucleotide has previously been introduced into a genome, genome editing technologies may be used to alter or modify the introduced polynucleotide sequence. Site specific modifications that can be introduced into the disclosed IPD103 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD103 polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the IPD103 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) Science 266:789 (cloning of the tomato Cf-9 gene for resistance to *Cladosporium fulvum*); Martin, et al., (1993) Science 262: 1432 (tomato Pto gene for resistance to *Pseudomonas syringae* pv. tomato encodes a protein kinase); Mindrinos, et al., (1994) Cell 78:1089 (*Arabidopsis* RSP2 gene for resistance to *Pseudomonas syringae*), McDowell and Woffenden, (2003) Trends Biotechnol. 21(4):178-83 and Toyoda, et al., (2002) Transgenic Res. 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) Gene 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens*, 7:1-13), from *Pseudomonas protegens* strain CHAO and Pf-5 (previously *fluorescens*) (Pechy-Tarr, (2008) *Environmental Microbiology* 10:2368-2386: Gen- Bank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and 5-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of 5-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of 5-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of US Patent Numbers 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945, 4,940,835; 5,866,775; 6,225,114; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) Biochem. J. 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in US Patent Numbers 6,288,306; 6,282,83 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from Delftia *acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), *Primula* A6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that, confers male fertility to be transcribed.

(A) Introduction of a deacetylase gene under the control of a tapetum-specific promoter and with the application of the chemical N-Ac-PPT (WO 2001/29237).

(B) Introduction of various stamen-specific promoters (WO 1992/13956, WO 1992/13957).

(C) Introduction of the barnase and the barstar gene (Paul, et al., (1992) Plant Mol. Biol. 19:611-622).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177,275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events with regulatory approval that are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments the stacked trait may be in the form of silencing of one or more polynucleotides of interest resulting in suppression of one or more target pest polypeptides. In some embodiments the silencing is achieved through the use of a suppression DNA construct.

In some embodiments one or more polynucleotide encoding the polypeptides of the IPD103 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment. The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) *Nature* 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) *Trends Genet.* 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease Ill enzyme referred to as dicer. Dicer is involved in the processing of the dsRNA into short pieces of dsRNA known as short interfering RNAs (siRNAs) (Berstein, et al., (2001) *Nature* 409:363). Short interfering RNAs derived from dicer activity are typically about 21 to about 23 nucleotides in length and comprise about 19 base pair duplexes (Elbashir, et al., (2001) *Genes Dev.* 15:188). Dicer has also been implicated in the excision of 21- and 22-nucleotide small temporal RNAs (stRNAs) from precursor RNA of conserved structure that are implicated in translational control (Hutvagner, et al., (2001) *Science* 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297:1833-1837; Jenuwein, (2002) *Science* 297:2215-2218 and Hall, et al., (2002) *Science* 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and Lygus can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the Lygus genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 Å protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PAT3. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the IPD103 polypeptide and desirably provide for improved protection of the pesticide from environmental degradation and inactivation.

Alternatively, the IPD103 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD103 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient or an agrochemical composition that contains at least one of the IPD103 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, Bacillus thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2, 2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluoroethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders *Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera*, etc., particularly *Lepidoptera* and *Coleoptera*.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenee (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guerin-Meneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guerin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); M. *sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gehin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/ Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stal (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schsffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug);

*Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*-Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) J. of Economic Entomology 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C.D.S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum,* liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD103 polypeptide or IPD103 chimeric polypeptide of the disclosure. In some embodiments methods are provided for killing an insect pest, comprising contacting the insect pest with an insecticidally-effective amount of a recombinant pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof.

In some embodiments methods are provided for controlling an insect pest population, comprising contacting the insect pest population, either simultaneously or sequentially, with an insecticidally-effective amount of a recombinant IPD103 polypeptide or IPD103 chimeric polypeptide of the disclosure. In some embodiments methods are provided for controlling an insect pest population, comprising contacting the insect pest population with an insecticidally-effective amount of a recombinant IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of a recombinant IPD103 polypeptide or chimeric IPD103 polypeptide of the disclosure. In some embodiments methods are provided for controlling an insect pest population resistant to a pesticidal protein, comprising contacting the insect pest population with an insecticidally-effective amount of a recombinant IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or a variant thereof.

In some embodiments methods are provided for protecting a plant from an insect pest, comprising expressing in the plant or cell thereof at least one recombinant polynucleotide encoding an IPD103 polypeptide or chimeric IPD103 polypeptide. In some embodiments methods are provided for protecting a plant from an insect pest, comprising expressing in the plant or cell thereof a recombinant polynucleotide encoding IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD103 polypeptides of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD103 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an IPD103 polypeptide and a Cry protein or other insecticidal protein to insects in the order Lepidoptera and/or Coleoptera having different modes of action.

In some embodiments the methods, of controlling Lepidoptera and/or Coleoptera insect infestation in a transgenic plant and promoting insect resistance management, comprise expression in the transgenic plant an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof and a Cry protein or other insecticidal protein to insects in the order Lepidoptera and/or Coleoptera, where the IPD103 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of an IPD103 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD103 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variants thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD103 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or variant thereof does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IPD103 polypeptide disclosed herein. Expression of the IPD103 polypeptide results in a reduced ability of a pest to infest or feed on the plant, thus improving plant yield.

Methods of Processing

Further provided are methods of processing a plant, plant part or seed to obtain a food or feed product from a plant, plant part or seed comprising an IPD103 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding an IPD103 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXPERIMENTALS

Example 1—Identification of Insecticidal Proteins Active Against Corn Earworm, European Corn Borer Fall Armyworm, Soybean Looper, and Velvet Bean Caterpillar from the Fern, *Athyrium niponicum* 'Red Beauty'

An insecticidal protein, IPD103Aa (SEQ ID NO: 2), was identified by protein purification, mass spectroscopy (MS) and PCR cloning from the commercial cultivar *Athyrium niponicum* 'Red Beauty', designated herein as NY15. Insecticidal activity against lepidopteran pests was observed from a protein extract from *Athyrium niponicum*, 'Red Beauty' with an artificial diet-based assay.

NY15 plant material was flash frozen in liquid nitrogen and stored at −80° C. The frozen sample was removed from storage and ground to a fine powder at liquid nitrogen temperatures with a GenoGrinder® 2010 (SPEX SamplePrep®, Metuchen, NJ). To extract protein, 5 mL Extraction Buffer (50 mM Tris, pH 8.0, 150 mM Potassium Chloride, 2.5 mM EDTA, 1.5% Polyvinylpolypyridone and "Complete, EDTA-free" protease inhibitor cocktail (Roche, Indianapolis, Indiana) was added per gram of fresh weight of NY15. The extracted material was clarified by centrifugation at 20,000 g for 10 min. The remaining cell pellet was re-extracted with ½ the volume of Extraction Buffer, centrifuged and the supernatants combined, filtered and desalted into 20 mM Tris, pH 8, using a Sephadex™ G25 (GE Healthcare, Piscataway, NJ) column and concentrated on 10 kDa molecular weight cutoff centrifugal concentrators (Sartorius Stedim, Goettingen, Germany).

Bioassays against Soybean Looper (SBL) (*Pseudoplusia includens*), Corn Earworm (CEW) (*Helicoverpa zea*) and European Corn Borer (ECB) (*Ostrinia nubialis*) were conducted using the desalted protein extract overlaid onto agar based Lepidoptera diet (Southland Products Inc., Lake Village, AR) in 96-well format. The sample was allowed to dry on top of the diet. A variable number of neonate insects (2-5) were placed individually into each well of the treated plate. The assay was run for four days at 27° C. and then scored for insect mortality, and various stages of stunting of insect growth. The scores were recorded numerically as dead (3), severely stunted (2) (little or no growth but alive and equivalent to a $1^{st}$ instar larvae), stunted (1) (growth to second instar but not equivalent to controls), or normal (0). The crude NY15 extract scored 1 against CEW in each of 4 replicates of the diet-based assay.

For protein purification, extract of NY15 was generated as described above and the supernatant desalted into 20 mM Tris, pH 8, before loading onto a 15 mL Capto™ Q column (GE Healthcare) that was equilibrated in the same buffer. A linear 10 column volume gradient from 0 M to 0.3 M NaCl in 50 mM Tris, pH 8.0 was applied. Eluted 1 mL fractions were assayed against CEW in the bioassay described above. Activity against CEW was detected in fractions eluting at ~7 to 11 mS/cm conductivity. These fractions were pooled and desalted into 20 mM Tris, pH 8.7 and loaded onto a 1 ml Mono Q™ column (GE Healthcare) equilibrated in the same buffer. A linear 20 CV gradient to 40% Elution Buffer (20 mM Tris+0.35 M NaCl, pH 8.7) was applied and 1 mL fractions were collected. Activity against CEW was detected in fractions eluting at ~8.5-13.3 $mS/cm^2$ conductivity. Active fractions were pooled and desalted into 25 mM BisTris, pH 7.2 and loaded on a 4 mL Mono P™ column (GE Healthcare). An isocratic gradient of 100% Polybuffer 74 was applied and 1 mL eluate fractions assayed against CEW. The fractions were submitted directly as well as after concentrating with 10 kDa MWCO units. There were three regions of activity associated with the Mono P™ run, where Mono P™ fractions 02-3, 07-8 and D12 all showed activity against CEW. The first two regions were active at 1× and 4× concentration while fraction D12 showed activity only after 4× concentration. Denaturing electrophoresis of the Mono P™ fractions on LDS polyacrylamide gels indicated that the abundance of a protein band at approximately 20 kDa correlated directly with the three regions of eluted CEW activity.

Protein sequencing and identification were performed by MS analysis after protein digestion. Proteins for MS identification were obtained from running sample on an LDS-PAGE gel stained with Coomassie™ Brilliant Blue G-250 stain. The bands of interest were excised from the gel, de-stained, reduced with dithiothreitol and then alkylated with iodoacetamide. Following overnight digestion with trypsin, the samples were subjected to nano-liquid chromatography/electrospray tandem mass spectrometry (nano-LC/ESI-MS/MS) on a Thermo Q Exactive™ Orbitrap™ mass spectrometer (Thermo Fisher Scientific®, 81 Wyman Street, Waltham, MA 02454) interfaced with an Eksigent™ NanoLC™ Ultra 1-D Plus nano-Ic system (AB Sciex™, 500 Old Connecticut Path, Framingham, MA 01701). Protein identification was done by database searches using Mascot® (Matrix Science, 10 Perrins Lane, London NW3 1QY UK). The searches were conducted against an in-house transcriptome database containing transcripts from the *Athyrium niponicum* 'Red Beauty', NY15 source plant and the public protein database Swiss-Prot using the Mascot search engine (Matrix Science). The amino acid sequences for all three gel bands aligned with the predicted protein from a NY15.

Example 2—Transcriptomic Sequencing of *Athyrium niponicum* 'Red Beauty' and Cloning of IPD103Aa A transcriptome for *Athyrium niponicum* 'Red Beauty' (NY15) was prepared as follows. Total RNA was isolated from frozen tissues with an RNeasy® kit (Qiagen®). Sequencing libraries from the resulting total RNAs were prepared using the TruSeq™ mRNA-Seq kit and protocol from Illumina®, Inc. (San Diego, CA). Briefly, mRNAs were isolated via attachment to oligo(dT) beads, fragmented to a mean size of 180 nt, reverse transcribed into cDNA by random hexamer prime, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 µl of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, MA) and checked for quality and quantity on the Agilent Bioanalyzer® DNA 7500 chip.

Normalized transcript libraries were sequenced according to manufacturer protocols on the Illumina® HiSeq® 2500. Libraries were pooled, hybridized and sequenced three per flowcell lane using onboard clustering methods followed by sequencing to a target depth of sixty million 75 bp paired end reads per normalized library.

Peptide sequences identified for IPD103Aa (SEQ ID NO: 2) by LCMS sequencing (described in Example 2) were searched against protein sequences predicted by open reading frames (ORFs) from the transcriptome assemblies for NY15. The peptides gave a perfect match to a transcript corresponding to IPD103Aa (SEQ ID NO: 2). The coding sequence was used to design the following primers: AGCATATGGCGGACAAAGCAGCAGCAGCAGCT AGAGAAGC (SEQ ID NO: 473) and CGACTCGAGATGGGTGCCGGCAGGCAGGCATATTGC (SEQ ID NO: 474) to clone the IPD103Aa polynucleotide sequence (SEQ ID NO: 1). This clone was produced by polymerase chain reaction using the Kappa HiFi™ polymerase (Kapa Bioscience, Wilmington, MA) and the cDNA prepared from the total RNA from *Athyrium niponicum* 'Red Beauty' using the SuperScript® II kit (Thermo Fischer Scientific, Waltham, MA) as the template. PCR products were gel purified, digested with NdeI and XhoI restriction enzymes (New England Biolabs) and ligated into pET14b (Novagen®) also digested with the same enzymes. Colonies were sequenced to confirm the clone.

Example 3—Purification of IPD103Aa Expressed in *E. coli*

The polynucleotide of SEQ ID NO: 1, encoding IPD103Aa (SEQ ID NO: 2) was subcloned into the pET14b vector (Novagen®) using the NdeI/XhoI restriction sites in frame with the coding sequence for an N-terminal 6×His tag followed by a thrombin cleavage site (SEQ ID NO: 40). Chemically competent OverExpress® C41(DE3) SOLOs cells (Lucigen®) were transformed with pET plasmid DNA, containing the IPD103Aa gene for recombinant protein expression. The transformed *E. coli* cells were grown overnight at 37° C. with ampicillin selection and then inoculated to a fresh 2×YT medium (1:25) and further grown to an optical density of about 0.8. Protein expression was induced by adding 0.3 mM IPTG and cells were further grown at 16° C. for 16 hours. The *E. coli* expressed proteins were purified by immobilized metal ion chromatography using HisPur™ Cobalt resin (Clonetech, Mountain View, CA) according to the manufacturer's protocols. The purified fractions were desalted using PD-10 columns (GE Life Sciences, Pittsburgh, USA) pre-equilibrated with PBS buffer. The eluted protein was used in diet bioassays to evaluate the protein activity on larvae of a diversity of Lepidoptera.

Example 4—Identification of IPD103Aa Homoloqs and Their Purification After Expression in *E. coli*

Gene identities may be determined by conducting BLAST™ (Basic Local Alignment Search Tool; Altschul, et al., (1993) J. Mol. Biol. 215:403-410; see also ncbi.nlm.nih-.gov/BLAST/, which can be accessed using the www prefix) searches under default parameters for similarity to sequences. The polynucleotide sequence for IPD103Aa (SEQ ID NO: 1) was analyzed. Gene identities conducted by BLAST™ in a DUPONT PIONEER internal plant transcriptomes database identified multiple homologs of IPD103Aa protein (SEQ ID NO: 2). The IPD13Aa homologs and the organism they were identified from are shown in Table 1.

TABLE 1

| Gene Name | Source | Organism | DNA Seq | AA Seq |
|---|---|---|---|---|
| IPD103Aa | NY15 | *Athyrium niponicum* 'Red Beauty' | SEQ ID NO: 1 | SEQ ID NO: 2 |
| IPD103Ab | NY15 | *Athyrium niponicum* 'Red Beauty' | SEQ ID NO: 3 | SEQ ID NO: 4 |
| IPD103Ac | PS9092AF | *Platycerium wandae* | SEQ ID NO: 5 | SEQ ID NO: 6 |
| IPD103Ad | PS12349 | *Pteris ensiformis* 'Evergemiensis' | SEQ ID NO: 7 | SEQ ID NO: 8 |
| IPD103Ae | PS12349 | *Pteris ensiformis* 'Evergemiensis' | SEQ ID NO: 9 | SEQ ID NO: 10 |
| IPD103Ba | PS9092AF | *Platycerium wandae* | SEQ ID NO: 11 | SEQ ID NO: 12 |
| IPD103Bb | PS9092AF | *Platycerium wandae* | SEQ ID NO: 13 | SEQ ID NO: 14 |
| IPD103Bc | PS12409 | *Athyrium filix-femina* | SEQ ID NO: 15 | SEQ ID NO: 16 |
| IPD103Bd | PS7897CF | *Colysis wrightii* | SEQ ID NO: 17 | SEQ ID NO: 18 |
| IPD103Be | PS8837CF | *Nephrolepis falcata* | SEQ ID NO: 19 | SEQ ID NO: 20 |
| IPD103Bf | PS11699 | *Nephrolepis cordifolia* | SEQ ID NO: 21 | SEQ ID NO: 22 |
| IPD103Bg | PS13327 | *Polystichum tsus-simense* | SEQ ID NO: 23 | SEQ ID NO: 24 |
| IPD103Bh | PS13327 | *Polystichum tsus-simense* | SEQ ID NO: 25 | SEQ ID NO: 26 |
| IPD103Bi | PS12861 | *Thelypteris palustris* | SEQ ID NO: 27 | SEQ ID NO: 28 |
| IPD103Bj | PS12410 | *Athyrium filix-femina* | SEQ ID NO: 29 | SEQ ID NO: 30 |
| IPD103Bk | PS12337 | *Nephrolepis cordifolia* | SEQ ID NO: 31 | SEQ ID NO: 32 |
| IPD103Ca | PS9092AF | *Platycerium wandae* | SEQ ID NO: 33 | SEQ ID NO: 34 |
| IPD103Da | PS9539 | *Tectaria milnei* | SEQ ID NO: 35 | SEQ ID NO: 36 |
| IPD103Db | PS12356 | *Davallia tyermannii* | SEQ ID NO: 37 | SEQ ID NO: 38 | cDNAs were generated from source organisms with identified homologs from the internal database by reverse transcription from total RNA. Homologs were PCR amplified from their respective cDNA's using primers designed to the coding sequences of each homolog (Table 2). The PCR products were digested with NdeI/XhoI (New England Biolabs, Ipswich, MA) and ligated into a pET14b (Novagen) plasmid digested by the same enzymes. Cloned PCR products were confirmed by sequencing. The amino acid sequence identity of the IPD103Aa homologs as calculated using the Needleman-Wunsch algorithm, as implemented in the Needle program (EMBOSS tool suite) are shown in Table 3.

TABLE 2

| Gene Name | Forward Primer SEQ ID | Forward Primer | Reverse Primer SEQ ID | Reverse Primer |
| --- | --- | --- | --- | --- |
| IPD103Aa | SEQ ID NO: 473 | AGCATATGGCGGACAAAGCAGCAGCAGCAGCTAGAGAAGC | SEQ ID NO: 474 | CGACTCGAGATGGGTGCCGGCAGGCAGGCATATTGC |
| IPD103Ab | SEQ ID NO: 475 | AGCATATGGCGGACCAAGCAGCAGCAGCTAGAGAAGC | SEQ ID NO: 474 | CGACTCGAGATGGGTGCCGGCAGGCAGGCATATTGC |
| IPD103Ac | SEQ ID NO: 476 | AACATATGGCCGAACCAGCAGCAGC | SEQ ID NO: 477 | TTCTCGAGTCAAGGGAGCGCCCCA |
| IPD103Ad | SEQ ID NO: 478 | AACATATGGCCGACCAAGGAGCAGCAG | SEQ ID NO: 479 | TTCTCGAGTCAAGGGAGCGCCCC |
| IPD103Ae | SEQ ID NO: 480 | AACATATGGCCGACCAAGCTGCAGC | SEQ ID NO: 479 | TTCTCGAGTCAAGGGAGCGCCCC |
| IPD103Ba | SEQ ID NO: 481 | AACATATGAGAGAGCGAGAGCGAGAGCG | SEQ ID NO: 477 | TTCTCGAGTCAAGGGAGCGCCCCA |
| IPD103Bb | SEQ ID NO: 482 | AACATATGGCCGAACCAGCAGCAGC | SEQ ID NO: 477 | TTCTCGAGTCAAGGGAGCGCCCCA |
| IPD103Bc | SEQ ID NO: 483 | AACATATGGCCGACAAAGCGCCTC | SEQ ID NO: 484 | TTCTCGAGTCAAGGGAGTGCCCCG |
| IPD103Bd | SEQ ID NO: 485 | AACATATGGCCGACCAAGTAGCAGCAG | SEQ ID NO: 479 | TTCTCGAGTCAAGGGAGCGCCCC |
| IPD103Be | SEQ ID NO: 486 | AACATATGGCCGACCCAGCAACAGC | SEQ ID NO: 479 | TTCTCGAGTCAAGGGAGCGcccc |
| IPD103Bf | SEQ ID NO: 487 | AACATATGCAGAGAGAGAGAGAGAGAGATGG | SEQ ID NO: 479 | TTCTCGAGTCAAGGGAGCGCCCC |
| IPD103Bg | SEQ ID NO: 488 | AACATATGGCCGACAAAGTAGCAGCAGC | SEQ ID NO: 479 | TTCTCGAGTCAAGGGAGCGCCCC |
| IPD103Bh | SEQ ID NO: 488 | AACATATGGCCGACAAAGTAGCAGCAGC | SEQ ID NO: 479 | TTCTCGAGTCAAGGGAGCGCCCC |
| IPD103Bi | SEQ ID NO: 488 | AACATATGGCCGACAAAGTAGCAGCAGC | SEQ ID NO: 489 | TTCTCGAGTCAAGGGAGTGCCCC |
| IPD103Ca | SEQ ID NO: 490 | AACATATGAGAGAGCGAGAGCGAGAGCG | SEQ ID NO: 477 | TTCTCGAGTCAAGGGAGCGCCCCA |
| IPD103Cb | SEQ ID NO: 491 | AACATATGGCCGATGACAAAGTAGCAAG | SEQ ID NO: 492 | TTCTCGAGTCAAGGGAGGGCCC |
| IPD103Da | SEQ ID NO: 493 | AACATATGGCCGATGAGGTAGCTGGTC | SEQ ID NO: 479 | TTCTCGAGTCAAGGGAGCGCCCC |
| IPD103Db | SEQ ID NO: 494 | AACATATGGACGCCGCTGCCG | SEQ ID NO: 495 | TTCTCGAGTCAAGGGAGCGCCC |

Table 3 provides a matrix of percent identity of IPD103 homolog proteins. The Needleman-Wunsch algorithm, as implemented in the Needle program (EMBOSS tool suite), was used to calculate pairwise identities.

TABLE 3

| | IPD103Ab SEQ ID NO: 4 | IPD103Ac SEQ ID NO: 6 | IPD103Ad SEQ ID NO: 8 | IPD103Ae SEQ ID NO: 10 | IPD103Ba SEQ ID NO: 12 | IPD103Bb SEQ ID NO: 14 | IPD103Bc SEQ ID NO: 16 | IPD103Bd SEQ ID NO: 18 | IPD103Be SEQ ID NO: 20 | IPD103Bf SEQ ID NO: 22 |
|---|---|---|---|---|---|---|---|---|---|---|
| IPD103Aa SEQ ID NO: 2 | 98.8 | 98.3 | 93.6 | 93.6 | 82.0 | 86.6 | 89.5 | 93.0 | 85.5 | 86.1 |
| IPD103Ab SEQ ID NO: 4 | — | 98.8 | 94.7 | 94.7 | 81.4 | 86.0 | 89.0 | 94.2 | 86.0 | 86.1 |
| IPD103Ac SEQ ID NO: 6 | — | — | 93.6 | 93.6 | 82.5 | 87.2 | 88.4 | 93.0 | 86.0 | 85.0 |
| IPD103Ad SEQ ID NO: 8 | — | — | — | 99.4 | 78.6 | 83.0 | 86.0 | 92.9 | 83.0 | 84.9 |
| IPD103Ae SEQ ID NO: 10 | — | — | — | — | 78.6 | 83.0 | 86.5 | 92.9 | 83.6 | 84.9 |
| IPD103Ba SEQ ID NO: 12 | — | — | — | — | — | 92.9 | 79.7 | 83.5 | 82.5 | 87.9 |
| IPD103Bb SEQ ID NO: 14 | — | — | — | — | — | — | 84.2 | 87.7 | 86.6 | 85.5 |
| IPD103Bc SEQ ID NO: 16 | — | — | — | — | — | — | — | 86.0 | 84.3 | 81.6 |
| IPD103Bd SEQ ID NO: 18 | — | — | — | — | — | — | — | — | 87.7 | 86.6 |
| IPD103Be SEQ ID NO: 20 | — | — | — | — | — | — | — | — | — | 85.6 |
| IPD103Bf SEQ ID NO: 22 | — | — | — | — | — | — | — | — | — | — |
| IPD103Bg SEQ ID NO: 24 | — | — | — | — | — | — | — | — | — | — |
| IPD103Bh SEQ ID NO: 26 | — | — | — | — | — | — | — | — | — | — |
| IPD103Bi SEQ ID NO: 28 | — | — | — | — | — | — | — | — | — | — |
| IPD103Bj SEQ ID NO: 30 | — | — | — | — | — | — | — | — | — | — |
| IPD103Bk SEQ ID NO: 32 | — | — | — | — | — | — | — | — | — | — |
| IPD103Ca SEQ ID NO: 34 | — | — | — | — | — | — | — | — | — | — |
| IPD103Da SEQ ID NO: 36 | — | — | — | — | — | — | — | — | — | — |

| | IPD103Bg SEQ ID NO: 24 | IPD103Bh SEQ ID NO: 26 | IPD103Bi SEQ ID NO: 28 | IPD103Bj SEQ ID NO: 30 | IPD103Bk SEQ ID NO: 32 | IPD103Ca SEQ ID NO: 34 | IPD103Da SEQ ID NO: 36 | IPD103Db SEQ ID NO: 38 |
|---|---|---|---|---|---|---|---|---|
| IPD103Aa SEQ ID NO: 2 | 87.4 | 87.4 | 85.0 | 89.0 | 90.1 | 81.4 | 72.0 | 61.8 |
| IPD103Ab SEQ ID NO: 4 | 86.3 | 86.3 | 84.4 | 88.4 | 90.1 | 80.9 | 72.2 | 62.2 |
| IPD103Ac SEQ ID NO: 6 | 85.7 | 85.7 | 83.8 | 87.8 | 89.0 | 82.0 | 71.6 | 62.2 |
| IPD103Ad SEQ ID NO: 8 | 83.9 | 83.9 | 83.8 | 85.4 | 88.9 | 78.0 | 71.8 | 62.0 |
| IPD103Ae SEQ ID NO: 10 | 83.3 | 83.3 | 83.8 | 86.0 | 88.9 | 78.0 | 71.1 | 62.4 |
| IPD103Ba SEQ ID NO: 12 | 76.2 | 76.2 | 73.9 | 79.1 | 84.6 | 98.9 | 64.1 | 57.9 |
| IPD103Bb SEQ ID NO: 14 | 80.5 | 80.5 | 79.2 | 83.6 | 89.5 | 94.0 | 67.1 | 61.0 |
| IPD103Bc SEQ ID NO: 16 | 92.5 | 92.5 | 82.1 | 99.4 | 85.4 | 79.1 | 71.8 | 59.3 |
| IPD103Bd SEQ ID NO: 18 | 84.5 | 84.5 | 82.1 | 85.4 | 90.6 | 82.4 | 71.1 | 62.6 |
| IPD103Be SEQ ID NO: 20 | 81.1 | 81.1 | 77.6 | 83.7 | 89.5 | 81.4 | 69.9 | 59.9 |
| IPD103Bf SEQ ID NO: 22 | 79.7 | 79.7 | 77.3 | 81.0 | 95.5 | 87.4 | 67.4 | 61.7 |
| IPD103Bg SEQ ID NO: 24 | — | 99.4 | 80.6 | 93.1 | 83.3 | 75.7 | 71.5 | 58.1 |
| IPD103Bh SEQ ID NO: 26 | — | — | 80.6 | 93.1 | 83.3 | 75.7 | 71.5 | 58.1 |
| IPD103Bi SEQ ID NO: 28 | — | — | — | 81.5 | 84.8 | 78.6 | 71.3 | 58.7 |
| IPD103Bj SEQ ID NO: 30 | — | — | — | — | 84.8 | 78.6 | 71.3 | 58.7 |
| IPD103Bk SEQ ID NO: 32 | — | — | — | — | — | 84.1 | 70.5 | 64.5 |

TABLE 3-continued

| | | | | | | | | |
|---|---|---|---|---|---|---|---|---|
| IPD103Ca SEQ ID NO: 34 | — | — | — | — | — | — | 63.0 | 57.4 |
| IPD103Da SEQ ID NO: 36 | — | — | — | — | — | — | — | 51.2 |

Example 5—Lepidoptera Assays with Purified Tagged Proteins Expressed in E. coli

Bioassays against the five pest species, Corn earworm (CEWT (*Helicoverpa zea*), European corn borer (ECB) (*Ostrinia nubialis*), fall armyworm (FAWAT (*Spodoptera frugiperda* JE Smith), Soybean looper (SBL) (*Pseudoplusia includens*), and velvet bean caterpillar (VBC) (*Anticarsia gemmatalis* Hübner) were conducted using a dilution series of purified N-6×His-IPD103Aa (SEQ ID NO: 40) or N-6× His IPD103Ab (SEQ ID NO: 507) polypeptides incorporated into an agar-based Lepidoptera diet (Southland Products Inc., Lake Village, AR) in a 96-well plate format. Four replicates were used per sample. Two to five neonate insects were placed into each well of the treated plate. After four days of incubation at 27° C. larvae were scored for mortality or severity of stunting. The scores were recorded numerically as dead (3), severely stunted (2) (little or no growth but alive and equivalent to a $1^{st}$ instar larvae), stunted (1) (growth to second instar but not equivalent to controls), or normal (0). Results from bioassays of a dilution series of N-6×His-tagged IPD103Aa (SEQ ID NO: 40) and N-6×His IPD103Ab (SEQ ID NO: 507) against the Lepidoptera pests are shown in Table 4. Values represent the mean larval inhibition score of 4 replicate assays.

TABLE 4

| | Dose (ppm) | CEW | ECB | FAW | SBL | VBC |
|---|---|---|---|---|---|---|
| NT-6×His | 1350 | 3 | 2 | 2 | 3 | 3 |
| IPD103Aa | 675 | 2.25 | 2 | 2 | 2 | 2 |
| SEQ ID | 338 | 2 | 2 | 2 | 1.5 | 2 |
| NO: 40 | 169 | 2 | 2 | 2 | 2 | 2 |
| | 84 | 2 | 2 | 0.75 | 2 | 2 |
| | 42 | 2 | 1.5 | 0 | 1 | 1 |
| | 21 | 1.5 | 1.5 | 0 | 0 | 0 |
| | 11 | 0.25 | 1 | 0 | 0 | 0 |
| Buffer Control | 0 | 0 | 0 | 0 | 0 | 0 |
| NT-6×His | 925 | 2.5 | 2 | 2 | 2 | 3 |
| IPD103Ab | 463 | 2 | 2 | 2 | 2 | 2.25 |
| SEQ ID | 231 | 2 | 2 | 1.25 | 2 | 2 |
| NO: 507 | 116 | 2 | 2 | 1.25 | 2 | 2 |
| | 58 | 2 | 2 | 1 | 2 | 2 |
| | 29 | 1.25 | 2 | 0 | 1 | 0.5 |
| | 14 | 0.75 | 2 | 0 | 0 | 0 |
| | 7 | 0.25 | 2 | 0 | 0 | 0 |
| Buffer Control | 0 | 0 | 0 | 0 | 0 | 0 |

Example 6—IPD103Aa and M20 Truncated IPD103Aa Variants with Multiple Amino Acid Substitutions at R10 and R42

To create variants of IPD103Aa (SEQ ID NO: 2) at amino acid residue R10 and R42, multiple amino acid changes were created by NNK mutagenesis. For mutations at Arg 42, a synthetic DNA (SEQ ID NO: 497) was generated compromising 5 nucleotides upstream of pET14 NdeI site and nucleotides 1-487 of IPD103Aa (SEQ ID NO: 1) where nt 124 and 125 were synthesized as either A, C, G or T and nt 126 was synthesized as either G or T to create a library of amino acid changes at the Arg42 position. The pET14b plasmid with the IPD103Aa gene (SEQ ID NO: 1) inserted in the NdeI/XhoI sites was amplified using the primers IPD103 start rev Gibson (SEQ ID NO: 498) and IPD103—for Gibson (SEQ ID NO: 499) using the Advantage® HF 2 PCR Kit (Clontech Laboratories, Inc. Mountain View, CA) to produce a plasmid that contained a 26 and a 30 nucleotide overlap sequence at either end that matched with the synthesized IPD103Aa R42 NNK gene (SEQ ID NO: 497). The IPD103Aa R42 NNK library was generated using the Gibson reaction (New England Biolabs, Ipswich MA) to combine the amplified pET14b IPD103Aa vector with the synthetic DNA. Clones were confirmed by DNA sequencing to identify the amino acid substitution at the Arg42 position.

For mutations at the Arg 10 residue, the primers IPD103Aa R10 NNK—for (SEQ ID NO: 500) and IPD103Aa_Rev primer (SEQ ID NO: 474) were used to amplify the IPD103Aa using the Advantage® HF 2 PCR Kit (Clontech Laboratories, Inc. Mountain View, CA). The PCR products were digested with NdeI/XhoI (New England Biolabs, Ipswich MA) and ligated into a pET14b (Novagen®) plasmid digested by the same enzymes to create the IPD103Aa R10 NNK library. The same reaction was performed on the IPD103Aa R42W (SEQ ID NO: 422) backbone to create a construct with mutations at R10 with R42W. Clones were confirmed by DNA sequencing to identify the amino acid substitution at the Arg10 position.

Combinations of the mutations at R10 and R42 were created in the IPD103Aa (SEQ ID NO: 1), IPD103Ab (SEQ ID NO: 4) backbone and the R42 mutations were created in the M20 start site IPD103Aa (SEQ ID NO: 417) backbone. To create the IPD103Aa M20 start site sequence (SEQ ID NO: 417) and produce Arg42 mutations in the IPD103Aa M20 start site sequence (SEQ ID NO: 417), the IPD103Aa M(20)DETE start (SEQ ID NO: 501) primer was used with the IPD103Aa_Rev primer (SEQ ID NO: 474) to amplify the IPD103Aa (SEQ ID NO: 2), IPD103Aa R42T (SEQ ID NO: 419), IPD103Aa R42W (SEQ ID NO: 422), and IPD103Aa R42Y (SEQ ID NO: 423) sequences with the Advantage® HF 2 PCR Kit (Clontech Laboratories, Inc. Mountain View, CA). The PCR products were digested with NdeI/XhoI (New England Biolabs, Ipswich MA) and ligated into a pET14b (Novagen) plasmid digested by the same enzymes. Clones were confirmed by DNA sequencing. To create the mutations on the IPD103Ab (SEQ ID NO: 3) backbone the primer, IPD103Ab R10 NNK for (SEQ ID NO: 502) and IPD103Aa_Rev primer (SEQ ID NO: 474) were used to amplify the IPD103Aa R42P (SEQ ID NO: 421), IPD103Aa R42T (SEQ ID NO: 419), and IPD103Aa R42L (SEQ ID NO: 420) sequences with the Advantage® HF 2 PCR Kit (Clontech Laboratories, Inc. Mountain View, CA). The PCR products were digested with NdeI/XhoI (New England Biolabs, Ipswich MA) and ligated into a pET14b (Novagen) plasmid digested by the same enzymes. Clones were confirmed by DNA sequencing. Specific mutations at R10 were combined with the IPD103Aa R42T (SEQ ID NO: 419), R42L (SEQ ID NO: 420), R42W (SEQ ID NO: 422) and R42Y (SEQ ID NO: 423) by amplifying the sequence using either the IPD103Aa R10A—for (SEQ ID NO: 503), IPD103Aa R10M—for primer (SEQ ID NO: 504), or the IPD103Aa R10S—for primer (SEQ ID NO: 505) with the IPD103Aa_Rev primer (SEQ ID NO: 474). The PCR products were digested with NdeI/XhoI (New England Biolabs, Ipswich MA) and ligated using (NEB) into a pET14b (Novagen) plasmid digested by the same enzymes. Clones were confirmed by DNA sequencing.

Sequence confirmed IPD103Aa R10 and R42 mutants were transformed into chemically competent OverExpress® C41 (DE3) SOLOs E. coli cells (Lucigen) for recombinant protein expression. The transformed E. coli cells were grown overnight at 37° C. with ampicillin selection and then inoculated to a fresh 2×YT medium (1:25) and further grown to an optical density of about 0.8. Protein expression was induced by adding 0.3 mM IPTG and cells were further grown at 16° C. for 16 hours. The E. coli expressed proteins were purified by immobilized metal ion chromatography using HisPur™ Cobalt resin (Thermo Fischer Scientific, Waltham, MA) according to the manufacturer's protocols. The purified fractions were desalted using PD-10 desalting columns (GE Life Sciences, Pittsburgh, PA) pre-equilibrated with PBS buffer. The eluted protein was run in diet assay to evaluate the insecticidal protein effects on larvae of a diversity of Lepidoptera. Bioassays were run against six pest species: Soybean Looper (SBL) (*Pseudoplusia includens*), Corn Earworm (CEW) (*Helicoverpa zea*), European Corn Borer (ECB) (*Ostrinia nubialis*), Fall Armyworm (FAW) (*Spodoptera frugiperda*), Velvetbean Caterpillar (VBC) (*Anticarsia gemmatalis*) and Black Cutworm (BCW) (*Agrotis ipsilon*) and were conducted using the purified protein at a concentration greater than 22 ug/$cm^2$ overlaid onto an agar-based Lepidoptera diet (Southland Products Inc., Lake Village, AR) in a 96-well plate format. Samples were allowed to dry on top of the diet and one to five neonate insects were placed into each well of the treated plate. After three days of incubation at 27° C. larvae were scored for mortality or severity of stunting. The scores were recorded numerically as dead (3), severely stunted (2) (little or no growth but alive and equivalent to a 1st instar larvae), stunted (1) (growth to second instar but not equivalent to controls), or normal (0). Activity is recorded as a "+" if an average score of 1 or greater was recorded at concentrations of purified protein greater than 22 μg/$cm^2$. Bioassay results are summarized in Table 5.

TABLE 5

| Backbone | R10 | R42 | Polypeptide | CEW | ECB | FAW | SBL | VBC | BCW | Additional amino acid change |
|---|---|---|---|---|---|---|---|---|---|---|
| M20 Start | | | SEQ ID NO: 445 | + | + | + | + | + | – | |
| IPD103Aa | | Gly | SEQ ID NO: 446 | – | + | + | – | – | nd | H163P |
| IPD103Aa | | Thr | SEQ ID NO: 447 | – | – | – | – | – | nd | A8G |
| IPD103Aa | | Leu | SEQ ID NO: 448 | + | + | – | – | + | nd | |
| IPD103Aa | | Pro | SEQ ID NO: 449 | + | – | – | – | – | nd | |
| IPD103Aa | | Trp | SEQ ID NO: 450 | + | + | – | – | + | nd | |
| IPD103Aa | | Tyr | SEQ ID NO: 451 | + | + | – | + | + | nd | |
| IPD103Aa | Tyr | | SEQ ID NO: 452 | + | + | + | + | + | + | K123E |
| IPD103Aa | Thr | | SEQ ID NO: 453 | + | + | + | + | + | – | |
| IPD103Aa | Ala | | SEQ ID NO: 454 | + | + | + | + | + | + | |
| IPD103Aa | Met | | SEQ ID NO: 455 | + | + | + | + | + | – | |
| IPD103Aa | Ser | | SEQ ID NO: 456 | + | + | + | + | + | – | |
| M20 start | | Thr | SEQ ID NO: 457 | + | + | + | + | + | nd | |
| M20 start | | Trp | SEQ ID NO: 458 | + | + | + | + | + | nd | |
| M20 start | | Tyr | SEQ ID NO: 459 | + | + | + | + | + | nd | |
| IPD103Ab | Cys | Pro | SEQ ID NO: 460 | + | + | + | + | + | nd | |
| IPD103Ab | Val | Pro | SEQ ID NO: 461 | + | + | – | + | + | nd | |
| IPD103Ab | Asp | Thr | SEQ ID NO: 462 | + | + | – | + | + | nd | |
| IPD103Ab | Gln | Leu | SEQ ID NO: 463 | + | + | + | + | + | nd | |
| IPD103Aa | Gly | Trp | SEQ ID NO: 464 | + | + | + | + | + | nd | |
| IPD103Aa | Ala | Thr | SEQ ID NO: 465 | + | + | + | + | + | nd | |
| IPD103Aa | Met | Thr | SEQ ID NO: 466 | + | + | + | + | + | nd | |
| IPD103Aa | Gly | Leu | SEQ ID NO: 467 | + | + | + | + | + | nd | |
| IPD103Aa | Ser | Leu | SEQ ID NO: 468 | + | + | + | + | + | nd | |
| IPD103Aa | Ala | Trp | SEQ ID NO: 469 | + | + | + | + | + | nd | |
| IPD103Aa | Met | Trp | SEQ ID NO: 470 | + | + | + | + | + | nd | |
| IPD103Aa | Met | Tyr | SEQ ID NO: 471 | + | + | + | + | + | nd | |
| IPD103Aa | Ala | Tyr | SEQ ID NO: 472 | + | + | + | + | + | nd | | nd—not determined

Example 7—Purification and Bioassay of IPD103 Homologs Expressed in *E. coli*

The genes encoding IPD103 homologs were subcloned into the pET14b vector (Novagen) using the NdeI/XhoI restriction sites in frame with an N-terminal 6×His tag followed by a thrombin cleavage site with the IPD103 homolog native stop codon. Chemically competent OverExpress® C41 (DE3) SOLOs cells (Lucigen) were transformed with pET14b plasmid DNA, containing the IPD103Aa homolog gene for recombinant protein expression. The transformed *E. coli* cells were grown overnight at 37° C. with ampicillin selection and then inoculated to a fresh 2×YT medium (1:100) and further grown to an optical density of about 0.8-1.2. Protein expression was induced by adding 1.0 mM IPTG and cells were further grown at 16° C. for 16 hours. The *E. coli* expressed proteins were purified by immobilized metal ion chromatography (IMAC) using Talon® Cobalt resin (Clonetech, Mountain View, CA) according to the manufacturer's protocols. The purified 1.5 mL fractions eluted in 250 mM imidazole were dialyzed into PBS buffer using 6K MWCO Flextubes (IBI, Peosta, IA) on a stir plate at 4 C overnight. The dialyzed protein was run in the diet assay to evaluate the insecticidal protein effects on larvae of a selection of Lepidoptera. The activity of a series of homologs of IPD103Aa is summarized in Table 6.

TABLE 6

| Homolog ID | AA Seq | CEW | ECB | FAW | SBL | VBC |
|---|---|---|---|---|---|---|
| IPD103Ab | SEQ ID NO: 4 | + | + | + | + | + |
| IPD103Ac | SEQ ID NO: 6 | + | + | + | + | + |
| IPD103Ad | SEQ ID NO: 8 | + | + | + | + | + |
| IPD103Ae | SEQ ID NO: 10 | + | + | + | + | + |
| IPD103Ba | SEQ ID NO: 12 | + | + | + | + | + |
| IPD103Bb | SEQ ID NO: 14 | + | + | + | − | + |
| IPD103Bc | SEQ ID NO: 16 | + | + | + | − | + |
| IPD103Bd | SEQ ID NO: 18 | + | + | + | + | + |
| IPD103Be | SEQ ID NO: 20 | + | + | + | + | + |
| IPD103Bf | SEQ ID NO: 22 | + | + | + | + | + |
| IPD103Bg | SEQ ID NO: 24 | + | + | + | + | + |
| IPD103Bh | SEQ ID NO: 26 | + | − | + | − | + |
| IPD103Bi | SEQ ID NO: 28 | + | + | + | + | + |
| IPD103Ca | SEQ ID NO: 34 | + | + | + | + | + |
| IPD103Da | SEQ ID NO: 36 | + | + | + | + | + |

Example 8—IPD103Aa Variants with Multiple Amino Acid Substitutions

To create variants of IPD103Aa (SEQ ID NO: 2) with multiple amino acid changes, variant libraries were generated by family shuffling (Chia-Chun J. Chang et al, 1999, Nature Biotechnology 17, 793-797) the polynucleotide sequences of SEQ ID NO: 1, SEQ ID NO: 19, and SEQ ID NO: 37, encoding IPD103Aa (SEQ ID NO: 12), IPD103Be (SEQ ID NO: 20), and IPD103 Da (SEQ ID NO: 38). Three libraries were constructed for generating IPD103 variants. In a first library (Library11), the native polynucleotide sequence of IPD103Aa (SEQ ID NO: 1) and the native polynucleotide sequence of IPD103Be (SEQ ID NO: 19) were used as library parents. In a second library, the native polynucleotide sequence of IPD103Be (SEQ ID NO: 19) and the polynucleotide sequence of SEQ ID NO: 496, encoding the IPD103 Da polypeptide, with codons optimized to increase the similarity to SEQ ID NO: 1 were used as library parents. In a third library, native polynucleotide sequences of IPD103Aa (SEQ ID NO: 1) and IPD103Be (SEQ ID NO: 19) and the codon-optimized polynucleotide sequence of IPD103 Da (SEQ ID NO: 496) were used as library parents. The second and third libraries were picked and screened together (Library123).

After transforming the library variants into E. coli cells, the colonies were picked and cultured in 24-well plates for protein expression. Cell lysates were generated by B-PER® Protein Extraction Reagent (Thermo Scientific, Rockford, IL) and screened for CEW and/or FAW insecticidal activity. The active variants were sequenced and the amino acid substitutions were identified. From library 11, 460 variants were screened and 110 active unique variants were sequence identified. From library 123, 552 variants were screened and 78 active unique variants were sequence identified.

The percent identity of the variant proteins compared to IPD103Aa (SEQ ID NO: 2), variant designation, nucleotide sequences, and amino acid sequences of the resulting active IPD103Aa polypeptide variants are summarized in Table 7. Table 8 summarizes the % identity of the active variants compared to IPD103Aa (SEQ ID NO: 2), the number of variants with each % identity, and the variant identification.

TABLE 7

| % Identity to IPD103Aa (SEQ ID NO: 2) | Variant | Polynucleotide | Polypeptide |
|---|---|---|---|
| 92 | IPD103-11Reary-01 | SEQ ID NO: 41 | SEQ ID NO: 229 |
| 90 | IPD103-11Reary-04 | SEQ ID NO: 42 | SEQ ID NO: 230 |
| 92 | IPD103-11Reary-05 | SEQ ID NO: 43 | SEQ ID NO: 231 |
| 92 | IPD103-11Reary-06 | SEQ ID NO: 44 | SEQ ID NO: 232 |
| 89 | IPD103-11Reary-08 | SEQ ID NO: 45 | SEQ ID NO: 233 |
| 94 | IPD103-11Reary-09 | SEQ ID NO: 46 | SEQ ID NO: 234 |
| 92 | IPD103-11Reary-10 | SEQ ID NO: 47 | SEQ ID NO: 235 |
| 91 | IPD103-11Reary-11 | SEQ ID NO: 48 | SEQ ID NO: 236 |
| 94 | IPD103-11Reary-13 | SEQ ID NO: 49 | SEQ ID NO: 237 |
| 98 | IPD103-11Reary-14 | SEQ ID NO: 50 | SEQ ID NO: 238 |
| 90 | IPD103-11Reary-15 | SEQ ID NO: 51 | SEQ ID NO: 239 |
| 95 | IPD103-11Reary-16 | SEQ ID NO: 52 | SEQ ID NO: 240 |
| 93 | IPD103-11Reary-17 | SEQ ID NO: 53 | SEQ ID NO: 241 |
| 92 | IPD103-11Reary-18 | SEQ ID NO: 54 | SEQ ID NO: 242 |
| 89 | IPD103-11Reary-19 | SEQ ID NO: 55 | SEQ ID NO: 243 |
| 90 | IPD103-11Reary-20 | SEQ ID NO: 56 | SEQ ID NO: 244 |
| 91 | IPD103-11Reary-21 | SEQ ID NO: 57 | SEQ ID NO: 245 |
| 94 | IPD103-11Reary-22 | SEQ ID NO: 58 | SEQ ID NO: 246 |
| 91 | IPD103-11Reary-24 | SEQ ID NO: 59 | SEQ ID NO: 247 |
| 98 | IPD103-11Reary-25 | SEQ ID NO: 60 | SEQ ID NO: 248 |
| 88 | IPD103-11Reary-26 | SEQ ID NO: 61 | SEQ ID NO: 249 |
| 95 | IPD103-11Reary-29 | SEQ ID NO: 62 | SEQ ID NO: 250 |
| 89 | IPD103-11Reary-31 | SEQ ID NO: 63 | SEQ ID NO: 251 |
| 90 | IPD103-11Reary-32 | SEQ ID NO: 64 | SEQ ID NO: 252 |
| 94 | IPD103-11Reary-33 | SEQ ID NO: 65 | SEQ ID NO: 253 |
| 95 | IPD103-11Reary-34 | SEQ ID NO: 66 | SEQ ID NO: 254 |
| 92 | IPD103-11Reary-35 | SEQ ID NO: 67 | SEQ ID NO: 255 |
| 92 | IPD103-11Reary-36 | SEQ ID NO: 68 | SEQ ID NO: 256 |
| 96 | IPD103-11Reary-37 | SEQ ID NO: 69 | SEQ ID NO: 257 |
| 87 | IPD103-11Reary-38 | SEQ ID NO: 70 | SEQ ID NO: 258 |
| 88 | IPD103-11Reary-39 | SEQ ID NO: 71 | SEQ ID NO: 259 |
| 92 | IPD103-11Reary-40 | SEQ ID NO: 72 | SEQ ID NO: 260 |
| 86 | IPD103-11Reary-41 | SEQ ID NO: 73 | SEQ ID NO: 261 |
| 92 | IPD103-11Reary-42 | SEQ ID NO: 74 | SEQ ID NO: 262 |
| 94 | IPD103-11Reary-43 | SEQ ID NO: 75 | SEQ ID NO: 263 |
| 91 | IPD103-11Reary-44 | SEQ ID NO: 76 | SEQ ID NO: 264 |
| 94 | IPD103-11Reary-45 | SEQ ID NO: 77 | SEQ ID NO: 265 |
| 89 | IPD103-11Reary-46 | SEQ ID NO: 78 | SEQ ID NO: 266 |

TABLE 7-continued

| % Identity to IPD103Aa (SEQ ID NO: 2) | Variant | Polynucleotide | Polypeptide |
|---|---|---|---|
| 89 | IPD103-123Reary-01 | SEQ ID NO: 79 | SEQ ID NO: 267 |
| 89 | IPD103-123Reary-02 | SEQ ID NO: 80 | SEQ ID NO: 268 |
| 94 | IPD103-123Reary-05 | SEQ ID NO: 81 | SEQ ID NO: 269 |
| 88 | IPD103-123Reary-06 | SEQ ID NO: 82 | SEQ ID NO: 270 |
| 92 | IPD103-123Reary-07 | SEQ ID NO: 83 | SEQ ID NO: 271 |
| 76 | IPD103-123Reary-08 | SEQ ID NO: 84 | SEQ ID NO: 272 |
| 82 | IPD103-123Reary-09 | SEQ ID NO: 85 | SEQ ID NO: 273 |
| 89 | IPD103-123Reary-10 | SEQ ID NO: 86 | SEQ ID NO: 274 |
| 90 | IPD103-123Reary-11 | SEQ ID NO: 87 | SEQ ID NO: 275 |
| 93 | IPD103-123Reary-12 | SEQ ID NO: 88 | SEQ ID NO: 276 |
| 87 | IPD103-123Reary-13 | SEQ ID NO: 89 | SEQ ID NO: 277 |
| 89 | IPD103-123Reary-14 | SEQ ID NO: 90 | SEQ ID NO: 278 |
| 84 | IPD103-123Reary-15 | SEQ ID NO: 91 | SEQ ID NO: 279 |
| 90 | IPD103-123Reary-16 | SEQ ID NO: 92 | SEQ ID NO: 280 |
| 81 | IPD103-123Reary-17 | SEQ ID NO: 93 | SEQ ID NO: 281 |
| 88 | IPD103-123Reary-18 | SEQ ID NO: 94 | SEQ ID NO: 282 |
| 81 | IPD103-123Reary-19 | SEQ ID NO: 95 | SEQ ID NO: 283 |
| 78 | IPD103-123Reary-21 | SEQ ID NO: 96 | SEQ ID NO: 284 |
| 85 | IPD103-123Reary-22 | SEQ ID NO: 97 | SEQ ID NO: 285 |
| 77 | IPD103-123Reary-23 | SEQ ID NO: 98 | SEQ ID NO: 286 |
| 75 | IPD103-123Reary-24 | SEQ ID NO: 99 | SEQ ID NO: 287 |
| 82 | IPD103-123Reary-25 | SEQ ID NO: 100 | SEQ ID NO: 288 |
| 92 | IPD103-123Reary-26 | SEQ ID NO: 101 | SEQ ID NO: 289 |
| 79 | IPD103-123Reary-28 | SEQ ID NO: 102 | SEQ ID NO: 290 |
| 90 | IPD103-123Reary-30 | SEQ ID NO: 103 | SEQ ID NO: 291 |
| 91 | IPD103-123Reary-31 | SEQ ID NO: 104 | SEQ ID NO: 292 |
| 84 | IPD103-123Reary-32 | SEQ ID NO: 105 | SEQ ID NO: 293 |
| 93 | IPD103-123Reary-33 | SEQ ID NO: 106 | SEQ ID NO: 294 |
| 85 | IPD103-123Reary-34 | SEQ ID NO: 107 | SEQ ID NO: 295 |
| 87 | IPD103-123Reary-35 | SEQ ID NO: 108 | SEQ ID NO: 296 |
| 88 | IPD103-123Reary-37 | SEQ ID NO: 109 | SEQ ID NO: 297 |
| 89 | IPD103-123Reary-38 | SEQ ID NO: 110 | SEQ ID NO: 298 |
| 75 | IPD103-123Reary-40 | SEQ ID NO: 111 | SEQ ID NO: 299 |
| 87 | IPD103lib11reary-01 | SEQ ID NO: 112 | SEQ ID NO: 300 |
| 89 | IPD103lib11reary-03 | SEQ ID NO: 113 | SEQ ID NO: 301 |
| 95 | IPD103lib11reary-07 | SEQ ID NO: 114 | SEQ ID NO: 302 |
| 93 | IPD103lib11reary-08 | SEQ ID NO: 115 | SEQ ID NO: 303 |
| 89 | IPD103lib11reary-09 | SEQ ID NO: 116 | SEQ ID NO: 304 |
| 90 | IPD103lib11reary-10 | SEQ ID NO: 117 | SEQ ID NO: 305 |
| 89 | IPD103lib11reary-11 | SEQ ID NO: 118 | SEQ ID NO: 306 |
| 93 | IPD103lib11reary-12 | SEQ ID NO: 119 | SEQ ID NO: 307 |
| 93 | IPD103lib11reary-13 | SEQ ID NO: 120 | SEQ ID NO: 308 |
| 90 | IPD103lib11reary-14 | SEQ ID NO: 121 | SEQ ID NO: 309 |
| 96 | IPD103lib11reary-15 | SEQ ID NO: 122 | SEQ ID NO: 310 |
| 92 | IPD103lib11reary-16 | SEQ ID NO: 123 | SEQ ID NO: 311 |
| 91 | IPD103lib11reary-17 | SEQ ID NO: 124 | SEQ ID NO: 312 |
| 97 | IPD103lib11reary-18 | SEQ ID NO: 125 | SEQ ID NO: 313 |
| 98 | IPD103lib11reary-19 | SEQ ID NO: 126 | SEQ ID NO: 314 |
| 90 | IPD103lib11reary-20 | SEQ ID NO: 127 | SEQ ID NO: 315 |
| 94 | IPD103lib11reary-21 | SEQ ID NO: 128 | SEQ ID NO: 316 |
| 87 | IPD103lib11reary-22 | SEQ ID NO: 129 | SEQ ID NO: 317 |
| 92 | IPD103lib11reary-23 | SEQ ID NO: 130 | SEQ ID NO: 318 |
| 92 | IPD103lib11reary-25 | SEQ ID NO: 131 | SEQ ID NO: 319 |
| 92 | IPD103lib11reary-27 | SEQ ID NO: 132 | SEQ ID NO: 320 |
| 90 | IPD103lib11reary-28 | SEQ ID NO: 133 | SEQ ID NO: 321 |
| 91 | IPD103lib11reary-29 | SEQ ID NO: 134 | SEQ ID NO: 322 |
| 89 | IPD103lib11reary-30 | SEQ ID NO: 135 | SEQ ID NO: 323 |
| 92 | IPD103lib11reary-31 | SEQ ID NO: 136 | SEQ ID NO: 324 |
| 91 | IPD103lib11reary-32 | SEQ ID NO: 137 | SEQ ID NO: 325 |
| 89 | IPD103lib11reary-33 | SEQ ID NO: 138 | SEQ ID NO: 326 |
| 93 | IPD103lib11reary-34 | SEQ ID NO: 139 | SEQ ID NO: 327 |
| 92 | IPD103lib11reary-35 | SEQ ID NO: 140 | SEQ ID NO: 328 |
| 88 | IPD103lib11reary-38 | SEQ ID NO: 141 | SEQ ID NO: 329 |
| 94 | IPD103lib11reary-39 | SEQ ID NO: 142 | SEQ ID NO: 330 |
| 96 | IPD103lib11reary-40 | SEQ ID NO: 143 | SEQ ID NO: 331 |
| 98 | IPD103lib11reary-41 | SEQ ID NO: 144 | SEQ ID NO: 332 |
| 91 | IPD103lib11reary-42 | SEQ ID NO: 145 | SEQ ID NO: 333 |
| 86 | IPD103lib11reary-43 | SEQ ID NO: 146 | SEQ ID NO: 334 |
| 95 | IPD103lib11reary-44 | SEQ ID NO: 147 | SEQ ID NO: 335 |
| 91 | IPD103lib11reary-45 | SEQ ID NO: 148 | SEQ ID NO: 336 |
| 89 | IPD103lib11reary-46 | SEQ ID NO: 149 | SEQ ID NO: 337 |
| 88 | IPD103lib11reary-47 | SEQ ID NO: 150 | SEQ ID NO: 338 |
| 89 | IPD103lib11reary-48 | SEQ ID NO: 151 | SEQ ID NO: 339 |
| 90 | IPD103lib11reary-49 | SEQ ID NO: 152 | SEQ ID NO: 340 |
| 95 | IPD103lib11reary-50 | SEQ ID NO: 153 | SEQ ID NO: 341 |
| 91 | IPD103lib11reary-51 | SEQ ID NO: 154 | SEQ ID NO: 342 |

TABLE 7-continued

| % Identity to IPD103Aa (SEQ ID NO: 2) | Variant | Polynucleotide | Polypeptide |
|---|---|---|---|
| 92 | IPD103lib11reary-52 | SEQ ID NO: 155 | SEQ ID NO: 343 |
| 91 | IPD103lib11reary-53 | SEQ ID NO: 156 | SEQ ID NO: 344 |
| 89 | IPD103lib11reary-54 | SEQ ID NO: 157 | SEQ ID NO: 345 |
| 96 | IPD103lib11reary-55 | SEQ ID NO: 158 | SEQ ID NO: 346 |
| 92 | IPD103lib11reary-56 | SEQ ID NO: 159 | SEQ ID NO: 347 |
| 93 | IPD103lib11reary-58 | SEQ ID NO: 160 | SEQ ID NO: 348 |
| 92 | IPD103lib11reary-59 | SEQ ID NO: 161 | SEQ ID NO: 349 |
| 90 | IPD103lib11reary-62 | SEQ ID NO: 162 | SEQ ID NO: 350 |
| 91 | IPD103lib11reary-63 | SEQ ID NO: 163 | SEQ ID NO: 351 |
| 91 | IPD103lib11reary-64 | SEQ ID NO: 164 | SEQ ID NO: 352 |
| 95 | IPD103lib11reary-65 | SEQ ID NO: 165 | SEQ ID NO: 353 |
| 96 | IPD103lib11reary-66 | SEQ ID NO: 166 | SEQ ID NO: 354 |
| 94 | IPD103lib11reary-67 | SEQ ID NO: 167 | SEQ ID NO: 355 |
| 93 | IPD103lib11reary-68 | SEQ ID NO: 168 | SEQ ID NO: 356 |
| 95 | IPD103lib11reary-69 | SEQ ID NO: 169 | SEQ ID NO: 357 |
| 93 | IPD103lib11reary-70 | SEQ ID NO: 170 | SEQ ID NO: 358 |
| 96 | IPD103lib11reary-73 | SEQ ID NO: 171 | SEQ ID NO: 359 |
| 89 | IPD103lib11reary-74 | SEQ ID NO: 172 | SEQ ID NO: 360 |
| 89 | IPD103lib11reary-75 | SEQ ID NO: 173 | SEQ ID NO: 361 |
| 88 | IPD103lib11reary-76 | SEQ ID NO: 174 | SEQ ID NO: 362 |
| 88 | IPD103lib11reary-78 | SEQ ID NO: 175 | SEQ ID NO: 363 |
| 96 | IPD103lib11reary-79 | SEQ ID NO: 176 | SEQ ID NO: 364 |
| 91 | IPD103lib11reary-80 | SEQ ID NO: 177 | SEQ ID NO: 365 |
| 91 | IPD103lib11reary-82 | SEQ ID NO: 178 | SEQ ID NO: 366 |
| 85 | IPD103lib11reary-83 | SEQ ID NO: 179 | SEQ ID NO: 367 |
| 93 | IPD103lib11reary-85 | SEQ ID NO: 180 | SEQ ID NO: 368 |
| 89 | IPD103lib11reary-86 | SEQ ID NO: 181 | SEQ ID NO: 369 |
| 94 | IPD103lib11reary-87 | SEQ ID NO: 182 | SEQ ID NO: 370 |
| 96 | IPD103lib11reary-88 | SEQ ID NO: 183 | SEQ ID NO: 371 |
| 78 | IPD103lib123reary-01 | SEQ ID NO: 184 | SEQ ID NO: 372 |
| 94 | IPD103lib123reary-05 | SEQ ID NO: 185 | SEQ ID NO: 373 |
| 85 | IPD103lib123reary-07 | SEQ ID NO: 186 | SEQ ID NO: 374 |
| 82 | IPD103lib123reary-11 | SEQ ID NO: 187 | SEQ ID NO: 375 |
| 75 | IPD103lib123reary-14 | SEQ ID NO: 188 | SEQ ID NO: 376 |
| 87 | IPD103lib123reary-15 | SEQ ID NO: 189 | SEQ ID NO: 377 |
| 81 | IPD103lib123reary-16 | SEQ ID NO: 190 | SEQ ID NO: 378 |
| 76 | IPD103lib123reary-17 | SEQ ID NO: 191 | SEQ ID NO: 379 |
| 88 | IPD103lib123reary-18 | SEQ ID NO: 192 | SEQ ID NO: 380 |
| 80 | IPD103lib123reary-19 | SEQ ID NO: 193 | SEQ ID NO: 381 |
| 84 | IPD103lib123reary-23 | SEQ ID NO: 194 | SEQ ID NO: 382 |
| 90 | IPD103lib123reary-27 | SEQ ID NO: 195 | SEQ ID NO: 383 |
| 86 | IPD103lib123reary-28 | SEQ ID NO: 196 | SEQ ID NO: 384 |
| 96 | IPD103lib123reary-29 | SEQ ID NO: 197 | SEQ ID NO: 385 |
| 83 | IPD103lib123reary-30 | SEQ ID NO: 198 | SEQ ID NO: 386 |
| 86 | IPD103lib123reary-31 | SEQ ID NO: 199 | SEQ ID NO: 387 |
| 76 | IPD103lib123reary-32 | SEQ ID NO: 200 | SEQ ID NO: 388 |
| 74 | IPD103lib123reary-34 | SEQ ID NO: 201 | SEQ ID NO: 389 |
| 82 | IPD103lib123reary-37 | SEQ ID NO: 202 | SEQ ID NO: 390 |
| 79 | IPD103lib123reary-38 | SEQ ID NO: 203 | SEQ ID NO: 391 |
| 75 | IPD103lib123reary-39 | SEQ ID NO: 204 | SEQ ID NO: 392 |
| 97 | IPD103lib123reary-40 | SEQ ID NO: 205 | SEQ ID NO: 393 |
| 76 | IPD103lib123reary-41 | SEQ ID NO: 206 | SEQ ID NO: 394 |
| 76 | IPD103lib123reary-42 | SEQ ID NO: 207 | SEQ ID NO: 395 |
| 96 | IPD103lib123reary-45 | SEQ ID NO: 208 | SEQ ID NO: 396 |
| 76 | IPD103lib123reary-46 | SEQ ID NO: 209 | SEQ ID NO: 397 |
| 78 | IPD103lib123reary-47 | SEQ ID NO: 210 | SEQ ID NO: 398 |
| 91 | IPD103lib123reary-48 | SEQ ID NO: 211 | SEQ ID NO: 399 |
| 92 | IPD103lib123reary-49 | SEQ ID NO: 212 | SEQ ID NO: 400 |
| 73 | IPD103lib123reary-52 | SEQ ID NO: 213 | SEQ ID NO: 401 |
| 81 | IPD103lib123reary-54 | SEQ ID NO: 214 | SEQ ID NO: 402 |
| 85 | IPD103lib123reary-55 | SEQ ID NO: 215 | SEQ ID NO: 403 |
| 76 | IPD103lib123reary-58 | SEQ ID NO: 216 | SEQ ID NO: 404 |
| 87 | IPD103lib123reary-59 | SEQ ID NO: 217 | SEQ ID NO: 405 |
| 73 | IPD103lib123reary-60 | SEQ ID NO: 218 | SEQ ID NO: 406 |
| 81 | IPD103lib123reary-62 | SEQ ID NO: 219 | SEQ ID NO: 407 |
| 74 | IPD103lib123reary-63 | SEQ ID NO: 220 | SEQ ID NO: 408 |
| 88 | IPD103lib123reary-65 | SEQ ID NO: 221 | SEQ ID NO: 409 |
| 76 | IPD103lib123reary-67 | SEQ ID NO: 222 | SEQ ID NO: 410 |
| 90 | IPD103lib123reary-68 | SEQ ID NO: 223 | SEQ ID NO: 411 |
| 75 | IPD103lib123reary-69 | SEQ ID NO: 224 | SEQ ID NO: 412 |
| 73 | IPD103lib123reary-70 | SEQ ID NO: 225 | SEQ ID NO: 413 |
| 90 | IPD103lib123reary-72 | SEQ ID NO: 226 | SEQ ID NO: 414 |
| 73 | IPD103lib123reary-73 | SEQ ID NO: 227 | SEQ ID NO: 415 |
| 74 | IPD103lib123reary-77 | SEQ ID NO: 228 | SEQ ID NO: 416 |

TABLE 8

| % Identity to IPD103Aa (SEQ ID NO: 2) | # of Unique Sequences | Variants |
|---|---|---|
| 98 | 4 | IPD103lib11reary-19, IPD103lib11reary-41, IPD103-11Reary-14, IPD103-11Reary-25 |
| 97 | 2 | IPD103lib123reary-40, IPD103lib11reary-18 |
| 96 | 10 | IPD103lib123reary-29, IPD103lib123reary-45, IPD103lib11reary-15, IPD103lib11reary-40, IPD103lib11reary-55, IPD103lib11reary-66, IPD103lib11reary-73, IPD103lib11reary-79, IPD103lib11reary-88, IPD103-11Reary-37 |
| 95 | 8 | IPD103lib11reary-07, IPD103lib11reary-44, IPD103lib11reary-50, IPD103lib11reary-65, IPD103lib11reary-69, IPD103-11Reary-16, IPD103-11Reary-29, IPD103-11Reary-34 |
| 94 | 12 | IPD103lib123reary-05, IPD103lib11reary-21, IPD103lib11reary-39, IPD103lib11reary-67, IPD103lib11reary-87, IPD103-11Reary-09, IPD103-11Reary-13, IPD103-11Reary-22, IPD103-11Reary-33, IPD103-11Reary-43, IPD103-11Reary-45, IPD103-123Reary-05 |
| 93 | 11 | IPD103lib11reary-08, IPD103lib11reary-12, IPD103lib11reary-13, IPD103lib11reary-34, IPD103lib11reary-58, IPD103lib11reary-68, IPD103lib11reary-70, IPD103lib11reary-85, IPD103-11Reary-17, IPD103-123Reary-12, IPD103-123Reary-33 |
| 92 | 21 | IPD103lib123reary-49, IPD103lib11reary-16, IPD103lib11reary-23, IPD103lib11reary-25, IPD103lib11reary-27, IPD103lib11reary-31, IPD103lib11reary-35, IPD103lib11reary-52, IPD103lib11reary-56, IPD103lib11reary-59, IPD103-11Reary-01, IPD103-11Reary-05, IPD103-11Reary-06, IPD103-11Reary-10, IPD103-11Reary-18, IPD103-11Reary-35, IPD103-11Reary-36, IPD103-11Reary-40, IPD103-11Reary-42, IPD103-123Reary-07, IPD103-123Reary-26 |
| 91 | 17 | IPD103lib123reary-48, IPD103lib11reary-17, IPD103lib11reary-29, IPD103lib11reary-32, IPD103lib11reary-42, IPD103lib11reary-45, IPD103lib11reary-51, IPD103lib11reary-53, IPD103lib11reary-63, IPD103lib11reary-64, IPD103lib11reary-80, IPD103lib11reary-82, IPD103-11Reary-11, IPD103-11Reary-21, IPD103-11Reary-24, IPD103-11Reary-44, IPD103-123Reary-31 |
| 90 | 16 | IPD103lib123reary-27, IPD103lib123reary-68, IPD103lib123reary-72, IPD103lib11reary-10, IPD103lib11reary-14, IPD103lib11reary-20, IPD103lib11reary-28, IPD103lib11reary-49, IPD103lib11reary-62, IPD103-11Reary-04, IPD103-11Reary-15, IPD103-11Reary-20, IPD103-11Reary-32, IPD103-123Reary-11, IPD103-123Reary-16, IPD103-123Reary-30 |
| 89 | 20 | IPD103lib11reary-03, IPD103lib11reary-09, IPD103lib11reary-11, IPD103lib11reary-30, IPD103lib11reary-33, IPD103lib11reary-46, IPD103lib11reary-48, IPD103lib11reary-54, IPD103lib11reary-74, IPD103lib11reary-75, IPD103lib11reary-86, IPD103-11Reary-08, IPD103-11Reary-19, IPD103-11Reary-31, IPD103-11Reary-46, IPD103-123Reary-01, IPD103-123Reary-02, IPD103-123Reary-10, IPD103-123Reary-14, IPD103-123Reary-38 |
| 88 | 11 | IPD103lib123reary-18, IPD103lib123reary-65, IPD103lib11reary-38, IPD103lib11reary-47, IPD103lib11reary-76, IPD103lib11reary-78, IPD103-11Reary-26, IPD103-11Reary-39, IPD103-123Reary-06, IPD103-123Reary-18, IPD103-123Reary-37 |
| 87 | 7 | IPD103lib123reary-15, IPD103lib123reary-59, IPD103lib11reary-01, IPD103lib11reary-22, IPD103-11Reary-38, IPD103-123Reary-13, IPD103-123Reary-35 |
| 86 | 4 | IPD103lib123reary-28, IPD103lib123reary-31, IPD103lib11reary-43, IPD103-11Reary-41 |
| 85 | 5 | IPD103lib123reary-55, IPD103lib123reary-07, IPD103lib11reary-83, IPD103-123Reary-22, IPD103-123Reary-34 |
| 84 | 3 | IPD103lib123reary-23, IPD103-123Reary-15, IPD103-123Reary-32 |
| 83 | 1 | IPD103lib123reary-30 |
| 82 | 4 | IPD103lib123reary-11, IPD103lib123reary-37, IPD103-123Reary-09, IPD103-123Reary-25 |
| 81 | 5 | IPD103lib123reary-16, IPD103lib123reary-54, IPD103lib123reary-62, IPD103-123Reary-17, IPD103-123Reary-19 |
| 80 | 1 | IPD103lib123reary-19 |
| 79 | 2 | IPD103lib123reary-38, IPD103-123Reary-28 |
| 78 | 3 | IPD103lib123reary-47, IPD103lib123reary-01, IPD103-123Reary-21 |
| 77 | 1 | IPD103-123Reary-23 |
| 76 | 8 | IPD103lib123reary-17, IPD103lib123reary-32, IPD103lib123reary-41, IPD103lib123reary-42, IPD103lib123reary-46, IPD103lib123reary-58, IPD103lib123reary-67, IPD103-123Reary-08 |
| 75 | 5 | IPD103lib123reary-14, IPD103lib123reary-39, IPD103lib123reary-69, IPD103-123Reary-24, IPD103-123Reary-40 |
| 74 | 3 | IPD103lib123reary-34, IPD103lib123reary-63, IPD103lib123reary-77 |
| 73 | 4 | IPD103lib123reary-52, IPD103lib123reary-60, IPD103lib123reary-70, IPD103lib123reary-73 |

Example 9—Vector Constructs for Expression of IPD103 Polypeptides in Plants

For testing in maize, expression vectors PHP79658, PHP70659, and PHP7600 were constructed to include a transgene cassette containing one of three different gene designs encoding IPD103Aa (SEQ ID NO: 2), the MMV ENH:MMV ENH:BYDV promoter (U.S. Ser. No. 62/260,819), linked to the PINII terminator (US-2014-0130205).

Example 10—Expression and Insect Bioassay on Transient Leaf Tissues

To confirm activity of IPD103Aa (SEQ ID NO: 2) and IPD103Ab (SEQ ID NO: 4) the corresponding genes were cloned into a transient expression system under control of the viral promoter dMMV or AtUBQ10 promoter (Dey, et. al., (1999) Plant Mol. Biol. 40:771-782; PCT Patent Publication WO2011133387; Norris S R et al (1993) Plant Mol Biol. 21(5):895-906)). The constructs were infiltrated into leaves. The agro-infiltration method of introducing an Agrobacterium cell suspension to plant cells of intact tissues so that reproducible infection and subsequent plant derived transgene expression may be measured or studied is well known in the art (Kapila, et. al., (1997) Plant Science 122:101-108). Briefly, the unifoliate stage of bush bean (common bean, Phaseolus vulgaris) or soybean (Glycine max), were agro-infiltrated with normalized bacterial cell cultures of test and control strains. Leaf discs were excised from each plantlet and infested with neonates of Soy Bean Looper (SBL) (Pseudoplusia includens), Corn Earworm, (CEW) (*Helicoverpa zea*), [FAW], Velvet Bean Caterpillar (VBC) (*Anticarsia gemmatalis*) or European Corn Borer (ECB) (*Ostrinia nubialis*). Leaf discs from a control were generated with *Agrobacterium* containing only empty expression vector. Leaf discs from a non-infiltrated plant were used as a second control. The consumption of green leaf tissue was scored after two (CEW, VBC), three (SBL) or four (ECB) days after infestation and given scores of 0 to 9 as indicated by Table 9. The transiently expressed IPD103Aa (SEQ ID NO: 2) and homologs protected bush bean leaf discs from consumption by the infested insects while total green tissue consumption was observed for the negative control and untreated tissue. Transient protein expression of IPD103Aa (SEQ ID NO: 2) and IPD103Ab (SEQ ID NO: 4) were confirmed by a mass spectrometry-based protein identification method using extracted protein lysates from infiltrated leave tissues (Patterson, (1998) 10(22):1-24, Current Protocol in Molecular Biology published by John Wiley & Son Inc). As shown in Table 10, IPD103Aa (SEQ ID NO: 2) and all the homologs tested resulted in protection of bush bean against leaf feeding damage from a diversity of Lepidoptera. A selection of IPD103 R10 mutants described in Table 5 were also transiently expressed in bush bean and shown to be active against Lepidoptera (Table 11). Larval feeding damage to soybean leaves transiently expressing insecticidal genes under the control of the viral promoter dMMV (Dey, et. al., (1999) *Plant Mol. Biol.* 40:771-782) was assessed using a scale described in Table 9. The effect of expression of IPD103 proteins was compared to non-agro-infiltrated controls and controls expressing DsRed2 fluorescence marker (Clontech, Mountain View, CA). Activity of selected IPD103 polypeptides, transiently expressed in bush bean, against leaf feeding damage from a selection of Lepidoptera is shown in Table 10. The average score and standard error (SE) for 6 replicate measurements are shown.

Activity of selected IPD103Aa R10 variants, transiently expressed in bush bean, against leaf feeding damage from a selection of Lepidoptera is shown in Table 11.

Activity of selected IPD103Aa polypeptides, transiently expressed in Soybean, against leaf feeding damage from a selection of Lepidoptera is shown in Table 12 The average leaf feeding score and standard deviation (StdDev) for 12 replicates/treatment is shown.

TABLE 9

| Leaf Feeding Score | % Consumed |
|---|---|
| 1 | 86-100 |
| 2 | 71-85 |
| 3 | 61-70 |
| 4 | 51-60 |
| 5 | 36-50 |
| 6 | 11-35 |
| 7 | 11-36 |
| 8 | 1-3 |
| 9 | 0 |

TABLE 10

| Gene | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|
| IPD103Aa SEQ ID NO: 2 | CEW | 7.7 | 0.3 | ECB | 5.2 | 1.1 | FAW | 4.7 | 0.4 |
| IPD103Ac SEQ ID NO: 6 | | 7.5 | 0.3 | | 6.7 | 0.7 | | 4.8 | 0.7 |
| IPD103Ad SEQ ID NO: 8 | | 8.2 | 0.3 | | 3.2 | 1.2 | | 4.5 | 0.3 |
| IPD103Ae SEQ ID NO: 10 | | 7.3 | 0.3 | | 2.0 | 0.7 | | 3.8 | 0.7 |
| IPD103Ba SEQ ID NO: 12 | | 6.0 | 0.4 | | 1.8 | 0.5 | | 3.2 | 0.2 |
| IPD103Bb SEQ ID NO: 14 | | 6.3 | 0.4 | | 5.8 | 0.2 | | 3.7 | 0.2 |
| IPD103Bc SEQ ID NO: 16 | | 7.0 | 0.6 | | 3.2 | 1.4 | | 3.7 | 0.2 |
| IPD103Bd SEQ ID NO: 18 | | 7.7 | 0.3 | | 7.5 | 0.3 | | 5.7 | 0.3 |
| IPD103Be SEQ ID NO: 20 | | 7.7 | 0.3 | | 5.8 | 0.8 | | 5.5 | 0.4 |
| IPD103Bf SEQ ID NO: 22 | | 7.3 | 0.6 | | 6.2 | 0.7 | | 4.3 | 0.6 |
| IPD103Bg SEQ ID NO: 24 | | 8.0 | 0.4 | | 4.2 | 1.2 | | 4.2 | 0.6 |
| IPD103Bh SEQ ID NO: 26 | | 8.0 | 0.4 | | 6.5 | 1.2 | | 6.0 | 0.8 |
| IPD103Ca SEQ ID NO: 34 | | 6.0 | 0.8 | | 3.8 | 1.5 | | 3.0 | 0.4 |
| IPD103Da SEQ ID NO: 36 | | 6.3 | 0.3 | | 3.3 | 1.1 | | 3.5 | 0.3 |
| Negative Control | | 3.7 | 1.1 | | 2.3 | 1.3 | | 2.2 | 0.2 |
| Untreated | | 3.5 | 0.4 | | 1.2 | 0.2 | | 2.8 | 0.3 |
| IPD103Aa SEQ ID NO: 2 | SBL | 6.0 | 0.4 | VBC | 8.0 | 0.0 | | | |
| IPD103Ac SEQ ID NO: 6 | | 5.2 | 0.2 | | 8.0 | 0.0 | | | |
| IPD103Ad SEQ ID NO: 8 | | 6.0 | 0.3 | | 8.2 | 0.2 | | | |
| IPD103Ae SEQ ID NO: 10 | | 6.0 | 0.4 | | 8.2 | 0.2 | | | |
| IPD103Ba SEQ ID NO: 12 | | 4.3 | 0.3 | | 5.7 | 0.7 | | | |
| IPD103Bb SEQ ID NO: 14 | | 3.8 | 0.3 | | 6.7 | 0.4 | | | |
| IPD103Bc SEQ ID NO: 16 | | 5.3 | 0.9 | | 6.5 | 0.2 | | | |
| IPD103Bd SEQ ID NO: 18 | | 6.0 | 0.4 | | 8.0 | 0.0 | | | |
| IPD103Be SEQ ID NO: 20 | | 5.3 | 0.2 | | 7.8 | 0.2 | | | |
| IPD103Bf SEQ ID NO: 22 | | 4.5 | 0.3 | | 7.7 | 0.2 | | | |
| IPD103Bg SEQ ID NO: 24 | | 5.7 | 0.6 | | 7.8 | 0.2 | | | |
| IPD103Bh SEQ ID NO: 26 | | 5.3 | 0.4 | | 8.5 | 0.2 | | | |
| IPD103Ca SEQ ID NO: 34 | | 3.8 | 0.4 | | 4.8 | 1.3 | | | |
| IPD103Da SEQ ID NO: 36 | | 4.5 | 0.5 | | 7.2 | 0.5 | | | |
| Negative Control | | 3.3 | 0.3 | | 1.0 | 0.0 | | | |
| Untreated | | 4.0 | 0.7 | | 2.7 | 1.1 | | | |

TABLE 11

| | SEQ ID | SBL | FAW | CEW | ECB |
|---|---|---|---|---|---|
| IPD103-R10Y | SEQ ID NO: 452 | − | + | + | − |
| IPD103-R10T | SEQ ID NO: 453 | + | + | + | + |
| IPD103-R10A | SEQ ID NO: 454 | + | + | + | + |

TABLE 11-continued

| | SEQ ID | SBL | FAW | CEW | ECB |
|---|---|---|---|---|---|
| IPD103-R10M | SEQ ID NO: 455 | + | + | + | + |
| IPD103-R10S | SEQ ID NO: 456 | + | + | + | + |
| IPD103lib11reary-54 | SEQ ID NO: 345 | + | + | + | + |
| IPD103Be | SEQ ID NO: 20 | + | + | + | + |
| IPD103Aa | SEQ ID NO: 2 | + | − | + | + |
| Empty | | − | − | − | − |

TABLE 12

| | | CEW | | SBL | | VBC | |
|---|---|---|---|---|---|---|---|
| | SEQ ID NO | Avg. Score | Std. DEV | Avg. Score | | Avg. Score | |
| IPD103Aa | SEQ ID NO: 2 | 7.8 | 0.5 | 7.8 | 0.8 | 7.2 | 0.7 |
| IPD103Bc | SEQ ID NO: 16 | 7.8 | 0.7 | 6.3 | 0.7 | 6.0 | 1.3 |
| IPD103Bd | SEQ ID NO: 18 | 8.2 | 0.4 | 7.8 | 0.6 | 6.8 | 1.8 |
| IPD103Be | SEQ ID NO: 20 | 6.8 | 0.6 | 6.7 | 0.8 | 6.4 | 1.2 |
| IPD103Bh | SEQ ID NO: 26 | 8.0 | 0.4 | 7.8 | 0.6 | 6.7 | 2.1 |
| IPD103Da | SEQ ID NO: 36 | 2.0 | 1.6 | 4.4 | 1.6 | 1.3 | 0.7 |
| DsRed control | | 1.0 | 0.0 | 1.3 | 0.5 | 1.0 | 0.0 |
| Neg. control | | 1.0 | 0.0 | 1.7 | 1.5 | 1.2 | 0.4 |

Example 11—*Agrobacterium*-Mediated Transformation of Maize and Regeneration of Transgenic Plants For *Agrobacterium*-mediated transformation of maize with IPD103Aa nucleotide sequences the method of Zhao was used (U.S. Pat. No. 5,981,840 and PCT Patent Publication Number WO 1998/32326; the contents of which are hereby incorporated by reference). Briefly, immature embryos were isolated from maize and the embryos contacted with a suspension of *Agrobacterium* under conditions whereby the bacteria are capable of transferring the PHP79658, PHP70659, and PHP7600 vectors to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of *Agrobacterium* without the addition of a selective agent for plant transformation (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus is recovered (step 4: the selection step). The immature embryos were cultured on solid medium with a selective agent resulting in the selective growth of transformed cells. The callus was then regenerated into plants (step 5: the regeneration step), and calli grown on selective medium or cultured on solid medium to regenerate the plants.

For detection of the IPD103 proteins in leaf tissue 4 lyophilized leaf punches/sample were pulverized and resuspended in 100 μL PBS containing 0.1% Tween 20 (PBST), 1% beta-mercaoptoethanol containing 1 tablet/7 mL complete Mini proteinase inhibitor (Roche 1183615301). The suspension was sonicated for 2 min and then centrifuged at 4° C., 20,000 g for 15 min. To a supernatant aliquot ⅓ volume of 3× NuPAGE® LDS Sample Buffer (Invitrogen™ (CA, USA), 1% B-ME containing 1 tablet/7 mL complete Mini proteinase inhibitor was added. The reaction was heated at 80° C. for 10 min and then centrifuged. A supernatant sample was loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane was incubated in PBST containing 5% skim milk powder for 2 hours before overnight incubation in affinity-purified rabbit anti-IPD103Aa polyclonal antibody in PBST overnight. The membrane was rinsed three times with PBST and then incubated in PBST for 15 min and then two times 5 min before incubating for 2 hours in PBST with goat anti-rabbit-HRP for 3 hours. The detected proteins were visualized using ECL Western Blotting Reagents (GE Healthcare cat #RPN2106) and visualized using a luminescent image analyzer (ImageQuant LAS 4000, GE Healthcare Transgenic maize plants positive for expression of the insecticidal proteins are tested for pesticidal activity using standard bioassays known in the art. Such methods include, for example, whole plant bioassays.

Example 12—Particle Bombardment Transformation and Regeneration of Transgenic Maize Plants Immature maize embryos from greenhouse donor plants are bombarded with a plasmid containing a nucleotide sequence encoding the insecticidal protein. The ears are husked and surface sterilized in 30% Clorox® bleach plus 0.5% Micro detergent for 20 minutes and rinsed two times with sterile water. The immature embryos are excised and placed embryo axis side down (scutellum side up), 25 embryos per plate, on 560Y medium for 4 hours and then aligned within the 2.5 cm target zone in preparation for bombardment. A plasmid vector DNA comprising the nucleotide sequence encoding the insecticidal protein operably linked to a promoter is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$ and 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment. The sample plates are bombarded at level #4 in a particle gun. All samples receive a single shot at 650 PSI, with a total of ten aliquots taken from each tube of prepared particles/DNA Following bombardment, the embryos are kept on 560Y medium for 2 days, then transferred to 56CR selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of an IPD103 polypeptide by assays known in the art, such as, for example, immunoassays and Western blotting.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054 and International Publication Number WO 2003/018810.

Bombardment medium (560Y) comprises 4.0 g/l N6 basal salts (SIGMA C-1416), 1.0 ml/l Eriksson's Vitamin Mix (1000.times.SIGMA-151 1), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH): 2.0 g/l Gelrite (added after bringing to volume with D-I $H_2O$) and 8.5 mg/l silver nitrate (added after sterilizing the medium and cooling to room temperature). Selection medium (560R) comprises 4.0 g/µl N6 basal salts (SIGMA C-1416), 1.0 ml/l Eriksson's Vitamin Mix (1000.times.SIGMA-151 1), 0.5 mg/l thiamine HCl, 30.0 g/l sucrose and 2.0 mg/l 2,4-D (brought to volume with D-I $H_2O$ following adjustment to pH 5.8 with KOH); 3.0 g/l Gelrite (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 1 1 1 17-074), 5.0 ml/l MS vitamins stock solution (0.100 g nicotinic acid, 0.02 g/µl thiamine HCL, 0.10 g/l pyridoxine HCL, and 0.40 g/l glycine brought to volume with polished D-I $H_2O$) (Murashige and Skoog, (1962) Physiol. Plant. 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/µl MS salts (GIBCO 1 1 1 17-074), 5.0 ml/l MS vitamins stock solution (0.100 g/µl nicotinic acid, 0.02 g/l thiamine HCL, 0.10 g/l pyridoxine HCL and 0.40 g/µl glycine brought to volume with polished D-I $H_2O$), 0.1 g/µl myoinositol and 40.0 g/µl sucrose (brought to volume with polished D-I $H_2O$ after adjusting pH to 5.6) and 6 g/l bacto-agar (added after bringing to volume with polished D-I $H_2O$), sterilized and cooled to 60° C.

Example 13—Insect Control Efficacy of Stable Transformed Corn Plants Against a Spectrum of Lepidopteran Insects Leaf discs were excised from transformed maize plants and tested for insecticidal activity of IPD103Aa polypeptides against the European Corn Borer (ECB) (*Ostrinia nubilalis*), Corn Earworm, (CEW) (*Helicoverpa zea*), and Fall Armyworm (*Spodoptera frugiperda*). The constructs, PHP79658, PHP79559 and PHP79660 for the expression of three IPD103Aa gene designs were used to generate transgenic maize events to test for efficacy against feeding damage caused by lepidopteran pests provided by expression of these polypeptides. FIG. 2 demonstrates that strong protection from leaf feeding by a broad spectrum of Lepidoptera pests was conferred by expression of IPD103Aa genes.

Example 14—Greenhouse Efficacy of IPD103 Polypeptide Events

Figure 4:
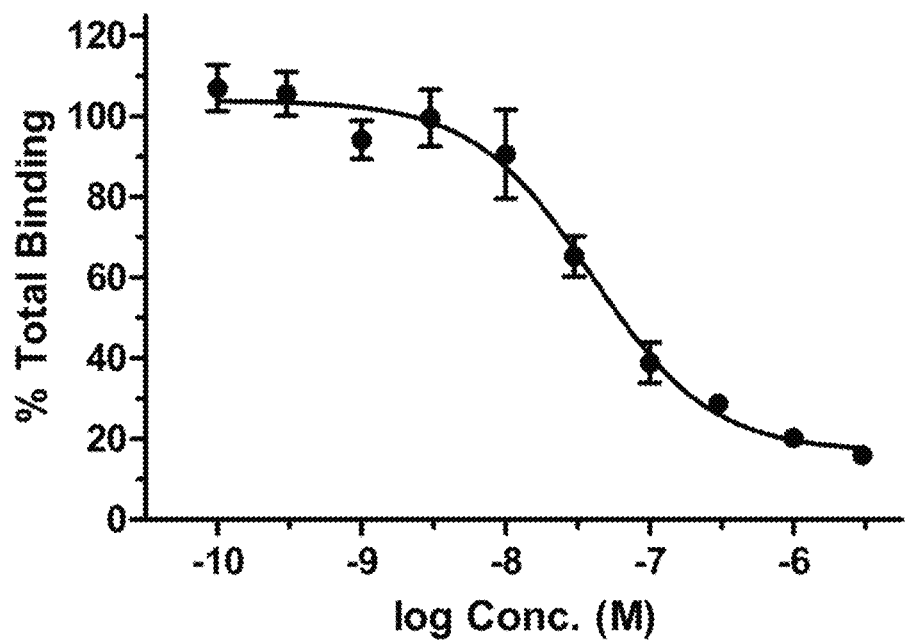
FIG. 4 shows a curve reflecting densitometry values of in-gel fluorescence, from the SDS-PAGE gel of Example 16, for homologous competition of 25 nM IPD103Aa$^{Alexa}$ binding to Helicoverpa zea (Corn Earworm) BBMVs normalized to the amount bound in the absence of unlabeled IPD103Aa (SEQ ID NO: 2). The solid line reflects the best fit of a square logistic equation to the data.

T0 greenhouse efficacy results for events generated from PHP79658, PHP79659 and PHP79660 constructs are shown in FIG. 4. Efficacy for events derived from all 3 constructs was observed relative to negative control events (Empty) as measured by corn ear protection from corn earworm (CEW). Ear protection was measured, using a grid, as the number of square centimeters (CEWSCM) of ear feeding damage. FIG. 4 shows that a large proportion of events from PHP79658, PHP79659 and PHP79660 performed better than the negative control and have earworm injury scores of 2 $cm^2$ or less Example 15—Transformation and Regeneration of Soybean (*Glycine max*)

Transgenic soybean lines are generated by the method of particle gun bombardment (Klein et al., Nature (London) 327:70-73 (1987); U.S. Pat. No. 4,945,050) using a BIO-RAD Biolistic PDS1000/He instrument and either plasmid or fragment DNA. The following stock solutions and media are used for transformation and regeneration of soybean plants:

Stock Solutions:
Sulfate 100× Stock:
  37.0 g $MgSO_4·7H_2O$, 1.69 g $MnSO_4·H_2O$, 0.86 g $ZnSO_4·7H_2O$, 0.0025 g $CuSO_4·5H_2O$
Halides 100× Stock:
  30.0 g $CaCl_2·2H_2O$, 0.083 g KI, 0.0025 g $CoCl_2·6H_2O$
P, B, Mo 100× Stock:
  18.5 g $KH_2PO_4$, 0.62 g $H_3BO_3$, 0.025 g $Na_2MoO_4·2H_2O$
Fe EDTA 100× Stock:
  3.724 g $Na_2EDTA$, 2.784 g $FeSO_4·7H_2O$
2,4-D Stock:
  10 mg/mL Vitamin
B5 vitamins, 1000× Stock:
  100.0 g myo-inositol, 1.0 g nicotinic acid, 1.0 g pyridoxine HCl, 10 g thiamine·HCL.
Media (Per Liter):
SB199 Solid Medium:
  1 package MS salts (Gibco/BRL—Cat. No. 11117-066), 1 mL B5 vitamins 1000× stock, 30 g Sucrose, 4 ml 2, 4-D (40 mg/L final concentration), pH 7.0, 2 g Gelrite
SB1 Solid Medium:
  1 package MS salts (Gibco/BRL—Cat. No. 11117-066), 1 mL B5 vitamins 1000× stock, 31.5 g Glucose, 2 mL 2, 4-D (20 mg/L final concentration), pH 5.7, 8 g TC agar
SB196:
  10 mL of each of the above stock solutions 1-4, 1 mL B5 Vitamin stock, 0.463 g (NH4)2 SO4, 2.83 g KNO3, 1 mL 2,4 D stock, 1 g asparagine, 10 g Sucrose, pH 5.7

SB71-4:
  Gamborg's B5 salts, 20 g sucrose, 5 g TC agar, pH 5.7.
SB103:
  1 pk. Murashige & Skoog salts mixture, 1 mL B5 Vitamin stock, 750 mg MgCl2 hexahydrate, 60 g maltose, 2 g gelrite, pH 5.7.
SB166:
  SB103 supplemented with 5 g per liter activated charcoal.

Soybean Embryogenic Suspension Culture Initiation:

Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2, 1-liter bottles of sterile distilled water and those less than 3 mm are placed on individual microscope slides. The small end of the seed is cut and the cotyledons pressed out of the seed coat. Cotyledons are transferred to plates containing SB199 medium (25-30 cotyledons per plate) for 2 weeks, then transferred to SB1 for 2-4 weeks. Plates are wrapped with fiber tape. After this time, secondary embryos are cut and placed into SB196 liquid medium for 7 days.

Culture Conditions:

Soybean embryogenic suspension cultures (cv. 93Y21) were maintained in 50 mL liquid medium SB196 on a rotary shaker, 100-150 rpm, 26° C. on 16:8 h day/night photoperiod at light intensity of 80-100 µE/m2/s. Cultures are subcultured every 7-14 days by inoculating up to % dime size quantity of tissue (clumps bulked together) into 50 mL of fresh liquid SB196.

Preparation of DNA for Bombardment:

In particle gun bombardment procedures it is possible to use purified 1) entire plasmid DNA; or 2) DNA fragments containing only the recombinant DNA expression cassette(s) of interest. For every seventeen bombardment transformations, 85 µL of suspension is prepared containing 1 to 90 picograms (µg) of plasmid DNA per base pair of each DNA plasmid. DNA plasmids or fragments are co-precipitated onto gold particles as follows. The DNAs in suspension are added to 50 µL of a 10-60 mg/mL 0.6 µm gold particle suspension and then combined with 50 µL CaCl$_2$ (2.5 M) and 20 µL spermidine (0.1 M). The mixture is vortexed for 5 sec, spun in a microfuge for 5 sec, and the supernatant removed. The DNA-coated particles are then washed once with 150 µL of 100% ethanol, vortexed and spun in a microfuge again, then resuspended in 85 µL of anhydrous ethanol. Five µL of the DNA-coated gold particles are then loaded on each macrocarrier disk.

Tissue Preparation and Bombardment with DNA:

Approximately 100 mg of two-week-old suspension culture is placed in an empty 60 mm×15 mm petri plate and the residual liquid removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Following bombardment, the tissue from each plate is divided between two flasks, placed back into liquid media, and cultured as described above.

Selection of Transformed Embryos and Plant Regeneration:

After bombardment, tissue from each bombarded plate is divided and placed into two flasks of SB196 liquid culture maintenance medium per plate of bombarded tissue. Seven days post bombardment, the liquid medium in each flask is replaced with fresh SB196 culture maintenance medium supplemented with 100 ng/mL selective agent (selection medium). For selection of transformed soybean cells the selective agent used can be a sulfonylurea (SU) compound with the chemical name, 2-chloro-N-((4-methoxy-6 methyl-1,3,5-triazine-2-yl)aminocarbonyl) benzenesulfonamide (common names: DPX-W4189 and Chlorsulfuron). Chlorsulfuron is the active ingredient in the DuPont sulfonylurea herbicide, GLEAN®. The selection medium containing SU is replaced every two weeks for 8 weeks. After the 8 week selection period, islands of green, transformed tissue are observed growing from untransformed, necrotic embryogenic clusters. These putative transgenic events are isolated and kept in SB196 liquid medium with SU at 100 ng/mL for another 5 weeks with media changes every 1-2 weeks to generate new, clonally propagated, transformed embryogenic suspension cultures. Embryos spend a total of around 13 weeks in contact with SU. Suspension cultures are subcultured and maintained as clusters of immature embryos and also regenerated into whole plants by maturation and germination of individual somatic embryos.

Somatic embryos became suitable for germination after four weeks on maturation medium (1 week on SB166 followed by 3 weeks on SB103). They are then removed from the maturation medium and dried in empty petri dishes for up to seven days. The dried embryos are then planted in SB71-4 medium where they are allowed to germinate under the same light and temperature conditions as described above. Germinated embryos are transferred to potting medium and grown to maturity for seed production.

Example 16—Testing Cross-Resistance of Cry1Ab and Cry1F-Selected European Corn Borer To determine if Cry1Ab or Cry1F-resistant insects were cross-resistant to N-6×His-IPD103Aa (SEQ ID NO: 40), European corn borer (ECB, *Ostrinia nubilalis*) larvae susceptible or resistant to Cry1Ab (Crespo A. et al., Pest Manag Sci 65: 1071-1081, 2009) or Cry1F (Siegfried B. et al., Pest Manag Sci 70: 725-733, 2014), were treated with N-6×His-IPD103Aa (SEQ ID NO: 40). The laboratory Cry1F-selected strain (Cry1F-R) originated from a combination of five field populations collected in 2007 and was selected for resistance using increasing amounts of lyophilized leaf tissue of Cry1F-expressing maize (Alves, A, US 2012/0148497 A1, 2012).

Larval susceptibility of ECB strains resistant to Cry1Ab (Cry1Ab-res) or Cry1F (Cry1F-res) and susceptible strains (SS) to the insecticidal proteins was determined using a diet incorporated bioassay method. Briefly, 25 μL of a sample was mixed with 75 μL of artificial diet per well in a 96-well plate. Each bioassay included eight concentrations of the sample as well as the negative buffer control, four replications for each concentration, and eight individuals for each replicate. One ECB neonate larva (<24 h after hatch) was placed in each assay well. Once infested, the plates were sealed with Mylar and ventilation holes were added to each well using #1 or #2 insect pins. Plates were incubated at 27° C., 50% RH, and a photoperiod of 16:8 hours (L:D). Mortality and larval growth inhibition (defined as inhibition if larva did not enter second instar within 6 days) by each sample were scored after a 6 day exposure. Concentrations resulting in 50% mortality (LC50) or inhibition of 50% of the individuals (IC50) were calculated based on Probit analysis. The resistance ratio (RR)=(LC50 of resistant ECB)/(LC50 of susceptible ECB) was >300 fold to Cry1Ab for the Cry1A-res colony and >1000 to Cry1F for the Cry1F-res colony. Table 13 shows that the Cry1A- or Cry1F-resistant ECB were not cross-resistant to N-6×His-IPD103Aa (SEQ ID NO: 40).

TABLE 13

N-6xHis-IPD103Aa (SEQ ID NO: 40) activity against ECB resistant to Cry1A or Cry1F

| ECB colony | LC/IC | ppm | Lower 95% CL | Upper 95% CL | Resistance Ratio |
|---|---|---|---|---|---|
| SS | LC50 | 128.7 | 97.1 | 187.5 | z |
|  | IC50 | 40.8 | 33.2 | 50 |  |
| Cry1A-res | LC50 | >256 (38% mortality) |  |  | >2 |
|  | IC50 | 194.5 | 143.3 | 314.9 | 4.8 |
| Cry1F-res | LC50 | ~256 |  |  | ~2 |
|  | IC50 | 168.8 | 117.7 | 293.2 | 4.1 |

Example 17—Testing Cross-Resistance of Cry1A-Selected Diamondback Moth

A diet overlay assay similar to the method described by Kain et al. (J. Econ. Entomol. 97: 2073-2078, 2004) was used to determine the susceptibility of diamondback moth (DBM, *Plutella xylostella*) to N-6×His-IPD103Aa (SEQ ID NO: 40). Eight concentrations of N-6×His-IPD103Aa (SEQ ID NO: 40) plus a control and three cups (replications) for each concentration were included in each bioassay with the resistant (Cry1A-res) or susceptible DBM colony. An aliquot of 0.2 mL of IPD103Aa solution was applied to and evenly distributed over the diet surface (surface area 7 cm²) of 30-mL plastic cups with 5 ml of artificial diet. Ten DBM neonates were transferred into each cup. Cups were covered with lids and held at 27° C., 50% RH, and a photoperiod of 16:8 (L:D) h and mortality or growth inhibition assessed after 5 days. Concentrations for 50% mortality (LC50) or inhibition of 50% of the individuals (IC50) were calculated based on Probit analysis. The RR was ~100 fold with Cry1A.88 for the Cry1A-res colony. Table 14 shows that the Cry1A resistant DBM were not cross-resistant to N-6×His-IPD103Aa (SEQ ID NO: 40).

TABLE 14

| DBM strain | LC/IC | μg/cm² | Lower 95% CL | Upper 95% CL | Resistance Ratio |
|---|---|---|---|---|---|
| SS | LC50 | 2.9 | 2.1 | 4.0 |  |
|  | IC50 | 1.7 | 1.3 | 2.2 |  |
| Cry1A-res | LC50 | 4.6 | 3.6 | 6.0 | 1.6 |
|  | IC50 | 1.7 | 1.2 | 2.2 | 1 |

Example 18—Site of Action of IPD103Aa

IPD103Aa (SEQ ID NO: 2) was evaluated for stability in the presence of midgut fluid extracts from *Helicoverpa zea* (Corn Earworm) and *Ostrinia nubilalis* (European Corn Borer) to determine if the full length state represents proforms of the proteins and whether midgut proteolysis is required for activation to a toxic state in vivo.

The direct binding of the IPD103Aa (SEQ ID NO: 2) to *Helicoverpa zea* (Corn Earworm) brush border membrane vesicles was tested for target site identification. FIG. 4 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 38 nM.

Figure 5:
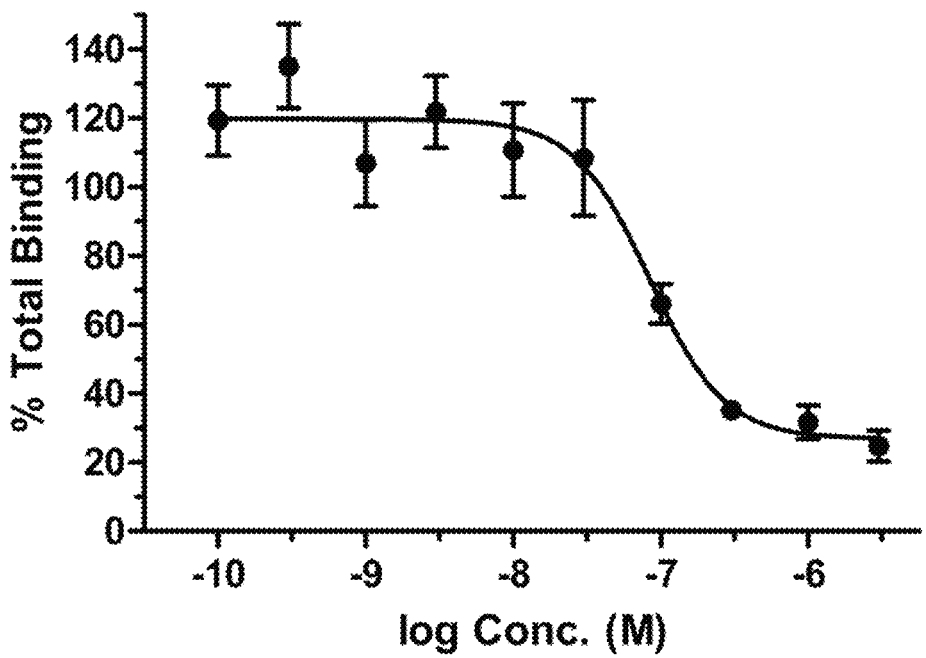
FIG. 5 shows a curve reflecting densitometry values of in-gel fluorescence, from the SDS-PAGE gel of Example 16, for homologous competition of 25 nM IPD103Aa$^{Alexa}$ binding to Ostrinia nubilalis (European Corn Borer) BBMVs normalized to the amount bound in the absence of unlabeled IPD103Aa (SEQ ID NO: 2). The solid line reflects the best fit of a square logistic equation to the data.

The direct binding of the IPD103Aa (SEQ ID NO: 2) to *Ostrinia nubilalis* (European Corn Borer) brush border membrane vesicles was tested for target site identification. FIG. 5 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 83 nM.

Example 19—Saturation Mutagenesis of IPD103Aa Variant

Saturation mutagenesis was performed at selected codons of the IPD103 polynucleotide of SEQ ID: 157 encoding the IPD103 variant IPD103lib11reary-54 of SEQ ID: 345 (Example 8-Table 7). Mutants were generated by site directed mutagenesis (QuikChange® Lightning Multi Site Directed Mutagenesis Kit, Agilent Technologies). After transforming the resulting library variants into *E. coli* cells, colonies were sequence identified. Unique clones were picked and cultured in 96-well plates for protein expression. Cell lysates were generated by B-PER® Protein Extraction Reagent from Thermo Scientific (3747 N Meridian Rd, Rockford, IL USA 61101) and screened for CEW insecticidal activity. Table 15 summarizes the amino acid substitutions identified at each mutagenized position of IPD103lib11reary-54 (SEQ ID: 345) and amino acid substitutions that retained insecticidal activity.

TABLE 15

| AA | Position | Identified substitutions | Active substitutions |
|---|---|---|---|
| A | 002 | G, V, L, I, P, S, T, C, N, Q, D, E, K, R | G, V, L, I, P, S, T, C, N, Q, E, K, R |
| D | 003 | G, A, V, L, I, W, F, P, S, T, C, E, R | G, A, V, L, I, W, F, P, S, T, C, E, R |
| P | 004 | G, A, L, W, S, Y, Q, D, E, K, R, H | G, A, L, W, S, Y, Q, D, E, K, R, H |
| A | 005 | G, V, L, P, S, C, Q, D, E, K, R | G, V, L, P, S, C, Q, D, E, K, R |
| T | 006 | G, A, V, L, I, P, S, N, Q, D, E, K, R | G, A, V, L, I, P, S, N, Q, D, E, K, R |
| A | 007 | G, V, L, W, F, P, T, C, D, K, R | G, V, L, W, F, P, T, C, D, K, R |
| A | 008 | G, L, W, P, S, T, Y, N, D, E, K, R | G, L, W, P, S, T, Y, N, D, E, K, R |
| R | 009 | G, A, V, L, I, W, F, P, S, T, N, D, E | G, A, V, L, I, W, F, P, S, T, N, D, E |
| E | 010 | G, A, V, L, M, W, S, K, R | G, A, V, L, M, W, S, K, R |
| A | 011 | G, V, W, P, S, T, C, Y, E, K, R, H | G, V, W, P, S, T, C, Y, E, K, R, H |
| E | 012 | G, V, L, W, P, S, T, Y, K, R, H | G, V, L, W, P, S, T, Y, K, R, H |
| E | 013 | G, V, L, I, M, W, F, S, D, K, R | G, V, L, I, M, W, F, S, D, K, R |
| E | 014 | G, A, V, L, F, S, T, C, Y, N, Q, R | G, A, V, L, F, S, T, C, Y, N, Q, R |

TABLE 15-continued

| AA | Position | Identified substitutions | Active substitutions |
|---|---|---|---|
| V | 015 | G, A, L, I, S, Q, D, E, K, R | G, A, L, I, S, Q, D, E, K, R |
| Q | 016 | G, A, V, L, I, W, F, P, S, T, D, R, H | G, A, V, L, I, W, F, P, S, T, D, R, H |
| E | 017 | G, A, V, L, M, S, T, C, D, K, R | G, A, V, L, M, S, T, C, D, K, R |
| T | 018 | G, V, L, I, M, W, P, S, C, Q, D, E, R | G, V, L, I, M, W, P, S, C, Q, D, E, R |
| L | 019 | G, A, W, F, P, S, T, C, Y, N, Q, E, K, R | G, W, F, P, S, T, C, Y, N, Q, E, K, R |
| M | 020 | A, V, L, I, W, F, P, S, T, Q, D, E, K, R, H | S, T |
| D | 021 | G, A, V, L, W, F, S, C, N, Q, K, R, H | G, A, V, C, N, H |
| E | 022 | G, A, V, L, M, W, P, S, Y, D, R, H | G, A, M, P, S, D |
| T | 023 | G, A, V, L, I, M, W, P, S, N, Q, E, K, R, H | V, I, S |
| E | 024 | G, V, L, M, W, P, C, Y, Q, K, R | V, M, W, P, C, Q |
| A | 025 | G, V, I, M, W, C, Y, E, R | G, V, I, M, C, E, R |
| V | 026 | G, A, L, I, M, W, S, T, Q, D, E, K, R, H | Q |
| G | 027 | A, V, L, I, M, W, P, S, C, D, K, R | |
| T | 028 | G, A, V, L, I, M, W, F, C, Q, E, K, R | A, V, I, M, C, Q, E |
| H | 029 | G, A, V, L, M, W, P, S, T, Y, N, Q, D, E, R | V, S |
| L | 030 | G, A, I, W, P, S, T, C, N, Q, D, E, K, R, H | I, P |
| D | 031 | G, A, V, L, M, F, S, T, E, R, H | S |
| F | 032 | G, A, V, L, I, M, W, P, T, N, Q, E, R, H | G, A, V, L, I, M, W, T, N, Q, E, H |
| V | 033 | G, L, M, W, F, P, S, T, C, Q, D, E, R, H | G, L, M, W, P, S, T, C, Q, E, R, H |
| A | 034 | G, V, L, I, M, W, F, S, T, C, Y, Q, E, K, R, H | G, V, L, M, S, T, C, Y, Q, E, K, R, H |
| G | 035 | A, V, L, I, M, P, S, T, N, Q, D, K, R, H | A, M, P, S, T, N, D |
| L | 036 | G, A, M, W, P, S, T, C, Q, D, E, R | A, M |
| E | 037 | G, A, V, L, M, S, N, D, K, R | G, A, V, L, M, S, N, D, K, R |
| V | 038 | G, L, M, W, S, T, Q, E, K, R, H | L, K |
| Q | 039 | G, A, L, P, S, C, Y, N, D, E, R | A, L, C, Y, N, D, E, R |
| P | 040 | G, A, V, I, M, F, S, T, C, Q, D, E, K, R | A |
| R | 041 | G, A, V, L, I, M, W, F, P, S, T, C, N, D, E | A, V, L, I, M, F, P, S, T, N, E |
| K | 042 | G, A, V, L, M, F, P, S, T, C, Y, Q, E, R, H | G, A, V, S, T, Q, E, R |
| V | 043 | G, L, I, M, W, P, S, T, E, K, R | M, T |
| I | 044 | G, A, V, L, M, W, P, S, T, Y, E, K, R | V, M |
| T | 045 | G, A, V, L, I, W, P, S, C, Q, E, K, R | A, S, E |
| V | 046 | G, A, L, F, S, C, Y, Q, E, K, R, H | L, Q, H |
| E | 047 | G, V, L, M, W, F, S, N, K, R | |
| V | 048 | A, L, I, M, W, P, S, D, E, R, H | A, L, I, M |
| D | 049 | G, A, V, L, M, W, F, P, S, Q, R, H | |
| A | 050 | G, V, L, M, W, P, S, E, K, R | G, V, L, M, W, P, S |
| A | 051 | G, V, L, M, W, S, T, C, Q, D, E, K, R | G, V, T, C, Q |
| A | 052 | G, V, L, I, M, P, S, T, C, N, Q, D, R | G, V, L, M, P, S, T, N, Q, D |
| V | 053 | G, L, W, F, S, C, Y, Q, E, K, R, H | L |
| I | 054 | G, A, V, L, W, S, T, C, Y, E, R, H | A, V, L, W, Y |
| Q | 055 | G, V, L, I, W, P, S, C, Y, E, K, R, H | G, V, L, I, S, C, Y, E, K, H |
| Q | 056 | G, A, V, L, W, P, S, T, N, E, K, R | G, A, L, S, T, N, E, K, R |
| I | 057 | G, A, V, L, M, W, P, S, T, Y, N, D, R | V, L, T |
| R | 058 | G, A, L, M, W, P, S, T, C, Y, Q, D, K | G, A, L, M, W, P, S, T, C, Y, Q, D, K |
| E | 059 | G, A, L, M, P, S, Y, N, D, K, R | G, A, L, M, S, Y, N, D, K, R |
| I | 060 | G, A, V, L, M, W, S, T, N, Q, E, R, H | V, L, M, W, T, N, Q, E |
| F | 061 | G, A, V, L, M, W, S, Q, E, R | A, L, M, S |
| Q | 062 | G, A, V, L, M, F, P, S, T, R | G, A, V, L, M, F, S, T, R |
| T | 063 | G, A, V, L, P, S, Y, N, D, E, K, R, H | G, A, V, L, S, Y, N, D, E, K, R, H |
| M | 064 | G, A, L, I, W, P, S, T, N, Q, E, K, R | A, L, I |
| A | 065 | G, V, L, M, W, F, S, T, Q, D, E, R, H | G, V, L, M, W, F, S, T, Q, D, E, R, H |
| R | 066 | G, A, V, L, I, P, S, T, C, N, D, K, H | G, A, V, I, P, S, T, C, N, D, K, H |
| H | 067 | G, A, V, L, W, F, S, C, N, K, R | G, W, F, N, K |
| F | 068 | G, A, V, L, W, S, T, N, Q, K, R, H | A, V, L, S, T, Q, H |
| N | 069 | G, A, V, L, M, W, F, S, Y, Q, D, E, K, R | G, A, V, L, F, Y, Q, D |
| S | 070 | G, W, F, T, C, Y, N, Q, K, R | G, F, T, C, Y, N, Q, K, R |
| T | 073 | G, A, V, L, I, M, W, F, P, S, Q, E, K, R | A, L, I, S, Q, E, K, R |
| R | 072 | G, A, V, L, M, F, S, T, Y, Q, D, K, H | G, A, V, L, M, F, S, T, Y, Q, D, K, H |
| V | 073 | G, A, L, I, M, F, P, S, T, N, E, R | A, L, I, S, T |
| V | 074 | G, A, L, I, W, P, S, T, N, E, K, R, H | G, L, I, W, P, S, T, E, K, H |
| R | 075 | G, A, V, I, M, W, F, P, S, T, C, N, D, E, K | P |

TABLE 15-continued

| AA | Position | Identified substitutions | Active substitutions |
|---|---|---|---|
| D | 076 | G, A, V, L, I, M, W, P, S, Y, N, E, R | G, A, W, P, S, Y, N |
| E | 077 | G, V, L, M, W, F, P, S, C, Y, N, Q, D, K, R, H | V, M, C, Y, N, Q, K, R, H |
| A | 078 | G, L, I, M, F, S, T, C, N, K, R, H | S, C, N |
| I | 079 | G, A, V, L, P, S, T, C, Y, N, D, E, K, R, H | G, V, P, Y, E |
| K | 080 | G, A, V, L, M, W, P, S, T, C, N, D, E, R | A, V, M, S, T, C, R |
| G | 081 | A, V, L, F, S, C, Y, N, D, E, R | A, V, L, S, C, N, D, R |
| I | 082 | G, A, V, L, M, S, Y, N, D, E, K, R | L, M |
| R | 083 | A, V, I, M, W, F, P, T, C, Q, D, K, H | K |
| D | 084 | G, A, V, L, I, M, P, S, C, E, R, H | |
| H | 085 | A, V, L, I, W, F, S, C, Y, N, Q, D, K, R | |
| F | 086 | G, A, V, L, I, P, S, T, C, Y, N, D, K, R | C |
| R | 087 | G, A, V, L, W, P, S, Q, E, K, H | V, L, Q |
| A | 088 | G, V, L, I, M, P, S, T, C, Y, N, Q, D, E, R, H | V, T, C, Y |
| A | 089 | G, V, L, I, M, F, P, S, C, Y, D, K, R, H | S |
| V | 090 | G, A, L, I, M, P, S, D, R | I, M |
| P | 091 | G, V, L, M, W, F, S, T, C, E, K, R, H | |
| T | 092 | G, A, V, L, I, W, S, Y, Q, E, R, H | V, L, S |
| R | 093 | G, A, V, L, M, F, P, S, T, C, D, E, K | P, S |
| N | 094 | G, A, V, L, M, W, P, T, Y, Q, D, E, R, H | |
| V | 095 | G, A, L, I, W, P, S, T, C, N, Q, D, K, R, H | I, T, C, R |
| V | 096 | G, L, M, W, P, S, T, Y, N, Q, R, H | L |
| V | 097 | G, A, L, W, F, P, T, Y, E, R | A |
| V | 098 | G, A, L, M, W, S, Y, Q, E, K, R | A |
| H | 099 | G, A, V, L, I, M, W, F, T, Y, N, D, E, R | G, A, V, I, T, Y, N, R |
| T | 100 | G, A, V, L, M, W, P, S, C, N, Q, K, R, H | G, A, V, P, S, C, N, Q, H |
| Q | 101 | G, A, V, L, I, S, T, D, E, K, R | L, I, T, D, E, K, R |
| H | 102 | G, A, L, M, P, S, T, N, Q, D, E, R | A, S, N, Q, E, R |
| V | 103 | G, A, L, M, W, F, P, S, T, N, D, E, R | G, A, L, M, W, F, P, S, T, R |
| H | 104 | G, A, L, M, P, S, C, D, K, R | G, A, L, M, S, C, D, K, R |
| T | 105 | G, A, V, L, I, M, F, P, S, C, Y, Q, D, R | A, L, M, S, C, Y, Q |
| L | 106 | I, F, P, S, T, Y, D, R, H | I, F |
| V | 107 | L, I, M, W, P, S, T, Y, D, E, K, R, H | L, I, M, P, S, T, Y, D, E, K, R, H |
| G | 108 | V, L, M, P, S, T, C, Q, D, K | S, Q, D |
| L | 109 | I, M, W, F, P, S, T, Y, N, Q, D, E, K, R | I, M, W, F, P, S, T, Y, N, Q, D, E, K, R |
| E | 110 | G, A, V, L, I, W, F, S, T, Q, K, R | A, V, L, I, S, T, Q, K, R |
| H | 111 | G, A, V, L, W, F, P, S, T, Y, N, Q, D, R | G, A, V, L, W, F, P, S, T, Y, N, Q, D, R |
| T | 112 | G, A, V, L, M, W, P, S, Q, R | G, A, V, L, M, W, P, S, Q, R |
| H | 113 | G, A, V, L, M, W, F, P, S, N, Q, D, R | G, V, L, M, F, S, N, Q, R |
| L | 114 | G, A, V, I, M, W, P, S, N, Q, E, K, R, H | V, I, M, P, Q |
| V | 115 | G, A, L, W, P, S, R, H | G, A, L, W, P, S, R, H |
| L | 116 | G, A, V, M, S, C, Y, Q, R, H | V, M |
| Q | 117 | G, A, V, L, W, P, S, T, E, K, R, H | G, A, V, L, S, T, E, K, R, H |
| T | 118 | G, A, L, W, P, C, Y, Q, E, K, R | A, C |
| G | 119 | A, V, L, I, M, W, F, S, C, Y, N, D, E, R, H | A, V, M, S, N, D, E, H |
| I | 120 | G, A, V, L, M, W, F, S, T, Q, D, E, K, R | G, A, V, L, M, W, F, S, T, Q, E, K, R |
| F | 121 | G, V, L, M, W, P, S, Y, Q, D, E, K, R | G, V, L, M, W, S, Y, Q, E, K |
| K | 122 | G, V, P, S, T, C, Y, N, Q, R | G, P, S, T, C, N, R |
| K | 123 | G, A, V, L, M, W, P, S, T, C, Y, E, R | G, A, W, P, T, Y |
| V | 124 | G, A, W, T, C, N, Q, D, E, R | A, W, T, C, N, Q, R |
| P | 125 | G, A, V, L, W, S, T, Y, Q, E, R | G, A, V, L, W, S, T, Y, Q, E, R |
| V | 126 | G, A, I, F, P, S, T, Y, Q, E | A, I, F, S, T |
| D | 127 | G, A, V, L, M, W, P, S, C, Q, R, H | A, V, L, M, W, S, C, Q, R, H |
| I | 128 | A, V, L, M, W, P, S, Q, D, E, K, R | V, L, M |
| Y | 129 | G, A, V, L, I, M, W, F, P, S, T, D, R, H | |
| V | 130 | G, A, L, M, W, F, S, T, Y, D, E, R | A, L |
| F | 131 | G, V, L, W, S, T, E, R | |
| K | 132 | G, A, V, L, M, P, S, C, Q, E, R, H | G, A, V, L, P, S, C, Q, E, R |
| S | 133 | G, A, L, M, W, P, T, C, Y, Q, D, K, R | G, L, M, P, T, C, Q, D, K, R |
| G | 134 | A, V, L, M, W, P, C, Y, Q, E, R | |
| V | 135 | G, A, L, M, P, S, T, Q, E, K, R | G, A, L, M, P, S, T, Q, E, K, R |
| F | 136 | G, A, V, I, M, P, S, T, C, Y, N, Q, K, R | I, M, C, Y, R |
| T | 137 | G, A, V, L, W, P, S, E, R | S |
| L | 138 | G, A, V, M, W, P, S, Q, D, K, R | V, M, S, Q |
| L | 139 | G, A, V, W, F, P, S, T, C, Y, Q, E, K, R, H | A, V |
| G | 140 | A, L, M, W, P, T, C, Q, D, R | |
| D | 141 | G, V, L, M, W, S, T, N, R | G, V, M, S, T, N, R |
| G | 142 | A, V, L, P, T, C, E, K, R | A, V |
| G | 143 | A, V, L, W, S, Q, E, R | A, W, S, Q, E |
| F | 144 | G, A, V, L, W, P, S, Q, D, K, R | G, A, V, L, W, P, S, Q, K, R |
| I | 145 | G, A, V, M, W, C, Q, E, R, H | G, A, V, M, W, C, Q, E, R, H |
| N | 146 | G, L, M, W, P, S, T, E, K, R | |
| W | 147 | G, V, M, P, S, C, E, R | |
| A | 148 | G, V, L, I, M, W, P, S, Y, Q, K, R | G, S |
| W | 149 | G, A, V, L, F, S, T, N, E | |
| G | 150 | A, V, L, I, W, S, T, Y, Q, E, K, R | I, Q |
| G | 151 | V, L, M, W, S, D, E, R | S |
| F | 152 | G, A, V, L, M, W, P, S, T, C, Q, D, R, H | W |
| V | 153 | G, A, L, I, M, W, P, S, N, E, K, R | A, L, I, P |

TABLE 15-continued

| AA | Position | Identified substitutions | Active substitutions |
|---|---|---|---|
| Q | 154 | G, V, L, W, F, P, S, T, N, D, E, K, R, H | G, V, L, W, F, P, S, T, N, D, E, K, R, H |
| E | 155 | G, V, L, M, F, P, S, N, Q, K, R | G, V, L, M, F, S, N, Q, K, R |
| V | 156 | G, A, L, M, F, P, S, Q, E, K, R | A, L, M, F, S, Q, E, K, R |
| A | 157 | G, V, L, I, M, W, P, S, T, N, Q, E, K, R, H | G, V, L, I, M, W, S, T, N, Q, E, K, R, H |
| G | 158 | A, V, W, P, T, C, E, K, R | A, V, W, P, T, C, E, K, R |
| K | 159 | G, A, V, L, I, W, P, S, T, Y, Q, R, H | G, A, V, L, P, S, T, Y, Q, R, H |
| R | 160 | G, A, V, L, I, M, F, S, T, C, Y, E, K | I, M, Y, K |
| I | 161 | G, A, V, L, M, W, F, P, S, T, Y, Q, D, E, R | A, V, L |
| H | 162 | G, A, L, I, W, F, P, S, T, C, Y, Q, K, R | G, A, L, I, W, F, S, T, C, Y, Q, K, R |
| F | 163 | A, L, S, T, C, Y, D, E | |
| R | 164 | G, V, L, I, M, W, F, P, S, T, Y, N, D | V, L, I, M, S, T, N, D |
| L | 165 | G, V, I, M, W, F, P, S, N, Q, E, K, R | G, V, I, M, W, F, P, S, N, Q, E, K, R |
| P | 166 | G, A, V, L, I, M, W, S, T, C, Y, N, Q, D, E, K, R, H | A, T, C, Q |
| P | 167 | G, A, V, L, M, W, S, T, C, Y, N, D, R, H | A, N, D |
| G | 168 | A, V, L, M, W, P, S, T, Q, R, H | |
| A | 169 | G, V, L, M, W, F, S, T, C, N, Q, R, H | G, S, T, C, Q |
| L | 170 | A, V, I, M, P, S, T, Y, Q, R, H | A, V, I, M, S, T, Y, Q, R, H |
| P | 171 | G, A, V, M, W, S, T, C, E, R | G, A, V, M, W, S, T, C, E, R |

Example 20 Identification of Amino Acid Positions Affecting the Protein Stability and Function of IPD103

Additional mutagenesis was performed on selected positions within IPD103lib11reary-54 (SEQ ID:157). Protein was purified from the single mutants and screened for activity on CEW. Table 16 summarizes additional amino acid substitutions identified, amino acid substitutions allowing retention of insecticidal activity, and amino acid substitutions resulting in reduced protein yields from E. coli.

TABLE 16

| AA | Position | Identified substitutions | Active substitutions | Reduced Expression substitutions |
|---|---|---|---|---|
| A | 002 | F, H, M, W, Y | F, H, M, W, Y | |
| A | 011 | D, F, L, M, N, Q | D, F, L, M, N, Q | |
| T | 018 | A, F, H, K, N, Y | A, H, K, N | |
| M | 020 | C, G, N, Y | | |
| D | 021 | E, I, M, P, T, Y | E, P, T | M |
| G | 027 | E, F, H, N, Q, T, Y | | F |
| D | 031 | I, K, P, Q | | |
| A | 034 | D, N, P | D, N, P | |
| A | 065 | C, I, K, N, P, Y | C, I, N, Y | K, P |
| R | 066 | E, F, M, Q, S, W, Y | E, F, M, S, W, Y | |
| F | 068 | C, D, E, I, M, P, Y | C, I, M | |
| S | 070 | A, D, E, H, I, L, M, P, V | A, D, E, H, L, M, V | I, P |
| N | 094 | C, F, I, K, S | | I, K |
| H | 104 | E, Q, T, W, Y | E, Q, T, W | |
| G | 140 | E, F, H, I, K, N, S, V, Y | S | I, N, V |
| W | 147 | A, D, F, H, I, K, L, N, Q, T, Y | F | D, K |
| W | 149 | C, D, H, I, K, M, P, Q, Y | | C, D, H, K, M, Q |
| Q | 154 | A, C, I, M | A | C, I, M |
| E | 155 | A, C, D, I, T, W | A, C, D, I, T, W | |
| G | 168 | C, D, E, F, I, K, N, Y | F | |

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

SEQUENCE LISTING

```
Sequence total quantity: 508
SEQ ID NO: 1              moltype = DNA   length = 516
FEATURE                   Location/Qualifiers
source                    1..516
                          mol_type = other DNA
                          organism = Athyrium niponicum
SEQUENCE: 1
atggcggaca aagcagcagc agcagctaga gaagctgaag aagaggtgga gacgacgatg   60
gacgagactg aggcggtggg gacgcacctg gacttcttgg gcgcggacgt gaagttgcaa  120
ccccgcaaca tcatcaccgt ggaggtggac gcggctgccg taatccaaca gatcagagag  180
atcttccaga caatgcgcg tcacttcaac tctacgaggg tggtgcggaa tgaagccatc   240
aagggcattc gagaccactt cagggccgcc gtcccgactc gcaacgtggt ggtcattcac  300
actcagcacg ttcacacact ggtgggcttg gagcacaccc acctcgtctt gcagaccggc  360
atcttcaaaa aggtccccgt cgacatctat gtcttcaagt ccggcgtctt caccaacctt  420
ggagacggag gcttcatcaa ctgggcatgg gtggcttcg tcgaccaggt cgtcggcaag   480
cgtatccact tccgcttgcc ccccggggcg ctccct                            516

SEQ ID NO: 2              moltype = AA   length = 172
FEATURE                   Location/Qualifiers
source                    1..172
                          mol_type = protein
                          organism = Athyrium niponicum
SEQUENCE: 2
MADKAAAAAR EAEEEVETTM DETEAVGTHL DFLGADVKLQ PRNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 3              moltype = DNA   length = 513
FEATURE                   Location/Qualifiers
source                    1..513
                          mol_type = other DNA
                          organism = Athyrium niponicum
SEQUENCE: 3
atggcggacc aagcagcagc agctagagaa gctgaagaag aggtggagac gacgatggac    60
gagactgagg cggtggggac gcacctggac ttcttgggcg cggacgtgaa gttgcaaccc   120
cgcaacatca tcaccgtgga ggtggacgcc gctgccgtaa tccaacagat cagagagatc   180
ttccagacaa tggcgcgtca cttcaactct acgagggtgg tgcgggatga agccatcaag   240
ggcattcgag accttcag gccgccgtc cgactcgca acgtggtggt cattcacact        300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg gcatggggt ggcttcgtcg accaggtcgt cggcaagcgt    480
atccacttcc gcttgccccc cggggcgctc cct                                513

SEQ ID NO: 4              moltype = AA   length = 171
FEATURE                   Location/Qualifiers
source                    1..171
                          mol_type = protein
                          organism = Athyrium niponicum
SEQUENCE: 4
MADQAAAARE AEEEVETTMD ETEAVGTHLD FLGADVKLQP RNIITVEVDA AAVIQQIREI    60
FQTMARHFNS TRVVRDEAIK GIRDHFRAAV PTRNVVVIHT QHVHTLVGLE HTHLVLQTGI   120
FKKVPVDIYV FKSGVFTNLG DGGFINWAWG GFVDQVVGKR IHFRLPPGAL P            171

SEQ ID NO: 5              moltype = DNA   length = 513
FEATURE                   Location/Qualifiers
source                    1..513
                          mol_type = other DNA
                          organism = Platycerium wandae
SEQUENCE: 5
atggccgaac agcagcagc agctagagaa gctgaagaag aggtggagac gacgatggac    60
gagactgagg cggtggggac gcacctggac ttcttgggcg cggacgtgaa gttgcaaccc   120
cgcaacatca tcaccgtgga ggtggacgcg ctgccgtaa tccaacagat cagagagatc    180
ttccagacaa tggcgcgtca cttcaactct acgagggtgg tgcgggatga agccatcaag   240
ggcattcgag accacttcag gccgccgtc cgactcgca acgtggtggt cattcacact     300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg gcatggggt ggcttcgtcg accaggtcgt cggcaagcgt    480
atccacttcc gcttgccccc cggggcgctc cct                                513

SEQ ID NO: 6              moltype = AA   length = 171
FEATURE                   Location/Qualifiers
source                    1..171
                          mol_type = protein
                          organism = Platycerium wandae
SEQUENCE: 6
MAEPAAAARE AEEEVETTMD ETEAVGTHLD FLGADVKLQP RNIITVEVDA AAVIQQIREI    60
FQTMARHFNS TRVVRDEAIK GIRDHFRAAV PTRNVVVIHT QHVHTLVGLE HTHLVLQTGI   120
FKKVPVDIYV FKSGVFTNLG DGGFINWAWG GFVDQVVGKR IHFRLPPGAL P            171
```

-continued

```
SEQ ID NO: 7              moltype = DNA  length = 510
FEATURE                   Location/Qualifiers
source                    1..510
                          mol_type = other DNA
                          organism = Pteris ensiformis
SEQUENCE: 7
atggccgacc aaggagcagc agctagagaa gctgaggaag aggtggagac gacgatggac    60
gagacggagg cggtggggac gcacctggac ttttggcgg acgtgaaggt gcagccccgc   120
aacatcatca ccgtggaggt ggacgccgct gccgtaatcc aacagatcag agagatcttc   180
caaaccatgg cacgtcactt caactctacg agggtggtgc gggatgaagc cattaagggc   240
attcgagacc acttcaggc cgccgttccg actcgcaacg tggtggtcat tcacactcag   300
cacgttcaaa cactggtggc cgtggagcac agccacatcg tcttgcagac cggcatcttc   360
aagaaggtcc ccgtcgacat ctatgttttc aagtccggcg tcttcaccaa ccttggagac   420
ggaggctaca tcaactgggc atggggtggc ttcgtagacc aggtcgtcgg caagcgtatc   480
cacttccgct tgccccccgg ggcgctccct                                    510

SEQ ID NO: 8              moltype = AA  length = 170
FEATURE                   Location/Qualifiers
source                    1..170
                          mol_type = protein
                          organism = Pteris ensiformis
SEQUENCE: 8
MADQGAAARE AEEEVETTMD ETEAVGTHLD FLADVKVQPR NIITVEVDAA AVIQQIREIF    60
QTMARHFNST RVVRDEAIKG IRDHFRAAVP TRNVVIHTQ HVQTLVAVEH SHIVLQTGIF    120
KKVPVDIYVF KSGVFTNLGD GGYINWAWGG FVDQVVGKRI HFRLPPGALP              170

SEQ ID NO: 9              moltype = DNA  length = 507
FEATURE                   Location/Qualifiers
source                    1..507
                          mol_type = other DNA
                          organism = Pteris ensiformis
SEQUENCE: 9
atggccgacc aagctgcagc tagagaagct gaggaagagg tggagacgac gatggacgag    60
acggaggcgg tggggacgca cctggacttt ttggcggacg tgaaggtgca gccccgcaac   120
atcatcaccg tggaggtgga cgccgctgcc gtaatccaac agatcagaga gatcttccaa   180
accatggcac gtcacttcaa ctctacgagg gtggtgcggg atgaagccat taagggcatt   240
cgagaccact tcagggccgc cgttccgact cgcaacgtgg tggtcattca cactcagcac   300
gttcaaacac tggtggccgt ggagcacagc cacatcgtgc tgcagaccgg catcttcaag   360
aaggtccccg tcgacatcta tgttttcaag tccggcgtct tcaccaacct tggagacgga   420
ggctacatca actgggcatg gggtggcttc gtagaccagg tcgtcggcaa gcgtatccac   480
ttccgcttgc ccccggggc gctccct                                       507

SEQ ID NO: 10             moltype = AA  length = 169
FEATURE                   Location/Qualifiers
source                    1..169
                          mol_type = protein
                          organism = Pteris ensiformis
SEQUENCE: 10
MADQAAAREA EEEVETTMDE TEAVGTHLDF LADVKVQPRN IITVEVDAAA VIQQIREIFQ    60
TMARHFNSTR VVRDEAIKGI RDHFRAAVPT RNVVIHTQH VQTLVAVEHS HIVLQTGIFK    120
KVPVDIYVFK SGVFTNLGDG GYINWAWGGF VDQVVGKRIH FRLPPGALP               169

SEQ ID NO: 11             moltype = DNA  length = 546
FEATURE                   Location/Qualifiers
source                    1..546
                          mol_type = other DNA
                          organism = Platycerium wandae
SEQUENCE: 11
atgagagagc gagagcgaga gcgagagaga gagatggccg aaccagcagc agcagcagct    60
aaaaaagctg aagaagaggt ggagatattt atggacgaca ctgaggcggt ggggacgcat   120
ctggacttct tggcgggctt gaaggtgcag ccccgcaaga tcatccgt ggaggtggac    180
cccgctgccg taatccagca gatcaggag atcttccaaa ccatggcacg tcacttcaac   240
tcgacgacgg tggtgcggga tgaagccatc aagggcattc gagaccactt cagggccgcc   300
gttccgactc gcaacgtggt ggtcgttcac actcagatca ttcacaccct ggagggcttg   360
gagcacacca accttgtctt gcagaccggc tcttcagaa aggtcccgt cgacatctac   420
gtcttcaagt ctggcgtctt caccctcctt ggagatggag gcttcatcaa ctgggcgtgg   480
ggtggcttc tagagcaggt cgtcggcaag cgtatccact tccgcttacc ccctggggcg   540
ctccct                                                              546

SEQ ID NO: 12             moltype = AA  length = 182
FEATURE                   Location/Qualifiers
source                    1..182
                          mol_type = protein
                          organism = Platycerium wandae
SEQUENCE: 12
MRERERERER EMAEPAAAAA KKAEEEVEIF MDDTEAVGTH LDFLAGLKVQ PRKIITVEVD    60
PAAVIQQIRE IFQTMARHFN STTVVRDEAI KGIRDHFRAA VPTRNVVVH TQIHTLEGL    120
EHTNLVLQTG LFRKVPVDIY VFKSGVFTLL GDGGFINWAW GGFVEQVVGK RIHFRLPPGA   180
```

```
LP                                                                   182

SEQ ID NO: 13           moltype = DNA  length = 513
FEATURE                 Location/Qualifiers
source                  1..513
                        mol_type = other DNA
                        organism = Platycerium wandae
SEQUENCE: 13
atggccgaac cagcagcagc agcagctaaa aaagctgaag aagaggtgga gatatttatg      60
gacgacactg aggcggtggg gacgcatctg gacttcttgg cgggcttgaa ggtgcagccc     120
cgcaagatca tcaccgtgga ggtggacccc gctgccgtaa tccagcagat aagagagatc     180
tttcaaaccc tggcacgtca cttcaactcg acgacggtgg tgcggatga agccatcaag      240
ggcattcgag accacttcag gccgccgtt ccgactcgca acgtggtggt cgttcacact      300
cagcacattc acacccctgga gggcttggag cacaccaacc ttgtcttgca gaccggccgc    360
ttcagaaagg tccccgtcga catctacgtc ttcaagtctg gcgtcttcac cctccttgga     420
gatggaggct tcatcaactg gcgtgggggt ggcttcgtag agcaggtcgt cggcaagcgt     480
atccacttcc gcttacccc tggggcgctc cct                                   513

SEQ ID NO: 14           moltype = AA  length = 171
FEATURE                 Location/Qualifiers
source                  1..171
                        mol_type = protein
                        organism = Platycerium wandae
SEQUENCE: 14
MAEPAAAAK KAEEEVEIFM DDTEAVGTHL DFLAGLKVQP RKIITVEVDP AAVIQQIREI       60
FQTLARHFNS TTVVRDEAIK GIRDHFRAAV PTRNVVVHT QHIHTLEGLE HTNLVLQTGR      120
FRKVPVDIYV FKSGVFTLLG DGGFINWAWG GFVEQVVGKR IHFRLPPGAL P              171

SEQ ID NO: 15           moltype = DNA  length = 513
FEATURE                 Location/Qualifiers
source                  1..513
                        mol_type = other DNA
                        organism = Athyrium filix-femina
SEQUENCE: 15
atggccgaca aagcgcctcc tcctgctaga gaagcagaag aagaggtgga ggagacgatg      60
gacgagactg aggcagtggg gacgcacctg gacttgatag cgcacctgag tgtgcaaccc     120
cgcggcatca tcaccgtgga ggtggacccc gccgctgtaa tccaacagat cagagagatc     180
ttccaaacca tggcacgtca tttcaactct acgagggtgg tacgggatga agccatcaag     240
ggcattcgag accacttcag gccgccgtc ccgactcgca acgtggtggt cattcacact      300
caaacacgttc acacactggt gggcttggag cacacccacc tcgtcttgca gaccggcatc    360
tttagaacgg tccccgtcga catctacgtc ttcaagtccg gcgtgttcac caacctcgga    420
gacggaggct tcatcaactg gcatgggggt ggcttcgtga ccgaggtcgt tgggaagcgt     480
gtccacttcc gcttgccccc cggggcactc cct                                  513

SEQ ID NO: 16           moltype = AA  length = 171
FEATURE                 Location/Qualifiers
source                  1..171
                        mol_type = protein
                        organism = Athyrium filix-femina
SEQUENCE: 16
MADKAPPPAR EAEEEVEETM DETEAVGTHL DLIAHLSVQP RGIITVEVDP AAVIQQIREI       60
FQTMARHFNS TRVVRDEAIK GIRDHFRAAV PTRNVVVIHT QHVHTLVGLE HTHLVLQTGI     120
FRTVPVDIYV FKSGVFTNLG DGGFINWHWG GFVTEVVGKR VHFRLPPGAL P              171

SEQ ID NO: 17           moltype = DNA  length = 510
FEATURE                 Location/Qualifiers
source                  1..510
                        mol_type = other DNA
                        organism = Colysis wrightii
SEQUENCE: 17
atggccgacc aagtagcagc agcgagaggg gctgaagaag aggtggagac gacgatggac      60
gagactgagg ctgtggggac gcacctggac ttccttggcg acgtgaaggt gcaacccggg    120
agcatcatca ccgtggaggt ggacgccgct gctgtaatcc aacagatcag agagatcttc    180
caaaccatgg cacgtcactt caactctacg agggacgaagc catcaaggg                240
attcgagacc acttccgggc cgccgtcccg actcgcaacg tggtggtcgt tcacactcag    300
cacgttcaca cactggtggg cctggagcac accaacatcg tcttgcagac cggcctcttc     360
aaaaaggtcc ccgtcgacat ctatgtcttc aagtccggcg tcttcaccct ccttggagac   420
ggaggcttca tcaactgggc atggggtggc ttcgtagacc aggtcgtcgg caagcgtatc     480
cacttccgct tgcccccgg ggcgctccct                                       510

SEQ ID NO: 18           moltype = AA  length = 170
FEATURE                 Location/Qualifiers
source                  1..170
                        mol_type = protein
                        organism = Colysis wrightii
SEQUENCE: 18
MADQVAAARG AEEEVETTMD ETEAVGTHLD FLADVKVQPR SIITVEVDAA AVIQQIREIF       60
QTMARHFNST RVVRDEAIKG IRDHFRAAVP TRNVVVHTQ HVHTLVGLEH TNIVLQTGLF     120
KKVPVDIYVF KSGVFTLLGD GGFINWAWGG FVDQVVGKRI HFRLPPGALP               170
```

```
SEQ ID NO: 19            moltype = DNA  length = 513
FEATURE                  Location/Qualifiers
misc_feature             1..513
                         note = IPD103 variant
misc_feature             484
                         note = n is a, c, g, or t
source                   1..513
                         mol_type = other DNA
                         organism = unidentified
SEQUENCE: 19
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacattc acacactgga gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg ggcatggggt ggcttcgtac aggaggtcgc cggcaagcgt   480
atcnacttcc gcttgccccc cggggcgctc cct                                513

SEQ ID NO: 20            moltype = AA  length = 171
FEATURE                  Location/Qualifiers
REGION                   1..171
                         note = IPD103 variant
SITE                     162
                         note = misc_feature - Xaa can be any naturally occurring
                          amino acid
source                   1..171
                         mol_type = protein
                         organism = unidentified
SEQUENCE: 20
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTNLVLQTGL   120
FKKVPVDIYV FKSGVFTLLG DGGFINWAWG GFVQEVAGKR IXFRLPPGAL P            171

SEQ ID NO: 21            moltype = DNA  length = 537
FEATURE                  Location/Qualifiers
source                   1..537
                         mol_type = other DNA
                         organism = Nephrolepsis cordifolia
SEQUENCE: 21
atgcagagag agagagagag agagatggcc gaccaagctg cagcagcagc tagagaagct    60
gaagaagagg tggaggtttt tatggacgag actgaggcgg tggggacgca cctggacttc   120
ttggcgggct tgaacgttca accccgcaag gtcatcaccg tggaggtgga cgccgctgcc   180
gtaatccaac agatcagaga gatcttccaa accatgcac gtcacttcaa ctcgacgagg   240
gtggtgcgtg atgaagccat caagggcatt cgcgaccact tcagggccgc tgtcccgact   300
cgcaacgtgg tggtcgttca cactcagcac attcacactc tggtggacgt ggagcacacc   360
aacctcgtct tgcagaccgg catcttcaaa aaggtccccg tcgacatcta tgtcttcaag   420
tccgcgtct tcaccctcct ggagacggc ggcttcatca ctgggcatg gggtggcttc   480
gtagaccagg ttgacggcaa gcgtatccac ttccgcttgc cccccgggc gctccct     537

SEQ ID NO: 22            moltype = AA  length = 179
FEATURE                  Location/Qualifiers
source                   1..179
                         mol_type = protein
                         organism = Nephrolepsis cordifolia
SEQUENCE: 22
MQREREREMA DQAAAAAREA EEEVEVFMDE TEAVGTHLDF LAGLNVQPRK VITVEVDAAA    60
VIQQIREIFQ TMARHFNSTR VVRDEAIKGI RDHFRAAVPT RNVVVVHTQH IHTLVDVEHT   120
NLVLQTGIFK KVPVDIYVFK SGVFTLLGDG GFINWAWGGF VDQVDGKRIH FRLPPGALP   179

SEQ ID NO: 23            moltype = DNA  length = 513
FEATURE                  Location/Qualifiers
source                   1..513
                         mol_type = other DNA
                         organism = Polystichium tsus-simense
SEQUENCE: 23
atggccgaca agtagcagc agcgcctcct cctgctagag aagcagaaga gaggtggag     60
gagacgatgg acgagactga ggcggtgggg acgcacctgg acttgatagc gaccctaccg   120
cgtggcatca tcaccgtgga ggtggactcc gcgccgtaa tccaacagat cagagagatc   180
ttccaaacca tggcacgtca tttcaactct acgagggtgg taaggaatga agccatcaag   240
ggcattcgag accacttcag ggccgccatc ccgactcgca acgtggtggt cattcacact   300
caaacgcttc acacactggt gggcttggag cacacccacc tcgtcttgca gaccggcatc   360
tttaaaaagg tccccgtcga cgtctacgtc ttcaagtccg gcgtgctcac caacctcgga   420
gacggaggct tcatcaactg gcatggggt ggcttcgtga ccgaggtcgt tgggaagcgt   480
gtccacttcc gcttgccccc cggggcgctc cct                                513

SEQ ID NO: 24            moltype = AA  length = 171
```

```
FEATURE                 Location/Qualifiers
source                  1..171
                        mol_type = protein
                        organism = Polystichium tsus-simense
SEQUENCE: 24
MADKVAAAPP PAREAEEEVE ETMDETEAVG THLDLIATLP RGIITVEVDS AAVIQQIREI    60
FQTMARHFNS TRVVRDEAIK GIRDHFRAAI PTRNVVVIHT QHVHTLVGLE HTHLVLQTGI   120
FKKVPVDVYV FKSGVLTNLG DGGFINWAWG GFVTEVVGKR VHFRLPPGAL P            171

SEQ ID NO: 25           moltype = DNA  length = 513
FEATURE                 Location/Qualifiers
source                  1..513
                        mol_type = other DNA
                        organism = Polystichium tsus-simense
SEQUENCE: 25
atggccgaca aagtagcagc agcgcctcct cctgctagag aagcagaaga agaggtggag    60
gagacgatgg acgagactga ggcggtgggg acgcacctgg acttgatagc aaccctaccg   120
cgtggcaatca tcaccgtgga ggtggacggc gccgccgtaa tccaacagat cagagagatc   180
ttccaaaacca tggcacgtca tttcaactct acgagggtgg taagggatga agccatcaag   240
ggcattcgag accacttcag ggccgccatc ccgactcgca acgtggtggt cattcacact    300
caaacgttc acacactggt gggcttggag cacacccacc tcgtcttgca gaccggcatc    360
tttaaaaagg tccccgtcga cgtctacgtc ttcaagtccg gcgtgctcac caaccctgga   420
gacggaggct tcatcaactg ggcatggggt ggcttcgtga ccgaggtcgt tgggaagcgt    480
gtccacttcc gcttgccccc cggggcgctc cct                                513

SEQ ID NO: 26           moltype = AA  length = 171
FEATURE                 Location/Qualifiers
source                  1..171
                        mol_type = protein
                        organism = Polystichium tsus-simense
SEQUENCE: 26
MADKVAAAPP PAREAEEEVE ETMDETEAVG THLDLIATLP RGIITVEVDG AAVIQQIREI    60
FQTMARHFNS TRVVRDEAIK GIRDHFRAAI PTRNVVVIHT QHVHTLVGLE HTHLVLQTGI   120
FKKVPVDVYV FKSGVLTNLG DGGFINWAWG GFVTEVVGKR VHFRLPPGAL P            171

SEQ ID NO: 27           moltype = DNA  length = 519
FEATURE                 Location/Qualifiers
source                  1..519
                        mol_type = other DNA
                        organism = Thelypteris palustris
SEQUENCE: 27
atggccgaca aagtagcagc agcttctcgg gctcaaggag cagaagaggt ggaggatctg    60
atggacgaga cagaggcggt ggggacgcac ctggactgca tgggcggcga cgtgaaggtg   120
caagcacgcg gcatcatcac cgtggaggtg gaccccgccg ccgtaatcca acagatcaga   180
gagatcttcc aaaaccctgg cacgtcacta aactctacga gggtggtacg ggatgcagcc   240
atcaaggcca ttcgagacca cttcagggcc gccgtcccga ctcgcaacgt ggtggtcatc    300
cacactcaac acgttcacac actggcggac gtagagcaca gccacctcgt cttgcagacc    360
ggcatcttca gaaggtcccc gtcgacatc tacgtcttca gtccggcgt gttcaccaac    420
ctcggcgacg gaggcttcat caactgggca tggggtggct acgtgacaga ggtcgttggg   480
aagcgtatcc acttccgctt gccccggggg cactccct                           519

SEQ ID NO: 28           moltype = AA  length = 173
FEATURE                 Location/Qualifiers
source                  1..173
                        mol_type = protein
                        organism = Thelypteris palustris
SEQUENCE: 28
MADKVAAASR AQGAEEVEDL MDETEAVGTH LDCMGGDVKV QARGIITVEV DPAAVIQQIR    60
EIFQTLARHY NSTRVVRDAA IKAIRDHFRA AVPTRNVVVI HTQHVHTLAD VEHSHLVLQT   120
GIFKKVPVDI YVFKSGVFTN LGDGGFINWA WGGYVTEVVG KRIHFRLPPG ALP          173

SEQ ID NO: 29           moltype = DNA  length = 513
FEATURE                 Location/Qualifiers
source                  1..513
                        mol_type = other DNA
                        organism = Athyrium filix-femina
SEQUENCE: 29
atggccgaca aagcgcctcc tcctgctaga gaagcagaaag aagaggtgga ggagacgatg    60
gacgagactg aggcagtggg gacgcacctg gacttgatag cgcacctgag tgtgcaaccc   120
cgcggcatca tcaccgtgga ggtggacccc gccgctgtaa tccaacagat cagagagatc   180
ttccaaaacca tggcacgtca tttcaactct acgagggtgg tacgggatga agccatcaag    240
ggcattcgag accacttcag ggccgccgtc ccgactcgca acgtggtggt cattcacact    300
caaacgttc acacactggt gggcttggag cacacccacc tcgtcttgca gaccggcatc    360
tttagaacgg tccccgtcga catctacgtc ttcaagtccg gcgtgctcac caaccctgga   420
gacggaggct tcatcaactg ggcatggggt ggcttcgtga ccgaggtcgt tgggaagcgt    480
gtccacttcc gcttgccccc cggggcactc cct                                513

SEQ ID NO: 30           moltype = AA  length = 171
FEATURE                 Location/Qualifiers
```

```
source                  1..171
                        mol_type = protein
                        organism = Athyrium filix-femina
SEQUENCE: 30
MADKAPPPAR EAEEEVEETM DETEAVGTHL DLIAHLSVQP RGIITVEVDP AAVIQQIREI    60
FQTMARHFNS TRVVRDEAIK GIRDHFRAAV PTRNVVVIHT QHVHTLVGLE HTHLVLQTGI   120
FRTVPVDIYV FKSGVLTNLG DGGFINWAWG GFVTEVVGKR VHFRLPPGAL P            171

SEQ ID NO: 31           moltype = DNA  length = 513
FEATURE                 Location/Qualifiers
source                  1..513
                        mol_type = other DNA
                        organism = Nephrolepis cordifolia
SEQUENCE: 31
atggccgacc aagctgcagc agcagctaga gaagctgaag aagaggtgga ggtttttatg    60
gacgagactg aggcggtggg gacgcacctg gacttcttgg cgggcttgaa cgttcaaccc   120
cgcaaggtca tcaccgtgga ggtggacgcc gctgccgtaa tccaacgat cagagagatc   180
ttccaaacca tggcacgtca cttcaactcg acgagggtgg tgcgggatga agccatcaag   240
ggcattcgcg accacttcag ggccgccgtc ccgactcgca acgtggtggt cgttcacact   300
cagcacattc acactctggt ggacgtggag cacaccaacc tcgtcttgca gaccggcatc   360
ttcaaaaagg tccccgtcga catctatgtc ttcaagtccg gcgtcttcac cctccttgga   420
gacggcggct tcatcaactg gcatggggt ggcttcgtag accaggttga cggcaagcgt   480
atccacttcc gcttgccccc cggggcgctc cct                               513

SEQ ID NO: 32           moltype = AA   length = 171
FEATURE                 Location/Qualifiers
source                  1..171
                        mol_type = protein
                        organism = Nephrolepis cordifolia
SEQUENCE: 32
MADQAAAAAR EAEEEVEVFM DETEAVGTHL DFLAGLNVQP RKVITVEVDA AAVIQQIREI    60
FQTMARHFNS TRVVRDEAIK GIRDHFRAAV PTRNVVVVHT QHIHTLVDVE HTNLVLQTGI   120
FKKVPVDIYV FKSGVFTLLG DGGFINWAWG GFVDQVDGKR IHFRLPPGAL P            171

SEQ ID NO: 33           moltype = DNA  length = 546
FEATURE                 Location/Qualifiers
source                  1..546
                        mol_type = other DNA
                        organism = Platycerium wandae
SEQUENCE: 33
atgagagagc gagagcgaga gcgagagaga gagatggccg aaccagcagc agcagcagct    60
aaaaaagctg aagaagaggt ggagatattt atggacgaca ctgaggcggt ggggacgcat   120
ctggacttct tggcgggctt gaaggtgcag ccccgcaaga tcatcaccgt ggaggtggac   180
cccgctgccg taatccagca gataagagag atctttcaaa ccctggcacg tcacttcaac   240
tcgacgacgg tggtgcggga tgaagccatc aagggcattc gagaccactt cagggccgcc   300
gttccgactc gcaacgtggt ggtcgttcac actcagcaca ttcacaccct ggagggcttg   360
gagcacacca accttgtctt gcagaccggc cgcttcaaga aggtccccgt cgacatctac   420
gtcttcaagt ctggcgtctt caccctcctt ggagatggag gcttcatcaa ctgggcgtgg   480
ggtggcttcg tggagcaggt cgtcggcaag cgtatccact tccgcttacc ccctggggcg   540
ctccct                                                              546

SEQ ID NO: 34           moltype = AA   length = 182
FEATURE                 Location/Qualifiers
source                  1..182
                        mol_type = protein
                        organism = Platycerium wandae
SEQUENCE: 34
MRERERERER EMAEPAAAAA KKAEEEVEIF MDDTEAVGTH LDFLAGLKVQ PRKIITVEVD    60
PAAVIQQIRE IFQTLARHFN STTVVRDEAI KGIRDHFRAA VPTRNVVVVH TQHIHTLEGL   120
EHTNLVLQTG RFRKVPVDIY VFKSGVFTLL GDGGFINWAW GGFVEQVVGK RIHFRLPPGA   180
LP                                                                  182

SEQ ID NO: 35           moltype = DNA  length = 513
FEATURE                 Location/Qualifiers
source                  1..513
                        mol_type = other DNA
                        organism = Tectaria milnei
SEQUENCE: 35
atggccgatg aggtagctgg tcatcacggt cctgcctgtg aagaagaaga agaaagagatg    60
ctgatggatg agactgaggc ggtgggggtg catgcaatcg atggcctgcc ggtgcaaaac   120
cgtagcatca ttaccgtgga ggtggacgcc gcagccgtaa tccagcagat cagagagata   180
tttgcatcga tgatcaagca ctacaactcc acgcgagtgg tgcgggatga ggccatcaag   240
tccattcgag accacttcag gctcgccgtg ccactcgca acgtggtggt gattcacact   300
cagcacgttc acactctgga cgccgtggag agctcttgcg aaccggtcta                360
ttcaaaaagg tgccagtgga catcttcgtc ttcaagtctg gcgtgttcac caacctggga   420
gacggggct tcatcaactg gcatggggt ggctacggcg tcaaccacac tgccaagcgt   480
gttgtcttca gtcggccccc tggggcgctc cct                               513

SEQ ID NO: 36           moltype = AA   length = 171
```

```
FEATURE                 Location/Qualifiers
source                  1..171
                        mol_type = protein
                        organism = Tectaria milnei
SEQUENCE: 36
MADEVAGHHG PACEEEEEEM LMDETEAVGV HAIDGLPVQN RSIITVEVDA AAVIQQIREI    60
FASMIKHYNS TRVVRDEAIK SIRDHFRLAV PTRNVVVIHT QHVHTLDAVE SSHLVLRTGL   120
FKKVPVDIFV FKSGVFTNLG DGGFINWAWG GYGVNHTAKR VVFSRPPGAL P            171

SEQ ID NO: 37           moltype = DNA  length = 375
FEATURE                 Location/Qualifiers
source                  1..375
                        mol_type = other DNA
                        organism = Davallia tyermannii
SEQUENCE: 37
atggacgccg ctgccgtaat ccagcagatt agagagatct tccaatccat ggcagatgac    60
ttcagctcga cgaaggtggt gcgggatgaa gccatcaagg gcattcgaga ccacttcagg   120
gccgccgtcc cgactcgcaa cgtggtggtc gttcacaccg cgcacattca cacacagctg   180
gtggacgtgg agcacaccaa actcgtcttg aagaccggca tcttcgaaaa ggtccccgtc   240
gacatctatg tcttcaagtc cggcgtcttc accctccttg gagacggagg ctacaacaac   300
tgggcatggg gtggcttcgt agaccaggtc gtcggcaagc gtatccactt ccgcttgccc   360
cccgggcgc tccct                                                     375

SEQ ID NO: 38           moltype = AA  length = 125
FEATURE                 Location/Qualifiers
source                  1..125
                        mol_type = protein
                        organism = Davallia tyermannii
SEQUENCE: 38
MDAAAVIQQI REIFQSMADD FSSTKVVRDE AIKGIRDHFR AAVPTRNVVV VHTPHIHTQL    60
VDVEHTKLVL KTGIFEKVPV DIYVFKSGVF TLLGDGGYNN WAWGGFVDQV VGKRIHFRLP   120
PGALP                                                               125

SEQ ID NO: 39           moltype = DNA  length = 579
FEATURE                 Location/Qualifiers
misc_feature            1..579
                        note = IPD103 variant
source                  1..579
                        mol_type = other DNA
                        organism = synthetic construct
SEQUENCE: 39
atgggcagca gccatcatca tcatcatcac agcagcggcc tggtgccgcg cggcagccat    60
atggcagaca aagcagcagc agcagctaga gaagctgaag aagaggtgga gacgacgatg   120
gacgagactg aggcggtggg gacgcacctg gacttcttgg gcgcggacgt gaagttgcaa   180
ccccgcaaca tcatcaccgt ggaggtggac gcggctgccg taatccaaca gatcagagag   240
atcttccaga caatggcgcg tcacttcaac tctacgaggg tggtgcggga tgaagccatc   300
aagggcattc gagaccactt cagggccgcc gtcccgactc gcaacgtggt ggtcattcac   360
actcagcacg ttcacacact ggtgggcttg agcacaccc acctcgtctt gcagaccggc   420
atcttcaaaa aggtccccgt cgacatctat gtcttcaagt ccggcgtctt caccaacttt   480
ggagacggag gcttcatcaa ctgggcatgg ggtggcttcg tcgaccaggt cgtcggcaag   540
cgtatccact tccgcttgcc ccccggggcg ctccccttga                         579

SEQ ID NO: 40           moltype = AA  length = 192
FEATURE                 Location/Qualifiers
REGION                  1..192
                        note = IPD103 variant
source                  1..192
                        mol_type = protein
                        organism = synthetic construct
SEQUENCE: 40
MGSSHHHHHH SSGLVPRGSH MADKAAAAAR EAEEEVETTM DETEAVGTHL DFLGADVKLQ    60
PRNIITVEVD AAAVIQQIRE IFQTMARHFN STRVVRDEAI KGIRDHFRAA VPTRNVVVIH   120
TQHVHTLVGL EHTHLVLQTG IFKKVPVDIY VFKSGVFTNL GDGGFINWAW GGFVDQVVGK   180
RIHFRLPPGA LP                                                       192

SEQ ID NO: 41           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 41
atggccgacc cagcaacagc agctagagaa gctgaagaag aggtggagac gacgatggac    60
gagactgagg cggtggggac gcacctggac ttcttgggcg cggacgtgaa gttgcaaccc   120
cgcaacatca tcaccgtgga ggtggacgcc gctgccgtaa tccagcagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cgttcacacc   300
cagcacattc acacactgga gggcttggag cacaccaacc tcgtcttgca gaccggcctc   360
```

```
ttcaaaaagg tccccgtcga catctacgtc ttcaagtccg gcgtcttcac cctccttgga    420
gacggaggct tcatcaactg ggcatggggt ggcttcgtac aggaggtcgc cggcaagcgt    480
atccacttcc gcttgccccc cggggcgctc cct                                513
```

| SEQ ID NO: 42 | moltype = DNA length = 510 |
|---|---|
| FEATURE | Location/Qualifiers |
| misc_feature | 1..510 |
| | note = IPD103 variant |
| source | 1..510 |
| | mol_type = other DNA |
| | organism = synthetic construct |

```
SEQUENCE: 42
atggccgacc cagcagcagc agctagagaa gctgaagaag aggtggagac gacgatggac     60
gagactgagg cggtggggac gcacctggac ttcgtgccgg gcttggaggt gcaaccccgc    120
aaggtcatca ccgtggaggt ggacgccgct gccgtaatcc agcagatcag agagatcttc    180
cagacaatgg cgcgtcactt caactctacg agggtggtgc gggatgaagc catcaagggc    240
attcgagacc acttcagggc cgccgtcccg actcgcaacg tggtggtcgt tcacacccag    300
cacattcaca cactggtggg cttggagcac acccacctcg tcttgcagac cggcatcttc    360
aaaaaggtcc ccgtcgacat ctatgtcttc aagtccggcg tcttcaccaa ccttggagac    420
ggaggcttca tcaactgggc atggggtggc ttcgtacagg aggtcgccgg caagcgtatc    480
cacttccgct tgcccccgg ggcgctccct                                    510
```

| SEQ ID NO: 43 | moltype = DNA length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 43
atggccgacc cagcaacagc agctagagaa gctgaagaag aggtgcagga gactttgatg     60
gacgagactg aggcggtggg gacgcacctg gacttcttgg gcgcggacgt gaagttgcaa    120
ccccgcaaca tcatcaccgt ggaggtggac gcggctgccg taatccagca gatcagagag    180
atcttccgaa ccatggcaag tcacttcaac tcgacgaggg tggtgcggga tgaagccatc    240
aagggcattc gagaccactt cagggccgcc gtcccgactc gcaacgtggt ggtcgttcac    300
actcagcacg ttcacacact ggtgggcttg agcacaccc acctcgtctt gcagaccggc    360
ctcttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact tccgcttgcc ccccggggcg ctccct                              516
```

| SEQ ID NO: 44 | moltype = DNA length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 44
atggcggaca aaacagcagc agcagctaga gaagctgaag aagaggtgca ggagactttg     60
atggacgaga ctgaggcggt ggggacgcac ctggacttcg tggcgggctt ggaggtgcaa    120
ccccgcaaca tcatcaccgt ggaggtggac gccgctgccg taatccagca gatcagagag    180
atcttccgaa ccatggcaag tcacttcaac tcgacgaggg tggtgcggga tgaagccatc    240
aagggcattc gagaccactt cagggccgcc gtcccgactc gcaacgtggt ggtcgttcac    300
acccagcaca ttcacacact ggagggcttg agcacaccac cctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

| SEQ ID NO: 45 | moltype = DNA length = 513 |
|---|---|
| FEATURE | Location/Qualifiers |
| misc_feature | 1..513 |
| | note = IPD103 variant |
| source | 1..513 |
| | mol_type = other DNA |
| | organism = synthetic construct |

```
SEQUENCE: 45
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cgttcacacc    300
cagcacattc acacactgga gggcttgagc acacccacc tcgtcttgca gaccggcctc    360
ttcaaaaagg tccccgtcga catctacgtc ttcaagtccg gcgtcttcac cctccttgga    420
gacggaggct tcatcaactg ggcatggggt ggcttcgtac aggaggtcgc cggcaagcgt    480
atccacttcc gcttgccccc cggggcgctc cct                                513
```

| SEQ ID NO: 46 | moltype = DNA length = 513 |
|---|---|
| FEATURE | Location/Qualifiers |
| misc_feature | 1..513 |

```
                          note = IPD103 variant
misc_feature              412
                          note = n is a, c, g, or t
source                    1..513
                          mol_type = other DNA
                          organism = synthetic construct
SEQUENCE: 46
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga acccatcaag   240
ggcattcgag accacttcag gccgccgtc ccgactcgca acgtggtggt cattcacact    300
cagcacgttc acacactggt gggcttggag cacacccacc tcgtattgca gaccggcatc   360
ttcaaaaagg tccccgtcga catttatgtc ttcaagtccg gtgttttcac cntcctcgga   420
gacggaggct tcatcaactg ggcatggggt ggcttcgtcg accaggtcgt cggcaagcgt   480
atccacttcc gcttgccccc cggggcggtc cct                                513

SEQ ID NO: 47             moltype = DNA   length = 513
FEATURE                   Location/Qualifiers
misc_feature              1..513
                          note = IPD103 variant
source                    1..513
                          mol_type = other DNA
                          organism = synthetic construct
SEQUENCE: 47
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtgtc cgttcacacc    300
cagcacattc acacactggt gggcttggag cacacccacc tcgtcttgca gaccggcatc   360
ttcaaaaagg tccccgtcga catctacgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 48             moltype = DNA   length = 513
FEATURE                   Location/Qualifiers
misc_feature              1..513
                          note = IPD103 variant
source                    1..513
                          mol_type = other DNA
                          organism = synthetic construct
SEQUENCE: 48
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cgttcacact    300
cagcacgttc acacactggt gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 49             moltype = DNA   length = 519
FEATURE                   Location/Qualifiers
misc_feature              1..519
                          note = IPD103 variant
source                    1..519
                          mol_type = other DNA
                          organism = synthetic construct
SEQUENCE: 49
atggcggaca aagcagcagc agcagctaga gaagctgaag aagaggtgca ggagactttg    60
atggacgaga ctgaggcggt ggggacgcac ctggacttct gggcgcgga cgtgaagttg   120
caacccgca acatcatcac cgtggaggtg gacgcggctg ctaatcca acagatcaga     180
gagatcttcc gaaccatggc aagtcacttc aactcgacga gggtggtgcg ggatgaagcc   240
atcaagggca ttcgagacca cttcaggccc gcgtcccga ctcgcaacgt ggtggtcgtt    300
cacacccagc acgttcacac actggtgggc ttggagcaca ccaacctcgt cttgcagacc   360
ggcctcttca aaaggtccc cgtcgacatc tatgtcttca gtccggcgt cttcaccctc    420
cttggagacg gaggcttcat caactgggca tggggtggct tcgtacagga ggtcgccggc   480
aagcgtatcc acttccgctt gccccccggg gcgctcct                          519

SEQ ID NO: 50             moltype = DNA   length = 516
FEATURE                   Location/Qualifiers
misc_feature              1..516
                          note = IPD103 variant
source                    1..516
                          mol_type = other DNA
                          organism = synthetic construct
SEQUENCE: 50
```

```
atggcggaca aagcagcagc agcagctaga gaagctgaag aagaggtgga gacgacgatg      60
gacgagactg aggcggtggg gacgcacctg gacttcttgg gcgcggacgt gaagttgcaa     120
ccccgcaaca tcatcaccgt ggaggtggac gcggctgccg taatccagca gatcagagag     180
atcttccgaa ccatggcaag tcacttcaac tcgacgaggg tggtgcggga tgaagccatc     240
aaggcattc  gagaccactt cagggccgcc gtcccgactc gcaacgtgtt ggtcattcac     300
actcagcacg ttcacacact ggtgggcttg gagcacaccc acctcgtctt gcagaccggc     360
ctcttcaaaa aggtccccgt cgacatctat gtcttcaagt ccggcgtctt caccctcctt     420
ggagacggag gcttcatcaa ctgggcatgg ggtggcttcg tcgaccaggt cgtcggcaag     480
cgtatccact tccgcttgcc ccccggggcg ctccct                               516

SEQ ID NO: 51           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 51
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaaggtca tcaccgtgga ggtggacgcg gctgccgtaa tccaacagat cagagagatc     180
ttccgaacca tggcaagtca cttcaactct acgagggtgg tgcggggatga agccatcaag     240
ggcattcgag accacttcag ggccgccgtc ccgactcgca acgtggtggt cgttcacacc     300
cagcacattc acacactgga gggcttggag cacacccacc tcgtcttgca gaccggcatc     360
ttcaaaaagg tccccgtcga catctacgtc ttcaagtccg gcgtcttcac cctccttgga     420
gacggaggct tcatcaactg gcatggggt ggcttcgtac aggaggtcgc cggcaagcgt     480
atccacttcc gcttgccccc cggggcgctc cct                                  513

SEQ ID NO: 52           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 52
atggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaacatca tcaccgtgga ggtggacgcc gctgccgtaa tccagcagat cagagagatc     180
ttccagacaa tggcgcgtca cttcaactct acgagggtgg tgcgggatga agccatcaag     240
ggcattcgag accacttcag ggccgccgtc ccgactcgca acgtggtggt cgttcacacc     300
cagcacgttc acacactggt gggcttggag cacacccacc tcgtcttgca gaccggcatc     360
ttcaaaaagg tccccgtcga catctacgtc ttcaagtccg gcgtcttcac cctccttgga     420
gacggaggct tcatcaactg ggcatggggt ggcttcgtcg accaggtcgt cggcaagcgt     480
atccacttcc gcttgccccc cggggcgctc cct                                  513

SEQ ID NO: 53           moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 53
atggcggaca aagcagcagc agcagctaga gaagctgaag aagaggtgca ggagactttg      60
atggacgaga ctgaggcggt ggggacgcac ctggacttcg tggcgggctt ggaggtgcaa     120
ccccgcaagg tcatcaccgt ggaggtggac gccgctgccg taatccagca gatcagagag     180
atcttccgaa ccatggcaag tcacttcaac tcgacgaggg tggtgcggga tgaagccatc     240
aaggcattc  gagaccactt cagggccgcc gtcccgactc gcaacgtgtt ggtcattcac     300
actcagcacg ttcacacact ggtgggcttg gagcacaccc acctcgtctt gcagaccggc     360
atcttcaaaa aggtccccgt cgacatctac gtcttcaagt ccggcgtctt caccctcctt     420
ggagacggag gcttcatcaa ctgggcatgg ggtggcttcg tcgaccaggt cgtcggcaag     480
cgtatccact tccgcttgcc ccccggggcg ctccct                               516

SEQ ID NO: 54           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 54
acggcggaca aagcagcagc agcagctaga gaagctgaag aagaggtgga gacgacgatg      60
gacgagactg aggcggtggg gacgcacctg gacttcgtgg cgggcttgga ggtgcaaccc     120
cgcaacatca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cgttcacact     300
cagcacgttc acacactggt gggcttggag cacacccacc tcgtcttgca gaccggcatc     360
ttcaaaaagg tccccgtcga catctacgtc ttcaagtccg gcgtcttcac cctccttgga     420
```

```
gacggaggct tcatcaactg ggcatggggt ggcttcgtac aggaggtcgc cggcaagcgt   480
atccacttcc gcttgccccc cggggcgctc cct                                513

SEQ ID NO: 55           moltype = DNA   length = 510
FEATURE                 Location/Qualifiers
misc_feature            1..510
                        note = IPD103 variant
source                  1..510
                        mol_type = other DNA
                        organism = synthetic construct
SEQUENCE: 55
atggccgacc cagcaacagc agctagagaa gctgaagaag aggtggagac gacgatggac   60
gagactgagg cggtggggac gcacctggac ttcgtggcgg gcttggaggt gcaacccgc   120
aaggtcatca ccgtggaggt ggacgccgct gccgtaatcc agcagatcag agagatcttc   180
cgaaccatgg caagtcactt caactcgacg agggtggtgc gggatgaagc catcaagggc   240
attcgagacc acttcaggc cgccgtcccg actcgcaacg tggtggtcgt tcacactcag   300
cacgttcaca cactggtggg cttggagcac acccacctcg tcttgcagac cggcctcttc   360
aaaaaggtcc ccgtcgacat ctacgtcttc aagtccggcg tcttcaccct ccttggagac   420
ggaggcttca tcaactgggc atgggtggc ttcgtcgacc aggtcgtcgg caagcgtatc   480
cacttccgct tgcccccgg ggcgctccct                                    510

SEQ ID NO: 56           moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 56
atggccgacc cagcaacagc agctagagaa gctgaagaag aggtgcagga gactttgatg   60
gacgagactg aggcggtggg gacgcacctg gacttcgtgg cgggcttgga ggtgcaaccc   120
cgcaacatca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacgttc acacactggt gggcttggag cacacccacc tcgtcttgca gaccggcatc   360
ttcaaaaagg tccccgtcga catctacgtc ttcaagtccg gcgtcttcac cctccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 57           moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 57
atggcggaca agcagcagc agcagctaga gaagctgaag aagaggtgga gacgacgatg   60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cgttcacacc   300
cagcacattc acacactggt gggcttggag cacacccacc tcgtcttgca gaccggcctc   360
ttcaaaaagg tccccgtcga catctacgtc ttcaagtccg gcgtcttcac cctccttgga   420
gacggaggct tcatcaactg ggcatggggt ggcttcgtac aggaggtcgc cggcaagcgt   480
atccacttcc gcttgccccc cggggcgctc cct                                513

SEQ ID NO: 58           moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 58
atggcggaca aaacagcagc agcagctaga gaagctgaag aagaggtgga gacgacgatg   60
gacgagactg aggcggtggg gacgcacctg gacttcttgg cgcggacgt gaagttgcaa   120
ccccgcaaca tcatcaccgt ggaggtggac gccgctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacaccc acctcgtctt gcagaccggc   360
atcttcaaaa aggtccccgt cgacatctat gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                             516

SEQ ID NO: 59           moltype = DNA   length = 513
FEATURE                 Location/Qualifiers
misc_feature            1..513
                        note = IPD103 variant
```

```
source                  1..513
                        mol_type = other DNA
                        organism = synthetic construct
SEQUENCE: 59
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaacatca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag gccgccgtc ccgactcgca acgtggtggt cattcacacc    300
cagcacgttc acacactggt gggcttggag cacacccacc tcgtcttgca gaccggcatc   360
ttcaaaaagg tccccgtcga catctacgtc ttcaagtccg gcgtcttcac cctccttgga   420
gacggaggct tcatcaactg ggcatggggt ggcttcgtcg accaggtcgt cggcaagcgt   480
atccacttcc gcttgccccc cggggcgctc cct                               513

SEQ ID NO: 60           moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 60
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg gtggcttcg tcgaccaggt cgtcggcaag    480
cgtatccact tccgcttgcc ccccggggcg ctccct                            516

SEQ ID NO: 61           moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 61
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgaggtgg tgcgggatga agccatcaag    240
ggcattcgag accacttcag gccgccgtc ccgactcgca acgtggtggt cgttcacacc    300
cagcacattc acacactgga gggcttggag cacaccaacc tcgtcttgca gaccggcctc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                               513

SEQ ID NO: 62           moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 62
atggcggaca aagcagcagc agcagctaga gaagctgaag aagaggtgga gactttgatg    60
gacgagactg aggcggtggg gacgcacctg gacttcttgg gcgcggacgt gaagttgcaa   120
ccccgcaaca tcatcaccgt ggaggtggac gccgctgccg taatccagca gatcagagag   180
atcttccgaa ccatggcaaa tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacaccc acctcgtctt gcagaccggc   360
ctcttcaaaa aggtccccgt cgacatctat gtcttcaagt ccggcgtctt caccaacctt   420
ggagacggag gcttcatcaa ctgggcatgg gtggcttcg tcgaccaggt cgtcggcaag    480
cgtatccact tccgcttgcc ccccggggcg ctccct                            516

SEQ ID NO: 63           moltype = DNA   length = 510
FEATURE                 Location/Qualifiers
misc_feature            1..510
                        note = IPD103 variant
source                  1..510
                        mol_type = other DNA
                        organism = synthetic construct
SEQUENCE: 63
atggccgacc cagcagcagc agctagagaa gctgaagaag aggtggagac gacgatggac    60
gagactgagg cggtggggac gcacctggac ttcgtggcgg gcttggaggt gcaacccgc    120
aaggtcatca ccgtggaggt ggacgcggct gccgtaatcc aacagatcag agagatcttc   180
```

```
cagacaatgg cgcgtcactt caactcgacg agggtggtgc gggatgaagc catcaagggc   240
attcgagacc acttcagggc cgccgtcccg actcgcaacg tggtggtcgt tcacactcag   300
cacgttcaca cactggtggg cttggagcac accaacctcg tcttgcagac cggcctcttc   360
aaaaaggtcc ccgtcgacat ctacgtcttc aagtccggcg tcttcaccct ccttggagac   420
ggaggcttca tcaactgggc atggggtggc ttcgtacagg aggtcgccgg caagcgtatc   480
cacttccgct gcccccccgg ggcgctccct                                    510

SEQ ID NO: 64           moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 64
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacattc acacactgga gggcttggag cacaccaacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtac aggaggtcgc cggcaagcgt   480
atccacttcc gcttgccccc cggggcgctc cct                                513

SEQ ID NO: 65           moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 65
atggcggaca aagcagcagc agcagctaga gaagctgaag aagaggtgga gacgacgatg    60
gacgagactg aggcggtggg gacgcacctg gacttcttgg cgcggacgt gaagttgcaa    120
ccccgcaagg tcatcaccgt ggaggtggac gccgctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcgttcac   300
actcagcaca ttcacacact ggagggcttg gagcacaccaa acctcgtctt gcagaccggc   360
atcttcaaaa aggtccccgt cgacatctac gtcttcaagt ccggcgtctt cacccctcctt   420
ggagacggag gcttcatcaa ctgggcatgg gtggcttcg tacaggaggt cgccggcaag   480
cgtatccact tccgcttgcc ccccggggcg ctccct                              516

SEQ ID NO: 66           moltype = DNA   length = 519
FEATURE                 Location/Qualifiers
misc_feature            1..519
                        note = IPD103 variant
source                  1..519
                        mol_type = other DNA
                        organism = synthetic construct
SEQUENCE: 66
atggcggaca aagcagcagc agcagctaga gaagctgaag aagaggtgca ggagactttg    60
atggacgaga ctgaggcggt ggggacgcac ctggacttct tgggcgcgga cgtgaagttg   120
caaccccgca aggtcatcac cgtggaggtg acgccgctg ccgtaatcca acagatcaga   180
gagatcttcc agacaatggc gcgtcacttc aactctacga gggtggtgcg ggatgaagcc   240
atcaagggca ttcgagacca cttcagggcc gccgtcccga ctcgcaacgt ggtagtcgtt   300
cacacccagc acattcacac actggagggc ttggagcaca cccacctcgt cttgcagacc   360
ggcatcttca aaaaggtccc cgtcgacatc tacgtcttca gtccggcgt cttcaccaac   420
cttggagacg gaggcttcat caactgggca tggggtggct tcgtacagga ggtcgccggc   480
aagcgtatcc acttccgctt gccccccggg gcgctccct                          519

SEQ ID NO: 67           moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 67
atggcggaca aagcagcagc agcagctaga gaagctgaag aagaggtgga gacgacgatg    60
gacgaaactg aggcggtggg gacgcacctg gacttcgtgg cgggcttgga ggtgcaaccc   120
cgcaaggtca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacgttc acacactggt gggctcggag cacacccacc tcgtcttgca gaccggcatc   360
ttcaaaaagg tccccgtcga catctatgtc ttcaagtccg gcgtcttcac cctccttgga   420
gacggaggct tcatcaactg gcatggggt ggcttcgtcg accaggtcgt cggcaagcgt   480
atccacttcc gcttgccccc cggggcgctc cct                                513
```

| SEQ ID NO: 68 | moltype = DNA length = 513 |
| --- | --- |
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 68

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacact   300
cagcacgttc acacactggt gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg gcatgggggt ggcttcgtcg accaggtcgt cggcaagcgt   480
atccacttcc gcttgccccc cggggcgctc cct                                513
```

| SEQ ID NO: 69 | moltype = DNA length = 516 |
| --- | --- |
| FEATURE | Location/Qualifiers |
| misc_feature | 1..516 |
| | note = IPD103 variant |
| source | 1..516 |
| | mol_type = other DNA |
| | organism = synthetic construct |

SEQUENCE: 69

```
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaagg tcatcaccgt ggaggtggac gccgctgccg taatccaaca gatcagagag   180
atcttccaga caatggcgcg tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggtgggcttg agcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccca                             516
```

| SEQ ID NO: 70 | moltype = DNA length = 513 |
| --- | --- |
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 70

```
atggccgacc cagcaacagc ggctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacattc acacactgga gggcttggag cacacccacc tcgtcttgca gaccggcatc   360
ttcaaaaagg tccccgtcga catctacgtc ttcaagtccg gcgtcttcac caaccttgga   420
gacggaggct tcatcaactg gcatgggggt ggcttcgtac aggaggtcgc cggcaagcgt   480
atccacttcc gcttgccccc cggggcgctc cct                                513
```

| SEQ ID NO: 71 | moltype = DNA length = 513 |
| --- | --- |
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 71

```
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cattcacact   300
cagcacgttc acacactggt gggcttggag cacaccaacc tcgtcttgca gaccggcatc   360
ttcaaaaagg tccccgtcga catctatgtc ttcaagtccg gcgtcttcac caaccttgga   420
gacggaggct tcatcaactg gcatgggggt ggcttcgtac aggaggtcgc cggcaagcgt   480
atccacttcc gcttgccccc cggggcgctc cct                                513
```

| SEQ ID NO: 72 | moltype = DNA length = 513 |
| --- | --- |
| FEATURE | Location/Qualifiers |
| misc_feature | 1..513 |
| | note = IPD103 variant |
| source | 1..513 |
| | mol_type = other DNA |
| | organism = synthetic construct |

```
SEQUENCE: 72
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc ccgactcgca acgtggtggt cgttcacacc    300
cagcacattc acacactgga gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtcg accaggtcgt cggcaagcgt    480
atccacttcc gcttgccccc cggggcgctc cct                                513

SEQ ID NO: 73        moltype = DNA   length = 513
FEATURE              Location/Qualifiers
misc_feature         1..513
                     note = IPD103 variant
source               1..513
                     mol_type = other DNA
                     organism = synthetic construct
SEQUENCE: 73
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacacc    300
cagcacattc acacactgga gggcttggag cacacccacc tcgtcttgca gaccggcatc   360
ttcaaaaagg tccccgtcga catctatgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 74        moltype = DNA   length = 513
FEATURE              Location/Qualifiers
misc_feature         1..513
                     note = IPD103 variant
source               1..513
                     mol_type = other DNA
                     organism = synthetic construct
SEQUENCE: 74
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacact    300
cagcacgttc acacactgga gggcttggag cacacccacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtcg accaggtcgt cggcaagcgt    480
atccacttcc gcttgccccc cggggcgctc cct                                513

SEQ ID NO: 75        moltype = DNA   length = 189
FEATURE              Location/Qualifiers
misc_feature         1..189
                     note = IPD103 variant
source               1..189
                     mol_type = other DNA
                     organism = synthetic construct
SEQUENCE: 75
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccagaca                                                            189

SEQ ID NO: 76        moltype = DNA   length = 513
FEATURE              Location/Qualifiers
misc_feature         1..513
                     note = IPD103 variant
source               1..513
                     mol_type = other DNA
                     organism = synthetic construct
SEQUENCE: 76
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacact    300
cagcacgttc acacactgga gggcttggag cacacccacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 77        moltype = DNA   length = 513
```

| FEATURE | Location/Qualifiers |
|---|---|
| misc_feature | 1..513 |
| | note = IPD103 variant |
| source | 1..513 |
| | mol_type = other DNA |
| | organism = synthetic construct |

SEQUENCE: 77

```
atggcggaca aagcagcagc agcagctaga gaagctgaag aagaggtgga gacgacgatg   60
gacgagactg aggcggtggg gacgcacctg gacttcgtgg cgggcttgga ggtgcaaccc  120
cgcaacatca tcaccgtgga ggtggacgcg gctgccgtaa tccaacagat cagagagatc  180
ttccagacaa tggcgcgtca cttcaactct acgagggtgg tgcgggatga agccatcaag  240
ggcattcgag accacttcag gccgccgtc ccgactcgca acgtggtggt cgttcacact   300
cagcacgttc acacactggt gggcttggag cacacccacc tcgtcttgca gaccggcctc  360
ttcaaaaagg tccccgtcga catctatgtc ttcaagtccg cgtcttcac caaccttgga   420
gacggaggct tcatcaactg gcatggggt ggcttcgtac aggaggtcgc cggcaagcgt   480
atccacttcc gcttgccccc cggggcgctc cct                               513
```

| SEQ ID NO: 78 | moltype = DNA length = 513 |
|---|---|
| FEATURE | Location/Qualifiers |
| misc_feature | 1..513 |
| | note = IPD103 variant |
| misc_feature | 55..56 |
| | note = n is a, c, g, or t |
| misc_feature | 165 |
| | note = n is a, c, g, or t |
| misc_feature | 195..196 |
| | note = n is a, c, g, or t |
| source | 1..513 |
| | mol_type = other DNA |
| | organism = synthetic construct |

SEQUENCE: 78

```
atggcggaca cagcagcagc agctgctaga gaagatgaag aagagctgga gacgnngatg   60
gacgagactg aggcggtggg gacgcacctg gacttcgtgg cgggcttgga ggtgcaaccc  120
cgcaaggtca tcaccgtgga ggtggacgcg gctgccgtaa tccancagat cagagagatc  180
ttccggacca tggcnngtca cttcaactct acgagggtgg tgcgggatga agccatcaag  240
ggcattcgag accacttcag gccgccgtc ccgactcgca acgtggtggt cgttcacacc   300
cagcacgttc acacactgga gggcttggag cacacccacc tcgtcttgca gaccggcatc  360
ttcaaaaagg tccccgtcga catctacgtc ttcaagtccg cgtcttcac catccttgga   420
gacggaggct tcatcaactg gcatggggt ggcttcgtcg accaggtcgt cggcaagcgt   480
atccacttcc gcttgccccc cggggcgctc cct                               513
```

| SEQ ID NO: 79 | moltype = DNA length = 510 |
|---|---|
| FEATURE | Location/Qualifiers |
| misc_feature | 1..510 |
| | note = IPD103 variant |
| source | 1..510 |
| | mol_type = other DNA |
| | organism = synthetic construct |

SEQUENCE: 79

```
atggcggaca aagcagcagc agctagagaa gctgaagaag aggtggagac gacgatggac   60
gagactgagg cggtggggac gcacctggac ttcgtggcgg gcttggaggt gcaacccgc   120
aacatcatca ccgtggaggt ggacgcggct gccgtaatcc aacagatcag agagatcttc  180
cagacaatgg cgcgtcactt caactctacg agggtggtgc gggatgaagc catcaagggc  240
attcgagacc acttcaggc cgccgtcccg actcgcaacg tggtggtcgt tcacacccag  300
cacattcaca cactgagggg cttggagcac accaacctg tcttgcagac cggcctcttc  360
aaaaaggtcc ccgtcgacat ctacgtcttc aagtccggcg tcttcaccaa cctgggagac  420
ggaggcttca tcaactgggc atggggtggc ttcgtacagg aggtcgccgg caagcgtatc  480
cacttccgct tgccccccgg ggcgctccct                                   510
```

| SEQ ID NO: 80 | moltype = DNA length = 510 |
|---|---|
| FEATURE | Location/Qualifiers |
| misc_feature | 1..510 |
| | note = IPD103 variant |
| source | 1..510 |
| | mol_type = other DNA |
| | organism = synthetic construct |

SEQUENCE: 80

```
atggcggaca aagcagcagc agcagctaga gaagctgaag aagaggagga ggaaatgctg   60
atggacgaga ctgaggcggt ggggtgcac gcgatcgacg gtctgccggt gcaaaaccgc  120
agcatcatca ccgtgaggt ggacgcggct gccgtaatcc agcagatcag agagatcttc  180
cgaaccatgg caagtcactt caactcgacg agggtggtgc gggatgaagc catcaagagc  240
attcgagacc acttcaggct cgccgtcccg actcgcaacg tggtggtcgt tcacacccag  300
cacgttcaca cactggtggg cttggagcac acccacctcg tcttgcagac cggcatcttc  360
aaaaaggtcc ccgtcgacat ctatgtcttc aagtccggcg tcttcaccaa cctgggagac  420
ggaggcttca tcaactgggc atggggtggc ttcgtcgacc aggtcgtcgg caagcgtatc  480
cacttccgct tgccccccgg ggcgctccct                                   510
```

| SEQ ID NO: 81 | moltype = DNA length = 513 |
|---|---|
| FEATURE | Location/Qualifiers |

```
misc_feature          1..513
                      note = IPD103 variant
source                1..513
                      mol_type = other DNA
                      organism = synthetic construct
SEQUENCE: 81
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactcg acgagggtgg tgcgggatga agccatcaag   240
ggcattcgag accacttcag ggccgccgtc ccgactcgca acgtggtggt cattcacacc   300
cagcacgttc acacactggt gggcttggag cacacccacc tcgtcttgcg gaccggcctg   360
ttcaaaaagg tccctgtcga catctacgtc ttcaagtccg gcgtcttcac caaccttgga   420
gacggaggct tcatcaactg gcatggggt ggcttcgtcg accaggtcgt cggcaagcgt   480
atccacttcc gcttgccccc cggggcgctc cct                              513

SEQ ID NO: 82         moltype = DNA  length = 510
FEATURE               Location/Qualifiers
misc_feature          1..510
                      note = IPD103 variant
source                1..510
                      mol_type = other DNA
                      organism = synthetic construct
SEQUENCE: 82
atggcggaca aagcagcagc agcagctaga gaagctgaag aagaggagga ggaaatgctg    60
atggacgaga ctgaggcggt ggggggtgcac gcgatcgacg gtctgccggt gcaaaaccgc   120
agcatcatca ccgtgaggt ggacgccgct gccgtaatcc agcagatcag agagatcttc   180
cgaaccatgg caagtcactt caactcgacg agggtggtgc gggatgaagc catcaagggc   240
attcgagacc acttcaggct cgccgtcccg actcgcaacg tggtggtcat tcacactcag   300
cacgttcaca cactggtggg cttggagcac acccacctc tcttgcagac cggcctcttc   360
aaaaaggtcc ccgtcgacat ctacgtcttc aagtccggcg tcttcaccaa cctgggagac   420
ggaggcttca tcaactgggc atggggtggc ttcgtacagg aggtcgccgg caagcgtatc   480
cacttccgct tgcccccgg ggcgctccct                                    510

SEQ ID NO: 83         moltype = DNA  length = 513
FEATURE               Location/Qualifiers
misc_feature          1..513
                      note = IPD103 variant
source                1..513
                      mol_type = other DNA
                      organism = synthetic construct
SEQUENCE: 83
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccagacaa tggcgcgtca cttcaactct acgagggtgg tgcgggatga agccatcaag   240
agcattcgag accacttcag ggccgccgtc ccgactcgca acgtggtggt cgttcacacc   300
cagcacattc acacactgga gggcttggag cacacccacc tcgtcttgca gaccggcctc   360
ttcaaaaagg tccccgtcga catctacgtc ttcaagtccg gcgtcttcac caaccttgga   420
gacggaggct tcatcaactg gcatggggt ggcttcgtcg accaggtcgt cggcaagcgt   480
atccacttcc gcttgccccc cggggcgctc cct                              513

SEQ ID NO: 84         moltype = DNA  length = 513
FEATURE               Location/Qualifiers
misc_feature          1..513
                      note = IPD103 variant
source                1..513
                      mol_type = other DNA
                      organism = synthetic construct
SEQUENCE: 84
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttcgcgtcaa tgatcaaaca ctacaactct acgagggtg tgcgggatga agccatcaag   240
ggcattcgag accacttcag ggccgccgtc ccgactcgca acgtggtggt cgttcacact   300
cagcacgttc acacactggt gggcttggag cacacccacc tcgtcttgca gaccggcctc   360
ttcaaaaagg tccccgtcga catctacgtc ttcaagtccg gcgtcttcac cctccttgga   420
gacggaggct tcatcaactg gcatggggt ggctacggcg tcaaccacac cgccaagcgt   480
gtcgtcttca gccggccccc cggggcgctc cct                              513

SEQ ID NO: 85         moltype = DNA  length = 519
FEATURE               Location/Qualifiers
misc_feature          1..519
                      note = IPD103 variant
source                1..519
                      mol_type = other DNA
                      organism = synthetic construct
SEQUENCE: 85
atggcggacg aagtagcagg tcaccatggt ccagcatgtg aagaagagga ggaggaaatg    60
```

```
ctgatggacg agactgaggc ggtggggacg cacctggact tcgtggcggg cttggaggtg   120
caaccccgca aggtcatcac cgtggaggtg gacgccgctg ccgtaatcca gcagatcaga   180
gagatcttcc gaaccatggc aagtcacttc aactctacga gggtggtgcg ggatgaagcc   240
atcaagggca ttcgagacca cttcaggggcc gccgtcccga ctcgcaacgt ggtggtcgtt   300
cacacccagc acattcacac actggagggc ttggagcaca cccacctcgt cttgcggacc   360
ggcctgttca aaaaggtccc tgtcgacatc tttgtcttca agtccggcgt cttcaccaac   420
cttggagacg gaggcttcat caactgggca tggggtggct acgtacagga ggtcgccggc   480
aagcgtatcc acttccgctt gccccccggg gcgctccct                          519

SEQ ID NO: 86            moltype = DNA    length = 522
FEATURE                  Location/Qualifiers
misc_feature             1..522
                         note = IPD103 variant
source                   1..522
                         mol_type = other DNA
                         organism = synthetic construct
SEQUENCE: 86
atggcggacg aagtagcagg tcaccatggt ccagcatgtg aagaagagga ggaggaaatg   60
ctgatggacg agactgaggc ggtggggacg cacctggact tcttgggcgc ggacgtgaag   120
ttgcaacccc gcaacatcat caccgtggag gtggacgcgg ctgccgtaat ccaacagatc   180
agagagatct tccagacaat ggcgcgtcac ttcaactcga cgagggtggt gcgggatgaa   240
gccatcaagg gcattcgaga ccacttcagg gccgccgtcc cgactcgcaa cgtggtggtc   300
gttcacaccc agcacattca cactggaggg cttggagc acaccaacct cgtcttgcag     360
accggcctct tcaaaaaggt ccccgtcgac atctatgtct tcaagtccgg cgtcttcacc   420
aaccttggag acgaggctt catcaactgg gcatggggtg gcttcgtaca ggaggtcgcc    480
ggcaagcgta tccacttccg cttgccccccc ggggcgctcc ct                     522

SEQ ID NO: 87            moltype = DNA    length = 516
FEATURE                  Location/Qualifiers
misc_feature             1..516
                         note = IPD103 variant
source                   1..516
                         mol_type = other DNA
                         organism = synthetic construct
SEQUENCE: 87
atggcggaca aagcagcagc agcagctaga gaagctgaag aagaggtgca ggagactttg   60
atggacgaga ctgaggcggt ggggacgcac ctggacttcg tggcgggctt ggaggtgcaa   120
ccccgcaagg tcatcaccgt ggaggtggac gcggctgccg taatccaaca gatcagagag   180
atcttccaga caatggcgcg tcacttcaac tcgacgaggg tggtgcggga tgaagccatc   240
aagggcattc gagaccactt cagggccgcc gtcccgactc gcaacgtggt ggtcattcac   300
actcagcacg ttcacacact ggacgccgtg gagtcctccc acctcgtctt gcggaccggc   360
ctgttcaaaa aggtccctgt cgacatctat gtcttcaagt ccggcgtctt caccaacctt   420
ggagacggag gcttcatcaa ctgggcatgg ggtggctacg tcgaccaggt cgtcggcaag   480
cgtatccact tccgcttgcc ccccggggcg ctccct                             516

SEQ ID NO: 88            moltype = DNA    length = 513
FEATURE                  Location/Qualifiers
misc_feature             1..513
                         note = IPD103 variant
source                   1..513
                         mol_type = other DNA
                         organism = synthetic construct
SEQUENCE: 88
atggcggaca aagcagcagc agcagctaga gaagctgaag aagaggtgga gacgacgatg   60
gacgagactg aggcggtggg gacgcacctg gacttcgtg cgggcttgga ggtgcaaccc    120
cgcaaggtca tcaccgtgga ggtggacgcg ctgccgtaa tccaacagat cagagagatc    180
ttccagacaa tggcgcgtca cttcaactct acgagggtgg tgcggatga agccatcaag    240
agcattcgag accacttcag gccgccgtc ccgactcgca acgtggtggt cattcacact    300
cagcacgttc acacactgga ggcttggag cacaccacc tcgtcttgca gaccggcctc    360
ttcaaaaagg tccccgtcga catctatgtc ttcaagtccg cgtcttcac caacctggga    420
gacggaggct tcatcaactg gcatggggt ggcttcgtac aggaggtcg cggcaagcgt     480
atccacttcc gcttgccccc cggggcgctc cct                                513

SEQ ID NO: 89            moltype = DNA    length = 513
FEATURE                  Location/Qualifiers
misc_feature             1..513
                         note = IPD103 variant
source                   1..513
                         mol_type = other DNA
                         organism = synthetic construct
SEQUENCE: 89
atggccgacc agcaacagc agctagagaa gctgaagaag ggtgcagga ctttgatg       60
gacgagactg aggcggtggg gacgcacctg gacttcgtg cgggcttgga ggtgcaaccc    120
cgcaaggtca tcaccgtgga ggtggacgcg ctgccgtaa tccaacagat cagagagatc    180
ttccgaacca tggcaagtca cttcaactcg acgagggtgg tgcggatga agccatcaag    240
ggcattcgag accacttcag ggccgccgtc ccgactcgca acgtggtggt cattcacact    300
cagcacgttc acacactgga cgccgtgag tcctcccacc tcgtcttgca gaccggcctc    360
ttcaaaaagg tccccgtcga catctatgtc ttcaagtccg cgtcttcac caacctggga    420
gacggaggct tcatcaactg gcatggggt ggcttcgtac accaggtcgt cggcaagcgt    480
```

```
atccacttcc gcttgccccc cggggcgctc cct                                513
```

SEQ ID NO: 90            moltype = DNA   length = 519
FEATURE                  Location/Qualifiers
misc_feature             1..519
                         note = IPD103 variant
source                   1..519
                         mol_type = other DNA
                         organism = synthetic construct
SEQUENCE: 90
```
atggcggacg aagtagcagg tcaccatggt ccagcatgtg aagaagaggt gcaggagact   60
ttgatggacg agactgaggc ggtggggacg cacctggact tcgtggcggg cttggaggtg  120
caaccccgca gcatcatcac cgtggaggtg gacgccgctg ccgtaatcca acagatcaga  180
gagatcttcc agacaatggc gcgtcacttc aactctacga gggtggtgcg ggatgaagcc  240
atcaagggca ttcgagacca cttcaggctc gccgtcccga ctcgcaacgt ggtggtcgtt  300
cacacccagc acgttcacac actggtgggc ttggagcaca cccacctcgt cttgcagacc  360
ggcatcttca aaaaggtccc cgtcgacatc tatgtcttca agtccggcgt cttcaccaac  420
ctgggagacg gaggcttcat caactgggca tggggtggct cgtcgacca ggtcgtcggc  480
aagcgtatcc acttccgctt gccccccggg gcgctccct                         519
```

SEQ ID NO: 91            moltype = DNA   length = 519
FEATURE                  Location/Qualifiers
misc_feature             1..519
                         note = IPD103 variant
source                   1..519
                         mol_type = other DNA
                         organism = synthetic construct
SEQUENCE: 91
```
aaggcggacg aagtagcagg tcaccatggt ccagcatgtg aagaagagga ggaggaaatg   60
ctgatggacg agactgaggc ggtggggacg cacctggact tcgtggcggg cttggaggtg  120
caaccccgca aggtcatcac cgtggaggtg gacgccgctg ccgtaatcca acagatcaga  180
gagatcttcc gaaccatggc aagtcactac aactctacga gggtggtgcg ggatgaagcc  240
atcaagggca ttcgagacca cttcaggccc gccgtcccga ctcgcaacgt ggtggtcatt  300
cacactcagc acgttcacac actggcgcc gtggagtcc cccacctcgt cttgcagacc  360
ggcatcttca aaaaggtccc cgtcgacatc tacgtcttca agtccggcgt cttcaccaac  420
ctgggagacg gaggcttcat caactgggca tggggtggct cgtcgacca ggtcgtcggc  480
aagcgtatcc acttccgctt gccccccggg gcgctccct                         519
```

SEQ ID NO: 92            moltype = DNA   length = 522
FEATURE                  Location/Qualifiers
misc_feature             1..522
                         note = IPD103 variant
source                   1..522
                         mol_type = other DNA
                         organism = synthetic construct
SEQUENCE: 92
```
atggcggacg aagtagcagg tcaccatggt ccagcatgtg aagaagagga ggaggaaatg   60
ctgatggacg agactgaggc ggtggggacg cacctggact tcttgggcgc ggacgtgaag  120
ttgcaaccccc gcaacatcat caccgtggag gtggacgcgg ctgccgtaat ccagcagatc  180
agagagatct tccagacaat ggcgcgtcac ttcaactcta cgagggtggt gcgggatgaa  240
gccatcaagg gcattcgaga ccacttcagg ccgccgtcc cgactcgcaa cgtggtgtcg  300
attcacactc agcacgttca cacactggac gccgtggagt cctcccacct cgtcttgcgg  360
accggcctgt tcaaaaaggt ccctgtcgac atctatgtct tcaagtccgg cgtcttcacc  420
aacctggag acgaggctt catcaactgg gcatggggtg gcttcgtcga ccaggtcgtc  480
ggcaagcgta tccacttccg cttgccccc ggggcgctcc ct                      522
```

SEQ ID NO: 93            moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 93
```
atggcggacg aagtagcagg tcaccatggt ccagcatgtg aagaagagga ggaggaaatg   60
ctgatggacg agactgaggc ggtggggggtg cacgcgatcg acgtctgcc ggtgcaaaac  120
cgcagcatca tcaccgtgga ggtggacgcc gctgccgtaa tccagcagat cagagagatc  180
ttccgaacca tggcaagtca cttcaactcg acgagggtgt gcgggatga agccatcaag  240
agcattcgag accacttcag gctcgccgtc ccgactcgca acgtggtggt cgttcacact  300
cagcacgttc acacactggt gggcttggag cacacccacc tcgtcttgcg gaccggcctc  360
ttcaaaaagg tccccgtcga catctacgtc ttcaagtccg gcgtcttcac cctccttgga  420
gacgaggct tcatcaactg ggcatggggt ggcttcgtac aggaggtcgc cggcaagcgt  480
atccacttcc gcttgccccc cggggcgctc cct                               513
```

SEQ ID NO: 94            moltype = DNA   length = 516
FEATURE                  Location/Qualifiers
misc_feature             1..516
                         note = IPD103 variant
source                   1..516

```
                        mol_type = other DNA
                        organism = synthetic construct
SEQUENCE: 94
atggcggacg aagtagcagg tcaccatggt ccagcatgtg aagaagaggt ggagacgacg    60
atggacgaga ctgaggcggt ggggacgcac ctgacttcg tggcgggctt ggaggtgcaa    120
ccccgcaagg tcatcaccgt ggaggtggac gcggctgccg taatccaaca gatcagagag   180
atcttccaga caatggcgcg tcacttcaac tctacgaggg tggtgcggga tgaagccatc   240
aagagcattc gagaccactt cagggccgcc gtcccgactc gcaacgtggt ggtcattcac   300
actcagcac ttcacacact ggagggcttg gagcacacca acctcgtctt gcagaccggc   360
atcttcaaaa aggtccccgt cgacatctac gtcttcaagt ccggcgtctt caccaacctg   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 95           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 95
atggcggacg aagtagcagg tcaccatggt ccagcatgtg aagaagagga ggagaaatg     60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcggatga agccatcaag   240
agcattcgag accacttcag ggccgccgtc ccgactcgca acgtggtgt cgttcacact   300
cagcacgttc acacactgga cgccgtggag tcctcccacc tcgtcttgcg gaccggcctg   360
ttcaaaaagg tccctgtcga catctacgtc ttcaagtccg gcgtcttcac caaccttgga   420
gacgaggct tcatcaactg gcatggggt ggcttcgtcg accaggtcgt cggcaagcgt    480
atccacttcc gcttgccccc cggggcgctc cct                                513

SEQ ID NO: 96           moltype = DNA  length = 517
FEATURE                 Location/Qualifiers
misc_feature            1..517
                        note = IPD103 variant
misc_feature            469
                        note = n is a, c, g, or t
misc_feature            494
                        note = n is a, c, g, or t
source                  1..517
                        mol_type = other DNA
                        organism = synthetic construct
SEQUENCE: 96
atggcggacg aagtagcagg tcaccatggt ccagcactga agaagaggag agagagatgg    60
atgatgacg agacgagacg aggcggtgca cctgcacgtg atcgccgtc tggaggtgca    120
accccgcagc atcatcaccg tggaggtgga cgccgctgcc gtaatccagc agatcagaga   180
gatcttccag acaatggcga gtcacttcaa ctctacgagg gtggtgcgga atgaagccat   240
caagggcatt cgagaccact tcagggccgc cgtcccgact cgcaacgtgg tggtcattca   300
cactcagcac gttcacacac tggaggccgt ggagtcctcc cacctcgtct tgcggaccgg   360
cctgttcaaa aaggtccctg tcgacatcta cgtcttcaag tccggcgtct tcaccctcct   420
tggagacgga ggcttcatca actgggcatg ggtggcttc gtcgtccang tcgtcggcaa    480
gcgtgtccac ttcngccggc ccccggggc gctccct                             517

SEQ ID NO: 97           moltype = DNA  length = 513
FEATURE                 Location/Qualifiers
misc_feature            1..513
                        note = IPD103 variant
misc_feature            412
                        note = n is a, c, g, or t
source                  1..513
                        mol_type = other DNA
                        organism = synthetic construct
SEQUENCE: 97
atggcggacc cagcaacagc agctagagaa gctgaagaag aggtgcagga gactttgatg    60
gacgagagtg aggcggtggg gacgcacctg gacttcgtgg cgggcttgga ggtgcaaccc   120
cgcaaggtca tcaccgtgga ggtggacgcc gctgccgtaa tccatcagat cagagagatc   180
ttccagacaa tggcgcgtca cttcaactct acgaggtgg tgcggatga agccatcaag    240
ggcatttgag accacttcag gccgctgtc ccgactcgca acgtggtggt cattcactcc    300
cagcacattc acacactgga gggcttggag cacaccaacc tcgtcttgca gaccggcatg   360
ttcaaaaagg tccccgtcga catctttgtc ttcaagtccg gcgtcttcac cntccttgga   420
gacgaggct tcatcaactg gcatggggt ggcttcgtac aggaggtcgt cggcaagcgt    480
atccacttcc gcttgccccc cggggcgctc cct                                513

SEQ ID NO: 98           moltype = DNA  length = 513
FEATURE                 Location/Qualifiers
misc_feature            1..513
                        note = IPD103 variant
source                  1..513
                        mol_type = other DNA
```

```
                        organism = synthetic construct
SEQUENCE: 98
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacattc acacactgga gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcggcg tcaaccacac cgccaagcgt   480
gtcgtcttca gccggccccc cggggcgctc cct                                513

SEQ ID NO: 99           moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 99
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
agcattcgag accacttcag ggccgccgtc ccgactcgca acgtggtggt cattcacact   300
cagcacgttc acacactgga cgccgtggag tcctcccacc tcgtcttgca gaccggcctc   360
ttcaaaaagg tccccgtcga catctttgtc ttcaagtccg gcgtcttcac caacctggga   420
gacggaggct tcatcaactg gcatggggt ggctacggcg tcaaccacac cgccaagcgt   480
gtcgtcttca gccggccccc cggggcgctc cct                                513

SEQ ID NO: 100          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 100
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
agcattcgag accacttcag ggccgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctatgtc ttcaagtccg gcgtcttcac caacctggga   420
gacggaggct tcatcaactg gcatgggggt ggcttcgtcg accaggtcgt cggcaagcgt   480
atccacttcc gcttgccccc cggggcgctc cct                                513

SEQ ID NO: 101          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 101
atggcggaca aagcagcagc agcagctaga gaagctgaag aagaggtgca ggagactttg    60
atggacgaga ctgaggcggt ggggacgcac ctggacttct tgggcgcgga cgtgaagttg   120
caaccccgca aggtcatcac cgtggaggtg gacgccgtcc cgtaatccca acagatcaga   180
gagatcttcc gaaccatggc aagtcacttc aactcgacga gggtggtgcg ggatgaagcc   240
atcaagggca ttcgagacca cttcagggcc gccgtcccga ctcgcaacgt ggtggtcgtt   300
cacacccagc acattcacac actggagggc ttggagcaca ccaacctcgt cttgcagacc   360
ggcatcttca aaaggtcccc gtcgacatc tacgtcttca agtccggcgt cttcacccctc   420
cttggagacg gaggcttcat caactgggca tggggtggct cgtacagga ggtcgccggc   480
aagcgtatcc acttccgctt gccccccggg gcgctccct                          519

SEQ ID NO: 102          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 102
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
agcattcgag accacttcag gctcgccgtc ccgactcgca acgtggtggt cattcacact   300
```

```
cagcacgttc acacactgga cgccgtggag tcctcccacc tcgtcttgcg gaccggcctg   360
ttcaaaaagg tccctgtcga catctttgtc ttcaagtccg gcgtcttcac caacctggga   420
gacggaggct tcatcaactg gcatgggggt ggcttcgtac aggaggtcgc cggcaagcgt   480
atccacttcc gcttgccccc cggggcgctc cct                                513

SEQ ID NO: 103            moltype = DNA  length = 522
FEATURE                   Location/Qualifiers
misc_feature              1..522
                          note = IPD103 variant
source                    1..522
                          mol_type = other DNA
                          organism = synthetic construct
SEQUENCE: 103
atggcggacg aagtagcagg tcaccatggt ccagcatgtg aagaagagga ggaggaaatg   60
ctgatggacg agactgaggc ggtgggggacg cacctggact tcttgggcgc ggacgtgaag   120
ttgcaaccc gcaaggtcat caccgtggag gtggacgccg ctgccgtaat ccaacagatc   180
agagagatct tccgaaccat ggcaagtcac ttcaactcga cgagggtggt gcgggatgaa   240
gccatcaagg gcattcgaga ccacttcagg gccgccgtcc gactcgcaa cgtggtggtc   300
gttcacactc agcacgttca cacactggtg ggcttggagc acaccaccct cgtcttgcag   360
accggcctct tcaaaaaggt ccccgtcgac atctatgtct tcaagtccgg cgtcttcacc   420
aacctggag acgaggctt catcaactgg gcatggggtg gcttcgtcga ccaggtcgtc   480
ggcaagcgta tccacttccg cttgccccc ggggcgctcc ct                      522

SEQ ID NO: 104            moltype = DNA  length = 507
FEATURE                   Location/Qualifiers
misc_feature              1..507
                          note = IPD103 variant
source                    1..507
                          mol_type = other DNA
                          organism = synthetic construct
SEQUENCE: 104
atggcggacg aagtagcagc agcagctaga gaagctgaag aagaggtgga gacgacgatg   60
gacgagactg aggcggtggg ggtgcacgcg atcgacggtc tgccggtgca aaaccgcagc   120
atcatcaccg tggaggtgga cgccgctgcc gtaatccagc agatcagaga gatcttccga   180
accatggcaa gtcacttcaa ctcgacgagg gtggtgcggg atgaagccat caagggcatt   240
cgagaccact tcaggctcgc cgtcccgact cgcaacgtgg tggtcattca cactcagcac   300
gttcacacac tggtgggctt ggagcacacc cacctcgtct gcagaccgg catcttcaaa   360
aaggtccccg tcgacatcta tgtcttcaag tccggcgtct tcaccaacct ggagacgga   420
ggcttcatca actgggcatg gggtggcttc gtcgaccagg tcgtcggcaa gcgtatccac   480
ttccgcttgc ccccgggc gctccct                                         507

SEQ ID NO: 105            moltype = DNA  length = 513
FEATURE                   Location/Qualifiers
misc_feature              1..513
                          note = IPD103 variant
source                    1..513
                          mol_type = other DNA
                          organism = synthetic construct
SEQUENCE: 105
atggcggaca aagcagcagc agcagctaga gaagctgaag aagaggtgga gacgacgatg   60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctacgtc ttcaagtccg gcgtcttcac caacctggga   420
gacgaggct tcatcaactg gcatgggggt ggcttcggcg tcaaccacac cgccaagcgt   480
gtcgtcttca gccggccccc cggggcgctc cct                                513

SEQ ID NO: 106            moltype = DNA  length = 516
FEATURE                   Location/Qualifiers
misc_feature              1..516
                          note = IPD103 variant
source                    1..516
                          mol_type = other DNA
                          organism = synthetic construct
SEQUENCE: 106
atggcggaca aagcagcagc agcagctaga gaagctgaag aagaggtgga gacgacgatg   60
gacgagactg aggcggtggg gacgcacctg gacttcttgg gcgcggacgt gaagttgcaa   120
ccccgcaagg tcatcaccgt ggaggtggac gccgctgccg taatccagca gatcagagag   180
atcttccgaa ccatggcaag tcacttcaac tcgacgaggg tggtgcggga tgaagccatc   240
aagggcattt gagaccactt cagggccgcc gtcccgactc gcaacgtggt ggtcgttcac   300
acccagcaca ttcacacact ggagggcttg gagcacacca acctcgtctt gcagaccggc   360
ctcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccct                             516

SEQ ID NO: 107            moltype = DNA  length = 516
FEATURE                   Location/Qualifiers
```

```
misc_feature            1..516
                        note = IPD103 variant
source                  1..516
                        mol_type = other DNA
                        organism = synthetic construct
SEQUENCE: 107
atggcggacg aagtagcagg tcaccatggt ccagcatgtg aagaagaggt ggagacgacg      60
atggacgaga ctgaggcggt ggggacgcac ctggacttcg tggcgggctt ggaggtgcaa     120
ccccgcaagg tcatcaccgt ggaggtggac gccgctgccg taatccagca gatcagagag     180
atcttccgaa ccatggcaag tcacttcaac tctacgaggg tggtgcggga tgaagccatc     240
aagagcattc gagaccactt cagggccgcc gtcccgactc gcaacgtggt ggtcgttcac     300
actcagcacg ttcacacact ggtgggcttg agcacacca acctcgtctt gcagaccggc      360
atcttcaaaa aggtccccgt cgacatctat gtcttcaagt ccggcgtctt caccaacctt     420
ggagacggag gcttcatcaa ctgggcatgg ggtggcttcg tacaggaggc cgccggcaag     480
cgtatccact tccgcttgcc ccccggggcg ctccct                              516

SEQ ID NO: 108          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 108
atggcggaca aagcagcagc agcagctaga gaagctgaag aagaggcgga gacgacgatg      60
gacgagactg aggcggtggg gacgcacctg gagttcgtcg cgggcttgga ggtgcaaccc     120
cgcagcatca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accccttcag gccgccgtc ccgactcgca acgtggtggt cgttcactcc      300
cagcacattc acacactggt gggcttggag cacacccacc tcgtgttgca gaccggctc      360
ttcaaaaagg tccccgtcga catctatctc ttcaagtccg gcgtcttcac cctccttgga     420
gacgaggct tcatcaactg gcatgggggt ggcttcgtac agcaggtcgc cggcaagcgt      480
atccacttcc gcttgccccc cggggcggtc ccc                                 513

SEQ ID NO: 109          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 109
atagccgacc cagcaacagc agctagagaa gctgaagaag aggtgcagga gactttgatg      60
gacgagactg aggcggtggg gacgcacctg gacttcgtgg cgggcttgga ggtgcaaccc     120
cgcaaggtca tcaccgtgga ggtggacgcc gctgccgtaa tccagcagat cagagagatc     180
ttccgaacca tggcaagtca cttcaactcg acgagggtgg tgcgggatga agccatcaag     240
ggcattcgag accacttcag ggccgccgtc ccgactcgca acgtggtggt cattcacact     300
cagcacgttc acacactggt gggcttggag cacacccacc tcgtcttgca gaccggcctc     360
ttcaaaaagg tccccgtcga catctacgtc ttcaagtccg gcgtcttcac cctccttgga     420
gacgaggct tcatcaactg gcatgggggt ggcttcgtac aggaggtcgc cggcaagcgt      480
atccacttcc gcttgccccc cggggcgctc cct                                 513

SEQ ID NO: 110          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 110
atggccgacc cagcaacagc agcagctaga gaagatgaag aagaggtgga gactttgatg      60
gacgagactg aggcggtggg gacgcacctg gacttcgtgg cgggcttgga ggtgcaaccc     120
cgcaacatca tcaccgtgga ggtggacgcc gctgccgtaa tccaacagat cagagagatc     180
ttccgaacca tggcaagtca cttcaactct acgagggtgg tgcgggatga agccatcaag     240
ggcattcgag accacttcag ggccgccgtc ccgactcgca acgtggtggt cattcacact     300
cagcacgttc acacactggt gggcttggag cacacccacc tcgttttgca gaccggcatc     360
ttcaaaaagg tccccgtcga catctatgtc ttcaagtccg gcgtcttcac caaccttgga     420
gacgaggct tcatcaactg gcatgggggt ggcttcgtac aggaggtcgc cggcaagcgt      480
gtcctcttca gccggccccc cggggcgctc cct                                 513

SEQ ID NO: 111          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 111
atggcggacg aagtagcagg tcaccatggt ccagcatgtg aagaagagga ggaggaaatg      60
```

```
ctgatggacg agactgaggc ggtgggggtg cacgcgatcg acggtctgcc ggtgcaaccc  120
cgcaaggtca tcaccgtgga ggtggacgcc gctgccgtaa tccagcagat cagagagatc  180
ttccgaacca tggcaagtca cttcaactcg acgagggtgg tgcgggatga agccatcaag  240
ggcattcgag accacttcag ggccgccgtc ccgactcgca acgtggtggt cattcacact  300
cagcacgttc acacactgga cgccgtggag tcctcccaca tcgtcttgcg gaccggcctg  360
ttcaaaaagg tccctgtcga catctttgtc ttcaagtccg cgtcttcac caaccttgga  420
gacggaggct tcatcaactg gcatggggt ggctacggcg tcaaccacac cgccaagcgt  480
gtcgtcttca gccggccccc cggggcgctc cct                                513

SEQ ID NO: 112           moltype = DNA  length = 513
FEATURE                  Location/Qualifiers
misc_feature             1..513
                         note = IPD103 variant
source                   1..513
                         mol_type = other DNA
                         organism = synthetic construct
SEQUENCE: 112
atggccgacc cagcaacagc agctagagaa gctgaagaag aggtgcagga gactttgatg  60
gacgagactg aggcggtggg gacgcacctg gacttcgtgg cgggcttgga ggtgcaaccc  120
cgcaaggtca tcaccgtgga ggtggacgcc gctgccgtaa tccagcagat cagagagatc  180
ttccagacaa tggcgcgtca cttcaactct acgagggtgg tgcgggatga agccatcaag  240
ggcattcgag accacttcag ggccgccgtc ccgactcgca acgtggtggt cgttcacacc  300
cagcacattc acacactggt gggcttggag cacaccaacc tcgtcttgca gaccggcctc  360
ttcaaaaagg tccccgtcga catctacgtc ttcaagtccg cgtcttcac cctccttgga  420
gacggaggct tcatcaactg gcatggggt ggcttcgtac aggaggtcgc cggcaagcgt  480
atccacttcc gcttgccccc cggggcgctc cct                                513

SEQ ID NO: 113           moltype = DNA  length = 513
FEATURE                  Location/Qualifiers
misc_feature             1..513
                         note = IPD103 variant
source                   1..513
                         mol_type = other DNA
                         organism = synthetic construct
SEQUENCE: 113
atggcggaca aagcagcagc agcagctaga gaagctgaag aagaggtgga gacgacgatg  60
gacgagactg aggcggtggg gacgcacctg gacttcgtgg cgggcttgga ggtgcaaccc  120
cgcaaggtca tcaccgtgga ggtggacgcc gctgccgtaa tccagcagat cagagagatc  180
ttccgaacca tggcaagtca cttcaactcg acgagggtgg tgcgggatga agccatcaag  240
ggcattcgag accacttcag ggccgccgtc ccgactcgca acgtggtggt cgttcacacc  300
cagcacattc acacactgga gggcttggag cacaccaacc tcgtcttgca gaccggcctc  360
ttcaaaaagg tccccgtcga catctacgtc ttcaagtccg cgtcttcac cctccttgga  420
gacggaggct tcatcaactg gcatggggt ggcttcgtac aggaggtcgc cggcaagcgt  480
atccacttcc gcttgccccc cggggcgctc cct                                513

SEQ ID NO: 114           moltype = DNA  length = 516
FEATURE                  Location/Qualifiers
misc_feature             1..516
                         note = IPD103 variant
source                   1..516
                         mol_type = other DNA
                         organism = synthetic construct
SEQUENCE: 114
atggcggaca aagcagcagc agcagctaga gaagctgaag aagaggtgga gacgacgatg  60
gacgagactg aggcggtggg gacgcacctg gacttcttgg gcgcggacgt gaagttgcaa  120
ccccgcaagg tcatcaccgt ggaggtggca gccgctgccg taatccagca gatcagagag  180
atcttccgaa ccatggcaag tcacttcaac tcgacgaggg tggtgcggga tgaagccatc  240
aagggcattc gagaccactt cagggccgcc gtcccgactc gcaacgtggt ggtcgttcac  300
acccacgacg ttcacacact ggtgggcttg gagcacacct ccgtcgtctt gcagaccggc  360
atcttcaaaa aggtccccgt cgacatctac gtcttcaagt ccggcgtctt caccaacctt  420
ggagacggag gcttcatcaa ctgggcatgg ggtggcttcg tacaggaggt cgccggcaag  480
cgtatccact tccgcttgcc ccccggggcg ctccct                            516

SEQ ID NO: 115           moltype = DNA  length = 513
FEATURE                  Location/Qualifiers
misc_feature             1..513
                         note = IPD103 variant
source                   1..513
                         mol_type = other DNA
                         organism = synthetic construct
SEQUENCE: 115
atggcggaca aagcagcagc agcagctaga gaagctgaag aagaggtgga gacgacgatg  60
gacgagactg aggcggtggg gacgcacctg gacttcgtgg cgggcttgga ggtgcaaccc  120
cgcaaggtca tcaccgtgga ggtggacgcg gctgccgtaa tccaacagat cagagagatc  180
ttccagacaa tggcgcgtca cttcaactct acgagggtgg tgcgggatga agccatcaag  240
ggcattcgag accacttcag ggccgccgtc ccgactcgca acgtggtggt cgttcacacc  300
cagcacattc acacactgga gggcttggag cacacccacc tcgtcttgca gaccggcctc  360
ttcaaaaagg tccccgtcga catctatgtc ttcaagtccg cgtcttcac caaccttgga  420
gacggaggct tcatcaactg gcatggggt ggcttcgtcg accaggtcgt cggcaagcgt  480
```

```
atccacttcc gcttgccccc cggggcgctc cct                                513
```

SEQ ID NO: 116         moltype = DNA  length = 510
FEATURE                Location/Qualifiers
misc_feature           1..510
                       note = IPD103 variant
source                 1..510
                       mol_type = other DNA
                       organism = synthetic construct
SEQUENCE: 116
```
atggccgacc cagcaacagc agctagagaa gctgaagaag aggtggagac gacgatggac   60
gagactgagg cggtggggac gcacctggac ttcgtggcgg gcttggaggt gcaaccccgc  120
aaggtcatca ccgtggaggt ggacgccgct gccgtaatcc aacagatcag agagatcttc  180
cagacaatgg cgcgtcactt caactctacg agggtggtgc gggatgaagc catcaagggc  240
attcgagacc acttcagggc cgccgtcccg actcgcaacg tggtggtcat tcacactcag  300
cacgttcaca cactggaggg cttggagcac accaacctcg tcttgcagac cggcatcttc  360
aaaaaggtcc ccgtcgacat ctacgtcttc aagtccggcg tcttcaccct ccttggagac  420
ggaggcttca tcaactgggc atggggtggc ttcgtacagg aggtcgccgg caagcgtatc  480
cacttccgct tgccccccgg ggcgctccct                                   510
```

SEQ ID NO: 117         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 117
```
atggcggaca aagcagcagc agcagctaga gaagctgaag aagaggtgca ggagactttg   60
atggacgaga ctgaggcggt ggggacgcac ctggacttcg tggcgggctt ggaggtgcaa  120
ccccgcaagg tcataccgt ggaggtggac gccgctgccg taatccaaca gatcagagag  180
atcttccgaa ccatggcaag tcacttcaac tcgacgaggg tggtgcggga tgaagccatc  240
aagggcattc gagaccactt cagggccgcc gtcccgactc gcaacgtggt ggtcgttcac  300
actcagcacg ttcacacatt ggagggcttg gagcacaccc acctcgtctt gcagaccggc  360
ctcttcaaaa aggtccccgt cgacatctat gtcttcaagt ccggcgtctt caccaacctt  420
ggagacggag gcttcatcaa ctgggcatgg ggtggcttcg tacaggaggt cgccggcaag  480
cgtatccact tccgcttgcc ccccggggcg ctccct                            516
```

SEQ ID NO: 118         moltype = DNA  length = 510
FEATURE                Location/Qualifiers
misc_feature           1..510
                       note = IPD103 variant
source                 1..510
                       mol_type = other DNA
                       organism = synthetic construct
SEQUENCE: 118
```
atggccgacc cagcaacagc agctagagaa gctgaagaag aggtggagac gacgatggac   60
gagactgagg cggtggggac gcacctggac ttcgtggcgg gcttggaggt gcaaccccgc  120
aacatcatca ccgtggaggt ggacgcggct gccgtaatcc agcagatcag agagatcttc  180
cagacaatgg cgagtcactt caactcgacg agggtggtgc gggatgaagc catcaagggc  240
attcgagacc acttcagggc cgccgtcccg actcgcaacg tggtggtcgt tcacacccag  300
cacattcaca cactggtggg cttggagcac acccacctcg tcttgcagac cggcctcttc  360
aaaaaggtcc ccgtcgacat ctacgtcttc aagtccggcg tcttcaccct ccttggagac  420
ggaggcttca tcaactgggc atggggtggc ttcgtacagg aggtcgccgg caagcgtatc  480
cacttccgct tgccccccgg ggcgctccct                                   510
```

SEQ ID NO: 119         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 119
```
atggccgacc cagcaacagc agctagagaa gctgaagaag aggtgcagga gactttgatg   60
gacgagactg aggcggtggg gacgcacctg gacttcttgg gcgcggacgt gaagttgcaa  120
ccccgcaaca tcatcaccgt ggaggtggac gccgctgccg taatccaaca gatcagagag  180
atcttccaga caatggcgcg tcacttcaac tctacgaggg tggtgcggga tgaagccatc  240
aagggcattc gagaccactt cagggccgcc gtcccgactc gcaacgtggt ggtcgttcac  300
actcagcacg ttcacacact ggtgggcttg gagcacaccc acctcgtctt gcagaccggc  360
ctcttcaaaa aggtccccgt cgacatctac gtcttcaagt ccggcgtctt caccctcctt  420
ggagacggag gcttcatcaa ctgggcatgg ggtggcttcg tacaggaggt cgccggcaag  480
cgtatccact tccgcttgcc ccccggggcg ctccct                            516
```

SEQ ID NO: 120         moltype = DNA  length = 513
FEATURE                Location/Qualifiers
misc_feature           1..513
                       note = IPD103 variant
source                 1..513

```
                        mol_type = other DNA
                        organism = synthetic construct
SEQUENCE: 120
atggcggaca aagcagcagc agcagctaga gaagctgaag aagaggtgga gacgacgatg   60
gacgagactg aggcggtggg gacgcacctg gacttcgtcg cgggcttgga ggtgcaaccc  120
cgcaaggtca tcaccgtgga ggtggacgcc gctgccgtaa tccagcagat cagagagatc  180
ttccgaacca tggcaagtca cttcaactcg acgagggtgg tgcgggatga agccatcaag  240
ggcattcgag accacttcag gccgccgtc ccgactcgca acgtggtggt cattcacacc  300
cagcacgttc acacactggt gggcttggag cacacccacc tcgtcttgca gaccggcctc  360
ttcaaaaagg tccccgtcga catctatgtc ttcaagtccg gcgtcttcac cctccttgga  420
gacgaggct tcatcaactg gcatggggt ggcttcgtcg accaggtcgt cggcaagcgt  480
atccacttcc gcttgccccc cggggcgctc cct                              513

SEQ ID NO: 121          moltype = DNA   length = 510
FEATURE                 Location/Qualifiers
misc_feature            1..510
                        note = IPD103 variant
source                  1..510
                        mol_type = other DNA
                        organism = synthetic construct
SEQUENCE: 121
atggccgacc cagcagcagc agctagagaa gctgaagaag aggtggagac gacgatggac   60
gagactgagg cggtggggac gcacctggac ttcgtggcgg gcttggaggt gcaaccccgc  120
aacatcatca ccgtggaggt ggacgcggct gccgtaatcc aacagatcag cgagatcttc  180
cgaaccatgc aagtcacttt caactcgacg agggtggtgc gggatgaagc catcaagggc  240
attcgagacc acttcaggc cgccgtcccg actcgcaacg tggtgtcg tcacaccag  300
cacattcaca cactggaggg cttggagcac acccacctcg tcttgcagac cggcatcttc  360
aaaaaggtcc ccgtcgacat ctacgtcttc aagtccggcg tcttcacccc ccttggagac  420
ggaggcttca tcaactgggc atgggtggc ttcgtcgacc aggtcgtcgg caagcgtatc  480
cacttccgct tgccccccgg ggcgctccct                                  510

SEQ ID NO: 122          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 122
atggcggaca aagcagcagc agcagctaga gaagctgaag aagaggtgga gacgacgatg   60
gacgagactg aggcggtggg gacgcacctg gacttcttgg gcgcggacgt gaagttgcaa  120
ccccgcaaca tcatcaccgt ggaggtggac gcggctgccg taatccaaca gatcagagag  180
atcttccaga caatgcgcg tcacttcaac tcgacgaggg ttgtgcggga tgaagccatc  240
aagggcattc gagaccactt cagggccgcc gtcccgactc gcaacgtggt ggtcgttcac  300
acccagcaca ttcacacact ggagggcttg agcacacca acctcgtctt gcagaccggc  360
ctcttcaaaa aggtccccgt cgacatctac gtcttcaagt ccggcgtctt caccctcctt  420
ggagacggag gcttcatcaa ctgggcatgg gtggcttcg tcgaccaggt cgtcggcaag  480
cgtatccact tccgcttgcc cccggggcg ctccct                            516

SEQ ID NO: 123          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 123
atggcggaca aagcagcagc agcagctaga gaagctgaag aagaggtgca ggagactttg   60
atggacgaga ctgaggcggt ggggacgcac ctggacttcg tggcgggctt ggaggtgcaa  120
ccccgcaagg tcatcaccgt ggaggtggac gccgctgccg taatccagca gatcagagag  180
atcttccgaa ccatggcaag tcacttcaac tcgacgaggg tggtgcggga tgaagccatc  240
aagggcattc gagaccactt cagggccgcc gtcccgactc gcaacgtggt ggtcattcac  300
actcagcacg ttcacacact ggagggcttg agcacaccc acctcgtctt gcagaccggc  360
ctcttcaaaa aggtccccgt cgacatctac gtcttcaagt ccggcgtctt caccctcctt  420
ggagacggag gcttcatcaa ctgggcatgg gtggcttcg tcgaccaggt cgtcggcaag  480
cgtatccact tccgcttgcc cccggggcg ctccct                            516

SEQ ID NO: 124          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 124
atggcggaca aagcagcagc agcagctaga gaagctgaag aagaggtgga gacgacgatg   60
gacgagactg aggcggtggg gacgcacctg gacttcgtgg cgggcttgga ggtgcaaccc  120
cgcaaggtca tcaccgtgga ggtggacgcc gctgccgtaa tccagcagat cagagagatc  180
ttccgaacca tggcaagtca cttcaactcg acgagggtgg tgcgggatga agccatcaag  240
```

```
ggcattcgag accacttcag ggccgccgtc ccgactcgca acgtggtggt cgttcacacc   300
cagcacattc acacactggt gggcttggag cacacccacc tcgtcttgca gaccggcatc   360
ttcaaaaagg tccccgtcga catctacgtc ttcaagtccg gcgtcttcac caaccttgga   420
gacgaggct tcatcaactg gcatggggt ggcttcgtac aggaggtcgc cggcaagcgt    480
atccacttcc gcttgccccc cggggcgctc cct                                513

SEQ ID NO: 125          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 125
atggcggaca aagcagcagc agcagctaga gaagctgaag aagaggtgga gacgacgatg   60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccgaa ccatggcaag tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
atcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccct                             516

SEQ ID NO: 126          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 126
atggcggaca aagcagcagc agcagctaga gaagctgaag aagaggtgga gacgacgatg   60
gacgagactg aggcggtggg gacgcacctg gacttcttgg gcgcggacgt gaagttgcaa   120
ccccgcaaca tcatcaccgt ggaggtggac gcggctggac gcggctgccg taatccaaca gatcagagag   180
atcttccaga caatgcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
atcttcaaaa aggtcccgt cgacatctac gtcttcaagt ccggcgtctt cacccctctt    420
ggagacggag gcttcatcaa ctgggcatgg ggtggcttcg tacaggaggt cgccggcaag   480
cgtatccact tccgcttgcc ccccggggcg ctccct                             516

SEQ ID NO: 127          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 127
atggcggaca aagcagcagc agcagctaga gaagctgaag aagaggtgga gacgacgatg   60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgaggtgg tgcgggatga agccatcaag   240
ggcattcgag accacttcag ggccgccgtc ccgactcgca acgtggtggt cgttcacacc   300
cagcacattc acacactgga gggcttggag cacacccacc tcgtcttgca gaccggcctc   360
ttcaaaaagg tccccgtcga catctacgtc ttcaagtccg gcgtcttcac caaccttgga   420
gacgaggct tcatcaactg gcatggggt ggcttcgtac aggaggtcgc cggcaagcgt    480
atccacttcc gcttgccccc cggggcgctc cct                                513

SEQ ID NO: 128          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 128
atggcggaca aagcagcagc agcagctaga gaagctgaag aagaggtgca ggagactttg   60
atggacgaga ctgaggcggt ggggacgcac ctggacttct tgggcgcgga cgtgaagttg   120
caaccccgca acatcatcac cgtggaggtg acgccgctg ccgtaatcca gcagatcaga    180
gagatcttcc gaaccatggc aagtcacttc aactctacga gggtggtgcg gatgaagcc   240
atcaaggcca ttcgagacca cttcagggcc gccgtcccga ctcgcaacgt ggtggtcgtt   300
cacacccagc acattcacac actgagggc ttggagcaca ccaccctcgt cttgcagacc    360
ggcctcttca aaaaggtccc cgtcgacatc tacgtcttca gtccggcgt cttcaccctc    420
cttggagacg gaggcttcat caactgggca tggggtggct tcgtacagga ggtcgccggc   480
aagcgtatcc acttccgctt gccccccggg gcgctccct                          519

SEQ ID NO: 129          moltype = DNA  length = 510
```

```
FEATURE                 Location/Qualifiers
misc_feature            1..510
                        note = IPD103 variant
source                  1..510
                        mol_type = other DNA
                        organism = synthetic construct
SEQUENCE: 129
atggccgacc cagcaacagc agctagagaa gctgaagaag aggtggagac gacgatggac    60
gagactgagg cggtggggac gcacctggac ttcgtggcgg gcttggaggt gcaacccgc    120
aaggtcatca ccgtggaggt ggacgccgct gccgtaatcc aacagatcag agagatcttc   180
cagacaatgg cgcgtcactt caactcgacg agggtggtgc gggatgaagc catcaagggc   240
attcgagacc acttcaggc gccgtcccg actcgcaacg tggtggtcgt tcacacccag     300
cacattcaca cactggaggg cttggagcac accaacctcg tcttgcagac cggcctcttc   360
aaaaaggtcc ccgtcgacat ctacgtcttc aagtccgcg tcttcaccct ccttggagac    420
ggaggcttca tcaactgggc atggggtggc ttcgtacagg aggtcgccgg caagcgtatc   480
cacttccgct tgccccccgg ggcgctccct                                    510

SEQ ID NO: 130          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 130
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag ggccgccgtc ccgactcgca acgtggtgt cattcacacc   300
cagcacattc acacactgga gggcttggag cacaccaacc tcgtcttgca gaccggcatc   360
ttcaaaaagg tccccgtcga catctatgtc ttcaagtccg cgtcttcac cctccttgga    420
gacggaggct tcatcaactg gcatggggt ggcttcgtcg accaggtcgt cggcaagcgt    480
atccacttcc gcttgccccc cggggcgctc cct                                513

SEQ ID NO: 131          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 131
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacaccaacc tcgtcttgca gaccggcatc   360
ttcaaaaagg tccccgtcga catctacgtc ttcaagtccg cgtcttcac cctccttgga    420
gacggaggct tcatcaactg gcatggggt ggcttcgtac aggaggtcgc cggcaagcgt    480
atccacttcc gcttgccccc cggggcgctc cct                                513

SEQ ID NO: 132          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 132
atggcggaca aagcagcagc agcagctaga gaagctgaag aagaggtgca ggagactttg    60
atggacgaga ctgaggcggt ggggacgcac ctggacttcg tggcgggctt ggaggtgcaa   120
ccccgcaagg tcatcaccgt ggaggtggac gccgctgccg taatccagca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggagggcttg gagcacacca acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccct                             516

SEQ ID NO: 133          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 133
```

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cattcacacc   300
cagcacattc acacactgga gggcttggag cacaccacc tcgtcttgca gaccggcctc    360
ttcaaaaagg tccccgtcga catctacgtc ttcaagtccg gcgtcttcac cctccttgga   420
gacggaggct tcatcaactg ggcatggggt ggcttcgtac aggaggtcgc cggcaagcgt   480
atccacttcc gcttgccccc cggggcgctc cct                                513

SEQ ID NO: 134         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 134
atggcggaca aagcagcagc agctagagaa gctgaagaag aggtgcagga gactttgatg    60
gacgagactg aggcggtggg gacgcacctg gacttcttgg gcgcggacgt gaagttgcaa   120
ccccgcaaca tcatcaccgt ggaggtggac gccgctgccg taatccagca gatcagagag   180
atcttccgaa ccatggcaag tcacttcaac tctacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacacca cctcgtcttg cagaccggc    360
ctcttcaaaa aggtccccgt cgacatctac gtcttcaagt ccggcgtctt caccctcctt   420
ggagacggag gcttcatcaa ctgggcatgg gtggcttcg tacaggaggt cgccggcaag    480
cgtatccact tccgcttgcc ccccggggcg ctccct                              516

SEQ ID NO: 135         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 135
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacact   300
cagcacgttc acacactgga gggcttggag cacaccaacc tcgtcttgca gaccggcctc   360
ttcaaaaagg tccccgtcga catctatgtc ttcaagtccg gcgtcttcac cctccttgga   420
gacggaggct tcatcaactg ggcatggggt ggcttcgtac aggaggtcgc cggcaagcgt   480
atccacttcc gcttgccccc cggggcgctc cct                                513

SEQ ID NO: 136         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 136
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactct acgagggtgg tgcgggatga agccatcaag   240
ggcattcgag accacttcag ggccgccgtc ccgactcgca acgtggtggt cgttcacacc   300
cagcacattc acacactgga gggcttggag cacaccacc tcgtcttgca gaccggcatc    360
ttcaaaaagg tccccgtcga catctacgtc ttcaagtccg gcgtcttcac cctccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 137         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 137
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cattcacacc   300
cagcacattc acacactgga gggcttggag cacaccaacc tcgtcttgca gaccggcctc   360
ttcaaaaagg tccccgtcga catctatgtc ttcaagtccg gcgtcttcac cctccttgga   420
```

```
gacggaggct tcatcaactg ggcatggggt ggcttcgtcg accaggtcgt cggcaagcgt    480
atccacttcc gcttgccccc cggggcgctc cct                                 513

SEQ ID NO: 138           moltype = DNA  length = 513
FEATURE                  Location/Qualifiers
misc_feature             1..513
                         note = IPD103 variant
source                   1..513
                         mol_type = other DNA
                         organism = synthetic construct
SEQUENCE: 138
atggccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaacatca tcaccgtgga ggtggacgcg gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cattcacacc    300
cagcacattc acacactgga gggcttggag cacaccaacc tcgtcttgca gaccggcatc    360
ttcaaaaagg tccccgtcga catctacgtc ttcaagtccg gcgtcttcac cctccttgga    420
gacggaggct tcatcaactg ggcatggggt ggcttcgtcg accaggtcgt cggcaagcgt    480
atccacttcc gcttgccccc cggggcgctc cct                                 513

SEQ ID NO: 139           moltype = DNA  length = 516
FEATURE                  Location/Qualifiers
misc_feature             1..516
                         note = IPD103 variant
source                   1..516
                         mol_type = other DNA
                         organism = synthetic construct
SEQUENCE: 139
atggcggaca aagcagcagc agcagctaga gaagctgaag aagaggtgca ggagactttg     60
atggacgaga ctgaggcggt ggggacgcac ctggacttcg tggcgggctt ggaggtgcaa    120
ccccgcaagg tcatcaccgt ggaggtggac gccgctgccg taatccagca gatcagagag    180
atcttccgaa ccatggcaag tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctac gtcttcaagt ccggcgtctt caccctcctt    420
ggagacggag gcttcatcaa ctgggcatgg ggtggcttcg tcgaccaggt cgtcggcaag    480
cgtatccact tccgcttgcc ccccggggcg ctccct                              516

SEQ ID NO: 140           moltype = DNA  length = 516
FEATURE                  Location/Qualifiers
misc_feature             1..516
                         note = IPD103 variant
source                   1..516
                         mol_type = other DNA
                         organism = synthetic construct
SEQUENCE: 140
atggcggaca agcagcagc agcagctaga gaagctgaag aagaggtgca ggagactttg      60
atggacgaga ctgaggcggt ggggacgcac ctggacttcg tggcgggctt ggaggtgcaa    120
ccccgcaagg tcatcaccgt ggaggtggac gccgctgccg taatccagca gatcagagag    180
atcttccgag acaatgcgcg tcacttcaac tctacgaggg tggtgcggga tgaagccatc    240
aagggcattc gagaccactt cagggccgcc gtcccgactc gcaacgtggt ggtcgttcac    300
actcagcacg ttcacacact ggtgggcttg gagcacaccc acctcgtctt gcagaccggc    360
atcttcaaaa aggtccccgt cgacatctac gtcttcaagt ccggcgtctt caccaacctt    420
ggagacggag gcttcatcaa ctgggcatgg ggtggcttcg tacaggaggt cgccggcaag    480
cgtatccact tccgcttgcc ccccggggcg ctccct                              516

SEQ ID NO: 141           moltype = DNA  length = 513
FEATURE                  Location/Qualifiers
misc_feature             1..513
                         note = IPD103 variant
source                   1..513
                         mol_type = other DNA
                         organism = synthetic construct
SEQUENCE: 141
atggccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggatga agccatcaag                 240
ggcattcgag accacttcag ggccgccgtc ccgactcgca acgtggtggt cgttcacact    300
cagcacgttc acacactgga gggcttggag cacaccaacc tcgtcttgca gaccggcatc    360
ttcaaaaagg tccccgtcga catctatgtc ttcaagtccg gcgtcttcac cctccttgga    420
gacggaggct tcatcaactg ggcatggggt ggcttcgtcg accaggtcgt cggcaagcgt    480
atccacttcc gcttgccccc cggggcgctc cct                                 513

SEQ ID NO: 142           moltype = DNA  length = 516
FEATURE                  Location/Qualifiers
misc_feature             1..516
                         note = IPD103 variant
```

```
source                      1..516
                            mol_type = other DNA
                            organism = synthetic construct
SEQUENCE: 142
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacacca acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                            516

SEQ ID NO: 143              moltype = DNA  length = 516
FEATURE                     Location/Qualifiers
misc_feature                1..516
                            note = IPD103 variant
source                      1..516
                            mol_type = other DNA
                            organism = synthetic construct
SEQUENCE: 143
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                            516

SEQ ID NO: 144              moltype = DNA  length = 516
FEATURE                     Location/Qualifiers
misc_feature                1..516
                            note = IPD103 variant
source                      1..516
                            mol_type = other DNA
                            organism = synthetic construct
SEQUENCE: 144
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccaga caatgcgcg tcacttcaac tcgacgaggg tggtgcggga tgaagccatc   240
aagggcattc gagaccactt cagggccgcc gtcccgactc gcaacgtggt ggtcgttcac   300
actcagcacg ttcacacact ggtgggcttg gagcacaccc acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tcgaccaggt cgccggcaag   480
cgtatccact tccgcttgcc ccccggggcg ctccct                            516

SEQ ID NO: 145              moltype = DNA  length = 516
FEATURE                     Location/Qualifiers
misc_feature                1..516
                            note = IPD103 variant
source                      1..516
                            mol_type = other DNA
                            organism = synthetic construct
SEQUENCE: 145
atggccgacc cagcaacagc agctagagaa gctgaagaag aggtgcagga cactttgatg    60
gacgagactg aggcggtggg gacgcacctg gacttcttgg gcgcggacgt gaagttgcaa   120
ccccgcaaca tcatcaccgt ggaggtggac gcggctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacacca acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                            516

SEQ ID NO: 146              moltype = DNA  length = 510
FEATURE                     Location/Qualifiers
misc_feature                1..510
                            note = IPD103 variant
source                      1..510
                            mol_type = other DNA
                            organism = synthetic construct
SEQUENCE: 146
atggccgacc cagcaacagc agctagagaa gctgaagaag aggtggagac gacgatggac    60
gagactgagg cggtggggac gcacctggac ttcgtggcgg gcttggaggt gcaacccgc   120
aaggtcatca ccgtggaggt ggacgccgct gccgtaatcc agcagatcag agatcttc    180
```

```
cgaaccatgg caagtcactt caactcgacg agggtggtgc gggatgaagc catcaagggc    240
attcgagacc acttcagggc cgccgtcccg actcgcaacg tggtggtcat tcacactcag    300
cacattcaca cactggaggg cttggagcac accaacctcg tcttgcagac cggcctcttc    360
aaaaaggtcc ccgtcgacat ctatgtcttc aagtccggcg tcttcaccct ccttggagac    420
ggaggcttca tcaactgggc atggggtggc ttcgtacagg aggtcgccgg caagcgtatc    480
cacttccgct gcccccccgg ggcgctccct                                     510

SEQ ID NO: 147         moltype = DNA   length = 513
FEATURE                Location/Qualifiers
misc_feature           1..513
                       note = IPD103 variant
source                 1..513
                       mol_type = other DNA
                       organism = synthetic construct
SEQUENCE: 147
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaaggtca tcaccgtgga ggtggacgcc gctgccgtaa tccaacagat cagagagatc    180
ttccagacaa tggcgcgtca cttcaactct acgagggtgg tgcgggatga agccatcaag    240
ggcattcgag accacttcag ggccgccgtc ccgactcgca acgtggtggt cattcacact    300
cagcacgttc acacactggt gggcttggag cacacccacc tcgtcttgca gaccggcctc    360
ttcaaaaagg tccccgtcga catctatgtc ttcaagtccg gcgtcttcac caaccttgga    420
gacggaggct tcatcaactg gcatggggt ggcttcgtcg accaggtcgt cggcaagcgt    480
atccacttcc gcttgccccc cggggcgctc cct                                 513

SEQ ID NO: 148         moltype = DNA   length = 513
FEATURE                Location/Qualifiers
misc_feature           1..513
                       note = IPD103 variant
misc_feature           127
                       note = n is a, c, g, or t
source                 1..513
                       mol_type = other DNA
                       organism = synthetic construct
SEQUENCE: 148
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaagntca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cgttcacacc    300
cagcacattc acacactggt gggcttggag cacaccaacc tcgtcttgca gaccggcatc    360
ttcaaaaagg tccccgtcga catctatgtc ttcaagtccg gcgtcttcac catccttgga    420
gacggaggct tcatcaactg gcatggggt ggcttcgtac aggaggtcgt cggcaagcgt    480
atccacttcc gcttgccccc cggggcgctc cct                                 513

SEQ ID NO: 149         moltype = DNA   length = 516
FEATURE                Location/Qualifiers
misc_feature           1..516
                       note = IPD103 variant
source                 1..516
                       mol_type = other DNA
                       organism = synthetic construct
SEQUENCE: 149
atggcggaca aagcagcagc agcagctaga gaagctgaag aagaggtgca ggagactttg     60
atggcgagaa ctgaggcggt ggggacgcac ctggacttcg tggcgggctt ggaggtgcaa    120
ccccgcaagg tcatcaccgt ggaggtggac gcggctgccg taatccaaca gatcagagag    180
atcttccgaa ccatggcaag tcacttcaac tcgacgaggg tggtgcggga tgaagccatc    240
aagggcattc gagaccactt cagggccgcc gtcccgactc gcaacgtggt ggtcgttcac    300
acccacacac ttcacacact ggagggcttg gagcacacca acctcgtctt gcagaccggc    360
atcttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact tccgcttgcc ccccggggcg ctccct                              516

SEQ ID NO: 150         moltype = DNA   length = 513
FEATURE                Location/Qualifiers
misc_feature           1..513
                       note = IPD103 variant
source                 1..513
                       mol_type = other DNA
                       organism = synthetic construct
SEQUENCE: 150
atggccgacc agcaacagc agctagagaa gctgaagaag aggtgcagga ctttgatg        60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag ggccgccgtc ccgactcgca acgtggtggt cattcacact    300
cagcacgttc acacactggt gggcttggag cacaccaacc tcgtcttgca gaccggcctc    360
ttcaaaaagg tccccgtcga catctatgtc ttcaagtccg gcgtcttcac caaccttgga    420
gacggaggct tcatcaactg gcatggggt ggcttcgtac aggaggtcgc cggcaagcgt    480
```

```
atccacttcc gcttgccccc cggggcgctc cct                            513

SEQ ID NO: 151         moltype = DNA  length = 510
FEATURE                Location/Qualifiers
misc_feature           1..510
                       note = IPD103 variant
misc_feature           32
                       note = n is a, c, g, or t
source                 1..510
                       mol_type = other DNA
                       organism = synthetic construct
SEQUENCE: 151
atggccgacc cagcaacagc agctagagaa gntgaagaag aggtggagac gacgatggac    60
gagactgagg cggtggggac gcacctggac ttcgtggcgg gcttggaggt gcaacccgc    120
aaggtcatca ccgtggaggt ggacgccgct gccgtaatcc agcagatcag agagatcttc   180
cgaaccatgg caagtcactt caactcgacg agggtggtgc gggatgaagc catcaagggc   240
attcgagacc acttcagggc cgccgtcccg actcgcaacg tggtggtcgt tcacacccag   300
cacattcaca cactggtggg cttggagcac acccacctcg tcttgcagac acgtcatcttc  360
aaaaaggtcc ccgtcgacat ttatgtcttc aagtccggcg tcttcaccct ccttggagac   420
ggaggcttca tcaactgggc atggggtggc ttcgtcgacc aggtcgtcgg caagcgtatc   480
cacttccgct tgccccccgg ggcgctccct                                    510

SEQ ID NO: 152         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 152
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcg ctgccgtaa tccaacagat cagagagatc   180
ttccagacaa tggcgcgtca cttcaactcg acgagggtg tgcgggatga agccatcaag    240
ggcattcgag accacttcag ggccgccgtc ccgactcgca acgtggtggt cgttcacact   300
cagcacgttc acacactgga gggcttggag cacacccacc tcgtcttgca gaccggcatc   360
ttcaaaaagg tccccgtcga catctacgtc ttcaagtccg gcgtcttcac cctccttgga   420
gacggaggct tcatcaactg gcatggggt ggcttcgtcg accaggtcgt cggcaagcgt   480
atccacttcc gcttgccccc cggggcgctc cct                               513

SEQ ID NO: 153         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 153
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgcca taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg agcacacca acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 154         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 154
atggcggaca aagcagcagc agcagctaga gaagctgaag aagaggtgca ggagactttg    60
atggacgaac tgaggcggt ggggacgcac ctggacttcg tggcgggctt ggaggtgcaa   120
ccccgcaaca tcatcaccgt ggaggtggac gccgctgccg taatccagca gatcagagag   180
atcttccgaa ccatggcaag tcacttcaac tctacgaggg tggtgcggga tgaagccatc   240
aagggcattc gagaccactt cagggccgcc gtcccgactc gcaacgtggt ggtcgttcac   300
acccagcaca ttcacacact ggtgggcttg agcacaccc acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tacaggaggt cgccggcaag   480
cgtatccact tccgcttgcc ccccggggcg ctccct                             516

SEQ ID NO: 155         moltype = DNA  length = 513
FEATURE                Location/Qualifiers
misc_feature           1..513
```

```
                        note = IPD103 variant
source                  1..513
                        mol_type = other DNA
                        organism = synthetic construct
SEQUENCE: 155
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccagacaa tggcgcgtca cttcaactcg acgagggtgg tgcgggatga agccatcaag   240
ggcattcgag accacttcag gccgccgtc cgactcgca acgtggtggt cgttcacacc     300
cagcacattc acacactgga gggcttggag cacaccaacc tcgtcttgca gaccggcctc   360
ttcaaaaagg tccccgtcga catctacgtc ttcaagtccg cgtcttcac caaccttgga    420
gacggaggct tcatcaactg gcatggggt ggcttcgtcg accaggtcgt cggcaagcgt    480
atccacttcc gcttgccccc cggggcgctc cct                                513

SEQ ID NO: 156          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 156
atggcggaca aagcagcagc agcagctaga gaagctgaag aagaggtgca ggagactttg    60
atggacgaga ctgaggcggt ggggacgcac ctggacttcg tggcgggctt ggaggtgcaa   120
ccccgcaagg tcatcaccgt ggaggtggac gccgctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
ctcttcaaaa aggtcccgt cgacatctac gtcttcaagt ccggcgtctt caccctcctt    420
ggagacggag gcttcatcaa ctgggcatgg ggtggcttcg tacaggaggt cgtcggcaag   480
cgtatccact ccgcttgcc ccccggggcg ctccct                              516

SEQ ID NO: 157          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 157
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag gccgccgtc cgactcgca acgtggtggt cgttcacact     300
cagcacgttc acacactggt gggcttggag cacaccacc tcgtcttgca gaccggcatt    360
ttcaaaaagg tccccgtcga catctacgtc ttcaagtccg cgtcttcac cctccttgga    420
gacggaggct tcatcaactg gcatggggt ggcttcgtac aggaggtcgc cggcaagcgt    480
atccacttcc gcttgccccc cggggcgctc cct                                513

SEQ ID NO: 158          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 158
atggccgaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccgaa ccacggcaag tcacttcaac tcgacgaggg tggtgcggga tgaagccatc   240
aagggcattc gagaccactt cagggccgcc gtcccgactc gcaacgtggt gtcattcac    300
tcccagcaca ttcacacatt ggagggcttg agcacaccc acctcgtctt gcagaccggc    360
atcttcaaaa aggtccccgt cgacatgtac gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccccga                            519

SEQ ID NO: 159          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 159
atggcggaca aagcagcagc agcagctaga gaagctgaag aagaggtgga gacgacgatg    60
gacgagactg aggcggtggg gacgcacctg gacttcgtgg cggcttga ggtgcaaccc     120
```

```
cgcaaggtca tcaccgtgga ggtggacgcc gctgccgtaa tccaacagat cagagagatc    180
ttccagacaa tggcgcgtca cttcaactcg acgagggtgg tgcgggatga agccatcaag    240
ggcattcgag accacttcag gccgccgtc ccgactcgca acgtggtggt cgttcacacc    300
cagcacgttc acacactggt gggcttggag cacacccacc tcgtcttgca gaccggcctc    360
ttcaaaaagg tccccgtcga catctacgtc ttcaagtccg gcgtcttcac cctccttgga    420
gacggaggct tcatcaactg ggcatggggt ggcttcgtac aggaggtcgc cggcaagcgt    480
atccacttcc gcttgccccc cggggcgctc cct                                 513

SEQ ID NO: 160         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 160
atggccgacc cagcaacagc agctagagaa gctgaagaag aggtgcagga gactttgatg     60
gacgagactg aggcggtggg gacgcacctg gacttcttgg gcgcggacgt gaagttgcaa    120
ccccgcaaca tcatcaccgt ggaggtggac gccgctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg agcacacaca acctcgtctt gcagaccggc    360
ctcttcaaaa aggtccccgt cgacatctac gtcttcaagt ccggcgtctt caccctcctt    420
ggagacggag gcttcatcaa ctgggcatgg gtggcttcg tacaggaggt cgccggcaag    480
cgtatccact ccgcttgcc cccggggcg ctccct                                516

SEQ ID NO: 161         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 161
atggccgacc cagcaacagc agctagagaa gctgaagaag aggtggagac gacgatggac     60
gagactgagg cggtggggac gcacctggac ttcttgggcg cggacgtgaa gttgcaaccc    120
cgcaacatca tcaccgtgga ggtggacgcg ctgccgtaa tccatcagat cagagagatc    180
ttccagacaa tggcgcgtca cttcaactct acgagggtgg tgcgggatga agccatcaag    240
ggcattcgag accacttcag gccgccgtc ccgactcgca acgtggtggt cgttcactcc    300
cagcacattc acacattggt gggcttggag cacacccacc tcgtcttgca gaccggcctc    360
ttcaaaaagg tccccgtcga catgtacgta ttcaagtccg gcgtcttcac caaccttgga    420
gacggaggct tcatcaactg gcatggggt ggcttcgtac aggaggtcgc cggcaagcgt    480
atccacttcc gcttgccccc cggggcgctc cct                                 513

SEQ ID NO: 162         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 162
atggcggacc cagcaacagc agctagagaa gatgaagaag aggtgcagga gactttgatg     60
gacgagactg aggcggtggg gacgcacctg gacttcttgg gcgcggacgt gaagttgcaa    120
ccccgcaaca tcatcaccgt ggaggtggac gcggctgccg taatccagca gatcagagag    180
atcttccgaa ccatggcaag tcacttcaac tcgacgaggg tggtgcggga tgaagccatc    240
aagggcattc gagaccactt cagggccgcc gtcccgactc gcaacgtggt ggtcgttcac    300
acccagcaca ttcacacact ggagggcttg agcacacccc acctcgtctt gcagaccggc    360
ctcttcaaaa aggtccccgt cgacatctac gtcttcaagt ccggcgtctt caccctcctt    420
ggagacggag gcttcatcaa ctgggcatgg gtggttttcg tacaggaggt cgccggcaag    480
cgtatccact ccgcttgcc cccggggcg ctccct                                516

SEQ ID NO: 163         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 163
atggcggaca agcagcagc agcagctaga gaagctgaag aagaggtgga gacgacgatg     60
gacgagactg aggcggtggg gacgcacctg gacttcgtgg cgggcttgga ggtgcaaccc    120
cgcaacatca tcaccgtgga ggtggacgcc gctgccgtaa tccagcagat cagagagatc    180
ttccgaacca tggcaagtca cttcaactcg acgagggtgg tgcgggatga agccatcaag    240
ggcattcgag accacttcag gccgccgtc ccgactcgca acgtggtggt cgttcacacc    300
cagcacattc acacactgga gggcttggag cacacccacc tcgtcttgca gaccggcatc    360
ttcaaaaagg tccccgtcga catctatgtc ttcaagtccg gcgtcttcac cctccttgga    420
gacggaggct tcatcaactg gcatggggt ggcttcgtac aggaggtcgc cggcaagcgt    480
atccacttcc gcttgccccc cggggcgctc cct                                 513
```

```
SEQ ID NO: 164          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 164
atggcggaca aagcagcaac agcagctaga gaagctgaag aagaggtgca ggagactttg   60
atggacgaga ctgaggcggt ggggacgcac ctggacttcg tggcgggctt ggaggtgcaa  120
ccccgcaaca tcatcaccgt ggaggtggac gccgctgccg taatccaaca gatcagagag  180
atcttccgga ccatggcaag tcacttcaac tctacgaggg tggtgcggga tgaagccatc  240
aagggcattc gagaccactt cagggccgcc gtcccgactc gcaacgtggt ggtcgttcac  300
acccagcaca ttcacacact ggagggcttg gagcacacca acctcgtctt gcagaccggc  360
atcttcaaaa aggtccccgt cgacatctac gtcttcaagt ccggcgtctt caccctcctt  420
ggagacggag gcttcatcaa ctgggcatgg ggtggcttcg tacagcaggt cgtcggcaag  480
cgtatccact tccgcttgcc ccccggggcg ctccct                            516

SEQ ID NO: 165          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 165
atggcggaca aagcagcagc agcagctaga gaagctgaag aagaggtgga gacgacgatg   60
gacgagactg aggcggtggg gacgcacctg gacttcttgg gcgcggacgt gaagttgcaa  120
ccccgcaagg tcatcaccgt ggaggtggac gccgctgccg taatccaaca gatcagagag  180
atcttccaga caatggcgcg tcacttcaac tcgacgaggg tggtgcggga tgaagccatc  240
aagggcattc gagaccactt cagggccgcc gtcccgactc gcaacgtggt ggtcattcac  300
actcagcaca ttcacacact ggagggcttg gagcacacca acctcgtctt gcagaccggc  360
ctcttcaaaa aggtccccgt cgacatctac gtcttcaagt ccggcgtctt caccctcctt  420
ggagacggag gcttcatcaa ctgggcatgg ggtggcttcg tcgacgaggt cgtcggcaag  480
cgtatccact tccgcttgcc ccccggggcg ctccct                            516

SEQ ID NO: 166          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 166
atggcggaca aagcagcagc agcagctaga gaagctgaag aagaggtgca ggagactttg   60
atggacgaga ctgaggcggt ggggacgcac ctggacttct tgggcgcgga cgtgaagttg  120
caaccccgca acatcatcac cgtggaggtg gacgcggctg ccgtaatcca gcagatcaga  180
gagatcttcc gaaccatggc aagtcacttc aactcgacga gggtggtgcg ggatgaagcc  240
atcaagggca ttcgagacca cttcagggcc gccgtcccga ctcgcaacgt ggtggtcatt  300
cacactcagc acgttcacac actggtgggc ttggagcacc cccacctcgt cttgctgatg  360
ggcatcttca aaaaggtccc cgtcgacatc tatgtcttca gtccggcgct tcaccaaac   420
cttggagacg gaggcttcat caactgggca tggggtggct tcgtacagga ggtcgccggc  480
aagcgtatcc acttccgctt gcccccgggg gcgctccct                         519

SEQ ID NO: 167          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 167
atggcggaca aagcagcagc agcagctaga gaagctgaag aagaggtgca ggagactttg   60
atggacgaga ctgaggcggt ggggacgcac ctggacttcg tggcgggctt ggaggtgcaa  120
ccccgcaaca tcatcaccgt ggaggtggac gcggctgccg taatccaaca gatcagagag  180
atcttccaga caatggcgcg tcacttcaac tcgacgaggg tggtgcggga tgaagccatc  240
aagggcattc gagaccactt cagggccgcc gtcccgactc gcaacgtggt ggtcattcac  300
actcagcacg ttcacacact ggtgggcttg gagcacaccc acctcgtctt gcagaccggc  360
atcttcaaaa aggtccccgt cgacatctat gtcttcaagt ccggcgtctt caccaaacttc  420
ggagacggag gcttcatcaa ctgggcatgg ggtggcttcg taggaggtc cgccggcaag   480
cgtatccact tccgcttgcc ccccggggcg ctccct                            516

SEQ ID NO: 168          moltype = DNA  length = 513
FEATURE                 Location/Qualifiers
misc_feature            1..513
                        note = IPD103 variant
source                  1..513
                        mol_type = other DNA
```

```
                    organism = synthetic construct
SEQUENCE: 168
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgaggtgg tgcgggatga agccatcaag    240
ggcattcgag accacttcag ggccgccgtc ccgactcgca acgtggtggt cattcacact   300
cagcacgttc acacactggt gggcttggag cacacccacc tcgtcttgca gaccggcctc   360
ttcaaaaagg tccccgtcga catctatgtc ttcaagtccg gcgtcttcac cctccttgga   420
gacggaggct tcatcaactg gcatggggt ggcttcgtcg accaggtcgt cggcaagcgt    480
atccacttcc gcttgccccc cggggcgctc cct                                513

SEQ ID NO: 169            moltype = DNA  length = 516
FEATURE                   Location/Qualifiers
misc_feature              1..516
                          note = IPD103 variant
source                    1..516
                          mol_type = other DNA
                          organism = synthetic construct
SEQUENCE: 169
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
acccagcaca ttcacacact ggagggcttg gagcacacca acctcgtctt gcagaccggc   360
ctcttcaaaa aggtccccgt cgacatctac gtcttcaagt ccggcgtctt caccctcctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 170            moltype = DNA  length = 516
FEATURE                   Location/Qualifiers
misc_feature              1..516
                          note = IPD103 variant
source                    1..516
                          mol_type = other DNA
                          organism = synthetic construct
SEQUENCE: 170
atggcggaca aagcagcagc agcagctaga gaagctgaag aagaggtgca ggagactttg    60
atggacgaga ctgaggcggt ggggacgcac ctggacttcg tggcgggctt ggaggtgcaa   120
ccccgcaaca tcatcaccgt ggaggtggac gcggctgccg taatccaaca gatcagagag   180
atcttccgaa ccatggcaag tcacttcaac tctacgaggg tggtgcggga tgaagccatc   240
aagggcattc gagaccactt cagggccgcc gtcccgactc gcaacgtggt cattcacacc  300
acccagcaca ttcacacact ggtgggcttg gagcacacca acctcgtctt gcagaccggc   360
ctcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 171            moltype = DNA  length = 516
FEATURE                   Location/Qualifiers
misc_feature              1..516
                          note = IPD103 variant
source                    1..516
                          mol_type = other DNA
                          organism = synthetic construct
SEQUENCE: 171
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgccg taatccaaca gatcagagag   180
atcttccgaga caatggcgcg tcacttcaac tctacgaggg tggtgcggga tgaagccatc   240
aagggcattc gagaccactt cagggccgcc gtcccgactc gcaacgtggt ggtcgttcac   300
acccagcacg ttcacacact ggagggcttg gagcacacca acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tacaggaggt cgccggcaag   480
cgtatccact ccgcttgcc ccccggggcg ctccct                              516

SEQ ID NO: 172            moltype = DNA  length = 513
FEATURE                   Location/Qualifiers
misc_feature              1..513
                          note = IPD103 variant
source                    1..513
                          mol_type = other DNA
                          organism = synthetic construct
SEQUENCE: 172
atggccgacc cagcaacagc agctagagaa gctgaagaag aggtgcagga ctttgatg     60
gacgagactg aggcggtggg gacgcacctg gacttcgtgg cgggcttgga ggtgcaaccc   120
cgcaaggtca tcaccgtgga ggtggacgcc gctgccgtaa tccagcagat cagagagatc   180
ttccgaacca tggcaagtca cttcaactcg acgaggtgg tgcgggatga agccatcaag    240
ggcattcgag accacttcag ggccgccgtc ccgactcgca acgtggtggt cgttcacacc   300
```

```
cagcacattc acacactgga gggcttggag cacacccacc tcgtcttgca gaccggcatc    360
ttcaaaaagg tccccgtcga catctacgtc ttcaagtccg gcgtcttcac caaccttgga    420
gacggaggct tcatcaactg gcatgggggt ggcttcgtcg accaggtcgt cggcaagcgt    480
atccacttcc gcttgccccc cggggcgctc cct                                 513

SEQ ID NO: 173            moltype = DNA   length = 516
FEATURE                   Location/Qualifiers
misc_feature              1..516
                          note = IPD103 variant
source                    1..516
                          mol_type = other DNA
                          organism = synthetic construct
SEQUENCE: 173
atggcggaca aagcagcagc agcagctaga gaagctgaag aagaggtgca ggagactttg     60
atggacgaga ctgaggcggt ggggacgcac ctggacttcg tggcgggctt ggaggtgcaa    120
ccccgcaagg tcatcaccgt ggaggtggac gccgctgccg taatccagca gatcagagag    180
atcttccgaa ccatggcaag tcacttcaac tcgacgaggt ggtgcggga tgaagccatc     240
aagggcattc gagaccactt cagggccgcc gtcccgactc gcaacgtggt ggtcgttcac    300
acccagcaca ttcacacact ggtgggcttg gagcacaccc acctcgtctt gcagaccggc    360
ctcttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact tccgcttgcc ccccggggcg ctccct                              516

SEQ ID NO: 174            moltype = DNA   length = 510
FEATURE                   Location/Qualifiers
misc_feature              1..510
                          note = IPD103 variant
source                    1..510
                          mol_type = other DNA
                          organism = synthetic construct
SEQUENCE: 174
atggccgacc cagcaacagc agctagagaa gctgaagaag aggtggagac gacgatggac     60
gagactgagg cggtggggac gcacctggac ttcgtggcgg gcttggaggt gcaacccgc     120
aaggtcatca ccgtggaggt ggacgccgct gccgtaatcc agcagatcag agagatcttg    180
cgaaccatgg caagtcactt caactcgacg aggtggtgc gggatgaagc catcaagggc    240
attcgagacc acttcagggc cgccgtcccg actcgcaacg tggtggtcgt tcacacccag    300
cacattcaca cactggaggg cttggaacac accaacctcg tcttgcagac cggcctcttc    360
aaaaaggtcc ccgtcgacat ctacgtcttc aagtccggcg tcttcaccaa ccttggagac    420
ggaggcttca tcaactgggc atggggtggc ttcgtcgacc aggtcgtcgg caagcgtatc    480
cacttccgct tgccccccgg ggcgctccct                                     510

SEQ ID NO: 175            moltype = DNA   length = 513
FEATURE                   Location/Qualifiers
misc_feature              1..513
                          note = IPD103 variant
source                    1..513
                          mol_type = other DNA
                          organism = synthetic construct
SEQUENCE: 175
atggccgacc cagcaacagc agctagagaa gctgaagaag aggtgcagga gactttgatg     60
gacgagactg aggcggtggg gacgcacctg gacttcgtgg cgggcttgga ggtgcaaccc    120
cgcaacatca tcaccgtgga ggtggacgcg ctgccgtaa tccaacagat cagagagatc    180
ttccagacaa tggcgcgtca cttcaactct acgagggtgg tgcgggatga agccatcaag    240
ggcattcgag accacttcag gccgccgtc ccgactcgca acgtggtggt cattcacgcc    300
cagcacattc acacactgga gggcttggag cacaccacc tcgtcttgca gaccggcatc    360
ttcaaaaagg tccccgtcga catctacgtc ttcaagtccg gcgtcttcac cctccttgga    420
gacggaggct tcatcaactg gcatgggggt ggcttcgtac aggaggtcgc cggcaagcgt    480
atccacttcc gcttgccccc cggggcgctc cct                                 513

SEQ ID NO: 176            moltype = DNA   length = 519
FEATURE                   Location/Qualifiers
misc_feature              1..519
                          note = IPD103 variant
source                    1..519
                          mol_type = other DNA
                          organism = synthetic construct
SEQUENCE: 176
atggcggaca aagcagcagc agcagctaga gaagctgaag aagaggtgca ggagactttg     60
atggacgaga ctgaggcggt ggggacgcac ctggacttct tgggcgcgga cgtgaagttg    120
caaccccgca acatcatcac cgtggaggtg acgccgctg ccgtaatcca gcagatcaga    180
gagatcttcc gaaccatggc aagtcacttc aactcgacga gggtggtgcg ggatgaagcc    240
atcaaggcat tcgagaccac ttcagggcc gccgtcccga ctcgcaacgt ggtggtcatt    300
cacactcagc acgttcacac actggtgggc ttggagcaca cccacctcgt cttgcagacc    360
ggcatcttca aaaaggtccc cgtcgacatc tatgtcttca gtccggcgt cttcaccctc    420
cttggagacg gaggcttcat caactgggca tggggtggct tcgtacagga ggtcgccggc    480
aagcgtatcc acttccgctt gccccccggg gcgctccct                           519

SEQ ID NO: 177            moltype = DNA   length = 513
FEATURE                   Location/Qualifiers
```

| misc_feature | 1..513 |
| | note = IPD103 variant |
| source | 1..513 |
| | mol_type = other DNA |
| | organism = synthetic construct |

SEQUENCE: 177

```
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccagcagat cagagagatc   180
ttccgaacca tggcaagtca cttcaactcg acgagggtgg tgcgggatga agccatcaag   240
ggcattcgag accacttcag gccgccgtc ccgactcgca acgtggtggt cgttcacacc    300
cagcacgttc acacactgga gggcttggag cacaccaacc tcgtcttgca gaccggcctc   360
ttcaaaaagg tccccgtcga catctatgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 178    moltype = DNA    length = 513
FEATURE           Location/Qualifiers
misc_feature      1..513
                  note = IPD103 variant
source            1..513
                  mol_type = other DNA
                  organism = synthetic construct
SEQUENCE: 178
ataaccgacc cagcaacagc agctagagaa gctgaagaag aggtggagac gacgatggac    60
gagactgagg cggtggggac gcacctggac ttcttgaggg cggacgtgaa gttgcaaccc   120
cgcaaggtca tcaccgtgga ggtggacgcc gctgccgtaa tccaacagat cagagagatc   180
ttccgaacca tggcaagtca cttcaactcg acgagggtgg tgcgggatga agccatcaag   240
ggcattcgag accacttcag gccgccgtc ccgactcgca acgtggtggt cattcacact    300
cagcacgttc acacactggt gggcttggag cacaccaacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtac aggaggtcgc cggcaagcgt    480
atccacttcc gcttgccccc cggggcgctc cct                                513

SEQ ID NO: 179    moltype = DNA    length = 519
FEATURE           Location/Qualifiers
misc_feature      1..519
                  note = IPD103 variant
source            1..519
                  mol_type = other DNA
                  organism = synthetic construct
SEQUENCE: 179
atggcggaca aagcagcagc agcagctaga gaagctgaag aagaggtgca ggagactttg    60
atggacgaga gtgaggcggt ggggacgcac ctggacttcg tggcgggctt ggaggtgcaa   120
ccccgcaagg tcatcacctt ggaggtggac gccgctgccg taatccagca gatcagagag   180
atcttccgaa ccatggcaag tcccttcaac tcgacgaggg tggtgcggga tgaagccatc   240
aaggcattc gagaccactt cagggccgcc gtcccgactc gcaacgtggt ggtcgttcac    300
tcccagcaca ttcacacatt ggagggattg agcacaccaa cttcgtcttg cagaccggc    360
ctcttcaaaa aggtccccgt ggacatgtac gtattcaagt ccggcgtctt caccaacctt   420
ggagacggag gcttcatcaa ctgggcatgg ggtggcttcg tacaggaggt cgccggcaag   480
cgtatccact tccgcttgcc ccccggggcg ctccctcga                          519

SEQ ID NO: 180    moltype = DNA    length = 513
FEATURE           Location/Qualifiers
misc_feature      1..513
                  note = IPD103 variant
source            1..513
                  mol_type = other DNA
                  organism = synthetic construct
SEQUENCE: 180
atggcggaca aagcagcagc agcaggtaga gaagatgaag aagaggtgga gacgacgatg    60
gacgagactg aggcggtggg gacgcacctg gacttcgtgg cgggcttgga ggtgcaaccc   120
cgcaacatca tcaccgtgga ggtggacgcg gctgccgtaa tccaacagat cagagagatc   180
ttccgaacca tggcaagcca cttcaactct acgagggtgg tgcgggatga agccatcaag   240
ggcattcgag accacttcag gccgccgtc ccgactcgca acgtggtggt cattcacact    300
cagcacgttc acacactggt gggcttggag cacacccacc tcgtcttgca gaccggcctc   360
ttcaaaaagg tccccgtcga catctacgtc ttcaagtccg gcgtcttcac cctccttgga   420
gacggaggct tcatcaactg gcatggggt ggcttcgtcg accaggtcgt cggcaagcgt    480
atccacttcc gcttgccccc cggggcgctc cct                                513

SEQ ID NO: 181    moltype = DNA    length = 513
FEATURE           Location/Qualifiers
misc_feature      1..513
                  note = IPD103 variant
source            1..513
                  mol_type = other DNA
                  organism = synthetic construct
SEQUENCE: 181
atggccgacc cagcaacagc agctagagaa gctgaagaag aggtgcagga gactttgatg    60
```

```
gacgagactg aggcggtggg gacgcacctg gacttcgtgg cgggcttgga ggtgcaaccc    120
cgcaaggtca tcaccgtgga ggtggacgcg gctgccgtaa tccaacagat cagagagatc    180
ttccagacaa tggcgcgtca cttcaactct acgagggtgg tgcggatgaa agccatcaag    240
ggcattcgag accacttcag ggccgccgtc ccgactcgca acgtggtggt cgttcacact    300
cagcacgttc acacactagt gggcttggag cacacccacc tcgtcttgca gaccggcctc    360
ttcaaaaagg tccccgtcga catctatgtc ttcaagtccg gcgtcttcac caaccttgga    420
gacggaggct tcatcaactg gcatgggggt ggcttcgtac aggaggtcgc cggcaagcgt    480
atccacttcc gcttgccccc cggggcgctc cct                                 513

SEQ ID NO: 182         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 182
atggcggaca aagcagcagc agcagctaga gaagctgaag aagaggtgga gacgacgatg     60
gacgagactg aggcggtggg gacgcacctg gacttcgtgg cgggcttgga ggtgcaaccc    120
cgcaacatca tcaccgtgga ggtggacgcg gctgccgtaa tccaacagat cagagagatc    180
ttccagacaa tggcgcgtca cttcaactct acgagggtgg tgcggatgaa agccatcaag    240
ggcattcgag accacttcag ggccgccgtc ccgactcgca acgtggtggt cgttcacact    300
cagcacattc acacactgga gggcttggag cacacccacc tcgtcttgca gaccggcatc    360
ttcaaaaagg tccccgtcga catctatgtc ttcaagtccg gcgtcttcac cctccttgga    420
gacgaggct tcatcaactg gcatgggggt ggcttcgtcg accaggtcgt cggcaagcgt     480
atccacttcc gcttgccccc cggggcgctc cct                                 513

SEQ ID NO: 183         moltype = DNA  length = 519
FEATURE                Location/Qualifiers
misc_feature           1..519
                       note = IPD103 variant
source                 1..519
                       mol_type = other DNA
                       organism = synthetic construct
SEQUENCE: 183
atggcggaca aagcagcagc agcagctaga gaagctgaag aagaggtgca ggagactttg     60
atggacgaga ctgaggcggt ggggacgcac ctggacttct tgggcgcgga cgtgaagttg    120
caaccccgca acatcatcac cgtggaggtg gacgcggctg ccgtaatcca gcagatcaga    180
gagatcttcc agacaatggc gcgtcacttc aactctacga gggtggtgcg ggatgaagcc    240
atcaagggca ttcgagacca cttcagggcc gccgtcccga ctcgcaacgt ggtggtcgtt    300
cacacccagc acattcacac actggagggc ttggagcaca cccacctcgt cttgcagacc    360
ggcctcttca aaaggtccc cgtcgacatc tacgtcttca gtccggcgt cttcaccctc     420
cttggagacg gaggcttcat caactgggca tggggtggct cgtcgacca ggtcgtcggc    480
aagcgtatcc acttccgctt gccccccggg gcgctccct                           519

SEQ ID NO: 184         moltype = DNA  length = 513
FEATURE                Location/Qualifiers
misc_feature           1..513
                       note = IPD103 variant
source                 1..513
                       mol_type = other DNA
                       organism = synthetic construct
SEQUENCE: 184
atgcggacg aagtagcagg tcaccatggt ccagcatgtg aagaaggagga ggaaatg        60
ctgatggacg agactgaggc ggtggggtg cacgcgatcg acggtctgcc ggtgcaaaac    120
cgcagcatca tcaccgtgga ggtggacgcg gctgccgtaa tccagcagat cagagagatc    180
ttccgaacca tggcaagtca cttcaactcg acgagggtgg tgcggatgaa agccatcaag    240
ggcattcgag accacttcag gctcgccgtc ccgactcgca acgtggtggt cgttcacact    300
cagcacgttc acacactggt gggcttggag cacacccacc tcgtcttgca gaccggcatc    360
ttcaaaaagg tccccgtcga catctatgtc ttcaagtccg gcgtcttcac cctccttgga    420
gacgaggct tcatcaactg gcatgggggt ggctacgcg tcaaccacac cgccaagcgt     480
gtcgtcttca gccggccccc cggggcgctc cct                                 513

SEQ ID NO: 185         moltype = DNA  length = 516
FEATURE                Location/Qualifiers
misc_feature           1..516
                       note = IPD103 variant
source                 1..516
                       mol_type = other DNA
                       organism = synthetic construct
SEQUENCE: 185
atggcggaca aagcagcagc agcagctaga gaagctgaag aagaggtgga gacgacgatg     60
gacgagactg aggcggtggg gacgcacctg gacttcttgg gcgcggacgt gaagttgcaa    120
ccccgcaaca tcaccgtg gaggtggac gccgctgccg taatccaaca gatcagagag        180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggacgccgtg gagtcctccc acctcgtctt gcggaccggc    360
ctgttcaaaa aggtccctgt cgacatcttt gtcttcaagt ccggcgtctt caccaacctt    420
ggagacggag gcttcatcaa ctgggcatgg ggtggcttcg tacaggaggt cgccggcaag    480
```

```
cgtatccact tccgcttgcc ccccggggcg ctccct                              516

SEQ ID NO: 186           moltype = DNA   length = 507
FEATURE                  Location/Qualifiers
misc_feature             1..507
                         note = IPD103 variant
source                   1..507
                         mol_type = other DNA
                         organism = synthetic construct
SEQUENCE: 186
atggcggaca aagcagcagc agcagctaga gaagctgaag aagaggtgga gacgacgatg    60
gacgagactg aggcggtggg ggtgcacgcg atcgacggtc tgccggtgca aaaccgcagc   120
atcatcaccg tggaggtgga cgccgctgcc gtaatccagc agatcagaga gatcttccga   180
accatggcaa gtcacttcaa ctcgacgagg gtggtcggga atgaagccat caagagcatt   240
cgagaccact tcaggctcgc cgtcccgact cgcaacgtgg tggtcgttca cacccagcac   300
gttcacacac tggacgccgt ggagtcctcc cacctcgtct gcggaccggg cctgttcaaa   360
aaggtccctg tcgacatctt tgtcttcaag tccggcgtct tcaccaacct gggagacgga   420
ggcttcatca actgggcatg gggtggcttc gtacaggagg tcgccggcaa gcgtatccac   480
ttccgcttgc ccccggggc gctccct                                        507

SEQ ID NO: 187           moltype = DNA   length = 516
FEATURE                  Location/Qualifiers
misc_feature             1..516
                         note = IPD103 variant
source                   1..516
                         mol_type = other DNA
                         organism = synthetic construct
SEQUENCE: 187
atggcggacg aagtagcagg tcaccatggt ccagcatgtg aagaagagga ggagacgacg    60
atggcagaga ctgaggcggt ggggacgcac ctgacttcg tggcgggctt ggaggtgcaa    120
ccccgcaagg tcatcaccgt ggaggtggac gccgctgccg taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
actcagcacg ttcacacact ggacgccgtg gagtcctccc acctcgtctt gcggaccggc   360
ctgttcaaaa aggtccctgt cgacatcttt gtcttcaagt ccggcgtctt caccaacctg   420
ggagacggag gcttcatcaa ctgggcatgg ggtggctacg tacaggaggt cgtcggcaag   480
cgtatccact tccgcttgcc ccccggggcg ctccct                             516

SEQ ID NO: 188           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 188
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
ggcattcgag accacttcag gctcgccgtc ccgactcgca acgtggtggt cgttcac     300
cagcacgttc acacactgga cgccgtggag tcctcccacc tcgtcttgcg gaccggcctg   360
ttcaaaaagg tccctgtcga catctttgtc ttcaagtccg gcgtcttcac caacctggga   420
gacgaggct tcatcaactg ggcatggggt ggctacggcg tcaaccacac cgccaagcgt   480
gtcgtcttca gccggcccc cggggcgctc cct                                 513

SEQ ID NO: 189           moltype = DNA   length = 510
FEATURE                  Location/Qualifiers
misc_feature             1..510
                         note = IPD103 variant
source                   1..510
                         mol_type = other DNA
                         organism = synthetic construct
SEQUENCE: 189
atggccgacc cagcaacagc agctagagaa gctgaagaag aggtggagac gacgatggac    60
gagactgagg cggtggggac gcacctggac ttcgtggcgg gcttggaggt gcaacccgc    120
aaggtcatca ccgtggaggt ggacgccgct gccgtaatcc agcagatcag agagatcttc   180
cagacaatgg cgcgtcactt caactctacg agggtggtg gggatgaagc catcaagggc    240
attcgagacc acttcaggtc ccgtcgccgg actcgcaacg tggtgtcat tcacactcag   300
cacgttcaca cactggacgc cgtggagtcc tcccacctcg tcttgcggac cggcctgttc   360
aaaaaggtcc ctgtcgacat cttttgtctt caagtccggc gtcttcacca acctgggaga   420
ggaggcttca tcaactgggc atgggtggc tacgtcgacc aggtcgtcgg caagcgtatc   480
cacttccgct tgccccccgg ggcgctccct                                    510

SEQ ID NO: 190           moltype = DNA   length = 516
FEATURE                  Location/Qualifiers
misc_feature             1..516
                         note = IPD103 variant
source                   1..516
```

```
                         mol_type = other DNA
                         organism = synthetic construct
SEQUENCE: 190
atggcggacg aagtagcagg tcaccatggt ccagcatgtg aagaagagga ggagaggacg    60
atggacgaga ctgaggcggt ggggacgcac ctggacttcg tggcgggctt ggaggtgcaa   120
ccccgcaagg tcatcaccgt ggaggtggac gccgctgccg taatccagca tatcagagag   180
atcttcggaa ccatggcaag tcacttcaac tcgacgaggg tggtgcggga tgaagccatc   240
aagggcattc gagaccactt cagggccgcc gtcccgactc gcaacgtggt ggtcgttcac   300
actcagcacg ttcacacact ggacgccgtg gagtcctccc acctcgtctt gcggaccggc   360
ctgttcaaaa aggtccctgt cgacatcttt gtcttcaagt ccggcgtctt caccaacctg   420
ggagacggag gcttcatcaa ctgggcatgg ggtggctacg tacaggaggt cgtcggcaag   480
cgtatcccact tccgcctgcc ccccggggcg ctccct                            516

SEQ ID NO: 191           moltype = DNA   length = 519
FEATURE                  Location/Qualifiers
misc_feature             1..519
                         note = IPD103 variant
source                   1..519
                         mol_type = other DNA
                         organism = synthetic construct
SEQUENCE: 191
atggcggacg aagtagcagg tcaccatggt ccagcatgtg aagaagagga ggaggaaatg    60
ctgatggacg agactgaggc ggtggggacg cacctggact tcgtggcggg cttggaggtg   120
caaccccgca aggtcatcac cgtggaggtg gacgccgctg ccgtaatcca gcagatcaga   180
gagatcttcc gaaccatggc aagtcacttc aactcgacga gggtggtgcg ggatgaagcc   240
atcaagggca ttcgagacca cttcaaggct gccgtcccga ctcgcaacgt ggtggtcgtt   300
cacactcagc acgttcacac actggacgcc gtggagtcct cccacctcgt cttgcggacc   360
ggcctgttca aaaaggtccc tgtcgacatc tttgtcttca gtccggcgt cttcaccaac   420
ctgggagacg gaggcttcat caactgggca tggggtggct acggcgtcaa ccacaccgcc   480
aagcgtgtcg tcttcagccg gcccccggg gcgctccct                           519

SEQ ID NO: 192           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 192
atggcggacg cagcagcagc agctgctaga gaagaagaag aagagcagga gacgacgatg    60
gacgagactg aggcggtggg gacgcacctg gacttcgtgg cgggcttgga ggtgcaaccc   120
cgcaacatca tcaccgtgga ggtggacgcg ctgccgtaa tccaacagat cagagagatc   180
ttccagtcaa tgatcagtca cttcaactcg acgagggtgg agccatcaag              240
ggcattcgag accacttcag ggtcgccgtc ccgactcgca acgtggtggt cattcacact   300
cagcacgttc acacactgga gggcgtggag tcctcccacc tcgtcttgca gaccgcatg   360
ttcaaaaagg tccccgtcga catctatgtc ttcagtccg gcgtcttcac catcctggga   420
gacggaggct tcatcaactg gcatgggt ggcttcggcg accaggtcgt cggcaagcgt   480
gtccacttcc gcctgccccc cggggcgctc cct                                513

SEQ ID NO: 193           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 193
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactct acgagggtgg tgcggatga agccatcaag    240
ggcattcgag accacttcag gccgccgtc ccgactcgca acgtggtggt cattcacact   300
cagcacgttc acacactggt gggcttggag cacacccacc tcgtcttgca gaccggcatc   360
ttcaaaaagg tccccgtcga catctttgtc ttcaagtccg gcgtcttcac caacctggga   420
gacggaggct tcatcaactg gcatgggt ggctacggcg tcaaccacac cgccaagcgt    480
gtcgtcttca gccggccccc cggggcgctc cct                                513

SEQ ID NO: 194           moltype = DNA   length = 519
FEATURE                  Location/Qualifiers
misc_feature             1..519
                         note = IPD103 variant
source                   1..519
                         mol_type = other DNA
                         organism = synthetic construct
SEQUENCE: 194
atggcggacg aagtagcagg tcaccatggt ccagcatgtg aagaagagga ggaggaaatg    60
ctgatggacg agactgaggc ggtggggacg cacctggact tcgtggcggg cttggaggtg   120
caaccccgca acatcatcac cgtggaggtg gacgccgctg ccgtaatcca acagatcaga   180
gagatcttcc agacaatggc gcgtcacttc aactctacga gggtggtgcg ggatgaagcc   240
```

```
atcaagggca ttcgagacca cttcagggcc gccgtcccga ctcgcaacgt ggtggtcatt    300
cacactcagc acgttcacac actggacgcc gtggagtcct cccacctcgt cttgcggacc    360
ggcctgttca aaaaggtccc tgtcgacatc tttgtcttca agtccggcgt cttcaccaac    420
ctgggagacg gaggcttcat caactgggca tggggtggct tcgtacagga ggtcgccggc    480
aagcgtatcc acttccgctt gcccccccggg gcgctccct                          519
```

| SEQ ID NO: 195 | moltype = DNA length = 513 |
| --- | --- |
| FEATURE | Location/Qualifiers |
| misc_feature | 1..513 |
| | note = IPD103 variant |
| source | 1..513 |
| | mol_type = other DNA |
| | organism = synthetic construct |

```
SEQUENCE: 195
atggcggaca aagcagcagc agcagctaga gaagctgaag aagaggtgga gacgacgatg    60
gacgagactg aggcggtggg gacgcacctg gacttcgtgg cgggcttgga ggtgcaaccc    120
cgcaaggtca tcaccgtgga ggtggacgcc gctgccgtaa tccagcagat cagagagatc    180
ttccgaacca tggcaagtca cttcaactcg acgagggtgg tgcgggatga agccatcaag    240
agcattcgag accacttcag ggccgccgtc ccgactcgca acgtggtggt cattcacact    300
cagcacgttc acacactgga gggcttggag cacaccaacc tcgtcttgca gaccggcctc    360
ttcaaaaagg tccccgtcga catctatgtc ttcaagtccg gcgtcttcac caacctggga    420
gacggaggct tcatcaactg gcgtgggggt ggcttcgtac aggaggtcgc cggcaagcgt    480
atccacttcc gcttgccccc cggggcgctc cct                                 513
```

| SEQ ID NO: 196 | moltype = DNA length = 510 |
| --- | --- |
| FEATURE | Location/Qualifiers |
| misc_feature | 1..510 |
| | note = IPD103 variant |
| source | 1..510 |
| | mol_type = other DNA |
| | organism = synthetic construct |

```
SEQUENCE: 196
atggcggacg aagcagcagc agcagctaga gaagctgaag aagaggagga ggaaatgctg    60
atggacgaga ctgaggcggt gggggtgcac gcgatcgacg gtctgccggt gcaaaaccgc    120
agcatcatca ccgtggaggt ggacgccgct gccgtaatcc aacagatcag agagatcttc    180
cgaaccatgg caagtcactt caactcgacg agggtggtgc gggatgaagc catcaagggc    240
attcgagacc acttcaggct cgccgtcccg actcgcaacg tggtggtcat tcacactcag    300
cacattcaca cactggtggg cttggagtcc tcccacctcg ccttgcggac cggcctgttc    360
aaaaaggtcc ctgtcgacat ctacgtcttc aagtccggcg tcttcaccct ccttggagac    420
ggaggcttca tcaactgggc atggggtggc ttcgtcgacc aggtcgtcgg caagcgtatc    480
cacttccgct tgccccccgg ggcgctccct                                     510
```

| SEQ ID NO: 197 | moltype = DNA length = 516 |
| --- | --- |
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 197
atggcggaca aagcagcagc agcagctaga gaagctgaag aagaggtgga gacgacgatg    60
gacgagactg aggcggtggg gacgcacctg gacttcttgg gcgcggacgt gaagttgcaa    120
ccccgcaaca tcatcaccgt ggaggtggac gccgctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacacca cctcgtcttc gcggaccggc    360
ctgttcaaaa aggtccccgt cgacatctac gtcttcaagt ccggcgtctt caccctcctt    420
ggagacggag gcttcatcaa ctgggcatgg ggtggcttcg tacaggaggt cgccggcaag    480
cgtatccact tccgcttgcc cccggggcg ctccct                               516
```

| SEQ ID NO: 198 | moltype = DNA length = 510 |
| --- | --- |
| FEATURE | Location/Qualifiers |
| misc_feature | 1..510 |
| | note = IPD103 variant |
| source | 1..510 |
| | mol_type = other DNA |
| | organism = synthetic construct |

```
SEQUENCE: 198
atggcggacg aagtagcagg tcaccatggt ccagcatgtg aagaagaggt ggagacgacg    60
atggacgaga ctgaggcggt gggggtgcac gcgatcgacg gtctgccggt gcaaaaccgc    120
agcatcatca ccgtggaggt ggacgccgct gccgtaatcc agcagatcag agagatcttc    180
cgaaccatgg caagtcactt caactcgacg agggtggtgc gggatgaagc catcaagggc    240
attcgagacc acttcaggct cgccgtcccg actcgcaacg tggtggtcgt tcacacccag    300
cacgttcaca cactggtggg cttggagcac accaacctcg tcgcagac cggcctcttc    360
aaaaaggtcc ccgtcgacat ctacgtcttc aagtccggcg tcttcaccct ccttggagac    420
ggaggcttca tcaactgggc atggggtggc ttcgtacagg aggtcgccgg caagcgtatc    480
cacttccgct tgccccccgg ggcgctccct                                     510
```

| SEQ ID NO: 199 | moltype = DNA length = 513 |
| --- | --- |

| FEATURE | Location/Qualifiers |
|---|---|
| misc_feature | 1..513 |
| | note = IPD103 variant |
| source | 1..513 |
| | mol_type = other DNA |
| | organism = synthetic construct |

SEQUENCE: 199

```
atggcggacg aagtagcagg tcaccatggt ccagcatgtg aagaagagga ggaggaaatg   60
ctgatggacg agactgaggc ggtgggggtg cacgcgatcg acggtctgcc ggtgcaaccc  120
cgcaaggtca tcaccgtgga ggtggacgcc gctgccgtaa tccaacagat cagagagatc  180
ttccagacaa tggcgcgtca cttcaactct acgagggtgg tgcgggatga agccatcaag  240
ggcattcgag accacttcag gccgccgtc ccgactcgca acgtggtggt cgttcacacc   300
cagcacattc acacactggt gggcttggag cacaccacc tcgtcttgca gaccggcctc  360
ttcaaaaagg tccccgtcga catctacgtc ttcaagtccg gcgtcttcac cctccttgga  420
gacggaggct tcatcaactg ggcatggggt ggcttcgtcg accaggtcgt cggcaagcgt  480
atccacttcc gcttgccccc cggggcgctc cct                              513
```

| SEQ ID NO: 200 | moltype = DNA length = 513 |
|---|---|
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 200

```
atggcggacg aagtagcagg tcaccatggt ccagcatgtg aagaagagga ggaggaaatg   60
ctgatggacg agactgaggc ggtgggggtg cacgcgatcg acggtctgcc ggtgcaaaac  120
cgcagcatca tcaccgtgga ggtggacgcc gctgccgtaa tccagcagat cagagagatc  180
ttccgaacca tggcaagtca cttcaactcg acgagggtgg tgcgggatga agccatcaag  240
agcattcgag accacttcag gctcgccgtc ccgactcgca acgtggtgt cattcacacc   300
cagcacgttc acacactgga gggcttggag tcctcccacc tcgtcttgcg gaccggcctc  360
ttcaaaaagg tccctgtcga catctttgtc ttcaagtccg gcgtcttcac caacctggga  420
gacggaggct tcatcaactg ggcatggggt ggctacggcg tcaaccacac cgccaagcgt  480
gtcgtcttca gccggccccc cggggcgctc cct                              513
```

| SEQ ID NO: 201 | moltype = DNA length = 513 |
|---|---|
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 201

```
atggcggacg aagtagcagg tcaccatggt ccagcatgtg aagaagagga ggaggaaatg   60
ctgatggacg agactgaggc ggtgggggtg cacgcgatcg acggtctgcc ggtgcaaaac  120
cgcagcatca tcaccgtgga ggtggacgcc gctgccgtaa tccaacagat cagagagatc  180
ttcgcgtcaa tgatcaaaca cttcaactcg acgagggtgg tgcgggatga agccatcaag  240
ggcattcgag accacttcag gccgccgtc ccgactcgca acgtggtggt cattcacact  300
cagcacgttc acacactgga cgccgtggag tcctcccacc tcgtcttgcg gaccggcctc  360
ttcaaaaagg tccctgtcga catctttgtc ttcaagtccg gcgtcttcac caacctggga  420
gacggaggct tcatcaactg ggcatggggt ggctacggcg tcaaccacac cgccaagcgt  480
gtcgtcttca gccggccccc cggggcgctc cct                              513
```

| SEQ ID NO: 202 | moltype = DNA length = 513 |
|---|---|
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 202

```
atggcggacg aagtagcagg tcaccatggt ccagcatgtg aagaagagga ggaggaaatg   60
ctgatggacg agactgaggc ggtgggggtg cacgcgatcg acggtctgcc ggtgcaaaac  120
cgcagcatca tcaccgtgga ggtggacgcc gctgccgtaa tccagcagat cagagagatc  180
ttccgaacca tggcaagtca cttcaactcg acgagggtgg tgcgggatga agccatcaag  240
agcattcgag accacttcag gccgccgtc ccgactcgca acgtggtggt cgttcacacc   300
cagcacattc acacactgga gggcttggag cacaccaacc tcgtcttgca gaccggcctc  360
ttcaaaaagg tccctgtcga catctacgtc ttcaagtccg gcgtcttcac caacctggga  420
gacggaggct tcatcaactg ggcatggggt ggcttcgtac aggaggtcgc cggcaagcgt  480
atccacttcc gcttgccccc cggggcgctc cct                              513
```

| SEQ ID NO: 203 | moltype = DNA length = 513 |
|---|---|
| FEATURE | Location/Qualifiers |
| misc_feature | 1..513 |
| | note = IPD103 variant |
| source | 1..513 |
| | mol_type = other DNA |
| | organism = synthetic construct |

SEQUENCE: 203

```
atggccgacc cagcaacagc agctagagaa gctgaagaag aggtgcagga gactttgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cattcacact   300
cagcacgttc acacactgga cgccgtggag tcctcccacc tcgtcttgcg gaccggcctg   360
ttcaaaaagg tccctgtcga catctttgtc ttcaagtccg gcgtcttcac cctccttgga   420
gacggaggct tcatcaactg gcatggggt ggctacggcg tcaaccacac cgccaagcgt   480
gtcgtcttca gccggccccc cggggcgctc cct                                513

SEQ ID NO: 204          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 204
atggcggacg aagtagcagg tcaccatggt ccagcatgtg aagaagagga ggaggaaatg    60
ctgatggacg agactgaggc ggtggggtg cacgcgatcg acggtctgcc ggtgcaaaac   120
cgcagcatca tcaccgtgga ggtggacgcg gctgccgtaa tccaacagat cagagagatc   180
ttccgaacca tggcaagtca cttcaactcg acgagggtgg tgcgggatga agccatcaag   240
ggcattcgag accacttcag gctcgccgtc ccgactcgca acgtggtggt cattcacact   300
cagcacgttc acacactgga cgccgtggag tcctcccacc tcgtcttgcg gaccggcctg   360
ttcaaaaagg tccctgtcga cattttgtc ttcaagtccg gtgttttcac caacctggga   420
gacggaggct tcatcaactg gcatggggt ggctacggcg tcaaccacac cgccaagcgt   480
gtcgtcttca gccggccccc cggggcgctc cct                                513

SEQ ID NO: 205          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 205
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgcgt taatccagca gatcagagag   180
atcttccgaa ccatggcaag tcacttcaac tcgacgaggg tggtgcggga tgaagccatc   240
aagggcattc gagaccactt cagggccgcc gtcccgactc gcaacgtggt ggtcgttcac   300
actcagcacg ttcacacact ggtgggcttg agcacaccc acctcgtctt gcagaccggc   360
ctcttcaaaa aggtccccgt cgacatctac gtcttcaagt ccggcgtctt cacccctctt   420
ggagacggag gcttcatcaa ctgggcatgg gtggcttcg tcgaccaggt cgtcggcaag   480
cgtatccact tccgcttgcc ccccggggcg ctccct                             516

SEQ ID NO: 206          moltype = DNA   length = 519
FEATURE                 Location/Qualifiers
misc_feature            1..519
                        note = IPD103 variant
source                  1..519
                        mol_type = other DNA
                        organism = synthetic construct
SEQUENCE: 206
atggcggacg aagtagcagg tcaccatggt ccagcatgtg aagaagagga ggaggaaatg    60
ctgatggacg agactgaggc ggtggggacg cacctggact tcgtggcggg cttggaggtg   120
caaaaccgca gcatcatcac cgtggaggtg gacgccgctg ccgtaatcca acagatcaga   180
gagatcttcc gaaccatggc aagtcacttc aactcgacga gggtggtgcg ggatgaagcc   240
atcaagggca ttcgagacca cttcaggctc gccgtcccga ctcgcaacgt ggtggtcgtt   300
cacactcagc acgttcacac actggcgcc gtggagtcct cccacctcgt cttgcggacc   360
ggcctgttca aaaaggtccc tgtcgacatc tttgtcttca gtccggcgt cttcaccaac   420
ctgggagacg gaggcttcat caactgggca tgggtggct acggcgtcaa ccacaccgcc   480
aagcgtgtcg tcttcagccg gccccccggg gcgctccct                          519

SEQ ID NO: 207          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 207
atggcggacg aagtagcagg tcaccatggt ccagcatgtg aagaagagga ggaggaaatg    60
ctgatggacg agactgaggc ggtggggtg cacgcgatcg acggtctgcc ggtgcaaaac   120
cgcagcatca tcaccgtgga ggtggacgcc gctgccgtaa tccaacagat cagagagatc   180
ttccgaacca tggcaagtca cttcaactcg acgagggtgg tgcgggatga agccatcaag   240
agcattcgag accacttcag gctcgccgtc ccgactcgca acgtggtggt cattcacact   300
cagcacgttc acacactgga cgccgtggag tcctcccacc tcgtcttgca gaccggcctc   360
ttcaaaaagg tccccgtcga catctacgtc ttcaagtccg gcgtcttcac caacctggga   420
```

```
gacggaggct tcatcaactg ggcatggggt ggctacggcg tcaaccacac cgccaagcgt    480
gtcgtcttca gccggccccc cggggcgctc cct                                 513

SEQ ID NO: 208           moltype = DNA   length = 516
FEATURE                  Location/Qualifiers
misc_feature             1..516
                         note = IPD103 variant
source                   1..516
                         mol_type = other DNA
                         organism = synthetic construct
SEQUENCE: 208
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gccgctgccg taatccaaca gatcagagag   180
atcttccgaa ccatggcaag tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg agcacaccc acctcgtctt gcagaccggc    360
ctcttcaaaa aggtccccgt cgacatctat gtcttcaagt ccggcgtctt caccaacctg   420
ggagacggag gcttcatcaa ctgggcatgg ggtggcttcg tacaggaggt cgccggcaag   480
cgtatccact tccgccggcc ccccgggcg ctccct                              516

SEQ ID NO: 209           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 209
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttcgcgtcaa tgatcaaaca ctacaactct acgagggtgg tgcgggatga agccatcaag   240
agcattcgag accacttcag ggccgccgtc ccgactcgca acgtggtggt cattcacac    300
cagcacgttc acacactgga gggcttggag cacaccaacc tcgtcttgca gaccggcctg   360
ttcaaaaagg tccctgtcga catctttgtc ttcaagtccg gcgtcttcac caacctggga   420
gacggaggct tcatcaactg ggcatggggt ggctacggcg tcaaccacac cgccaagcgt   480
gtcgtcttca gccggccccc cggggcgctc cct                                513

SEQ ID NO: 210           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 210
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactgga cgccgtggag tcctcccacc tcgtcttgca gaccggcctc   360
ttcaaaaagg tccccgtcga catctatgtc ttcaagtccg gcgtcttcac caaccttgga   420
gacggaggct tcatcaactg ggcatggggt ggctacggcg tcaaccacac cgccaagcgt   480
gtcgtcttca gccggccccc cggggcgctc cct                                513

SEQ ID NO: 211           moltype = DNA   length = 513
FEATURE                  Location/Qualifiers
misc_feature             1..513
                         note = IPD103 variant
source                   1..513
                         mol_type = other DNA
                         organism = synthetic construct
SEQUENCE: 211
atggccgacc agcaacagc agctagagaa gctgaagaag aggtggagac gacgatggac    60
gagactgagg cggtggggac gcacctggac ttcttgggcg cggacgtgaa gttgcaaccc   120
cgcaacatca tcaccgtgga ggtggacgcg gctgccgtaa tccagcagat cagagagatc   180
ttccagacaa tggcgcgtca cttcaactct acgagggtgg tgcgggatga agccatcaag   240
ggcattcgag accacttcag gctcgccgtc ccgactcgca acgtggtggt cattcacacc   300
cagcacgttc acacactgga cgccgtggag tcctcccgcc tcgtcttgcg gaccggcctg   360
ttcaaaaagg tccctgtcga catctttgtc ttcaagtccg gcgtcttcac caacctggga   420
gacggaggct tcatcaactg ggcatggggt ggcttcgtcg accaggtcgt cggcaagcgt   480
atccacttcc gcttgccccc cggggcgctc cct                                513

SEQ ID NO: 212           moltype = DNA   length = 519
FEATURE                  Location/Qualifiers
misc_feature             1..519
                         note = IPD103 variant
```

```
source                      1..519
                            mol_type = other DNA
                            organism = synthetic construct
SEQUENCE: 212
atggcggaca aagcagcagc agcagctaga gaagctgaag aagaggtgca ggagactttg      60
atggacgaga ctgaggcggt ggggacgcac ctggacttct tgggcgcgga cgtgaagttg     120
caaccccgca aggtcatcac cgtggaggtg gacgcggctg ccgtaatcca gcagatcaga     180
gagatcttcc gaaccatggc aagtcacttc aactctacga gggtggtgcg ggatgaagcc     240
atcaagggca ttcgagacca cttcagggcc gccgtcccga ctcgcaacgt ggtggtcgtt     300
cacactcagc acgttcacac actggacgcc gtggagtcct cccacctcgt cttgcggacg     360
ggcctgttca aaaaggtccc cgtcgacatc tacgtcttca gtccggcgt cttcaccctc      420
cttggagacg ggggcttcat caactgggca tggggtggct tcgtcgacca ggtcgtcggc     480
aagcgtatcc acttccgctt gccccccggg gcgctccct                            519

SEQ ID NO: 213              moltype = DNA  length = 513
FEATURE                     Location/Qualifiers
misc_feature                1..513
                            note = IPD103 variant
source                      1..513
                            mol_type = other DNA
                            organism = synthetic construct
SEQUENCE: 213
atggcggacg aagtagcagg tcaccatggt ccagcatgtg aagaagagga ggaggaaatg      60
ctgatggacg agactgaggc ggtggggggtg cacgcgatcg acggtctgcc ggtgcaaaac    120
cgcagcatca tcaccgtgga ggtggacgcc gctgccgtaa tccaacagat cagagagatc     180
ttcgcgtcaa tgatcaaaca ctacaactct acgagggtgg tgcgggatga agccatcaag     240
ggcattcgag accacttcag ggccgccgtc ccgactcgca acgtggtggt cgttcacacc     300
cagcacgttc acacactgga cgccgtggag tcctcccacc tcgtcttgcg gaccggcctg     360
ttcaaaaagg tccctgtcga catctacgtc ttcaagtccg gcgtcttcac cctccttgga     420
gacggaggct tcatcaactg gcatggggt ggctacggcg tcaaccacac cgccaagcgt      480
gtcgtcttca gccggccccc cggggcgctc cct                                  513

SEQ ID NO: 214              moltype = DNA  length = 519
FEATURE                     Location/Qualifiers
misc_feature                1..519
                            note = IPD103 variant
source                      1..519
                            mol_type = other DNA
                            organism = synthetic construct
SEQUENCE: 214
atggcggacg aagtagcagg tcaccatggt ccagcatgtg aagaagagga ggaggaaatg      60
ctgatggacg agactgaggc ggtggggacg cacctggact tcgtggcggg cttggaggtg     120
caaccccgca aggtcatcac cgtggaggtg gacgccgctg ccgtaatcca acagatcaga     180
gagatcttcc agacaatggc gcgtcactac aactctacga gggtggtgcg ggatgaagcc     240
atcaagagca ttcgagacca cttcagggcc gccgtcccga ctcgcaacgt ggtggtcgtt     300
cacccccagc acattcacac actggacgcc gtggagtcct cccacctcgt cttgcggacc     360
ggcctgttca aaaggtccc tgtcgacatc tttgtcttca gtccggcgt cttcaccaac       420
ctgggagacg gaggcttcat caactgggca tggggtggct tcgtacagga ggtcgccggc     480
aagcgtatcc acttccgctt gccccccggg gcgctccct                            519

SEQ ID NO: 215              moltype = DNA  length = 513
FEATURE                     Location/Qualifiers
misc_feature                1..513
                            note = IPD103 variant
source                      1..513
                            mol_type = other DNA
                            organism = synthetic construct
SEQUENCE: 215
atggcggaca aagcagcagc agcagctaga gaagctgaag aagaggtgga gacgacgatg      60
gacgagactg aggcggtggg ggtgcacctg gacttcgtgg cgggcttgga ggtgcaaccc     120
cgcaaggtca tcaccgtgga ggtggacgcc gctgccgtaa tccaacagat cagagagatc     180
ttcgggtcca tgatcaatca cttcaactct acgagggtgg tgcgggatga agccatcaag     240
ggcattcgag accacttcag ggccgccgtc ccgactcgca acgtggtggt cattcacact     300
cagcacgttc acacactggt ggccgtggag tcctcccacc tcgtcttgca gaccggcctc     360
ttcaaaaagg tccccgtcga catctacgtc ttcaagtccg gcgtcttcac cctccttgga     420
gacggaggct tcatcaactg gcatggggt ggcttcggac tcgagctcgc cggcaagcgt      480
gtccacttcc gccggccccc cggggcgctc cct                                  513

SEQ ID NO: 216              moltype = DNA  length = 513
FEATURE                     Location/Qualifiers
misc_feature                1..513
                            note = IPD103 variant
source                      1..513
                            mol_type = other DNA
                            organism = synthetic construct
SEQUENCE: 216
atggcggacg aagtagcagg tcaccatggt ccagcatgtg aagaagagga ggaggaaatg      60
ctgatggacg agactgaggc ggtggggggtg cacgcgatcg acggtctgcc ggtgcaaaac    120
cgcagcatca tcaccgtgga ggtggacgcc gctgccgtaa tccaacagat cagagagatc     180
```

```
ttccgaacca tggcaagtca cttcaactcg acgagggtgg tgcgggatga agccatcaag   240
agcattcgag accacttcag gctcgccgtc ccgactcgca acgtggtggt cgttcacacc   300
cagcacattc acacactgga gggcttggag cacaccaacc tcgtcttgca gaccggcctc   360
ttcaaaaagg tccccgtcga catctacgtc ttcaagtccg gcgtcttcac caacctggga   420
gacggaggct tcatcaactg gcatggggt ggctacggcg tcaaccacac cgccaagcgt    480
gtcgtcttca gccggccccc cggggcgctc cct                                513

SEQ ID NO: 217          moltype = DNA  length = 510
FEATURE                 Location/Qualifiers
misc_feature            1..510
                        note = IPD103 variant
source                  1..510
                        mol_type = other DNA
                        organism = synthetic construct
SEQUENCE: 217
atggcggaca aagcagcagc agcagctaga gaagctgaag aagaggtgca ggagactttg   60
atggacgaga ctgaggcggt gggggtgcac gcgatcgacg tctgccggt gcaaaaccgc    120
agcatcatca ccgtggaggt ggacgccgct gccgtaatcc agcagatcag agagatcttc   180
gcgtcaatga tcaaacacta caactctacg agggtggtgc gggatgaagc catcaagagc   240
attcgagacc acttcaggct cgccgtcccg actcgcaacg tggtggtcat tcacactcag   300
cacgttcaca cactggtggg cttggagcac acccacctct cttgcagac cggcctcttc    360
aaaaaggtcc ccgtcgacat ctacgtcttc aagtccggcg tcttcaccct ccttggagac   420
ggaggcttca tcaactgggc atggggtggc ttcgtcgacc aggtcgtcgg caagcgtatc   480
cacttccgct tgccccccgg ggcgctccct                                    510

SEQ ID NO: 218          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 218
atggcggacg aagtagcagg tcaccatggt ccagcatgtg aagaagagga ggaggaaatg   60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtgg tgcgggatga agccatcaag   240
agcattcgag accacttcag gctcgccgtc ccgactcgca acgtggtggt cgttcacact   300
cagcacgttc acacactgga cgccgtggag tcctccccac cgtcttgcg gaccggcctc    360
ttcaaaaagg tccctgtcga catctttgtc ttcaagtccg gcgtcttcac cctccttgga   420
gacggaggct tcatcaactg gcatggggt ggctacggcg tcaaccacac cgccaagcgt    480
gtcgtcttca gccggccccc cggggcgctc cct                                513

SEQ ID NO: 219          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 219
atggcggacg aagtagcagg tcaccatggt ccagcatgtg aagaagagga ggaggaaatg   60
ctgatgacg agactgaggc ggtggggacg cacctggact tcgtggcggg cttggaggtg    120
caaccccgca aggtcatcac cgtggaggtg acgccgctg ccgtaatcca gcagatcaga    180
gagatcttcc gaaccatggc aagtcacttc aactcgacga gggtggtgcg ggatgaagcc   240
atcaagggca ttcgagacca cttcaggcc gccgtcccga ctcgcaacgt ggtggtcatt   300
cacactcagc acgttcacac actggacgcc gtggagtcct cccacctcgt cttgcggacc    360
ggcctgttca aaaggtccc tgtcgacatc tttgtcttca gtccggcgt cttcaccctc     420
cttggagacg gaggcttcat caactgggca tggggtggct acgtacagga ggtcgtcggc   480
aagcgtatcc acttccgctt gccccccggg gcgctccct                          519

SEQ ID NO: 220          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 220
atggcggacg aagtagcagg tcaccatggt ccagcatgtg aagaagagga ggaggaaatg   60
ctgatgacg agactgaggc ggtgggggtg cacgcgatcg acggtctgcc ggtgcaaccc    120
cgcaaggtca tcaccgtgga ggtggacgcc gctgccgtaa tccaacagat cagagagatc   180
ttccgcgtca atgatcaaaca ctacaactct acgagggtgg tgcgggatga agccatcaag   240
agcattcgag accacttcag gctcgccgtc ccgactcgca acgtggtggt cgttcacacc   300
cagcacattc acacactgga gggcttggag cacaccaacc tcgtcttgcg gaccggcctc   360
ttcaaaaagg tccctgtcga catctacgtc ttcaagtccg gcgtcttcac cctccttgga   420
gacggaggct tcatcaactg gcatggggt ggctacggcg tcaaccacac cgccaagcgt    480
gtcgtcttca gccggccccc cggggcgctc cct                                513
```

```
SEQ ID NO: 221          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 221
atggcggaca aagcagcagc agcagctaga gaagctgaag aagaggtgga gacgacgatg    60
gacgagactg aggcggtggg gacgcacctg gacttcgtgg cgggcttgga ggtgcaaccc   120
cgcaaggtca tcaccgtgga ggtggacgcc gctgccgtaa tccaacagat cagagagatc   180
ttccgaacca tggcaagtca cttcaactcg acgagggtgg tgcgggatga agccatcaag   240
ggcattcgag accacttcag ggccgccgtc ccgactcgca acgtggtggt cgttcacacc   300
cagcacattc acacactgga cgccgtggag tcctcccacc tcgtcttgcg gaccggcctc   360
ttcaaaaagg tccccgtcga catctatgtc ttcaagtccg gcgtcttcac cctccttgga   420
gacggaggct tcatcaactg gcatggggt ggcttcgtcg accaggtcgt cggcaagcgt    480
atccacttcc gcttgccccc cggggcgctc cct                                513

SEQ ID NO: 222          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 222
atggcggacg aagtagcagg tcaccatggt ccagcatgtg aagaagagga ggaggaaatg    60
ctgatgacg agactgaggc ggtgggggtg cacgcgatcg acggtctgcc ggtgcaaaac    120
cgcagcatca tcaccgtgga ggtggacgcc gctgccgtaa tccagcagat cagagagatc   180
ttccaaacca tggcaagtca cttcaactcg acgagggtgg tgcgggatga agccatcaag   240
agcattcgag accacttcag gctcgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctatgtc ttcaagtccg gcgtcttcac caacctggga   420
gacggaggct tcatcaactg gcatggggt ggctacggcg tcaaccacac cgccaagcgt    480
gtcgtcttca gccggccccc cggggcgctc cct                                513

SEQ ID NO: 223          moltype = DNA   length = 522
FEATURE                 Location/Qualifiers
misc_feature            1..522
                        note = IPD103 variant
source                  1..522
                        mol_type = other DNA
                        organism = synthetic construct
SEQUENCE: 223
atggcggacg aagtagcagg tcaccatggt ccagcatgtg aagaagagga ggaggaaatg    60
ctgatgacg agactgaggc ggtgggacg cacctggact tcttgggcgc ggacgtgaag    120
ttgcaacccc gcaacatcat caccgtggag gtggacgcg ctgccgtaat ccaacagatc   180
agagagatct tccagacaat ggcgcgtcac ttcaactcga cgagggtggt gcgggatgaa   240
gccatcaagg gcattcgaga ccacttcagg gccgccgtcc cgactcgcaa cgtggtggtc   300
gttcacaccc agcacattca cacactggag gcttgagc acaccaacct cgtcttgcag   360
accggcctct tcaaaaaggt ccccgtcgac atctatgtct tcaagtccgg cgtcttcacc   420
aaccttggag acggaggctt catcaactgg catgggtg gcttcgtaca ggaggtcgcc    480
ggcaagcgta tccacttccg cttgcccccc ggggcgctcc ct                      522

SEQ ID NO: 224          moltype = DNA   length = 511
FEATURE                 Location/Qualifiers
misc_feature            1..511
                        note = IPD103 variant
source                  1..511
                        mol_type = other DNA
                        organism = synthetic construct
SEQUENCE: 224
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc ctgccgtaat ccaacagatc agagagatct   180
tcgaaccatg gcaagtcact tcaactcgac gagggtggtg cgggatgaag ccatcaagag   240
cattcgagac cacttcaggc tcgccgtccc gactcgcaac gtggtggtca ttcacactca   300
gcacgttcac acactggacg ccgtggagtc ctcccacctc gtcttgcgga ccggcctgtt   360
caaaaaggtc cctgtcgaca tctacgtctt caagtccggc gtcttcacca accttggaga   420
cggaggcttc atcaactggg catggggtgg ctacggcgtc aaccacaccg ccaagcgtgt   480
cgtcttcagc cggccccccg gggcgctccc t                                  511

SEQ ID NO: 225          moltype = DNA   length = 513
FEATURE                 Location/Qualifiers
misc_feature            1..513
                        note = IPD103 variant
source                  1..513
                        mol_type = other DNA
                        organism = synthetic construct
```

```
SEQUENCE: 225
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttcgcgtcaa tgatcaaaca ctacaactct acgagggtgg tgcgggatga agccatcaag   240
agcattcgag accacttcag gctcgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctacgtc ttcaagtccg gcgtcttcac taacctggga   420
gacggaggct tcatcaactg ggcatggggt ggctacggcg tcaaccacac cgccaagcgt   480
gtcgtcttca gccggccccc cggggcgctc cct                                513

SEQ ID NO: 226          moltype = DNA   length = 510
FEATURE                 Location/Qualifiers
misc_feature            1..510
                        note = IPD103 variant
source                  1..510
                        mol_type = other DNA
                        organism = synthetic construct
SEQUENCE: 226
atggcggaca aagcagcagc agcagctaga gaagctgaag aagaggtgca ggagactttg    60
atggacgaga ctgaggcggt gggggtgcac gcgatcgacg tctgccggt gcaacccgc    120
aacatcatca ccgtggaggt ggacgcggct gccgtaatcc aacagatcag agagatcttc   180
cgaaccatgg caagtcactt caactcgacg agggtggtgc gggatgaagc catcaagggc   240
attcgagacc acttcaggc cgccgtcccg actcgcaacg tggtggtcgt tcacactcag   300
cacgttcaca cactggtggg cttggagcac acccacctcg tcttgcagac cggcctcttc   360
ataaaggtcc ccgtcgacat ctacgtcttc aagtccggcg tcttcaccct ccttggagac   420
ggaggcttca tcaactgggc atgggggtgg ttcgtcgacc aggtcgtcgg caagcgtatc   480
cacttccgct tgcccccccgg ggcgctccct                                   510

SEQ ID NO: 227          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 227
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccaacagat cagagagatc   180
ttcgcgtcaa tgatcaaaca ctacaactct acgagggtgg tgcgggatga agccatcaag   240
agcattcgag accacttcag gctcgccgtc ccgactcgca acgtggtggt cattcacact   300
cagcacgttc acacactgga cgccgtggag tcctcccacc tcgtcttgcg gaccggcctg   360
ttcaaaaagg tccccgtcga catctacgtc ttcaagtccg gcgtcttcac cctccttgga   420
gacggaggct tcatcaactg ggcatggggt ggctacggcg tcaaccacac cgccaagcgt   480
gtcgtcttca gccggccccc cggggcgctc cct                                513

SEQ ID NO: 228          moltype = DNA   length = 513
FEATURE                 Location/Qualifiers
misc_feature            1..513
                        note = IPD103 variant
source                  1..513
                        mol_type = other DNA
                        organism = synthetic construct
SEQUENCE: 228
atggcggacg aagtagcagg tcaccatggt ccagcatgtg aagaagagga ggaggaaatg    60
ctgatggacg agactgaggc ggtgggggtg cacgcgatcg acggtctgcc ggtgcaaaac   120
cgcagcatca tcaccgtgga ggtggacgcc gctgccgtaa tccagcagat cagagagatc   180
ttccgaacca tggcaagtca cttcaactcg acgagggtg tgcgggatga agccatcaag   240
agcattcgag accacttcag gctcgccgtc ccgactcgca acgtggtggt cgttcacact   300
cagcacgttc acacactgga cgccgtggag tcctcccacc tcgtcttgcg gaccggcctg   360
ttcaaaaagg tccctgtcga catctttgtc ttcaagtccg gcgtcttcac caaccttgga   420
gacggaggct tcatcaactg ggcatggggt ggctacggcg tcaaccacac cgccaagcgt   480
gtcgtcttca gccggccccc cggggcgctc cct                                513

SEQ ID NO: 229          moltype = AA    length = 171
FEATURE                 Location/Qualifiers
REGION                  1..171
                        note = IPD103 variant
source                  1..171
                        mol_type = protein
                        organism = synthetic construct
SEQUENCE: 229
MADPATAARE AEEEVETTMD ETEAVGTHLD FLGADVKLQP RNIITVEVDA AAVIQQIREI    60
FQTMARHFNS TRVVRDEAIK GIRDHFRAAV PTRNVVVHT QHIHTLEGLE HTNLVLQTGL   120
FKKVPVDIYV FKSGVFTLLG DGGFINWAWG GFVQEVAGKR IHFRLPPGAL P            171

SEQ ID NO: 230          moltype = AA    length = 170
FEATURE                 Location/Qualifiers
```

```
REGION                    1..170
                          note = IPD103 variant
source                    1..170
                          mol_type = protein
                          organism = synthetic construct
SEQUENCE: 230
MADPAAARE AEEEVETTMD ETEAVGTHLD FVAGLEVQPR KVITVEVDAA AVIQQIREIF    60
QTMARHFNST RVVRDEAIKG IRDHFRAAVP TRNVVVVHTQ HIHTLVGLEH THLVLQTGIF  120
KKVPVDIYVF KSGVFTNLGD GGFINWAWGG FVQEVAGKRI HFRLPPGALP             170

SEQ ID NO: 231            moltype = AA  length = 172
FEATURE                   Location/Qualifiers
REGION                    1..172
                          note = IPD103 variant
source                    1..172
                          mol_type = protein
                          organism = synthetic construct
SEQUENCE: 231
MADPATAARE AEEEVQETLM DETEAVGTHL DFLGADVKLQ PRNIITVEVD AAAVIQQIRE   60
IFRTMASHFN STRVVRDEAI KGIRDHFRAA VPTRNVVVVH TQHVHTLVGL EHTHLVLQTG  120
LFKKVPVDIY VFKSGVFTLL GDGGFINWAW GGFVQEVAGK RIHFRLPPGA LP          172

SEQ ID NO: 232            moltype = AA  length = 172
FEATURE                   Location/Qualifiers
REGION                    1..172
                          note = IPD103 variant
source                    1..172
                          mol_type = protein
                          organism = synthetic construct
SEQUENCE: 232
MADKTAAAAR EAEEEVQETL MDETEAVGTH LDFVAGLEVQ PRNIITVEVD AAAVIQQIRE   60
IFRTMASHFN STRVVRDEAI KGIRDHFRAA VPTRNVVVVH TQHIHTLEGL EHTNLVLQTG  120
IFKKVPVDIY VFKSGVFTNL GDGGFINWAW GGFVDQVVGK RIHFRLPPGA LP          172

SEQ ID NO: 233            moltype = AA  length = 171
FEATURE                   Location/Qualifiers
REGION                    1..171
                          note = IPD103 variant
source                    1..171
                          mol_type = protein
                          organism = synthetic construct
SEQUENCE: 233
MADKAAAAAR EAEEEVETTM DETEAVGTHL DFVAGLEVQP RKVITVEVDA AAVIQQIREI   60
FRTMASHFNS TRVVRDEAIK GIRDHFRAAV PTRNVVVVHT QHIHTLEGLE HTHLVLQTGL  120
FKKVPVDIYV FKSGVFTLLG DGGFINWAWG GFVQEVAGKR IHFRLPPGAL P           171

SEQ ID NO: 234            moltype = AA  length = 171
FEATURE                   Location/Qualifiers
REGION                    1..171
                          note = IPD103 variant
SITE                      138
                          note = misc_feature - Xaa can be any naturally occurring
                           amino acid
source                    1..171
                          mol_type = protein
                          organism = synthetic construct
SEQUENCE: 234
MADKAAAAAR EAEEEVETTM DETEAVGTHL DFVAGLEVQP RKVITVEVDA AAVIQQIREI   60
FQTMARHFNS TRVVRDEPIK GIRDHFRAAV PTRNVVVIHT QHVHTLVGLE HTHLVLQTGI  120
FKKVPVDIYV FKSGVFTXLG DGGFINWAWG GFVDQVVGKR IHFRLPPGAV P           171

SEQ ID NO: 235            moltype = AA  length = 171
FEATURE                   Location/Qualifiers
REGION                    1..171
                          note = IPD103 variant
source                    1..171
                          mol_type = protein
                          organism = synthetic construct
SEQUENCE: 235
MADKAAAAAR EAEEEVETTM DETEAVGTHL DFVAGLEVQP RNIITVEVDA AAVIQQIREI   60
FRTMASHFNS TRVVRDEAIK GIRDHFRAAV PTRNVVVVHT QHIHTLVGLE HTHLVLQTGI  120
FKKVPVDIYV FKSGVFTLLG DGGFINWAWG GFVQEVAGKR IHFRLPPGAL P           171

SEQ ID NO: 236            moltype = AA  length = 171
FEATURE                   Location/Qualifiers
REGION                    1..171
                          note = IPD103 variant
source                    1..171
                          mol_type = protein
```

```
                    organism = synthetic construct
SEQUENCE: 236
MADKAAAAAR EAEEEVETTM DETEAVGTHL DFVAGLEVQP RKVITVEVDA AAVIQQIREI      60
FQTMARHFNS TRVVRDEAIK GIRDHFRAAV PTRNVVVVHT QHVHTLVGLE HTNLVLQTGL     120
FKKVPVDIYV FKSGVFTLLG DGGFINWAWG GFVQEVAGKR IHFRLPPGAL P             171

SEQ ID NO: 237          moltype = AA   length = 173
FEATURE                 Location/Qualifiers
REGION                  1..173
                        note = IPD103 variant
source                  1..173
                        mol_type = protein
                        organism = synthetic construct
SEQUENCE: 237
MADKAAAAAR EAEEEVQETL MDETEAVGTH LDFLGADVKL QPRNIITVEV DAAAVIQQIR      60
EIFRTMASHF NSTRVVRDEA IKGIRDHFRA AVPTRNVVVV HTQHVHTLVG LEHTNLVLQT     120
GLFKKVPVDI YVFKSGVFTL LGDGGFINWA WGGFVQEVAG KRIHFRLPPG ALP            173

SEQ ID NO: 238          moltype = AA   length = 172
FEATURE                 Location/Qualifiers
REGION                  1..172
                        note = IPD103 variant
source                  1..172
                        mol_type = protein
                        organism = synthetic construct
SEQUENCE: 238
MADKAAAAAR EAEEEVETTM DETEAVGTHL DFLGADVKLQ PRNIITVEVD AAAVIQQIRE      60
IFRTMASHFN STRVVRDEAI KGIRDHFRAA VPTRNVVVIH TQHVHTLVGL EHTHLVLQTG     120
LFKKVPVDIY VFKSGVFTLL GDGGFINWAW GGFVDQVVGK RIHFRLPPGA LP             172

SEQ ID NO: 239          moltype = AA   length = 171
FEATURE                 Location/Qualifiers
REGION                  1..171
                        note = IPD103 variant
source                  1..171
                        mol_type = protein
                        organism = synthetic construct
SEQUENCE: 239
MADKAAAAAR EAEEEVETTM DETEAVGTHL DFVAGLEVQP RKVITVEVDA AAVIQQIREI      60
FRTMASHFNS TRVVRDEAIK GIRDHFRAAV PTRNVVVVHT QHIHTLEGLE HTHLVLQTGI     120
FKKVPVDIYV FKSGVFTLLG DGGFINWAWG GFVQEVAGKR IHFRLPPGAL P              171

SEQ ID NO: 240          moltype = AA   length = 171
FEATURE                 Location/Qualifiers
REGION                  1..171
                        note = IPD103 variant
source                  1..171
                        mol_type = protein
                        organism = synthetic construct
SEQUENCE: 240
MADKAAAAAR EAEEEVETTM DETEAVGTHL DFVAGLEVQP RNIITVEVDA AAVIQQIREI      60
FQTMARHFNS TRVVRDEAIK GIRDHFRAAV PTRNVVVVHT QHVHTLVGLE HTHLVLQTGI     120
FKKVPVDIYV FKSGVFTLLG DGGFINWAWG GFVDQVVGKR IHFRLPPGAL P              171

SEQ ID NO: 241          moltype = AA   length = 172
FEATURE                 Location/Qualifiers
REGION                  1..172
                        note = IPD103 variant
source                  1..172
                        mol_type = protein
                        organism = synthetic construct
SEQUENCE: 241
MADKAAAAAR EAEEEVQETL MDETEAVGTH LDFVAGLEVQ PRKVITVEVD AAAVIQQIRE      60
IFRTMASHFN STRVVRDEAI KGIRDHFRAA VPTRNVVVIH TQHVHTLVGL EHTHLVLQTG     120
IFKKVPVDIY VFKSGVFTLL GDGGFINWAW GGFVDQVVGK RIHFRLPPGA LP             172

SEQ ID NO: 242          moltype = AA   length = 171
FEATURE                 Location/Qualifiers
REGION                  1..171
                        note = IPD103 variant
source                  1..171
                        mol_type = protein
                        organism = synthetic construct
SEQUENCE: 242
TADKAAAAAR EAEEEVETTM DETEAVGTHL DFVAGLEVQP RNIITVEVDA AAVIQQIREI      60
FRTMASHFNS TRVVRDEAIK GIRDHFRAAV PTRNVVVVHT QHVHTLVGLE HTHLVLQTGI     120
FKKVPVDIYV FKSGVFTLLG DGGFINWAWG GFVQEVAGKR IHFRLPPGAL P              171

SEQ ID NO: 243          moltype = AA   length = 170
```

```
FEATURE                 Location/Qualifiers
REGION                  1..170
                        note = IPD103 variant
source                  1..170
                        mol_type = protein
                        organism = synthetic construct
SEQUENCE: 243
MADPATAARE AEEEVETTMD ETEAVGTHLD FVAGLEVQPR KVITVEVDAA AVIQQIREIF    60
RTMASHFNST RVVRDEAIKG IRDHFRAAVP TRNVVVVHTQ HVHTLVGLEH THLVLQTGLF   120
KKVPVDIYVF KSGVFTLLGD GGFINWAWGG FVDQVVGKRI HFRLPPGALP             170

SEQ ID NO: 244          moltype = AA  length = 171
FEATURE                 Location/Qualifiers
REGION                  1..171
                        note = IPD103 variant
source                  1..171
                        mol_type = protein
                        organism = synthetic construct
SEQUENCE: 244
MADPATAARE AEEEVQETLM DTEAVGTHL DFVAGLEVQP RNIITVEVDA AAVIQQIREI    60
FRTMASHFNS TRVVRDEAIK GIRDHFRAAV PTRNVVVVHT QHVHTLVGLE HTHLVLQTGI  120
FKKVPVDIYV FKSGVFTLLG DGGFINWAWG GFVDQVVGKR IHFRLPPGAL P           171

SEQ ID NO: 245          moltype = AA  length = 171
FEATURE                 Location/Qualifiers
REGION                  1..171
                        note = IPD103 variant
source                  1..171
                        mol_type = protein
                        organism = synthetic construct
SEQUENCE: 245
MADKAAAAAR EAEEEVETTM DTEAVGTHL DFVAGLEVQP RKVITVEVDA AAVIQQIREI    60
FQTMARHFNS TRVVRDEAIK GIRDHFRAAV PTRNVVVVHT QHIHTLVGLE HTHLVLQTGL  120
FKKVPVDIYV FKSGVFTLLG DGGFINWAWG GFVQEVAGKR IHFRLPPGAL P           171

SEQ ID NO: 246          moltype = AA  length = 172
FEATURE                 Location/Qualifiers
REGION                  1..172
                        note = IPD103 variant
source                  1..172
                        mol_type = protein
                        organism = synthetic construct
SEQUENCE: 246
MADKTAAAAR EAEEEVETTM DTEAVGTHL DFLGADVKLQ PRNIITVEVD AAAVIQQIRE    60
IFRTMASHFN STRVVRDEAI KGIRDHFRAA VPTRNVVVVH TQHIHTLEGL EHTHLVLQTG  120
IFKKVPVDIY VFKSGVFTLL GDGGFINWAW GGFVQEVAGK RIHFRLPPGA LP          172

SEQ ID NO: 247          moltype = AA  length = 171
FEATURE                 Location/Qualifiers
REGION                  1..171
                        note = IPD103 variant
source                  1..171
                        mol_type = protein
                        organism = synthetic construct
SEQUENCE: 247
MADPATAARE AEEEVQETLM DTEAVGTHL DFVAGLEVQP RNIITVEVDA AAVIQQIREI    60
FRTMASHFNS TRVVRDEAIK GIRDHFRAAV PTRNVVVIHT QHVHTLVGLE HTHLVLQTGI  120
FKKVPVDIYV FKSGVFTLLG DGGFINWAWG GFVDQVVGKR IHFRLPPGAL P           171

SEQ ID NO: 248          moltype = AA  length = 172
FEATURE                 Location/Qualifiers
REGION                  1..172
                        note = IPD103 variant
source                  1..172
                        mol_type = protein
                        organism = synthetic construct
SEQUENCE: 248
MADKAAAAAR EAEEEVETTM DTEAVGTHL DFLGADVKLQ PRNIITVEVD AAAVIQQIRE    60
IFRTMASHFN STRVVRDEAI KGIRDHFRAA VPTRNVVVVH TQHIHTLVGL EHTHLVLQTG  120
IFKKVPVDIY VFKSGVFTNL GDGGFINWAW GGFVDQVVGK RIHFRLPPGA LP          172

SEQ ID NO: 249          moltype = AA  length = 171
FEATURE                 Location/Qualifiers
REGION                  1..171
                        note = IPD103 variant
source                  1..171
                        mol_type = protein
                        organism = synthetic construct
SEQUENCE: 249
```

```
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTNLVLQTGL   120
FKKVPVDIYV FKSGVFTNLG DGGFINWAWG GFVDQVVGKR IHFRLPPGAL P           171

SEQ ID NO: 250          moltype = AA   length = 172
FEATURE                 Location/Qualifiers
REGION                  1..172
                        note = IPD103 variant
source                  1..172
                        mol_type = protein
                        organism = synthetic construct
SEQUENCE: 250
MADKAAAAAR EAEEEVETLM DETEAVGTHL DFLGADVKLQ PRNIITVEVD AAAVIQQIRE    60
IFRTMANHFN STRVVRDEAI KGIRDHFRAA VPTRNVVVVH TQHIHTLEGL EHTNLVLQTG   120
LFKKVPVDIY VFKSGVFTNL GDGGFINWAW GGFVDQVVGK RIHFRLPPGA LP          172

SEQ ID NO: 251          moltype = AA   length = 170
FEATURE                 Location/Qualifiers
REGION                  1..170
                        note = IPD103 variant
source                  1..170
                        mol_type = protein
                        organism = synthetic construct
SEQUENCE: 251
MADPAAAARE AEEEVETTMD ETEAVGTHLD FVAGLEVQPR KVITVEVDAA AVIQQIREIF    60
QTMARHFNST RVVRDEAIKG IRDHFRAAVP TRNVVVVHTQ HVHTLVGLEH TNLVLQTGLF   120
KKVPVDIYVF KSGVFTLLGD GGFINWAWGG FVQEVAGKRI HFRLPPGALP             170

SEQ ID NO: 252          moltype = AA   length = 171
FEATURE                 Location/Qualifiers
REGION                  1..171
                        note = IPD103 variant
source                  1..171
                        mol_type = protein
                        organism = synthetic construct
SEQUENCE: 252
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTNLVLQTGI   120
FKKVPVDIYV FKSGVFTNLG DGGFINWAWG GFVQEVAGKR IHFRLPPGAL P           171

SEQ ID NO: 253          moltype = AA   length = 172
FEATURE                 Location/Qualifiers
REGION                  1..172
                        note = IPD103 variant
source                  1..172
                        mol_type = protein
                        organism = synthetic construct
SEQUENCE: 253
MADKAAAAAR EAEEEVETTM DETEAVGTHL DFLGADVKLQ PRKVITVEVD AAAVIQQIRE    60
IFQTMARHFN STRVVRDEAI KGIRDHFRAA VPTRNVVVVH TQHIHTLEGL EHTHLVLQTG   120
LFKKVPVDIY VFKSGVFTLL GDGGFINWAW GGFVQEVAGK RIHFRLPPGA LP          172

SEQ ID NO: 254          moltype = AA   length = 173
FEATURE                 Location/Qualifiers
REGION                  1..173
                        note = IPD103 variant
source                  1..173
                        mol_type = protein
                        organism = synthetic construct
SEQUENCE: 254
MADKAAAAAR EAEEEVQETL MDETEAVGTH LDFLGADVKL QPRKVITVEV DAAAVIQQIR    60
EIFQTMARHF NSTRVVRDEA IKGIRDHFRA AVPTRNVVVV HTQHIHTLEG LEHTHLVLQT   120
GIFKKVPVDI YVFKSGVFTN LGDGGFINWA WGGFVQEVAG KRIHFRLPPG ALP         173

SEQ ID NO: 255          moltype = AA   length = 171
FEATURE                 Location/Qualifiers
REGION                  1..171
                        note = IPD103 variant
source                  1..171
                        mol_type = protein
                        organism = synthetic construct
SEQUENCE: 255
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHVHTLVGSE HTHLVLQTGI   120
FKKVPVDIYV FKSGVFTLLG DGGFINWAWG GFVDQVVGKR IHFRLPPGAL P           171

SEQ ID NO: 256          moltype = AA   length = 171
FEATURE                 Location/Qualifiers
REGION                  1..171
```

```
                        note = IPD103 variant
source                  1..171
                        mol_type = protein
                        organism = synthetic construct
SEQUENCE: 256
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHVHTLVGLE HTNLVLQTGL   120
FKKVPVDIYV FKSGVFTLLG DGGFINWAWG GFVDQVVGKR IHFRLPPGAL P            171

SEQ ID NO: 257          moltype = AA  length = 172
FEATURE                 Location/Qualifiers
REGION                  1..172
                        note = IPD103 variant
source                  1..172
                        mol_type = protein
                        organism = synthetic construct
SEQUENCE: 257
MADKAAAAAR EAEEEVETTM DETEAVGTHL DFLGADVKLQ PRKVITVEVD AAAVIQQIRE    60
IFQTMARHFN STRVVRDEAI KGIRDHFRAA VPTRNVVVVH TQHIHTLVGL EHTHLVLQTG   120
IFKKVPVDIY VFKSGVFTNL GDGGFINWAW GGFVQEVAGK RIHFRLPPGA LP           172

SEQ ID NO: 258          moltype = AA  length = 171
FEATURE                 Location/Qualifiers
REGION                  1..171
                        note = IPD103 variant
source                  1..171
                        mol_type = protein
                        organism = synthetic construct
SEQUENCE: 258
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTHLVLQTGI   120
FKKVPVDIYV FKSGVFTNLG DGGFINWAWG GFVQEVAGKR IHFRLPPGAL P            171

SEQ ID NO: 259          moltype = AA  length = 171
FEATURE                 Location/Qualifiers
REGION                  1..171
                        note = IPD103 variant
source                  1..171
                        mol_type = protein
                        organism = synthetic construct
SEQUENCE: 259
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVIHT QHVHTLVGLE HTHLVLQTGI   120
FKKVPVDIYV FKSGVFTNLG DGGFINWAWG GFVQEVAGKR IHFRLPPGAL P            171

SEQ ID NO: 260          moltype = AA  length = 171
FEATURE                 Location/Qualifiers
REGION                  1..171
                        note = IPD103 variant
source                  1..171
                        mol_type = protein
                        organism = synthetic construct
SEQUENCE: 260
MADKAAAAAR EAEEEVETTM DETEAVGTHL DFVAGLEVQP RKVITVEVDA AAVIQQIREI    60
FQTMARHFNS TRVVRDEAIK GIRDHFRAAV PTRNVVVVHT QHIHTLEGLE HTNLVLQTGL   120
FKKVPVDIYV FKSGVFTLLG DGGFINWAWG GFVDQVVGKR IHFRLPPGAL P            171

SEQ ID NO: 261          moltype = AA  length = 171
FEATURE                 Location/Qualifiers
REGION                  1..171
                        note = IPD103 variant
source                  1..171
                        mol_type = protein
                        organism = synthetic construct
SEQUENCE: 261
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTHLVLQTGI   120
FKKVPVDIYV FKSGVFTLLG DGGFINWAWG GFVQEVAGKR IHFRLPPGAL P            171

SEQ ID NO: 262          moltype = AA  length = 171
FEATURE                 Location/Qualifiers
REGION                  1..171
                        note = IPD103 variant
source                  1..171
                        mol_type = protein
                        organism = synthetic construct
SEQUENCE: 262
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHVHTLEGLE HTHLVLQTGL   120
```

```
FKKVPVDIYV FKSGVFTLLG DGGFINWAWG GFVDQVVGKR IHFRLPPGAL P        171

SEQ ID NO: 263              moltype = AA  length = 171
FEATURE                     Location/Qualifiers
REGION                      1..171
                            note = IPD103 variant
source                      1..171
                            mol_type = protein
                            organism = synthetic construct
SEQUENCE: 263
MADKAAAAAR EAEEEVETTM DETEAVGTHL DFVAGLEVQP RKVITVEVDA AAVIQQIREI  60
FQTMARHFNS TRVVRDEAIK GIRDHFRAAV PTRNVVVVHT QHVHTLEGLE HTHLVLQTGI 120
FKKVPVDIYV FKSGVFTNLG DGGFINWAWG GFVDQVVGKR IHFRLPPGAL P         171

SEQ ID NO: 264              moltype = AA  length = 171
FEATURE                     Location/Qualifiers
REGION                      1..171
                            note = IPD103 variant
source                      1..171
                            mol_type = protein
                            organism = synthetic construct
SEQUENCE: 264
MADKAAAAAR EAEEEVETTM DETEAVGTHL DFVAGLEVQP RKVITVEVDA AAVIQQIREI  60
FRTMASHFNS TRVVRDEAIK GIRDHFRAAV PTRNVVVVHT QHVHTLEGLE HTHLVLQTGI 120
FKKVPVDIYV FKSGVFTLLG DGGFINWAWG GFVQEVAGKR IHFRLPPGAL P         171

SEQ ID NO: 265              moltype = AA  length = 171
FEATURE                     Location/Qualifiers
REGION                      1..171
                            note = IPD103 variant
source                      1..171
                            mol_type = protein
                            organism = synthetic construct
SEQUENCE: 265
MADKAAAAAR EAEEEVETTM DETEAVGTHL DFVAGLEVQP RNIITVEVDA AAVIQQIREI  60
FQTMARHFNS TRVVRDEAIK GIRDHFRAAV PTRNVVVVHT QHVHTLVGLE HTHLVLQTGL 120
FKKVPVDIYV FKSGVFTNLG DGGFINWAWG GFVQEVAGKR IHFRLPPGAL P         171

SEQ ID NO: 266              moltype = AA  length = 171
FEATURE                     Location/Qualifiers
REGION                      1..171
                            note = IPD103 variant
SITE                        19
                            note = misc_feature - Xaa can be any naturally occurring
                             amino acid
SITE                        55
                            note = misc_feature - Xaa can be any naturally occurring
                             amino acid
SITE                        66
                            note = misc_feature - Xaa can be any naturally occurring
                             amino acid
source                      1..171
                            mol_type = protein
                            organism = synthetic construct
SEQUENCE: 266
MADTAAAAAR EDEEELETXM DETEAVGTHL DFVAGLEVQP RKVITVEVDA AAVIXQIREI  60
FRTMAXHFNS TRVVRDEAIK GIRDHFRAAV PTRNVVVVHT QHVHTLEGLE HTHLVLQTGI 120
FKKVPVDIYV FKSGVFTILG DGGFINWAWG GFVDQVVGKR IHFRLPPGAL P         171

SEQ ID NO: 267              moltype = AA  length = 170
FEATURE                     Location/Qualifiers
REGION                      1..170
                            note = IPD103 variant
source                      1..170
                            mol_type = protein
                            organism = synthetic construct
SEQUENCE: 267
MADKAAAARE AEEEVETTMD ETEAVGTHLD FVAGLEVQPR NIITVEVDAA AVIQQIREIF  60
QTMARHFNST RVVRDEAIKG IRDHFRAAVP TRNVVVVHTQ HIHTLEGLEH TNLVLQTGLF 120
KKVPVDIYVF KSGVFTNLGD GGFINWAWGG FVQEVAGKRI HFRLPPGALP          170

SEQ ID NO: 268              moltype = AA  length = 170
FEATURE                     Location/Qualifiers
REGION                      1..170
                            note = IPD103 variant
source                      1..170
                            mol_type = protein
                            organism = synthetic construct
SEQUENCE: 268
```

```
MADKAAAAAR EAEEEEEEML MDETEAVGVH AIDGLPVQNR SIITVEVDAA AVIQQIREIF    60
RTMASHFNST RVVRDEAIKS IRDHFRLAVP TRNVVVVHTQ HVHTLVGLEH THLVLQTGIF   120
KKVPVDIYVF KSGVFTNLGD GGFINWAWGG FVDQVVGKRI HFRLPPGALP              170

SEQ ID NO: 269          moltype = AA  length = 171
FEATURE                 Location/Qualifiers
REGION                  1..171
                        note = IPD103 variant
source                  1..171
                        mol_type = protein
                        organism = synthetic construct
SEQUENCE: 269
MADKAAAAAR EAEEEVETTM DETEAVGTHL DFVAGLEVQP RKVITVEVDA AAVIQQIREI    60
FQTMARHFNS TRVVRDEAIK GIRDHFRAAV PTRNVVVIHT QHVHTLVGLE HTHLVLRTGL   120
FKKVPVDIYV FKSGVFTNLG DGGFINWAWG GFVDQVVGKR IHFRLPPGAL P            171

SEQ ID NO: 270          moltype = AA  length = 170
FEATURE                 Location/Qualifiers
REGION                  1..170
                        note = IPD103 variant
source                  1..170
                        mol_type = protein
                        organism = synthetic construct
SEQUENCE: 270
MADKAAAAAR EAEEEEEEML MDETEAVGVH AIDGLPVQNR SIITVEVDAA AVIQQIREIF    60
RTMASHFNST RVVRDEAIKG IRDHFRLAVP TRNVVVIHTQ HVHTLVGLEH THLVLQTGLF   120
KKVPVDIYVF KSGVFTNLGD GGFINWAWGG FVQEVAGKRI HFRLPPGALP              170

SEQ ID NO: 271          moltype = AA  length = 171
FEATURE                 Location/Qualifiers
REGION                  1..171
                        note = IPD103 variant
source                  1..171
                        mol_type = protein
                        organism = synthetic construct
SEQUENCE: 271
MADKAAAAAR EAEEEVETTM DETEAVGTHL DFVAGLEVQP RKVITVEVDA AAVIQQIREI    60
FQTMARHFNS TRVVRDEAIK SIRDHFRAAV PTRNVVVVHT QHIHTLEGLE HTHLVLQTGL   120
FKKVPVDIYV FKSGVFTNLG DGGFINWAWG GFVDQVVGKR IHFRLPPGAL P            171

SEQ ID NO: 272          moltype = AA  length = 171
FEATURE                 Location/Qualifiers
REGION                  1..171
                        note = IPD103 variant
source                  1..171
                        mol_type = protein
                        organism = synthetic construct
SEQUENCE: 272
MADEVAGHHG PACEEEEEEM LMDETEAVGV HAIDGLPVQN RSIITVEVDA AAVIQQIREI    60
FASMIKHYNS TRVVRDEAIK GIRDHFRAAV PTRNVVVVHT QHVHTLVGLE HTHLVLQTGL   120
FKKVPVDIYV FKSGVFTLLG DGGFINWAWG GYGVNHTAKR VVFSRPPGAL P            171

SEQ ID NO: 273          moltype = AA  length = 173
FEATURE                 Location/Qualifiers
REGION                  1..173
                        note = IPD103 variant
source                  1..173
                        mol_type = protein
                        organism = synthetic construct
SEQUENCE: 273
MADEVAGHHG PACEEEEEEM LMDETEAVGT HLDFVAGLEV QPRKVITVEV DAAAVIQQIR    60
EIFRTMASHF NSTRVVRDEA IKGIRDHFRA AVPTRNVVVV HTQHIHTLEG LEHTHLVLRT   120
GLFKKVPVDI FVFKSGVFTN LGDGGFINWA WGGYVQEVAG KRIHFRLPPG ALP          173

SEQ ID NO: 274          moltype = AA  length = 174
FEATURE                 Location/Qualifiers
REGION                  1..174
                        note = IPD103 variant
source                  1..174
                        mol_type = protein
                        organism = synthetic construct
SEQUENCE: 274
MADEVAGHHG PACEEEEEEM LMDETEAVGT HLDFLGADVK LQPRNIITVE VDAAAVIQQI    60
REIFQTMARH FNSTRVVRDE AIKGIRDHFR AAVPTRNVVV VHTQHIHTLE GLEHTNLVLQ   120
TGLFKKVPVD IYVFKSGVFT NLGDGGFINW AWGGFVQEVA GKRIHFRLPP GALP         174

SEQ ID NO: 275          moltype = AA  length = 172
FEATURE                 Location/Qualifiers
REGION                  1..172
```

```
                     note = IPD103 variant
source               1..172
                     mol_type = protein
                     organism = synthetic construct
SEQUENCE: 275
MADKAAAAAR EAEEEVQETL MDETEAVGTH LDFVAGLEVQ PRKVITVEVD AAAVIQQIRE    60
IFQTMARHFN STRVVRDEAI KGIRDHFRAA VPTRNVVVIH TQHVHTLDAV ESSHLVLRTG   120
LFKKVPVDIY VFKSGVFTNL GDGGFINWAW GGYVDQVVGK RIHFRLPPGA LP           172

SEQ ID NO: 276       moltype = AA   length = 171
FEATURE              Location/Qualifiers
REGION               1..171
                     note = IPD103 variant
source               1..171
                     mol_type = protein
                     organism = synthetic construct
SEQUENCE: 276
MADKAAAAAR EAEEEVETTM DETEAVGTHL DFVAGLEVQP RKVITVEVDA AAVIQQIREI    60
FQTMARHFNS TRVVRDEAIK SIRDHFRAAV PTRNVVVIHT QHVHTLVGLE HTHLVLQTGL   120
FKKVPVDIYV FKSGVFTNLG DGGFINWAWG GFVQEVVGKR IHFRLPPGAL P            171

SEQ ID NO: 277       moltype = AA   length = 171
FEATURE              Location/Qualifiers
REGION               1..171
                     note = IPD103 variant
source               1..171
                     mol_type = protein
                     organism = synthetic construct
SEQUENCE: 277
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVIHT QHVHTLDAVE SSHLVLQTGL   120
FKKVPVDIYV FKSGVFTNLG DGGFINWAWG GFVDQVVGKR IHFRLPPGAL P            171

SEQ ID NO: 278       moltype = AA   length = 173
FEATURE              Location/Qualifiers
REGION               1..173
                     note = IPD103 variant
source               1..173
                     mol_type = protein
                     organism = synthetic construct
SEQUENCE: 278
MADEVAGHHG PACEEEVQET LMDETEAVGT HLDFVAGLEV QPRSIITVEV DAAAVIQQIR    60
EIFQTMARHF NSTRVVRDEA IKGIRDHFRL AVPTRNVVVV HTQHVHTLVG LEHTHLVLQT   120
GIFKKVPVDI YVFKSGVFTN LGDGGFINWA WGGFVDQVVG KRIHFRLPPG ALP          173

SEQ ID NO: 279       moltype = AA   length = 173
FEATURE              Location/Qualifiers
REGION               1..173
                     note = IPD103 variant
source               1..173
                     mol_type = protein
                     organism = synthetic construct
SEQUENCE: 279
KADEVAGHHG PACEEEEEEM LMDETEAVGT HLDFVAGLEV QPRKVITVEV DAAAVIQQIR    60
EIFRTMASHY NSTRVVRDEA IKGIRDHFRA AVPTRNVVVI HTQHVHTLDA VESSHLVLQT   120
GIFKKVPVDI YVFKSGVFTN LGDGGFINWA WGGFVDQVVG KRIHFRLPPG ALP          173

SEQ ID NO: 280       moltype = AA   length = 174
FEATURE              Location/Qualifiers
REGION               1..174
                     note = IPD103 variant
source               1..174
                     mol_type = protein
                     organism = synthetic construct
SEQUENCE: 280
MADEVAGHHG PACEEEEEEM LMDETEAVGT HLDFLGADVK LQPRNIITVE VDAAAVIQQI    60
REIFQTMARH FNSTRVVRDE AIKGIRDHFR AAVPTRNVVV IHTQHVHTLD AVESSHLVLR   120
TGLFKKVPVD IYVFKSGVFT NLGDGGFINW AWGGFVDQVV GKRIHFRLPP GALP         174

SEQ ID NO: 281       moltype = AA   length = 171
FEATURE              Location/Qualifiers
REGION               1..171
                     note = IPD103 variant
source               1..171
                     mol_type = protein
                     organism = synthetic construct
SEQUENCE: 281
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVVHT QHVHTLVGLE HTHLVLRTGL   120
```

```
FKKVPVDIYV FKSGVFTLLG DGGFINWAWG GFVQEVAGKR IHFRLPPGAL P          171

SEQ ID NO: 282           moltype = AA  length = 172
FEATURE                  Location/Qualifiers
REGION                   1..172
                         note = IPD103 variant
source                   1..172
                         mol_type = protein
                         organism = synthetic construct
SEQUENCE: 282
MADEVAGHHG PACEEEVETT MDETEAVGTH LDFVAGLEVQ PRKVITVEVD AAAVIQQIRE  60
IFQTMARHFN STRVVRDEAI KSIRDHFRAA VPTRNVVVIH TQHVHTLEGL EHTNLVLQTG  120
IFKKVPVDIY VFKSGVFTNL GDGGFINWAW GGFVDQVVGK RIHFRLPPGA LP          172

SEQ ID NO: 283           moltype = AA  length = 171
FEATURE                  Location/Qualifiers
REGION                   1..171
                         note = IPD103 variant
source                   1..171
                         mol_type = protein
                         organism = synthetic construct
SEQUENCE: 283
MADEVAGHHG PACEEEEEM LMDETEAVGV HAIDGLPVQN RSIITVEVDA AAVIQQIREI   60
FRTMASHFNS TRVVRDEAIK SIRDHFRAAV PTRNVVVVHT QHVHTLDAVE SSHLVLRTGL  120
FKKVPVDIYV FKSGVFTNLG DGGFINWAWG GFVDQVVGKR IHFRLPPGAL P          171

SEQ ID NO: 284           moltype = AA  length = 172
FEATURE                  Location/Qualifiers
REGION                   1..172
                         note = IPD103 variant
source                   1..172
                         mol_type = protein
                         organism = synthetic construct
SEQUENCE: 284
MADEVAGHHG PASEEEEERM MDETETEAVH LHVIAGLEVQ PRSIITVEVD AAAVIQQIRE  60
IFQTMASHFN STRVVRDEAI KGIRDHFRAA VPTRNVVVIH TQHVHTLEAV ESSHLVLRTG  120
LFKKVPVDIY VFKSGVFTLL GDGGFINWAW GGFVVHVVGK RVHFSRPPGA LP          172

SEQ ID NO: 285           moltype = AA  length = 171
FEATURE                  Location/Qualifiers
REGION                   1..171
                         note = IPD103 variant
source                   1..171
                         mol_type = protein
                         organism = synthetic construct
SEQUENCE: 285
MADPATAARE AEEEVQETLM DESEAVGTHL DFVAGLEVQP RKVITVEVDA AAVIHQIREI  60
FQTMARHFNS TRVVRDEAIK GIRDHFRAAV PTRNVVVIHS QHIHTLEGLE HTNLVLQTGM  120
FKKVPVDIFV FKSGVFTLLG DGGFINWAWG GFVQEVVGKR IHFRLPPGAL P          171

SEQ ID NO: 286           moltype = AA  length = 171
FEATURE                  Location/Qualifiers
REGION                   1..171
                         note = IPD103 variant
source                   1..171
                         mol_type = protein
                         organism = synthetic construct
SEQUENCE: 286
MADEVAGHHG PACEEEEEEM LMDETEAVGV HAIDGLPVQN RSIITVEVDA AAVIQQIREI  60
FRTMASHFNS TRVVRDEAIK GIRDHFRAAV PTRNVVVVHT QHIHTLEGLE HTNLVLQTGL  120
FKKVPVDIYV FKSGVFTLLG DGGFINWAWG GFGVNHTAKR VVFSRPPGAL P          171

SEQ ID NO: 287           moltype = AA  length = 171
FEATURE                  Location/Qualifiers
REGION                   1..171
                         note = IPD103 variant
source                   1..171
                         mol_type = protein
                         organism = synthetic construct
SEQUENCE: 287
MADEVAGHHG PACEEEEEEM LMDETEAVGV HAIDGLPVQN RSIITVEVDA AAVIQQIREI  60
FRTMASHFNS TRVVRDEAIK SIRDHFRAAV PTRNVVVIHT QHVHTLDAVE SSHLVLQTGL  120
FKKVPVDIFV FKSGVFTNLG DGGFINWAWG GYGVNHTAKR VVFSRPPGAL P          171

SEQ ID NO: 288           moltype = AA  length = 171
FEATURE                  Location/Qualifiers
REGION                   1..171
                         note = IPD103 variant
source                   1..171
```

```
                        mol_type = protein
                        organism = synthetic construct
SEQUENCE: 288
MADEVAGHHG PACEEEEEEM LMDETEAVGV HAIDGLPVQN RSIITVEVDA AAVIQQIREI    60
FRTMASHFNS TRVVRDEAIK SIRDHFRAAV PTRNVVVIHT QHVHTLDAVE SSHLVLRTGL   120
FKKVPVDIYV FKSGVFTNLG DGGFINWAWG GFVDQVVGKR IHFRLPPGAL P            171

SEQ ID NO: 289          moltype = AA  length = 173
FEATURE                 Location/Qualifiers
REGION                  1..173
                        note = IPD103 variant
source                  1..173
                        mol_type = protein
                        organism = synthetic construct
SEQUENCE: 289
MADKAAAAAR EAEEEVQETL MDETEAVGTH LDFLGADVKL QPRKVITVEV DAAAVIQQIR    60
EIFRTMASHF NSTRVVRDEA IKGIRDHFRA AVPTRNVVVV HTQHIHTLEG LEHTNLVLQT   120
GIFKKVPVDI YVFKSGVFTL LGDGGFINWA WGGFVQEVAG KRIHFRLPPG ALP          173

SEQ ID NO: 290          moltype = AA  length = 171
FEATURE                 Location/Qualifiers
REGION                  1..171
                        note = IPD103 variant
source                  1..171
                        mol_type = protein
                        organism = synthetic construct
SEQUENCE: 290
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVIHT QHVHTLDAVE SSHLVLRTGL   120
FKKVPVDIFV FKSGVFTNLG DGGFINWAWG GFVQEVAGKR IHFRLPPGAL P            171

SEQ ID NO: 291          moltype = AA  length = 174
FEATURE                 Location/Qualifiers
REGION                  1..174
                        note = IPD103 variant
source                  1..174
                        mol_type = protein
                        organism = synthetic construct
SEQUENCE: 291
MADEVAGHHG PACEEEEEEM LMDETEAVGT HLDFLGADVK LQPRKVITVE VDAAAVIQQI    60
REIFRTMASH FNSTRVVRDE AIKGIRDHFR AAVPTRNVVV VHTQHVHTLV GLEHTHLVLQ   120
TGLFKKVPVD IYVFKSGVFT NLGDGGFINW AWGGFVDQVV GKRIHFRLPP GALP         174

SEQ ID NO: 292          moltype = AA  length = 169
FEATURE                 Location/Qualifiers
REGION                  1..169
                        note = IPD103 variant
source                  1..169
                        mol_type = protein
                        organism = synthetic construct
SEQUENCE: 292
MADEVAAAAR EAEEEVETTM DETEAVGVHA IDGLPVQNRS IITVEVDAAA VIQQIREIFR    60
TMASHFNSTR VVRDEAIKGI RDHFRLAVPT RNVVVIHTQH VHTLVGLEHT HLVLQTGIFK   120
KVPVDIYVFK SGVFTNLGDG GFINWAWGGF VDQVVGKRIH FRLPPGALP               169

SEQ ID NO: 293          moltype = AA  length = 171
FEATURE                 Location/Qualifiers
REGION                  1..171
                        note = IPD103 variant
source                  1..171
                        mol_type = protein
                        organism = synthetic construct
SEQUENCE: 293
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVIHT QHVHTLDAVE SSHLVLRTGL   120
FKKVPVDIYV FKSGVFTNLG DGGFINWAWG GFGVNHTAKR VVFSRPPGAL P            171

SEQ ID NO: 294          moltype = AA  length = 172
FEATURE                 Location/Qualifiers
REGION                  1..172
                        note = IPD103 variant
source                  1..172
                        mol_type = protein
                        organism = synthetic construct
SEQUENCE: 294
MADKAAAAAR EAEEEVETTM DETEAVGTHL DFLGADVKLQ PRKVITVEVD AAAVIQQIRE    60
IFRTMASHFN STRVVRDEAI KGIRDHFRAA VPTRNVVVVH TQHIHTLEGL EHTNLVLQTG   120
LFKKVPVDIY VFKSGVFTNL GDGGFINWAW GGFVQEVAGK RIHFRLPPGA LP           172
```

| SEQ ID NO: 295 | moltype = AA   length = 172 |
| --- | --- |
| FEATURE | Location/Qualifiers |
| REGION | 1..172 |
| | note = IPD103 variant |
| source | 1..172 |
| | mol_type = protein |
| | organism = synthetic construct |

SEQUENCE: 295
```
MADEVAGHHG PACEEEVETT MDETEAVGTH LDFVAGLEVQ PRKVITVEVD AAAVIQQIRE   60
IFRTMASHFN STRVVRDEAI KSIRDHFRAA VPTRNVVVVH TQHVHTLVGL EHTNLVLQTG  120
IFKKVPVDIY VFKSGVFTNL GDGGFINWAW GGFVQEAAGK RIHFRLPPGA LP         172
```

| SEQ ID NO: 296 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

SEQUENCE: 296
```
MADKAAAAAR EAEEEAETTM DETEAVGTHL ELMAGLEVQP RSIITVEVDA AAVIQQIREI   60
FRTMASHFNS TRVVRDEAIK GIRDPFRAAV PTRNVVVVHS QHIHTLVGLE HTHLVLQTGM  120
FKKVPVDIYL FKSGVFTLLG DGGFINWAWG GFVQQVAGKR IHFRLPPGAV P          171
```

| SEQ ID NO: 297 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

SEQUENCE: 297
```
IADPATAARE AEEEVQETLM DETEAVGTHL DFVAGLEVQP RKVITVEVDA AAVIQQIREI   60
FRTMASHFNS TRVVRDEAIK GIRDHFRAAV PTRNVVVIHT QHVHTLVGLE HTHLVLQTGL  120
FKKVPVDIYV FKSGVFTLLG DGGFINWAWG GFVQEVAGKR IHFRLPPGAL P          171
```

| SEQ ID NO: 298 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

SEQUENCE: 298
```
MADPATAAAR EDEEEVETLM DETEAVGTHL DFVAGLEVQP RNIITVEVDA AAVIQQIREI   60
FRTMASHFNS TRVVRDEAIK GIRDHFRAAV PTRNVVVIHT QHVHTLVGLE HTHLVLQTGI  120
FKKVPVDIYV FKSGVFTNLG DGGFINWAWG GFVQEVAGKR VLFSRPPGAL P          171
```

| SEQ ID NO: 299 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

SEQUENCE: 299
```
MADEVAGHHG PACEEEEEM LMDETEAVGV HAIDGLPVQP RKVITVEVDA AAVIQQIREI   60
FRTMASHFNS TRVVRDEAIK GIRDHFRAAV PTRNVVVIHT QHVHTLDAVE SSHLVLRTGL  120
FKKVPVDIFV FKSGVFTNLG DGGFINWAWG GYGVNHTAKR VVFSRPPGAL P          171
```

| SEQ ID NO: 300 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

SEQUENCE: 300
```
MADPATAARE AEEEVQETLM DETEAVGTHL DFVAGLEVQP RKVITVEVDA AAVIQQIREI   60
FQTMARHFNS TRVVRDEAIK GIRDHFRAAV PTRNVVVVHT QHIHTLVGLE HTNLVLQTGL  120
FKKVPVDIYV FKSGVFTLLG DGGFINWAWG GFVQEVAGKR IHFRLPPGAL P          171
```

| SEQ ID NO: 301 | moltype = AA   length = 171 |
| --- | --- |
| FEATURE | Location/Qualifiers |
| REGION | 1..171 |
| | note = IPD103 variant |
| source | 1..171 |
| | mol_type = protein |
| | organism = synthetic construct |

```
SEQUENCE: 301
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTNLVLQTGL   120
FKKVPVDIYV FKSGVFTLLG DGGFINWAWG GFVQEVAGKR IHFRLPPGAL P            171

SEQ ID NO: 302            moltype = AA   length = 172
FEATURE                   Location/Qualifiers
REGION                    1..172
                          note = IPD103 variant
source                    1..172
                          mol_type = protein
                          organism = synthetic construct
SEQUENCE: 302
MADKAAAAAR EAEEEVETTM DETEAVGTHL DFLGADVKLQ PRKVITVEVD AAAVIQQIRE    60
IFRTMASHFN STRVVRDEAI KGIRDHFRAA VPTRNVVVVH TQHVHTLVGL EHTNLVLQTG   120
IFKKVPVDIY VFKSGVFTNL GDGGFINWAW GGFVQEVAGK RIHFRLPPGA LP           172

SEQ ID NO: 303            moltype = AA   length = 171
FEATURE                   Location/Qualifiers
REGION                    1..171
                          note = IPD103 variant
source                    1..171
                          mol_type = protein
                          organism = synthetic construct
SEQUENCE: 303
MADKAAAAAR EAEEEVETTM DETEAVGTHL DFVAGLEVQP RKVITVEVDA AAVIQQIREI    60
FQTMARHFNS TRVVRDEAIK GIRDHFRAAV PTRNVVVVHT QHIHTLEGLE HTHLVLQTGL   120
FKKVPVDIYV FKSGVFTNLG DGGFINWAWG GFVDQVVGKR IHFRLPPGAL P            171

SEQ ID NO: 304            moltype = AA   length = 170
FEATURE                   Location/Qualifiers
REGION                    1..170
                          note = IPD103 variant
source                    1..170
                          mol_type = protein
                          organism = synthetic construct
SEQUENCE: 304
MADPATAARE AEEEVETTMD ETEAVGTHLD FVAGLEVQPR KVITVEVDAA AVIQQIREIF    60
QTMARHFNST RVVRDEAIKG IRDHFRAAVP TRNVVVIHTQ HVHTLEGLEH TNLVLQTGIF   120
KKVPVDIYVF KSGVFTLLGD GGFINWAWGG FVQEVAGKRI HFRLPPGALP              170

SEQ ID NO: 305            moltype = AA   length = 172
FEATURE                   Location/Qualifiers
REGION                    1..172
                          note = IPD103 variant
source                    1..172
                          mol_type = protein
                          organism = synthetic construct
SEQUENCE: 305
MADKAAAAAR EAEEEVQETL MDETEAVGTH LDFVAGLEVQ PRKVITVEVD AAAVIQQIRE    60
IFRTMASHFN STRVVRDEAI KGIRDHFRAA VPTRNVVVVH TQHVHTLEGL EHTHLVLQTG   120
LFKKVPVDIY VFKSGVFTNL DGGFINWAW GGFVQEVAGK RIHFRLPPGA LP            172

SEQ ID NO: 306            moltype = AA   length = 170
FEATURE                   Location/Qualifiers
REGION                    1..170
                          note = IPD103 variant
source                    1..170
                          mol_type = protein
                          organism = synthetic construct
SEQUENCE: 306
MADPATAARE AEEEVETTMD ETEAVGTHLD FVAGLEVQPR NIITVEVDAA AVIQQIREIF    60
QTMASHFNST RVVRDEAIKG IRDHFRAAVP TRNVVVHTQ HIHTLVGLEH THLVLQTGLF    120
KKVPVDIYVF KSGVFTLLGD GGFINWAWGG FVQEVAGKRI HFRLPPGALP              170

SEQ ID NO: 307            moltype = AA   length = 172
FEATURE                   Location/Qualifiers
REGION                    1..172
                          note = IPD103 variant
source                    1..172
                          mol_type = protein
                          organism = synthetic construct
SEQUENCE: 307
MADPATAARE AEEEVQETLM DETEAVGTHL DFLGADVKLQ PRNIITVEVD AAAVIQQIRE    60
IFQTMARHFN STRVVRDEAI KGIRDHFRAA VPTRNVVVVH TQHVHTLVGL EHTNLVLQTG   120
LFKKVPVDIY VFKSGVFTLL GDGGFINWAW GGFVQEVAGK RIHFRLPPGA LP           172

SEQ ID NO: 308            moltype = AA   length = 171
FEATURE                   Location/Qualifiers
```

```
REGION                      1..171
                            note = IPD103 variant
source                      1..171
                            mol_type = protein
                            organism = synthetic construct
SEQUENCE: 308
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVIHT QHVHTLVGLE HTHLVLQTGL   120
FKKVPVDIYV FKSGVFTLLG DGGFINWAWG GFVDQVVGKR IHFRLPPGAL P            171

SEQ ID NO: 309              moltype = AA  length = 170
FEATURE                     Location/Qualifiers
REGION                      1..170
                            note = IPD103 variant
source                      1..170
                            mol_type = protein
                            organism = synthetic construct
SEQUENCE: 309
MADPAAAARE AEEEVETTMD ETEAVGTHLD FVAGLEVQPR NIITVEVDAA AVIQQISEIF    60
RTMASHFNST RVVRDEAIKG IRDHFRAAVP TRNVVVVHTQ HIHTLEGLEH THLVLQTGIF   120
KKVPVDIYVF KSGVFTLLGD GGFINWAWGG FVDQVVGKRI HFRLPPGALP              170

SEQ ID NO: 310              moltype = AA  length = 172
FEATURE                     Location/Qualifiers
REGION                      1..172
                            note = IPD103 variant
source                      1..172
                            mol_type = protein
                            organism = synthetic construct
SEQUENCE: 310
MADKAAAAAR EAEEEVETTM DETEAVGTHL DFLGADVKLQ PRNIITVEVD AAAVIQQIRE    60
IFQTMARHFN STRVVRDEAI KGIRDHFRAA VPTRNVVVVH TQHIHTLEGL EHTNLVLQTG   120
LFKKVPVDIY VFKSGVFTLL GDGGFINWAW GGFVDQVVGK RIHFRLPPGA LP            172

SEQ ID NO: 311              moltype = AA  length = 172
FEATURE                     Location/Qualifiers
REGION                      1..172
                            note = IPD103 variant
source                      1..172
                            mol_type = protein
                            organism = synthetic construct
SEQUENCE: 311
MADKAAAAAR EAEEEVQETL MDETEAVGTH LDFVAGLEVQ PRKVITVEVD AAAVIQQIRE    60
IFRTMASHFN STRVVRDEAI KGIRDHFRAA VPTRNVVVIH TQHVHTLEGL EHTHLVLQTG   120
LFKKVPVDIY VFKSGVFTLL GDGGFINWAW GGFVDQVVGK RIHFRLPPGA LP            172

SEQ ID NO: 312              moltype = AA  length = 171
FEATURE                     Location/Qualifiers
REGION                      1..171
                            note = IPD103 variant
source                      1..171
                            mol_type = protein
                            organism = synthetic construct
SEQUENCE: 312
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHIHTLVGLE HTHLVLQTGI   120
FKKVPVDIYV FKSGVFTNLG DGGFINWAWG GFVQEVAGKR IHFRLPPGAL P             171

SEQ ID NO: 313              moltype = AA  length = 172
FEATURE                     Location/Qualifiers
REGION                      1..172
                            note = IPD103 variant
source                      1..172
                            mol_type = protein
                            organism = synthetic construct
SEQUENCE: 313
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVIH TQHVHTLVGL EHTHLVLQTG   120
IFKKVPVDIY VFKSGVFTNL GDGGFINWAW GGFVQEVAGK RIHFRLPPGA LP            172

SEQ ID NO: 314              moltype = AA  length = 172
FEATURE                     Location/Qualifiers
REGION                      1..172
                            note = IPD103 variant
source                      1..172
                            mol_type = protein
                            organism = synthetic construct
SEQUENCE: 314
MADKAAAAAR EAEEEVETTM DETEAVGTHL DFLGADVKLQ PRNIITVEVD AAAVIQQIRE    60
```

```
IFQTMARHFN STRVVRDEAI KGIRDHFRAA VPTRNVVVIH TQHVHTLVGL EHTHLVLQTG  120
IFKKVPVDIY VFKSGVFTLL GDGGFINWAW GGFVQEVAGK RIHFRLPPGA LP          172

SEQ ID NO: 315           moltype = AA  length = 171
FEATURE                  Location/Qualifiers
REGION                   1..171
                         note = IPD103 variant
source                   1..171
                         mol_type = protein
                         organism = synthetic construct
SEQUENCE: 315
MADKAAAAAR EAEEEVETTM DETEAVGTHL DFVAGLEVQP RKVITVEVDA AAVIQQIREI  60
FRTMASHFNS TRVVRDEAIK GIRDHFRAAV PTRNVVVHT QHIHTLEGLE HTHLVLQTGL   120
FKKVPVDIYV FKSGVFTNLG DGGFINWAWG GFVQEVAGKR IHFRLPPGAL P           171

SEQ ID NO: 316           moltype = AA  length = 173
FEATURE                  Location/Qualifiers
REGION                   1..173
                         note = IPD103 variant
source                   1..173
                         mol_type = protein
                         organism = synthetic construct
SEQUENCE: 316
MADKAAAAAR EAEEEVQETL MDETEAVGTH LDFLGADVKL QPRNIITVEV DAAAVIQQIR  60
EIFRTMASHF NSTRVVRDEA IKGIRDHFRA AVPTRNVVVV HTQHIHTLEG LEHTHLVLQT  120
GLFKKVPVDI YVFKSGVFTL LGDGGFINWA WGGFVQEVAG KRIHFRLPPG ALP         173

SEQ ID NO: 317           moltype = AA  length = 170
FEATURE                  Location/Qualifiers
REGION                   1..170
                         note = IPD103 variant
source                   1..170
                         mol_type = protein
                         organism = synthetic construct
SEQUENCE: 317
MADPATAARE AEEEVETTMD ETEAVGTHLD FVAGLEVQPR KVITVEVDAA AVIQQIREIF  60
QTMARHFNST RVVRDEAIKG IRDHFRAAVP TRNVVVHTQ HIHTLEGLEH TNLVLQTGLF   120
KKVPVDIYVF KSGVFTLLGD GGFINWAWGG FVQEVAGKRI HFRLPPGALP             170

SEQ ID NO: 318           moltype = AA  length = 171
FEATURE                  Location/Qualifiers
REGION                   1..171
                         note = IPD103 variant
source                   1..171
                         mol_type = protein
                         organism = synthetic construct
SEQUENCE: 318
MADKAAAAAR EAEEEVETTM DETEAVGTHL DFVAGLEVQP RKVITVEVDA AAVIQQIREI  60
FRTMASHFNS TRVVRDEAIK GIRDHFRAAV PTRNVVVIHT QHIHTLEGLE HTNLVLQTGI  120
FKKVPVDIYV FKSGVFTLLG DGGFINWAWG GFVDQVVGKR IHFRLPPGAL P           171

SEQ ID NO: 319           moltype = AA  length = 171
FEATURE                  Location/Qualifiers
REGION                   1..171
                         note = IPD103 variant
source                   1..171
                         mol_type = protein
                         organism = synthetic construct
SEQUENCE: 319
MADKAAAAAR EAEEEVETTM DETEAVGTHL DFVAGLEVQP RKVITVEVDA AAVIQQIREI  60
FRTMASHFNS TRVVRDEAIK GIRDHFRAAV PTRNVVVIHT QHVHTLVGLE HTHLVLQTGI  120
FKKVPVDIYV FKSGVFTLLG DGGFINWAWG GFVQEVAGKR IHFRLPPGAL P           171

SEQ ID NO: 320           moltype = AA  length = 172
FEATURE                  Location/Qualifiers
REGION                   1..172
                         note = IPD103 variant
source                   1..172
                         mol_type = protein
                         organism = synthetic construct
SEQUENCE: 320
MADKAAAAAR EAEEEVQETL MDETEAVGTH LDFVAGLEVQ PRKVITVEVD AAAVIQQIRE  60
IFQTMARHFN STRVVRDEAI KGIRDHFRAA VPTRNVVVIH TQHVHTLEGL EHTNLVLQTG  120
IFKKVPVDIY VFKSGVFTNL GDGGFINWAW GGFVQEVAGK RIHFRLPPGA LP          172

SEQ ID NO: 321           moltype = AA  length = 171
FEATURE                  Location/Qualifiers
REGION                   1..171
                         note = IPD103 variant
```

```
-continued source                        1..171
                              mol_type = protein
                              organism = synthetic construct
SEQUENCE: 321
MADKAAAAAR EAEEEVETTM DETEAVGTHL DFVAGLEVQP RKVITVEVDA AAVIQQIREI     60
FRTMASHFNS TRVVRDEAIK GIRDHFRAAV PTRNVVVIHT QHIHTLEGLE HTHLVLQTGL    120
FKKVPVDIYV FKSGVFTLLG DGGFINWAWG GFVQEVAGKR IHFRLPPGAL P             171

SEQ ID NO: 322                moltype = AA   length = 172
FEATURE                       Location/Qualifiers
REGION                        1..172
                              note = IPD103 variant
source                        1..172
                              mol_type = protein
                              organism = synthetic construct
SEQUENCE: 322
MADKAAAARE AEEEVQETLM DETEAVGTHL DFLGADVKLQ PRNIITVEVD AAAVIQQIRE     60
IFRTMASHFN STRVVRDEAI KGIRDHFRAA VPTRNVVVH TQHIHTLEGL AEHTNLVLQTG    120
LFKKVPVDIY VFKSGVFTLL GDGGFINWAW GGFVQEVAGK RIHFRLPPGA LP            172

SEQ ID NO: 323                moltype = AA   length = 171
FEATURE                       Location/Qualifiers
REGION                        1..171
                              note = IPD103 variant
source                        1..171
                              mol_type = protein
                              organism = synthetic construct
SEQUENCE: 323
MADKAAAAAR EAEEEVETTM DETEAVGTHL DFVAGLEVQP RKVITVEVDA AAVIQQIREI     60
FRTMASHFNS TRVVRDEAIK GIRDHFRAAV PTRNVVVVHT QHVHTLEGLE HTNLVLQTGL    120
FKKVPVDIYV FKSGVFTLLG DGGFINWAWG GFVQEVAGKR IHFRLPPGAL P             171

SEQ ID NO: 324                moltype = AA   length = 171
FEATURE                       Location/Qualifiers
REGION                        1..171
                              note = IPD103 variant
source                        1..171
                              mol_type = protein
                              organism = synthetic construct
SEQUENCE: 324
MADKAAAAAR EAEEEVETTM DETEAVGTHL DFVAGLEVQP RKVITVEVDA AAVIQQIREI     60
FRTMASHFNS TRVVRDEAIK GIRDHFRAAV PTRNVVVIHT QHIHTLEGLE HTNLVLQTGI    120
FKKVPVDIYV FKSGVFTLLG DGGFINWAWG GFVDQVVGKR IHFRLPPGAL P             171

SEQ ID NO: 325                moltype = AA   length = 171
FEATURE                       Location/Qualifiers
REGION                        1..171
                              note = IPD103 variant
source                        1..171
                              mol_type = protein
                              organism = synthetic construct
SEQUENCE: 325
MADKAAAAAR EAEEEVETTM DETEAVGTHL DFVAGLEVQP RKVITVEVDA AAVIQQIREI     60
FRTMASHFNS TRVVRDEAIK GIRDHFRAAV PTRNVVVIHT QHIHTLEGLE HTNLVLQTGL    120
FKKVPVDIYV FKSGVFTLLG DGGFINWAWG GFVDQVVGKR IHFRLPPGAL P             171

SEQ ID NO: 326                moltype = AA   length = 171
FEATURE                       Location/Qualifiers
REGION                        1..171
                              note = IPD103 variant
source                        1..171
                              mol_type = protein
                              organism = synthetic construct
SEQUENCE: 326
MADPATAARE AEEEVQETLM DETEAVGTHL DFVAGLEVQP RNIITVEVDA AAVIQQIREI     60
FRTMASHFNS TRVVRDEAIK GIRDHFRAAV PTRNVVVIHT QHIHTLEGLE HTNLVLQTGI    120
FKKVPVDIYV FKSGVFTLLG DGGFINWAWG GFVDQVVGKR IHFRLPPGAL P             171

SEQ ID NO: 327                moltype = AA   length = 172
FEATURE                       Location/Qualifiers
REGION                        1..172
                              note = IPD103 variant
source                        1..172
                              mol_type = protein
                              organism = synthetic construct
SEQUENCE: 327
MADKAAAARE AEEEVQETL MDETEAVGTH LDFVAGLEVQ PRKVITVEVD AAAVIQQIRE      60
IFRTMASHFN STRVVRDEAI KGIRDHFRAA VPTRNVVVIH TQHVHTLVGL EHTHLVLQTG    120
IFKKVPVDIY VFKSGVFTLL GDGGFINWAW GGFVDQVVGK RIHFRLPPGA LP            172
```

```
SEQ ID NO: 328           moltype = AA   length = 172
FEATURE                  Location/Qualifiers
REGION                   1..172
                         note = IPD103 variant
source                   1..172
                         mol_type = protein
                         organism = synthetic construct
SEQUENCE: 328
MADKAAAAAR EAEEEVQETL MDETEAVGTH LDFVAGLEVQ PRKVITVEVD AAAVIQQIRE    60
IFQTMARHFN STRVVRDEAI KGIRDHFRAA VPTRNVVVVH TQHVHTLVGL EHTHLVLQTG   120
IFKKVPVDIY VFKSGVFTNL GDGGFINWAW GGFVQEVAGK RIHFRLPPGA LP          172

SEQ ID NO: 329           moltype = AA   length = 171
FEATURE                  Location/Qualifiers
REGION                   1..171
                         note = IPD103 variant
source                   1..171
                         mol_type = protein
                         organism = synthetic construct
SEQUENCE: 329
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHVHTLEGLE HTNLVLQTGI   120
FKKVPVDIYV FKSGVFTLLG DGGFINWAWG GFVDQVVGKR IHFRLPPGAL P           171

SEQ ID NO: 330           moltype = AA   length = 172
FEATURE                  Location/Qualifiers
REGION                   1..172
                         note = IPD103 variant
source                   1..172
                         mol_type = protein
                         organism = synthetic construct
SEQUENCE: 330
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVVH TQHIHTLEGL EHTNLVLQTG   120
LFKKVPVDIY VFKSGVFTLL GDGGFINWAW GGFVQEVAGK RIHFRLPPGA LP          172

SEQ ID NO: 331           moltype = AA   length = 172
FEATURE                  Location/Qualifiers
REGION                   1..172
                         note = IPD103 variant
source                   1..172
                         mol_type = protein
                         organism = synthetic construct
SEQUENCE: 331
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVVH TQHVHTLVGL EHTHLVLQTG   120
LFKKVPVDIY VFKSGVFTLL GDGGFINWAW GGFVQEVAGK RIHFRLPPGA LP          172

SEQ ID NO: 332           moltype = AA   length = 172
FEATURE                  Location/Qualifiers
REGION                   1..172
                         note = IPD103 variant
source                   1..172
                         mol_type = protein
                         organism = synthetic construct
SEQUENCE: 332
MADKAAAAAR EAEEEVETTM DETEAVGTHL DFLGADVKLQ PRNIITVEVD AAAVIQQIRE    60
IFQTMARHFN STRVVRDEAI KGIRDHFRAA VPTRNVVVVH TQHVHTLVGL EHTHLVLQTG   120
LFKKVPVDIY VFKSGVFTLL GDGGFINWAW GGFVDQVAGK RIHFRLPPGA LP          172

SEQ ID NO: 333           moltype = AA   length = 172
FEATURE                  Location/Qualifiers
REGION                   1..172
                         note = IPD103 variant
source                   1..172
                         mol_type = protein
                         organism = synthetic construct
SEQUENCE: 333
MADPATAARE AEEEVQETLM DETEAVGTHL DFLGADVKLQ PRNIITVEVD AAAVIQQIRE    60
IFRTMASHFN STRVVRDEAI KGIRDHFRAA VPTRNVVVVH TQHIHTLEGL EHTNLVLQTG   120
LFKKVPVDIY VFKSGVFTLL GDGGFINWAW GGFVQEVAGK RIHFRLPPGA LP          172

SEQ ID NO: 334           moltype = AA   length = 170
FEATURE                  Location/Qualifiers
REGION                   1..170
                         note = IPD103 variant
source                   1..170
                         mol_type = protein
```

```
                    organism = synthetic construct
SEQUENCE: 334
MADPATAARE AEEEVETTMD ETEAVGTHLD FVAGLEVQPR KVITVEVDAA AVIQQIREIF    60
RTMASHFNST RVVRDEAIKG IRDHFRAAVP TRNVVIHTQ HIHTLEGLEH TNLVLQTGLF    120
KKVPVDIYVF KSGVFTLLGD GGFINWAWGG FVQEVAGKRI HFRLPPGALP             170

SEQ ID NO: 335          moltype = AA   length = 171
FEATURE                 Location/Qualifiers
REGION                  1..171
                        note = IPD103 variant
source                  1..171
                        mol_type = protein
                        organism = synthetic construct
SEQUENCE: 335
MADKAAAAAR EAEEEVETTM DETEAVGTHL DFVAGLEVQP RKVITVEVDA AAVIQQIREI    60
FQTMARHFNS TRVVRDEAIK GIRDHFRAAV PTRNVVVIHT QHVHTLVGLE HTHLVLQTGL   120
FKKVPVDIYV FKSGVFTNLG DGGFINWAWG GFVDQVVGKR IHFRLPPGAL P            171

SEQ ID NO: 336          moltype = AA   length = 171
FEATURE                 Location/Qualifiers
REGION                  1..171
                        note = IPD103 variant
SITE                    43
                        note = misc_feature - Xaa can be any naturally occurring
                         amino acid
source                  1..171
                        mol_type = protein
                        organism = synthetic construct
SEQUENCE: 336
MADKAAAAAR EAEEEVETTM DETEAVGTHL DFVAGLEVQP RKXITVEVDA AAVIQQIREI    60
FRTMASHFNS TRVVRDEAIK GIRDHFRAAV PTRNVVVIHT QHIHTLVGLE HTNLVLQTGI   120
FKKVPVDIYV FKSGVFTILG DGGFINWAWG GFVQEVVGKR IHFRLPPGAL P            171

SEQ ID NO: 337          moltype = AA   length = 172
FEATURE                 Location/Qualifiers
REGION                  1..172
                        note = IPD103 variant
source                  1..172
                        mol_type = protein
                        organism = synthetic construct
SEQUENCE: 337
MADKAAAAAR EAEEEVQETL MDETEAVGTH LDFVAGLEVQ PRKVITVEVD AAAVIQQIRE    60
IFRTMASHFN STRVVRDEAI KGIRDHFRAA VPTRNVVVVH TQHIHTLEGL EHTNLVLQTG   120
IFKKVPVDIY VFKSGVFTLL GDGGFINWAW GGFVQEVAGK RIHFRLPPGA LP           172

SEQ ID NO: 338          moltype = AA   length = 171
FEATURE                 Location/Qualifiers
REGION                  1..171
                        note = IPD103 variant
source                  1..171
                        mol_type = protein
                        organism = synthetic construct
SEQUENCE: 338
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVIHT QHVHTLVGLE HTNLVLQTGL   120
FKKVPVDIYV FKSGVFTNLG DGGFINWAWG GFVQEVAGKR IHFRLPPGAL P            171

SEQ ID NO: 339          moltype = AA   length = 170
FEATURE                 Location/Qualifiers
REGION                  1..170
                        note = IPD103 variant
source                  1..170
                        mol_type = protein
                        organism = synthetic construct
SEQUENCE: 339
MADPATAARE AEEEVETTMD ETEAVGTHLD FVAGLEVQPR KVITVEVDAA AVIQQIREIF    60
RTMASHFNST RVVRDEAIKG IRDHFRAAVP TRNVVVHTQ HIHTLVGLEH THLVLQTGIF   120
KKVPVDIYVF KSGVFTLLGD GGFINWAWGG FVDQVVGKRI HFRLPPGALP             170

SEQ ID NO: 340          moltype = AA   length = 171
FEATURE                 Location/Qualifiers
REGION                  1..171
                        note = IPD103 variant
source                  1..171
                        mol_type = protein
                        organism = synthetic construct
SEQUENCE: 340
MADPATAARE AEEEVQETLM DETEAVGTHL DFVAGLEVQP RKVITVEVDA AAVIQQIREI    60
FQTMARHFNS TRVVRDEAIK GIRDHFRAAV PTRNVVVVHT QHVHTLEGLE HTHLVLQTGI   120
```

```
FKKVPVDIYV FKSGVFTLLG DGGFINWAWG GFVDQVVGKR IHFRLPPGAL P         171

SEQ ID NO: 341           moltype = AA  length = 172
FEATURE                  Location/Qualifiers
REGION                   1..172
                         note = IPD103 variant
source                   1..172
                         mol_type = protein
                         organism = synthetic construct
SEQUENCE: 341
MADKAAAAAR EAEEEVETTM DETEAVGTHL DFLGADVKLQ PRNIITVEVD AAAVIQQIRE  60
IFRTMASHFN STRVVRDEAI KGIRDHFRAA VPTRNVVVVH TQHIHTLEGL EHTNLVLQTG 120
LFKKVPVDIY VFKSGVFTLL GDGGFINWAW GGFVDQVVGK RIHFRLPPGA LP        172

SEQ ID NO: 342           moltype = AA  length = 172
FEATURE                  Location/Qualifiers
REGION                   1..172
                         note = IPD103 variant
source                   1..172
                         mol_type = protein
                         organism = synthetic construct
SEQUENCE: 342
MADKAAAAAR EAEEEVQETL MDETEAVGTH LDFVAGLEVQ PRNIITVEVD AAAVIQQIRE  60
IFRTMASHFN STRVVRDEAI KGIRDHFRAA VPTRNVVVVH TQHIHTLVGL EHTHLVLQTG 120
LFKKVPVDIY VFKSGVFTLL GDGGFINWAW GGFVQEVAGK RIHFRLPPGA LP        172

SEQ ID NO: 343           moltype = AA  length = 171
FEATURE                  Location/Qualifiers
REGION                   1..171
                         note = IPD103 variant
source                   1..171
                         mol_type = protein
                         organism = synthetic construct
SEQUENCE: 343
MADKAAAAAR EAEEEVETTM DETEAVGTHL DFVAGLEVQP RKVITVEVDA AAVIQQIREI  60
FQTMARHFNS TRVVRDEAIK GIRDHFRAAV PTRNVVVVHT QHIHTLEGLE HTNLVLQTGL 120
FKKVPVDIYV FKSGVFTNLG DGGFINWAWG GFVDQVVGKR IHFRLPPGAL P         171

SEQ ID NO: 344           moltype = AA  length = 172
FEATURE                  Location/Qualifiers
REGION                   1..172
                         note = IPD103 variant
source                   1..172
                         mol_type = protein
                         organism = synthetic construct
SEQUENCE: 344
MADKAAAAAR EAEEEVQETL MDETEAVGTH LDFVAGLEVQ PRKVITVEVD AAAVIQQIRE  60
IFRTMASHFN STRVVRDEAI KGIRDHFRAA VPTRNVVVIH TQHVHTLVGL EHTHLVLQTG 120
LFKKVPVDIY VFKSGVFTLL GDGGFINWAW GGFVQEVVGK RIHFRLPPGA LP        172

SEQ ID NO: 345           moltype = AA  length = 171
FEATURE                  Location/Qualifiers
REGION                   1..171
                         note = IPD103 variant
source                   1..171
                         mol_type = protein
                         organism = synthetic construct
SEQUENCE: 345
MADPATAARE AEEEVQETLM DETEAVGTHL DFVAGLEVQP RKVITVEVDA AAVIQQIREI  60
FQTMARHFNS TRVVRDEAIK GIRDHFRAAV PTRNVVVVHT QHVHTLVGLE HTHLVLQTGI 120
FKKVPVDIYV FKSGVFTLLG DGGFINWAWG GFVQEVAGKR IHFRLPPGAL P         171

SEQ ID NO: 346           moltype = AA  length = 173
FEATURE                  Location/Qualifiers
REGION                   1..173
                         note = IPD103 variant
source                   1..173
                         mol_type = protein
                         organism = synthetic construct
SEQUENCE: 346
MADKAAAAAR EAEEEVETTM DETEAVGTHL DFLGADVKLQ PRNIITVEVD AAAVIQQIRE  60
IFRTTASHFN STRVVRDEAI KGIRDHFRAA VPTRNVVVIH SQHIHTLEGL EHTHLVLQTG 120
IFKKVPVDMY VFKSGVFTNL GDGGFINWAW GGFVDQVVGK RIHFRLPPGA LPR       173

SEQ ID NO: 347           moltype = AA  length = 171
FEATURE                  Location/Qualifiers
REGION                   1..171
                         note = IPD103 variant
source                   1..171
```

```
                        mol_type = protein
                        organism = synthetic construct
SEQUENCE: 347
MADKAAAAAR EAEEEVETTM DETEAVGTHL DFVAGLEVQP RKVITVEVDA AAVIQQIREI    60
FQTMARHFNS TRVVRDEAIK GIRDHFRAAV PTRNVVVVHT QHVHTLVGLE HTHLVLQTGL   120
FKKVPVDIYV FKSGVFTLLG DGGFINWAWG GFVQEVAGKR IHFRLPPGAL P            171

SEQ ID NO: 348          moltype = AA   length = 172
FEATURE                 Location/Qualifiers
REGION                  1..172
                        note = IPD103 variant
source                  1..172
                        mol_type = protein
                        organism = synthetic construct
SEQUENCE: 348
MADPATAARE AEEEVQETLM DETEAVGTHL DFLGADVKLQ PRNIITVEVD AAAVIQQIRE    60
IFQTMARHFN STRVVRDEAI KGIRDHFRAA VPTRNVVVIH TQHVHTLVGL EHTNLVLQTG   120
LFKKVPVDIY VFKSGVFTLL GDGGFINWAW GGFVQEVAGK RIHFRLPPGA LP           172

SEQ ID NO: 349          moltype = AA   length = 171
FEATURE                 Location/Qualifiers
REGION                  1..171
                        note = IPD103 variant
source                  1..171
                        mol_type = protein
                        organism = synthetic construct
SEQUENCE: 349
MADPATAARE AEEEVETTMD ETEAVGTHLD FLGADVKLQP RNIITVEVDA AAVIHQIREI    60
FQTMARHFNS TRVVRDEAIK GIRDHFRAAV PTRNVVVVHS QHIHTLVGLE HTHLVLQTGL   120
FKKVPVDMYV FKSGVFTNLG DGGFINWAWG GFVQEVAGKR IHFRLPPGAL P            171

SEQ ID NO: 350          moltype = AA   length = 172
FEATURE                 Location/Qualifiers
REGION                  1..172
                        note = IPD103 variant
source                  1..172
                        mol_type = protein
                        organism = synthetic construct
SEQUENCE: 350
MADPATAARE DEEEVQETLM DETEAVGTHL DFLGADVKLQ PRNIITVEVD AAAVIQQIRE    60
IFRTMASHFN STRVVRDEAI KGIRDHFRAA VPTRNVVVVH TQHIHTLEGL EHTHLVLQTG   120
LFKKVPVDIY VFKSGVFTLL GDGGFINWAW GGFVQEVAGK RIHFRLPPGA LP           172

SEQ ID NO: 351          moltype = AA   length = 171
FEATURE                 Location/Qualifiers
REGION                  1..171
                        note = IPD103 variant
source                  1..171
                        mol_type = protein
                        organism = synthetic construct
SEQUENCE: 351
MADKAAAAAR EAEEEVETTM DETEAVGTHL DFVAGLEVQP RNIITVEVDA AAVIQQIREI    60
FRTMASHFNS TRVVRDEAIK GIRDHFRAAV PTRNVVVVHT QHIHTLEGLE HTHLVLQTGI   120
FKKVPVDIYV FKSGVFTLLG DGGFINWAWG GFVQEVAGKR IHFRLPPGAL P            171

SEQ ID NO: 352          moltype = AA   length = 172
FEATURE                 Location/Qualifiers
REGION                  1..172
                        note = IPD103 variant
source                  1..172
                        mol_type = protein
                        organism = synthetic construct
SEQUENCE: 352
MADKAATAAR EAEEEVQETL MDETEAVGTH LDFVAGLEVQ PRNIITVEVD AAAVIQQIRE    60
IFRTMASHFN STRVVRDEAI KGIRDHFRAA VPTRNVVVVH TQHIHTLEGL EHTNLVLQTG   120
IFKKVPVDIY VFKSGVFTLL GDGGFINWAW GGFVQQVVGK RIHFRLPPGA LP           172

SEQ ID NO: 353          moltype = AA   length = 172
FEATURE                 Location/Qualifiers
REGION                  1..172
                        note = IPD103 variant
source                  1..172
                        mol_type = protein
                        organism = synthetic construct
SEQUENCE: 353
MADKAAAAAR EAEEEVETTM DETEAVGTHL DFLGADVKLQ PRKVITVEVD AAAVIQQIRE    60
IFQTMARHFN STRVVRDEAI KGIRDHFRAA VPTRNVVVIH TQHIHTLEGL EHTHLVLQTG   120
LFKKVPVDIY VFKSGVFTLL GDGGFINWAW GGFVDEVVGK RIHFRLPPGA LP           172
```

```
SEQ ID NO: 354           moltype = AA  length = 173
FEATURE                  Location/Qualifiers
REGION                   1..173
                         note = IPD103 variant
source                   1..173
                         mol_type = protein
                         organism = synthetic construct
SEQUENCE: 354
MADKAAAAAR EAEEEVQETL MDETEAVGTH LDFLGADVKL QPRNIITVEV DAAAVIQQIR    60
EIFRTMASHF NSTRVVRDEA IKGIRDHFRA AVPTRNVVVI HTQHVHTLVG LEHTHLVLLT   120
GIFKKVPVDI YVFKSGVFTN LGDGGFINWA WGGFVQEVAG KRIHFRLPPG ALP          173

SEQ ID NO: 355           moltype = AA  length = 172
FEATURE                  Location/Qualifiers
REGION                   1..172
                         note = IPD103 variant
source                   1..172
                         mol_type = protein
                         organism = synthetic construct
SEQUENCE: 355
MADKAAAAAR EAEEEVQETL MDETEAVGTH LDFVAGLEVQ PRNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVQEVAGK RIHFRLPPGA LP           172

SEQ ID NO: 356           moltype = AA  length = 171
FEATURE                  Location/Qualifiers
REGION                   1..171
                         note = IPD103 variant
source                   1..171
                         mol_type = protein
                         organism = synthetic construct
SEQUENCE: 356
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVIHT QHVHTLVGLE HTHLVLQTGL   120
FKKVPVDIYV FKSGVFTLLG DGGFINWAWG GFVDQVVGKR IHFRLPPGAL P            171

SEQ ID NO: 357           moltype = AA  length = 172
FEATURE                  Location/Qualifiers
REGION                   1..172
                         note = IPD103 variant
source                   1..172
                         mol_type = protein
                         organism = synthetic construct
SEQUENCE: 357
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVVH TQHIHTLEGL EHTNLVLQTG   120
LFKKVPVDIY VFKSGVFTLL GDGGFINWAW GGFVDQVVGK RIHFRLPPGA LP           172

SEQ ID NO: 358           moltype = AA  length = 172
FEATURE                  Location/Qualifiers
REGION                   1..172
                         note = IPD103 variant
source                   1..172
                         mol_type = protein
                         organism = synthetic construct
SEQUENCE: 358
MADKAAAAAR EAEEEVQETL MDETEAVGTH LDFVAGLEVQ PRNIITVEVD AAAVIQQIRE    60
IFRTMASHFN STRVVRDEAI KGIRDHFRAA VPTRNVVVIH TQHIHTLVGL EHTNLVLQTG   120
LFKKVPVDIY VFKSGVFTNL GDGGFINWAW GGFVDQVVGK RIHFRLPPGA LP           172

SEQ ID NO: 359           moltype = AA  length = 172
FEATURE                  Location/Qualifiers
REGION                   1..172
                         note = IPD103 variant
source                   1..172
                         mol_type = protein
                         organism = synthetic construct
SEQUENCE: 359
MADKAAAAAR EAEEEVETTM DETEAVGTHL DFLGADVKLQ PRNIITVEVD AAAVIQQIRE    60
IFQTMARHFN STRVVRDEAI KGIRDHFRAA VPTRNVVVVH TQHVHTLEGL EHTNLVLQTG   120
IFKKVPVDIY VFKSGVFTNL GDGGFINWAW GGFVQEVAGK RIHFRLPPGA LP           172

SEQ ID NO: 360           moltype = AA  length = 171
FEATURE                  Location/Qualifiers
REGION                   1..171
                         note = IPD103 variant
source                   1..171
                         mol_type = protein
                         organism = synthetic construct
```

```
SEQUENCE: 360
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVVHT QHIHTLEGLE HTHLVLQTGI  120
FKKVPVDIYV FKSGVFTNLG DGGFINWAWG GFVDQVVGKR IHFRLPPGAL P           171

SEQ ID NO: 361         moltype = AA  length = 172
FEATURE                Location/Qualifiers
REGION                 1..172
                       note = IPD103 variant
source                 1..172
                       mol_type = protein
                       organism = synthetic construct
SEQUENCE: 361
MADKAAAAAR EAEEEVQETL MDETEAVGTH LDFVAGLEVQ PRKVITVEVD AAAVIQQIRE    60
IFRTMASHFN STRVVRDEAI KGIRDHFRAA VPTRNVVVVH TQHIHTLVGL EHTHLVLQTG  120
LFKKVPVDIY VFKSGVFTLL GDGGFINWAW GGFVQEVAGK RIHFRLPPGA LP          172

SEQ ID NO: 362         moltype = AA  length = 170
FEATURE                Location/Qualifiers
REGION                 1..170
                       note = IPD103 variant
source                 1..170
                       mol_type = protein
                       organism = synthetic construct
SEQUENCE: 362
MADPATAARE AEEEVETTMD ETEAVGTHLD FVAGLEVQPR KVITVEVDAA AVIQQIREIF    60
RTMASHFNST RVVRDEAIKG IRDHFRAAVP TRNVVVVHTQ HIHTLEGLEH TNLVLQTGLF  120
KKVPVDIYVF KSGVFTNLGD GGFINWAWGG FVDQVVGKRI HFRLPPGALP             170

SEQ ID NO: 363         moltype = AA  length = 171
FEATURE                Location/Qualifiers
REGION                 1..171
                       note = IPD103 variant
source                 1..171
                       mol_type = protein
                       organism = synthetic construct
SEQUENCE: 363
MADPATAARE AEEEVQETLM DETEAVGTHL DFVAGLEVQP RNIITVEVDA AAVIQQIREI    60
FQTMARHFNS TRVVRDEAIK GIRDHFRAAV PTRNVVVIHA QHIHTLEGLE HTNLVLQTGI  120
FKKVPVDIYV FKSGVFTLLG DGGFINWAWG GFVQEVAGKR IHFRLPPGAL P           171

SEQ ID NO: 364         moltype = AA  length = 173
FEATURE                Location/Qualifiers
REGION                 1..173
                       note = IPD103 variant
source                 1..173
                       mol_type = protein
                       organism = synthetic construct
SEQUENCE: 364
MADKAAAAAR EAEEEVQETL MDETEAVGTH LDFLGADVKL QPRNIITVEV DAAAVIQQIR    60
EIFRTMASHF NSTRVVRDEA IKGIRDHFRA AVPTRNVVVI HTQHVHTLVG LEHTHLVLQT  120
GIFKKVPVDI YVFKSGVFTL LGDGGFINWA WGGFVQEVAG KRIHFRLPPG ALP         173

SEQ ID NO: 365         moltype = AA  length = 171
FEATURE                Location/Qualifiers
REGION                 1..171
                       note = IPD103 variant
source                 1..171
                       mol_type = protein
                       organism = synthetic construct
SEQUENCE: 365
MADKAAAAAR EAEEEVETTM DETEAVGTHL DFVAGLEVQP RNIITVEVDA AAVIQQIREI    60
FRTMASHFNS TRVVRDEAIK GIRDHFRAAV PTRNVVVVHT QHVHTLEGLE HTNLVLQTGL  120
FKKVPVDIYV FKSGVFTLLG DGGFINWAWG GFVQEVAGKR IHFRLPPGAL P           171

SEQ ID NO: 366         moltype = AA  length = 171
FEATURE                Location/Qualifiers
REGION                 1..171
                       note = IPD103 variant
source                 1..171
                       mol_type = protein
                       organism = synthetic construct
SEQUENCE: 366
ITDPATAARE AEEEVETTMD ETEAVGTHLD FLGADVKLQP RKVITVEVDA AAVIQQIREI    60
FRTMASHFNS TRVVRDEAIK GIRDHFRAAV PTRNVVVIHT QHVHTLVGLE HTNLVLQTGL  120
FKKVPVDIYV FKSGVFTLLG DGGFINWAWG GFVQEVAGKR IHFRLPPGAL P           171

SEQ ID NO: 367         moltype = AA  length = 173
FEATURE                Location/Qualifiers
```

```
REGION                  1..173
                        note = IPD103 variant
source                  1..173
                        mol_type = protein
                        organism = synthetic construct
SEQUENCE: 367
MADKAAAAAR EAEEEVQETL MDESEAVGTH LDFVAGLEVQ PRKVITLEVD AAAVIQQIRE    60
IFRTMASPFN STRVVRDEAI KGIRDHFRAA VPTRNVVVVH SQHIHTLEGL EHTNFVLQTG   120
LFKKVPVDMY VFKSGVFTNL GDGGFINWAW GGFVQEVAGK RIHFRLPPGA LPR          173

SEQ ID NO: 368          moltype = AA  length = 171
FEATURE                 Location/Qualifiers
REGION                  1..171
                        note = IPD103 variant
source                  1..171
                        mol_type = protein
                        organism = synthetic construct
SEQUENCE: 368
MADKAAAAGR EDEEEVETTM DETEAVGTHL DFVAGLEVQP RNIITVEVDA AAVIQQIREI    60
FRTMASHFNS TRVVRDEAIK GIRDHFRAAV PTRNVVVIHT QHVHTLVGLE HTHLVLQTGL   120
FKKVPVDIYV FKSGVFTLLG DGGFINWAWG GFVDQVVGKR IHFRLPPGAL P            171

SEQ ID NO: 369          moltype = AA  length = 171
FEATURE                 Location/Qualifiers
REGION                  1..171
                        note = IPD103 variant
source                  1..171
                        mol_type = protein
                        organism = synthetic construct
SEQUENCE: 369
MADPATAARE AEEEVQETLM DETEAVGTHL DFVAGLEVQP RKVITVEVDA AAVIQQIREI    60
FQTMARHFNS TRVVRDEAIK GIRDHFRAAV PTRNVVVVHT QHVHTLVGLE HTHLVLQTGL   120
FKKVPVDIYV FKSGVFTNLG DGGFINWAWG GFVQEVAGKR IHFRLPPGAL P            171

SEQ ID NO: 370          moltype = AA  length = 171
FEATURE                 Location/Qualifiers
REGION                  1..171
                        note = IPD103 variant
source                  1..171
                        mol_type = protein
                        organism = synthetic construct
SEQUENCE: 370
MADKAAAAAR EAEEEVETTM DETEAVGTHL DFVAGLEVQP RNIITVEVDA AAVIQQIREI    60
FQTMARHFNS TRVVRDEAIK GIRDHFRAAV PTRNVVVVHT QHIHTLEGLE HTHLVLQTGI   120
FKKVPVDIYV FKSGVFTLLG DGGFINWAWG GFVDQVVGKR IHFRLPPGAL P            171

SEQ ID NO: 371          moltype = AA  length = 173
FEATURE                 Location/Qualifiers
REGION                  1..173
                        note = IPD103 variant
source                  1..173
                        mol_type = protein
                        organism = synthetic construct
SEQUENCE: 371
MADKAAAAAR EAEEEVQETL MDETEAVGTH LDFLGADVKL QPRNIITVEV DAAAVIQQIR    60
EIFQTMARHF NSTRVVRDEA IKGIRDHFRA AVPTRNVVVV HTQHIHTLEG LEHTHLVLQT   120
GLFKKVPVDI YVFKSGVFTL LGDGGFINWA WGGFVDQVVG KRIHFRLPPG ALP          173

SEQ ID NO: 372          moltype = AA  length = 171
FEATURE                 Location/Qualifiers
REGION                  1..171
                        note = IPD103 variant
source                  1..171
                        mol_type = protein
                        organism = synthetic construct
SEQUENCE: 372
MADEVAGHHG PACEEEEEM LMDETEAVGV HAIDGLPVQN RSIITVEVDA AAVIQQIREI     60
FRTMASHFNS TRVVRDEAIK GIRDHFRLAV PTRNVVVVHT QHVHTLVGLE HTHLVLQTGI   120
FKKVPVDIYV FKSGVFTLLG DGGFINWAWG GYGVNHTAKR VVFSRPPGAL P            171

SEQ ID NO: 373          moltype = AA  length = 172
FEATURE                 Location/Qualifiers
REGION                  1..172
                        note = IPD103 variant
source                  1..172
                        mol_type = protein
                        organism = synthetic construct
SEQUENCE: 373
MADKAAAAAR EAEEEVETTM DETEAVGTHL DFLGADVKLQ PRNIITVEVD AAAVIQQIRE    60
```

```
IFQTMARHFN STRVVRDEAI KGIRDHFRAA VPTRNVVVIH TQHVHTLDAV ESSHLVLRTG    120
LFKKVPVDIF VFKSGVFTNL GDGGFINWAW GGFVQEVAGK RIHFRLPPGA LP           172

SEQ ID NO: 374          moltype = AA  length = 169
FEATURE                 Location/Qualifiers
REGION                  1..169
                        note = IPD103 variant
source                  1..169
                        mol_type = protein
                        organism = synthetic construct
SEQUENCE: 374
MADKAAAAAR EAEEEVETTM DETEAVGVHA IDGLPVQNRS IITVEVDAAA VIQQIREIFR    60
TMASHFNSTR VVRDEAIKSI RDHFRLAVPT RNVVVVHTQH VHTLDAVESS HLVLRTGLFK   120
KVPVDIFVFK SGVFTNLGDG GFINWAWGGF VQEVAGKRIH FRLPPGALP               169

SEQ ID NO: 375          moltype = AA  length = 172
FEATURE                 Location/Qualifiers
REGION                  1..172
                        note = IPD103 variant
source                  1..172
                        mol_type = protein
                        organism = synthetic construct
SEQUENCE: 375
MADEVAGHHG PACEEEEETT MDETEAVGTH LDFVAGLEVQ PRKVITVEVD AAAVIQQIRE    60
IFRTMASHFN STRVVRDEAI KGIRDHFRAA VPTRNVVVVH TQHVHTLDAV ESSHLVLRTG   120
LFKKVPVDIF VFKSGVFTNL GDGGFINWAW GGYVQEVVGK RIHFRLPPGA LP           172

SEQ ID NO: 376          moltype = AA  length = 171
FEATURE                 Location/Qualifiers
REGION                  1..171
                        note = IPD103 variant
source                  1..171
                        mol_type = protein
                        organism = synthetic construct
SEQUENCE: 376
MADEVAGHHG PACEEEEEEM LMDETEAVGV HAIDGLPVQN RSIITVEVDA AAVIQQIREI    60
FRTMASHFNS TRVVRDEAIK GIRDHFRLAV PTRNVVVIHT QHVHTLDAVE SSHLVLRTGL   120
FKKVPVDIFV FKSGVFTNLG DGGFINWAWG GYGVNHTAKR VVFSRPPGAL P            171

SEQ ID NO: 377          moltype = AA  length = 170
FEATURE                 Location/Qualifiers
REGION                  1..170
                        note = IPD103 variant
source                  1..170
                        mol_type = protein
                        organism = synthetic construct
SEQUENCE: 377
MADPATAARE AEEEVETTMD ETEAVGTHLD FVAGLEVQPR KVITVEVDAA AVIQQIREIF    60
QTMARHFNST RVVRDEAIKG IRDHFRAAVP TRNVVVIHTQ HVHTLDAVES SHLVLRTGLF   120
KKVPVDIFVF KSGVFTNLGD GGFINWAWGG YVDQVVGKRI HFRLPPGALP              170

SEQ ID NO: 378          moltype = AA  length = 172
FEATURE                 Location/Qualifiers
REGION                  1..172
                        note = IPD103 variant
source                  1..172
                        mol_type = protein
                        organism = synthetic construct
SEQUENCE: 378
MADEVAGHHG PACEEEEERT MDETEAVGTH LDFVAGLEVQ PRKVITVEVD AAAVIQHIRE    60
IFGTMASHFN STRVVRDEAI KGIRDHFRAA VPTRNVVVVH TQHVHTLDAV ESSHLVLRTG   120
LFKKVPVDIF VFKSGVFTNL GDGGFINWAW GGYVQEVVGK RIHFRLPPGA LP           172

SEQ ID NO: 379          moltype = AA  length = 173
FEATURE                 Location/Qualifiers
REGION                  1..173
                        note = IPD103 variant
source                  1..173
                        mol_type = protein
                        organism = synthetic construct
SEQUENCE: 379
MADEVAGHHG PACEEEEEEM LMDETEAVGT HLDFVAGLEV QPRKVITVEV DAAAVIQQIR    60
EIFRTMASHF NSTRVVRDEA IKGIRDHFRL AVPTRNVVVV HTQHVHTLDA VESSHLVLRT   120
GLFKKVPVDI FVFKSGVFTN LGDGGFINWA WGGYGVNHTA KRVVFSRPPG ALP          173

SEQ ID NO: 380          moltype = AA  length = 171
FEATURE                 Location/Qualifiers
REGION                  1..171
                        note = IPD103 variant
```

```
source                      1..171
                            mol_type = protein
                            organism = synthetic construct
SEQUENCE: 380
MADAAAAAAR EEEEEQETTM DETEAVGTHL DFVAGLEVQP RNIITVEVDA AAVIQQIREI     60
FQSMISHFNS TRVVRDEAIK GIRDHFRVAV PTRNVVVIHT QHVHTLEGVE SSHLVLQTGM    120
FKKVPVDIYV FKSGVFTILG DGGFINWAWG GFGDQVVGKR VHFRLPPGAL P            171

SEQ ID NO: 381              moltype = AA  length = 171
FEATURE                     Location/Qualifiers
REGION                      1..171
                            note = IPD103 variant
source                      1..171
                            mol_type = protein
                            organism = synthetic construct
SEQUENCE: 381
MADEVAGHHG PACEEEEEEM LMDETEAVGV HAIDGLPVQN RSIITVEVDA AAVIQQIREI     60
FRTMASHFNS TRVVRDEAIK GIRDHFRAAV PTRNVVVIHT QHVHTLVGLE HTHLVLQTGI    120
FKKVPVDIFV FKSGVFTNLG DGGFINWAWG GYGVNHTAKR VVFSRPPGAL P            171

SEQ ID NO: 382              moltype = AA  length = 173
FEATURE                     Location/Qualifiers
REGION                      1..173
                            note = IPD103 variant
source                      1..173
                            mol_type = protein
                            organism = synthetic construct
SEQUENCE: 382
MADEVAGHHG PACEEEEEEM LMDETEAVGT HLDFVAGLEV QPRNIITVEV DAAAVIQQIR     60
EIFQTMARHF NSTRVVRDEA IKGIRDHFRA AVPTRNVVVI HTQHVHTLDA VESSHLVLRT    120
GLFKKVPVDI FVFKSGVFTN LGDGGFINWA WGGFVQEVAG KRIHFRLPPG ALP          173

SEQ ID NO: 383              moltype = AA  length = 171
FEATURE                     Location/Qualifiers
REGION                      1..171
                            note = IPD103 variant
source                      1..171
                            mol_type = protein
                            organism = synthetic construct
SEQUENCE: 383
MADKAAAAAR EAEEEVETTM DETEAVGTHL DFVAGLEVQP RKVITVEVDA AAVIQQIREI     60
FRTMASHFNS TRVVRDEAIK SIRDHFRAAV PTRNVVVIHT QHVHTLEGLE HTNLVLQTGL    120
FKKVPVDIYV FKSGVFTNLG DGGFINWAWG GFVQEVAGKR IHFRLPPGAL P            171

SEQ ID NO: 384              moltype = AA  length = 170
FEATURE                     Location/Qualifiers
REGION                      1..170
                            note = IPD103 variant
source                      1..170
                            mol_type = protein
                            organism = synthetic construct
SEQUENCE: 384
MADEAAAAAR EAEEEEEMLMDETEAVGVH AIDGLPVQNR SIITVEVDAA AVIQQIREIF      60
RTMASHFNST RVVRDEAIKG IRDHFRLAVP TRNVVVIHTQ HIHTLVGLES SHLALRTGLF    120
KKVPVDIYVF KSGVFTLLGD GGFINWAWGG FVDQVVGKRI HFRLPPGALP              170

SEQ ID NO: 385              moltype = AA  length = 172
FEATURE                     Location/Qualifiers
REGION                      1..172
                            note = IPD103 variant
source                      1..172
                            mol_type = protein
                            organism = synthetic construct
SEQUENCE: 385
MADKAAAAAR EAEEEVETTM DETEAVGTHL DFLGADVKLQ PRNIITVEVD AAAVIQQIRE     60
IFQTMARHFN STRVVRDEAI KGIRDHFRAA VPTRNVVVIH TQHVHTLVGL EHTNLVLRTG    120
LFKKVPVDIY VFKSGVFTLL GDGGFINWAW GGFVQEVAGK RIHFRLPPGA LP           172

SEQ ID NO: 386              moltype = AA  length = 170
FEATURE                     Location/Qualifiers
REGION                      1..170
                            note = IPD103 variant
source                      1..170
                            mol_type = protein
                            organism = synthetic construct
SEQUENCE: 386
MADEVAGHHG PACEEEVETT MDETEAVGVH AIDGLPVQNR SIITVEVDAA AVIQQIREIF     60
RTMASHFNST RVVRDEAIKG IRDHFRLAVP TRNVVVVHTQ HVHTLEGLEH TNLVLQTGLF    120
KKVPVDIYVF KSGVFTLLGD GGFINWAWGG FVQEVAGKRI HFRLPPGALP              170
```

```
SEQ ID NO: 387         moltype = AA  length = 171
FEATURE                Location/Qualifiers
REGION                 1..171
                       note = IPD103 variant
source                 1..171
                       mol_type = protein
                       organism = synthetic construct
SEQUENCE: 387
MADEVAGHHG PACEEEEEEM LMDETEAVGV HAIDGLPVQP RKVITVEVDA AAVIQQIREI    60
FQTMARHFNS TRVVRDEAIK GIRDHFRAAV PTRNVVVVHT QHIHTLVGLE HTHLVLQTGL   120
FKKVPVDIYV FKSGVFTLLG DGGFINWAWG GFVDQVVGKR IHFRLPPGAL P           171

SEQ ID NO: 388         moltype = AA  length = 171
FEATURE                Location/Qualifiers
REGION                 1..171
                       note = IPD103 variant
source                 1..171
                       mol_type = protein
                       organism = synthetic construct
SEQUENCE: 388
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVIHT QHVHTLEGLE SSHLVLRTGL   120
FKKVPVDIFV FKSGVFTNLG DGGFINWAWG GYGVNHTAKR VVFSRPPGAL P           171

SEQ ID NO: 389         moltype = AA  length = 171
FEATURE                Location/Qualifiers
REGION                 1..171
                       note = IPD103 variant
source                 1..171
                       mol_type = protein
                       organism = synthetic construct
SEQUENCE: 389
MADEVAGHHG PACEEEEEEM LMDETEAVGV HAIDGLPVQN RSIITVEVDA AAVIQQIREI    60
FASMIKHFNS TRVVRDEAIK GIRDHFRAAV PTRNVVVIHT QHVHTLDAVE SSHLVLRTGL   120
FKKVPVDIFV FKSGVFTNLG DGGFINWAWG GYGVNHTAKR VVFSRPPGAL P           171

SEQ ID NO: 390         moltype = AA  length = 171
FEATURE                Location/Qualifiers
REGION                 1..171
                       note = IPD103 variant
source                 1..171
                       mol_type = protein
                       organism = synthetic construct
SEQUENCE: 390
MADEVAGHHG PACEEEEEEM LMDETEAVGV HAIDGLPVQN RSIITVEVDA AAVIQQIREI    60
FRTMASHFNS TRVVRDEAIK SIRDHFRAAV PTRNVVVIHT QHIHTLEGLE HTNLVLQTGL   120
FKKVPVDIYV FKSGVFTNLG DGGFINWAWG GFVQEVAGKR IHFRLPPGAL P           171

SEQ ID NO: 391         moltype = AA  length = 171
FEATURE                Location/Qualifiers
REGION                 1..171
                       note = IPD103 variant
source                 1..171
                       mol_type = protein
                       organism = synthetic construct
SEQUENCE: 391
MADPATAARE AEEEVQETLM DETEAVGTHL DFVAGLEVQP RKVITVEVDA AAVIQQIREI    60
FRTMASHFNS TRVVRDEAIK GIRDHFRAAV PTRNVVVIHT QHVHTLDAVE SSHLVLRTGL   120
FKKVPVDIFV FKSGVFTLLG DGGFINWAWG GYGVNHTAKR VVFSRPPGAL P           171

SEQ ID NO: 392         moltype = AA  length = 171
FEATURE                Location/Qualifiers
REGION                 1..171
                       note = IPD103 variant
source                 1..171
                       mol_type = protein
                       organism = synthetic construct
SEQUENCE: 392
MADEVAGHHG PACEEEEEEM LMDETEAVGV HAIDGLPVQN RSIITVEVDA AAVIQQIREI    60
FRTMASHFNS TRVVRDEAIK GIRDHFRLAV PTRNVVVIHT QHVHTLDAVE SSHLVLRTGL   120
FKKVPVDIFV FKSGVFTNLG DGGFINWAWG GYGVNHTAKR VVFSRPPGAL P           171

SEQ ID NO: 393         moltype = AA  length = 172
FEATURE                Location/Qualifiers
REGION                 1..172
                       note = IPD103 variant
source                 1..172
                       mol_type = protein
```

```
                       organism = synthetic construct
SEQUENCE: 393
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVVH TQHVHTLVGL EHTHLVLQTG   120
LFKKVPVDIY VFKSGVFTLL GDGGFINWAW GGFVDQVVGK RIHFRLPPGA LP          172

SEQ ID NO: 394            moltype = AA   length = 173
FEATURE                   Location/Qualifiers
REGION                    1..173
                          note = IPD103 variant
source                    1..173
                          mol_type = protein
                          organism = synthetic construct
SEQUENCE: 394
MADEVAGHHG PACEEEEEEM LMDETEAVGT HLDFVAGLEV QNRSIITVEV DAAAVIQQIR    60
EIFRTMASHF NSTRVVRDEA IKGIRDHFRL AVPTRNVVVV HTQHVHTLDA VESSHLVLRT   120
GLFKKVPVDI FVFKSGVFTN LGDGGFINWA WGGYGVNHTA KRVVFSRPPG ALP         173

SEQ ID NO: 395            moltype = AA   length = 171
FEATURE                   Location/Qualifiers
REGION                    1..171
                          note = IPD103 variant
source                    1..171
                          mol_type = protein
                          organism = synthetic construct
SEQUENCE: 395
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVIHT QHVHTLDAVE SSHLVLQTGL   120
FKKVPVDIYV FKSGVFTNLG DGGFINWAWG GYGVNHTAKR VVFSRPPGAL P           171

SEQ ID NO: 396            moltype = AA   length = 172
FEATURE                   Location/Qualifiers
REGION                    1..172
                          note = IPD103 variant
source                    1..172
                          mol_type = protein
                          organism = synthetic construct
SEQUENCE: 396
MADKAAAAAR EAEEEVETTM DETEAVGTHL DFLGADVKLQ PRNIITVEVD AAAVIQQIRE    60
IFRTMASHFN STRVVRDEAI KGIRDHFRAA VPTRNVVVIH TQHVHTLVGL EHTHLVLQTG   120
LFKKVPVDIY VFKSGVFTNL GDGGFINWAW GGFVQEVAGK RIHFRRPPGA LP          172

SEQ ID NO: 397            moltype = AA   length = 171
FEATURE                   Location/Qualifiers
REGION                    1..171
                          note = IPD103 variant
source                    1..171
                          mol_type = protein
                          organism = synthetic construct
SEQUENCE: 397
MADEVAGHHG PACEEEEEEM LMDETEAVGV HAIDGLPVQN RSIITVEVDA AAVIQQIREI    60
FASMIKHYNS TRVVRDEAIK SIRDHFRAAV PTRNVVVIHT QHVHTLEGLE HTNLVLQTGL   120
FKKVPVDIFV FKSGVFTNLG DGGFINWAWG GYGVNHTAKR VVFSRPPGAL P           171

SEQ ID NO: 398            moltype = AA   length = 171
FEATURE                   Location/Qualifiers
REGION                    1..171
                          note = IPD103 variant
source                    1..171
                          mol_type = protein
                          organism = synthetic construct
SEQUENCE: 398
MADEVAGHHG PACEEEEEEM LMDETEAVGV HAIDGLPVQN RSIITVEVDA AAVIQQIREI    60
FQTMARHFNS TRVVRDEAIK GIRDHFRAAV PTRNVVVIHT QHVHTLDAVE SSHLVLQTGL   120
FKKVPVDIYV FKSGVFTNLG DGGFINWAWG GYGVNHTAKR VVFSRPPGAL P           171

SEQ ID NO: 399            moltype = AA   length = 171
FEATURE                   Location/Qualifiers
REGION                    1..171
                          note = IPD103 variant
source                    1..171
                          mol_type = protein
                          organism = synthetic construct
SEQUENCE: 399
MADPATAARE AEEEVETTMD ETEAVGTHLD FLGADVKLQP RNIITVEVDA AAVIQQIREI    60
FQTMARHFNS TRVVRDEAIK GIRDHFRLAV PTRNVVVIHT QHVHTLDAVE SSRLVLRTGL   120
FKKVPVDIFV FKSGVFTNLG DGGFINWAWG GFVDQVVGKR IHFRLPPGAL P           171

SEQ ID NO: 400            moltype = AA   length = 173
```

```
FEATURE                 Location/Qualifiers
REGION                  1..173
                        note = IPD103 variant
source                  1..173
                        mol_type = protein
                        organism = synthetic construct
SEQUENCE: 400
MADKAAAAAR EAEEEVQETL MDETEAVGTH LDFLGADVKL QPRKVITVEV DAAAVIQQIR  60
EIFRTMASHF NSTRVVRDEA IKGIRDHFRA AVPTRNVQVV HTQHVHTLDA VESSHLVLRT 120
GLFKKVPVDI YVFKSGVFTL LGDGGFINWA WGGFVDQVVG KRIHFRLPPG ALP        173

SEQ ID NO: 401          moltype = AA   length = 171
FEATURE                 Location/Qualifiers
REGION                  1..171
                        note = IPD103 variant
source                  1..171
                        mol_type = protein
                        organism = synthetic construct
SEQUENCE: 401
MADEVAGHHG PACEEEEEEM LMDETEAVGV HAIDGLPVQN RSIITVEVDA AAVIQQIREI  60
FASMIKHYNS TRVVRDEAIK GIRDHFRAAV PTRNVVVVHT QHVHTLDAVE SSHLVLRTGL 120
FKKVPVDIYV FKSGVFTLLG DGGFINWAWG GYGVNHTAKR VVFSRPPGAL P          171

SEQ ID NO: 402          moltype = AA   length = 173
FEATURE                 Location/Qualifiers
REGION                  1..173
                        note = IPD103 variant
source                  1..173
                        mol_type = protein
                        organism = synthetic construct
SEQUENCE: 402
MADEVAGHHG PACEEEEEEM LMDETEAVGT HLDFVAGLEV QPRKVITVEV DAAAVIQQIR  60
EIFQTMARHY NSTRVVRDEA IKSIRDHFRA AVPTRNVVVV HTQHIHTLDA VESSHLVLRT 120
GLFKKVPVDI FVFKSGVFTN LGDGGFINWA WGGFVQEVAG KRIHFRLPPG ALP        173

SEQ ID NO: 403          moltype = AA   length = 171
FEATURE                 Location/Qualifiers
REGION                  1..171
                        note = IPD103 variant
source                  1..171
                        mol_type = protein
                        organism = synthetic construct
SEQUENCE: 403
MADKAAAAAR EAEEEVETTM DETEAVGVHL DFVAGLEVQP RKVITVEVDA AAVIQQIREI  60
FGSMINHFNS TRVVRDEAIK GIRDHFRAAV PTRNVVVIHT QHVHTLVAVE SSHLVLQTGL 120
FKKVPVDIYV FKSGVFTLLG DGGFINWAWG GFGLELAGKR VHFRRPPGAL P          171

SEQ ID NO: 404          moltype = AA   length = 171
FEATURE                 Location/Qualifiers
REGION                  1..171
                        note = IPD103 variant
source                  1..171
                        mol_type = protein
                        organism = synthetic construct
SEQUENCE: 404
MADEVAGHHG PACEEEEEEM LMDETEAVGV HAIDGLPVQN RSIITVEVDA AAVIQQIREI  60
FRTMASHFNS TRVVRDEAIK SIRDHFRLAV PTRNVVVVHT QHIHTLEGLE HTNLVLQTGL 120
FKKVPVDIYV FKSGVFTNLG DGGFINWAWG GYGVNHTAKR VVFSRPPGAL P          171

SEQ ID NO: 405          moltype = AA   length = 170
FEATURE                 Location/Qualifiers
REGION                  1..170
                        note = IPD103 variant
source                  1..170
                        mol_type = protein
                        organism = synthetic construct
SEQUENCE: 405
MADKAAAAAR EAEEEVQETL MDETEAVGVH AIDGLPVQNR SIITVEVDAA AVIQQIREIF  60
ASMIKHYNST RVVRDEAIKS IRDHFRLAVP TRNVVVIHTQ HVHTLVGLEH THLVLQTGLF 120
KKVPVDIYVF KSGVFTLLGD GGFINWAWGG FVDQVVGKRI HFRLPPGALP            170

SEQ ID NO: 406          moltype = AA   length = 171
FEATURE                 Location/Qualifiers
REGION                  1..171
                        note = IPD103 variant
source                  1..171
                        mol_type = protein
                        organism = synthetic construct
SEQUENCE: 406
```

```
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVVHT QHVHTLDAVE SSHLVLRTGL   120
FKKVPVDIFV FKSGVFTLLG DGGFINWAWG GYGVNHTAKR VVFSRPPGAL P           171

SEQ ID NO: 407         moltype = AA   length = 173
FEATURE                Location/Qualifiers
REGION                 1..173
                       note = IPD103 variant
source                 1..173
                       mol_type = protein
                       organism = synthetic construct
SEQUENCE: 407
MADEVAGHHG PACEEEEEEM LMDETEAVGT HLDFVAGLEV QPRKVITVEV DAAAVIQQIR    60
EIFRTMASHF NSTRVVRDEA IKGIRDHFRA AVPTRNVVVI HTQHVHTLDA VESSHLVLRT   120
GLFKKVPVDI FVFKSGVFTL LGDGGFINWA WGGYVQEVVG KRIHFRLPPG ALP          173

SEQ ID NO: 408         moltype = AA   length = 171
FEATURE                Location/Qualifiers
REGION                 1..171
                       note = IPD103 variant
source                 1..171
                       mol_type = protein
                       organism = synthetic construct
SEQUENCE: 408
MADEVAGHHG PACEEEEEEM LMDETEAVGV HAIDGLPVQP RKVITVEVDA AAVIQQIREI    60
FASMIKHYNS TRVVRDEAIK GIRDHFRLAV PTRNVVVVHT QHIHTLEGLE HTNLVLRTGL   120
FKKVPVDIYV FKSGVFTLLG DGGFINWAWG GYGVNHTAKR VVFSRPPGAL P           171

SEQ ID NO: 409         moltype = AA   length = 171
FEATURE                Location/Qualifiers
REGION                 1..171
                       note = IPD103 variant
source                 1..171
                       mol_type = protein
                       organism = synthetic construct
SEQUENCE: 409
MADKAAAAAR EAEEEVETTM DETEAVGTHL DFVAGLEVQP RKVITVEVDA AAVIQQIREI    60
FRTMASHFNS TRVVRDEAIK GIRDHFRAAV PTRNVVVVHT QHIHTLDAVE SSHLVLRTGL   120
FKKVPVDIYV FKSGVFTLLG DGGFINWAWG GFVDQVVGKR IHFRLPPGAL P           171

SEQ ID NO: 410         moltype = AA   length = 171
FEATURE                Location/Qualifiers
REGION                 1..171
                       note = IPD103 variant
source                 1..171
                       mol_type = protein
                       organism = synthetic construct
SEQUENCE: 410
MADEVAGHHG PACEEEEEEM LMDETEAVGV HAIDGLPVQN RSIITVEVDA AAVIQQIREI    60
FQTMASHFNS TRVVRDEAIK SIRDHFRLAV PTRNVVVIHT QHVHTLDAVE SSHLVLRTGL   120
FKKVPVDIYV FKSGVFTNLG DGGFINWAWG GYGVNHTAKR VVFSRPPGAL P           171

SEQ ID NO: 411         moltype = AA   length = 174
FEATURE                Location/Qualifiers
REGION                 1..174
                       note = IPD103 variant
source                 1..174
                       mol_type = protein
                       organism = synthetic construct
SEQUENCE: 411
MADEVAGHHG PACEEEEEEM LMDETEAVGT HLDFLGADVK LQPRNIITVE VDAAAVIQQI    60
REIFQTMARH FNSTRVVRDE AIKGIRDHFR AAVPTRNVVV VHTQHIHTLE GLEHTNLVLQ   120
TGLFKKVPVD IYVFKSGVFT NLGDGGFINW AWGGFVQEVA GKRIHFRLPP GALP         174

SEQ ID NO: 412         moltype = AA   length = 171
FEATURE                Location/Qualifiers
REGION                 1..171
                       note = IPD103 variant
source                 1..171
                       mol_type = protein
                       organism = synthetic construct
SEQUENCE: 412
MADEVAGHHG PACEEEEEEM LMDETEAVGV HAIDGLPVQN RSIITVEVDA AAVIQQIREI    60
FRTMASHFNS TRVVRDEAIK SIRDHFRLAV PTRNVVVIHT QHVHTLDAVE SSHLVLRTGL   120
FKKVPVDIYV FKSGVFTNLG DGGFINWAWG GYGVNHTAKR VVFSRPPGAL P           171

SEQ ID NO: 413         moltype = AA   length = 171
FEATURE                Location/Qualifiers
REGION                 1..171
```

```
                        note = IPD103 variant
source                  1..171
                        mol_type = protein
                        organism = synthetic construct
SEQUENCE: 413
MADEVAGHHG PACEEEEEEM LMDETEAVGV HAIDGLPVQN RSIITVEVDA AAVIQQIREI   60
FASMIKHYNS TRVVRDEAIK SIRDHFRLAV PTRNVVVIHT QHVHTLDAVE SSHLVLRTGL  120
FKKVPVDIYV FKSGVFTNLG DGGFINWAWG GYGVNHTAKR VVFSRPPGAL P          171

SEQ ID NO: 414          moltype = AA  length = 170
FEATURE                 Location/Qualifiers
REGION                  1..170
                        note = IPD103 variant
source                  1..170
                        mol_type = protein
                        organism = synthetic construct
SEQUENCE: 414
MADKAAAAAR EAEEEVQETL MDETEAVGVH AIDGLPVQPR NIITVEVDAA AVIQQIREIF   60
RTMASHFNST RVVRDEAIKG IRDHFRAAVP TRNVVVVHTQ HVHTLVGLEH THLVLQTGLF  120
IKVPVDIYVF KSGVFTLLGD GGFINWAWGG FVDQVVGKRI HFRLPPGALP            170

SEQ ID NO: 415          moltype = AA  length = 171
FEATURE                 Location/Qualifiers
REGION                  1..171
                        note = IPD103 variant
source                  1..171
                        mol_type = protein
                        organism = synthetic construct
SEQUENCE: 415
MADEVAGHHG PACEEEEEEM LMDETEAVGV HAIDGLPVQN RSIITVEVDA AAVIQQIREI   60
FASMIKHYNS TRVVRDEAIK SIRDHFRLAV PTRNVVVIHT QHVHTLDAVE SSHLVLQTGL  120
FKKVPVDIYV FKSGVFTLLG DGGFINWAWG GYGVNHTAKR VVFSRPPGAL P          171

SEQ ID NO: 416          moltype = AA  length = 171
FEATURE                 Location/Qualifiers
REGION                  1..171
                        note = IPD103 variant
source                  1..171
                        mol_type = protein
                        organism = synthetic construct
SEQUENCE: 416
MADEVAGHHG PACEEEEEEM LMDETEAVGV HAIDGLPVQN RSIITVEVDA AAVIQQIREI   60
FRTMASHFNS TRVVRDEAIK SIRDHFRLAV PTRNVVVVHT QHVHTLDAVE SSHLVLRTGL  120
FKKVPVDIFV FKSGVFTNLG DGGFINWAWG GYGVNHTAKR VVFSRPPGAL P          171

SEQ ID NO: 417          moltype = DNA  length = 459
FEATURE                 Location/Qualifiers
misc_feature            1..459
                        note = IPD103 variant
source                  1..459
                        mol_type = other DNA
                        organism = synthetic construct
SEQUENCE: 417
atggacgaga ctgaggcggt ggggacgcac ctggacttct tgggcgcgga cgtgaagttg   60
caacccgca acatcatcac cgtggaggtg gacgcggctg ccgtaatcca acagatcaga  120
gagatcttcc agacaatggc gcgtcacttc aactctacga gggtggtgcg ggatgaagcc  180
atcaagggca ttcgagacca cttcagggcc gccgtcccga ctcgcaacgt ggtggtcatt  240
cacactcagc acgttcacac actggtgggc ttggagcaca cccacctcgt cttgcagacc  300
ggcatcttca aaaaggtccc cgtcgacatc tatgtcttca gtccggcgt cttcaccaac  360
cttggagacg gaggcttcat caactgggca tggggtggct cgtcgacca ggtcgtcggc  420
aagcgtatcc acttccgctt gccccccggg gcgctccct                        459

SEQ ID NO: 418          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 418
atggcggaca aagcagcagc agcagctaga gaagctgaag aagaggtgga gacgacgatg   60
gacgagactg aggcggtggg gacgcacctg gacttcttgg gcgcgacgt gaagttgcaa  120
cccgggaaca tcatcaccgt ggaggtggac gcggctgccg taatccaaca gatcagagag  180
atcttccaga caatggcgcg tcacttcaac tctacgaggg tggtgcggga tgaagcatc  240
aagggcattc gagaccactt cagggccgcc gtcccgactc gcaacgtggt ggtcattcac  300
actcagcacg ttcacacact ggtgggcttg agcacaccc acctcgtctt gcagaccggc  360
atcttcaaaa aggtccccgt cgacatctat gtcttcaagt ccggcgtctt caccaacctt  420
ggagacggag gcttcatcaa ctgggcatgg ggtggcttcg tcgaccaggt cgtcggcaag  480
cgtatcccct tccgcttgcc cccgggggcg ctccct                           516
```

SEQ ID NO: 419          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 419
atggcggaca aagcagcagc aggagctaga gaagctgaag aagaggtgga gacgacgatg    60
gacgagactg aggcggtggg gacgcacctg gacttcttgg gcgcggacgt gaagttgcaa   120
cccacgaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 420          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 420
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
cccctgaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 421          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 421
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
cccctaaca tcatcaccgt ggaggtggac gcggctgccg taatccaaca gatcagagag    180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 422          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 422
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccctggaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 423          moltype = DNA   length = 516
FEATURE                 Location/Qualifiers
misc_feature            1..516
                        note = IPD103 variant
source                  1..516
                        mol_type = other DNA

```
                        organism = synthetic construct
SEQUENCE: 423
atggcggaca aagcagcagc agcagctaga gaagctgaag aagaggtgga gacgacgatg    60
gacgagactg aggcggtggg gacgcacctg gacttcttgg gcgcggacgt gaagttgcaa   120
ccctataaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 424          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 424
atggcggaca aagcagcagc agcagcttat gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 425          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 425
atggcggaca aagcagcagc agcagcagct acggaagctg aagaagaggt ggagacgacg    60
atggacgaga ctgaggcggt ggggacgcac ctggacttct tgggcgcgga cgtgaagttg   120
caaccccgca acatcatcac cgtggaggtg gacgcggctg ccgtaatcca acagatcaga   180
gagatcttcc agacaatggc gcgtcacttc aactctacga gggtggtgcg ggatgaagcc   240
atcaagggca ttcgagacca cttcaaggcc gccgtcccga ctcgcaacgt ggtggtcatt   300
cacactcagc acgttcacac actggtgggc ttggagcaca cccacctcgt cttgcagacc   360
ggcatcttca aaaaggtccc cgtcgacatc tatgtcttca gtccggcgt cttcaccaac   420
cttggagacg gaggcttcat caactgggca tggggtggct cgtcgacca ggtcgtcggc   480
aagcgtatcc acttccgctt gccccccggg gcgctccct                          519

SEQ ID NO: 426          moltype = DNA  length = 516
FEATURE                 Location/Qualifiers
misc_feature            1..516
                        note = IPD103 variant
source                  1..516
                        mol_type = other DNA
                        organism = synthetic construct
SEQUENCE: 426
atggcggaca aagcagcagc agcagctgcc gaagctgaag aagaggtgga gacgacgatg    60
gacgagactg aggcggtggg gacgcacctg gacttcttgg gcgcggacgt gaagttgcaa   120
ccccgcaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact tccgcttgcc ccccggggcg ctccct                             516

SEQ ID NO: 427          moltype = DNA  length = 519
FEATURE                 Location/Qualifiers
misc_feature            1..519
                        note = IPD103 variant
source                  1..519
                        mol_type = other DNA
                        organism = synthetic construct
SEQUENCE: 427
atggcggaca aagcagcagc agcagcagct atggaagctg aagaagaggt ggagacgacg    60
atggacgaga ctgaggcggt ggggacgcac ctggacttct tgggcgcgga cgtgaagttg   120
caaccccgca acatcatcac cgtggaggtg gacgcggctg ccgtaatcca acagatcaga   180
gagatcttcc agacaatggc gcgtcacttc aactctacga gggtggtgcg ggatgaagcc   240
atcaagggca ttcgagacca cttcagggcc gccgtcccga ctcgcaacgt ggtggtcatt   300
```

```
cacactcagc acgttcacac actggtgggc ttggagcaca cccacctcgt cttgcagacc   360
ggcatcttca aaaaggtccc cgtcgacatc tatgtcttca agtccggcgt cttcaccaac   420
cttggagacg gaggcttcat caactgggca tggggtggct tcgtcgacca ggtcgtcggc   480
aagcgtatcc acttccgctt gccccccggg gcgctccct                          519

SEQ ID NO: 428           moltype = DNA   length = 519
FEATURE                  Location/Qualifiers
misc_feature             1..519
                         note = IPD103 variant
source                   1..519
                         mol_type = other DNA
                         organism = synthetic construct
SEQUENCE: 428
atggcggaca aagcagcagc agcagcagct agtgaagctg aagaagaggt ggagacgacg   60
atggacgaga ctgaggcggt ggggacgcac ctggacttct tgggcgcgga cgtgaagttg  120
caaccccgca acatcatcac cgtggaggtg gacgcggctg ccgtaatcca acagatcaga  180
gagatcttcc agacaatggc gcgtcacttc aactctacga gggtggtgcg ggatgaagcc  240
atcaagggca ttcgagacca cttcagggcc gccgtcccga ctcgcaacgt ggtggtcatt  300
cacactcagc acgttcacac actggtgggc ttggagcaca cccacctcgt cttgcagacc  360
ggcatcttca aaaaggtccc cgtcgacatc tatgtcttca agtccggcgt cttcaccaac  420
cttggagacg gaggcttcat caactgggca tggggtggct tcgtcgacca ggtcgtcggc  480
aagcgtatcc acttccgctt gccccccggg gcgctccct                         519

SEQ ID NO: 429           moltype = DNA   length = 459
FEATURE                  Location/Qualifiers
misc_feature             1..459
                         note = IPD103 variant
source                   1..459
                         mol_type = other DNA
                         organism = synthetic construct
SEQUENCE: 429
atggacgaga ctgaggcggt ggggacgcac ctggacttct tgggcgcgga cgtgaagttg   60
caacccacga acatcatcac cgtggaggtg gacgcggctg ccgtaatcca acagatcaga  120
gagatcttcc agacaatggc gcgtcacttc aactctacga gggtggtgcg ggatgaagcc  180
atcaagggca ttcgagacca cttcagggcc gccgtcccga ctcgcaacgt ggtggtcatt  240
cacactcagc acgttcacac actggtgggc ttggagcaca cccacctcgt cttgcagacc  300
ggcatcttca aaaaggtccc cgtcgacatc tatgtcttca agtccggcgt cttcaccaac  360
cttggagacg gaggcttcat caactgggca tggggtggct tcgtcgacca ggtcgtcggc  420
aagcgtatcc acttccgctt gccccccggg gcgctccct                         459

SEQ ID NO: 430           moltype = DNA   length = 459
FEATURE                  Location/Qualifiers
misc_feature             1..459
                         note = IPD103 variant
source                   1..459
                         mol_type = other DNA
                         organism = synthetic construct
SEQUENCE: 430
atggacgaga ctgaggcggt ggggacgcac ctggacttct tgggcgcgga cgtgaagttg   60
caaccctgga acatcatcac cgtggaggtg gacgcggctg ccgtaatcca acagatcaga  120
gagatcttcc agacaatggc gcgtcacttc aactctacga gggtggtgcg ggatgaagcc  180
atcaagggca ttcgagacca cttcagggcc gccgtcccga ctcgcaacgt ggtggtcatt  240
cacactcagc acgttcacac actggtgggc ttggagcaca cccacctcgt cttgcagacc  300
ggcatcttca aaaaggtccc cgtcgacatc tatgtcttca agtccggcgt cttcaccaac  360
cttggagacg gaggcttcat caactgggca tggggtggct tcgtcgacca ggtcgtcggc  420
aagcgtatcc acttccgctt gccccccggg gcgctccct                         459

SEQ ID NO: 431           moltype = DNA   length = 459
FEATURE                  Location/Qualifiers
misc_feature             1..459
                         note = IPD103 variant
source                   1..459
                         mol_type = other DNA
                         organism = synthetic construct
SEQUENCE: 431
atggacgaga ctgaggcggt ggggacgcac ctggacttct tgggcgcgga cgtgaagttg   60
caacccata  acatcatcac cgtggaggtg gacgcggctg ccgtaatcca acagatcaga  120
gagatcttcc agacaatggc gcgtcacttc aactctacga gggtggtgcg ggatgaagcc  180
atcaagggca ttcgagacca cttcagggcc gccgtcccga ctcgcaacgt ggtggtcatt  240
cacactcagc acgttcacac actggtgggc ttggagcaca cccacctcgt cttgcagacc  300
ggcatcttca aaaaggtccc cgtcgacatc tatgtcttca agtccggcgt cttcaccaac  360
cttggagacg gaggcttcat caactgggca tggggtggct tcgtcgacca ggtcgtcggc  420
aagcgtatcc acttccgctt gccccccggg gcgctccct                         459

SEQ ID NO: 432           moltype = DNA   length = 513
FEATURE                  Location/Qualifiers
misc_feature             1..513
                         note = IPD103 variant
source                   1..513
```

```
                        mol_type = other DNA
                        organism = synthetic construct
SEQUENCE: 432
atggcggacc aagcagcagc agcttgtgaa gctgaagaag aggtggagac gacgatggac    60
gagactgagg cggtggggac gcacctggac ttccttgggcg cggacgtgaa gttgcaaccc   120
cctaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 433          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 433
atggcggacc aagcagcagc agctgtggaa gctgaagaag aggtggagac gacgatggac    60
gagactgagg cggtggggac gcacctggac ttccttgggcg cggacgtgaa gttgcaaccc   120
cctaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 434          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 434
atggcggacc aagcagcagc agctgacgaa gctgaagaag aggtggagac gacgatggac    60
gagactgagg cggtggggac gcacctggac ttccttgggcg cggacgtgaa gttgcaaccc   120
acgaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 435          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 435
atggcggacc aagcagcagc agctcaagaa gctgaagaag aggtggagac gacgatggac    60
gagactgagg cggtggggac gcacctggac ttccttgggcg cggacgtgaa gttgcaaccc   120
ctgaacatca tcaccgtgga ggtggacgcg gctgccgtaa tccaacagat cagagagatc   180
ttccagacaa tggcgcgtca cttcaactct acgagggtgg tgcgggatga agccatcaag   240
ggcattcgag accacttcag ggccgccgtc ccgactcgca acgtggtggt cattcacact   300
cagcacgttc acacactggt gggcttggag cacacccacc tcgtcttgca gaccggcatc   360
ttcaaaaagg tccccgtcga catctatgtc ttcaagtccg gcgtcttcac caaccttgga   420
gacggaggct tcatcaactg ggcatggggt ggcttcgtcg accaggtcgt cggcaagcgt   480
atccacttcc gcttgccccc cggggcgctc cct                                513

SEQ ID NO: 436          moltype = DNA  length = 513
FEATURE                 Location/Qualifiers
misc_feature            1..513
                        note = IPD103 variant
source                  1..513
                        mol_type = other DNA
                        organism = synthetic construct
SEQUENCE: 436
atggcggacc aagcagcagc agctggcgaa gctgaagaag aggtggagac gacgatggac    60
gagactgagg cggtggggac gcacctggac ttccttgggcg cggacgtgaa gttgcaaccc   120
ctgaacatca tcaccgtgga ggtggacgcg gctgccgtaa tccaacagat cagagagatc   180
ttccagacaa tggcgcgtca cttcaactct acgagggtgg tgcgggatga agccatcaag   240
```

```
ggcattcgag accacttcag ggccgccgtc ccgactcgca acgtggtggt cattcacact    300
cagcacgttc acacactggt gggcttggag cacacccacc tcgtcttgca gaccggcatc    360
ttcaaaaagg tccccgtcga catctatgtc ttcaagtccg gcgtcttcac caaccttgga    420
gacgaggcct tcatcaactg gcatggggt ggcttcgtcg accaggtcgt cggcaagcgt    480
atccacttcc gcttgccccc cggggcgctc cct                                 513
```

| SEQ ID NO: 437 | moltype = DNA   length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 437
atggcggaca aagcagcagc agcagctagg gcagctgaag aagaggtgga gacgacgatg    60
gacgagactg aggcggtggg gacgcacctg gacttcttgg gcgcggacgt gaagttgcaa    120
ccctggaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

| SEQ ID NO: 438 | moltype = DNA   length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 438
atggcggaca aagcagcagc agcagctgcc gaagctgaag aagaggtgga gacgacgatg    60
gacgagactg aggcggtggg gacgcacctg gacttcttgg gcgcggacgt gaagttgcaa    120
cccacgaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

| SEQ ID NO: 439 | moltype = DNA   length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 439
atggcggaca aagcagcagc agcagctatg gaagctgaag aagaggtgga gacgacgatg    60
gacgagactg aggcggtggg gacgcacctg gacttcttgg gcgcggacgt gaagttgcaa    120
cccacgaaca tcatcaccgt ggaggtggac gcggctgccg taatccaaca gatcagagag    180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

| SEQ ID NO: 440 | moltype = DNA   length = 516 |
|---|---|
| FEATURE | Location/Qualifiers |
| misc_feature | 1..516 |
| | note = IPD103 variant |
| source | 1..516 |
| | mol_type = other DNA |
| | organism = synthetic construct |

```
SEQUENCE: 440
atggcggaca aagcagcagc agcagctagt gaagctgaag aagaggtgga gacgacgatg    60
gacgagactg aggcggtggg gacgcacctg gacttcttgg gcgcggacgt gaagttgcaa    120
ccctgaaca tcatcaccgt ggaggtggac gcggctgccg taatccaaca gatcagagag     180
atcttccaga caatggcgcg tcacttcaac tctacgaggg tggtgcggga tgaagccatc    240
aagggcattc gagaccactt cagggccgcc gtcccgactc gcaacgtggt ggtcattcac    300
actcagcacg ttcacacact ggtgggcttg gagcacaccc acctcgtctt gcagaccggc    360
atcttcaaaa aggtccccgt cgacatctat gtcttcaagt ccggcgtctt caccaacctt    420
ggagacggag gcttcatcaa ctgggcatgg ggtggcttcg tcgaccaggt cgtcggcaag    480
cgtatccact tccgcttgcc ccccggggcg ctccct                              516
```

| SEQ ID NO: 441 | moltype = DNA   length = 516 |
|---|---|

```
FEATURE                 Location/Qualifiers
misc_feature            1..516
                        note = IPD103 variant
source                  1..516
                        mol_type = other DNA
                        organism = synthetic construct
SEQUENCE: 441
atggcggaca aagcagcagc agcagctgcc gaagctgaag aagaggtgga gacgacgatg    60
gacgagactg aggcggtggg gacgcacctg gacttcttgg gcgcggacgt gaagttgcaa   120
ccctggaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 442          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 442
atggcggaca aagcagcagc agcagctatg gaagctgaag aagaggtgga gacgacgatg    60
gacgagactg aggcggtggg gacgcacctg gacttcttgg gcgcggacgt gaagttgcaa   120
ccctggaaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 443          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 443
atggcggaca aagcagcagc agcagctatg gaagctgaag aagaggtgga gacgacgatg    60
gacgagactg aggcggtggg gacgcacctg gacttcttgg gcgcggacgt gaagttgcaa   120
ccctataaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 444          moltype = DNA   length = 516
FEATURE                 Location/Qualifiers
misc_feature            1..516
                        note = IPD103 variant
source                  1..516
                        mol_type = other DNA
                        organism = synthetic construct
SEQUENCE: 444
atggcggaca aagcagcagc agcagctgcc gaagctgaag aagaggtgga gacgacgatg    60
gacgagactg aggcggtggg gacgcacctg gacttcttgg gcgcggacgt gaagttgcaa   120
ccctataaca tcatcaccgt ggaggtggac gcggctgccg taatccaaca gatcagagag   180
atcttccaga caatggcgcg tcacttcaac tctacgaggg tggtgcggga tgaagccatc   240
aagggcattc gagaccactt cagggccgcc gtcccgactc gcaacgtggt ggtcattcac   300
actcagcacg ttcacacact ggtgggcttg gagcacaccc acctcgtctt gcagaccggc   360
atcttcaaaa aggtccccgt cgacatctat gtcttcaagt ccggcgtctt caccaacctt   420
ggagacggag gcttcatcaa ctgggcatgg ggtggcttcg tcgaccaggt cgtcggcaag   480
cgtatccact ccgcttgcc ccccggggcg ctccct                              516

SEQ ID NO: 445          moltype = AA   length = 153
FEATURE                 Location/Qualifiers
REGION                  1..153
                        note = IPD103 variant
source                  1..153
                        mol_type = protein
                        organism = synthetic construct
SEQUENCE: 445
```

```
MDETEAVGTH LDFLGADVKL QPRNIITVEV DAAAVIQQIR EIFQTMARHF NSTRVVRDEA    60
IKGIRDHFRA AVPTRNVVVI HTQHVHTLVG LEHTHLVLQT GIFKKVPVDI YVFKSGVFTN   120
LGDGGFINWA WGGFVDQVVG KRIHFRLPPG ALP                               153

SEQ ID NO: 446          moltype = AA   length = 172
FEATURE                 Location/Qualifiers
REGION                  1..172
                        note = IPD103 variant
source                  1..172
                        mol_type = protein
                        organism = synthetic construct
SEQUENCE: 446
MADKAAAAAR EAEEEVETTM DETEAVGTHL DFLGADVKLQ PGNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIPFRLPPGA LP           172

SEQ ID NO: 447          moltype = AA   length = 172
FEATURE                 Location/Qualifiers
REGION                  1..172
                        note = IPD103 variant
source                  1..172
                        mol_type = protein
                        organism = synthetic construct
SEQUENCE: 447
MADKAAAGAR EAEEEVETTM DETEAVGTHL DFLGADVKLQ PTNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 448          moltype = AA   length = 172
FEATURE                 Location/Qualifiers
REGION                  1..172
                        note = IPD103 variant
source                  1..172
                        mol_type = protein
                        organism = synthetic construct
SEQUENCE: 448
MADKAAAAAR EAEEEVETTM DETEAVGTHL DFLGADVKLQ PLNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 449          moltype = AA   length = 172
FEATURE                 Location/Qualifiers
REGION                  1..172
                        note = IPD103 variant
source                  1..172
                        mol_type = protein
                        organism = synthetic construct
SEQUENCE: 449
MADKAAAAAR EAEEEVETTM DETEAVGTHL DFLGADVKLQ PPNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 450          moltype = AA   length = 172
FEATURE                 Location/Qualifiers
REGION                  1..172
                        note = IPD103 variant
source                  1..172
                        mol_type = protein
                        organism = synthetic construct
SEQUENCE: 450
MADKAAAAAR EAEEEVETTM DETEAVGTHL DFLGADVKLQ PWNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 451          moltype = AA   length = 172
FEATURE                 Location/Qualifiers
REGION                  1..172
                        note = IPD103 variant
source                  1..172
                        mol_type = protein
                        organism = synthetic construct
SEQUENCE: 451
MADKAAAAAR EAEEEVETTM DETEAVGTHL DFLGADVKLQ PYNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 452          moltype = AA   length = 172
FEATURE                 Location/Qualifiers
REGION                  1..172
```

```
                        note = IPD103 variant
source                  1..172
                        mol_type = protein
                        organism = synthetic construct
SEQUENCE: 452
MADKAAAAAY EAEEEVETTM DETEAVGTHL DFLGADVKLQ PRNIITVEVD AAAVIQQIRE       60
IFQTMARHFN STRVVRDEAI KGIRDHFRAA VPTRNVVVIH TQHVHTLVGL EHTHLVLQTG      120
IFKKVPVDIY VFKSGVFTNL GDGGFINWAW GGFVDQVVGK RIHFRLPPGA LP             172

SEQ ID NO: 453          moltype = AA   length = 173
FEATURE                 Location/Qualifiers
REGION                  1..173
                        note = IPD103 variant
source                  1..173
                        mol_type = protein
                        organism = synthetic construct
SEQUENCE: 453
MADKAAAAAA TEAEEEVETT MDETEAVGTH LDFLGADVKL QPRNIITVEV DAAAVIQQIR       60
EIFQTMARHF NSTRVVRDEA IKGIRDHFRA AVPTRNVVVI HTQHVHTLVG LEHTHLVLQT      120
GIFKKVPVDI YVFKSGVFTN LGDGGFINWA WGGFVDQVVG KRIHFRLPPG ALP            173

SEQ ID NO: 454          moltype = AA   length = 172
FEATURE                 Location/Qualifiers
REGION                  1..172
                        note = IPD103 variant
source                  1..172
                        mol_type = protein
                        organism = synthetic construct
SEQUENCE: 454
MADKAAAAAA EAEEEVETTM DETEAVGTHL DFLGADVKLQ PRNIITVEVD AAAVIQQIRE       60
IFQTMARHFN STRVVRDEAI KGIRDHFRAA VPTRNVVVIH TQHVHTLVGL EHTHLVLQTG      120
IFKKVPVDIY VFKSGVFTNL GDGGFINWAW GGFVDQVVGK RIHFRLPPGA LP             172

SEQ ID NO: 455          moltype = AA   length = 173
FEATURE                 Location/Qualifiers
REGION                  1..173
                        note = IPD103 variant
source                  1..173
                        mol_type = protein
                        organism = synthetic construct
SEQUENCE: 455
MADKAAAAAA MEAEEEVETT MDETEAVGTH LDFLGADVKL QPRNIITVEV DAAAVIQQIR       60
EIFQTMARHF NSTRVVRDEA IKGIRDHFRA AVPTRNVVVI HTQHVHTLVG LEHTHLVLQT      120
GIFKKVPVDI YVFKSGVFTN LGDGGFINWA WGGFVDQVVG KRIHFRLPPG ALP            173

SEQ ID NO: 456          moltype = AA   length = 173
FEATURE                 Location/Qualifiers
REGION                  1..173
                        note = IPD103 variant
source                  1..173
                        mol_type = protein
                        organism = synthetic construct
SEQUENCE: 456
MADKAAAAAA SEAEEEVETT MDETEAVGTH LDFLGADVKL QPRNIITVEV DAAAVIQQIR       60
EIFQTMARHF NSTRVVRDEA IKGIRDHFRA AVPTRNVVVI HTQHVHTLVG LEHTHLVLQT      120
GIFKKVPVDI YVFKSGVFTN LGDGGFINWA WGGFVDQVVG KRIHFRLPPG ALP            173

SEQ ID NO: 457          moltype = AA   length = 153
FEATURE                 Location/Qualifiers
REGION                  1..153
                        note = IPD103 variant
source                  1..153
                        mol_type = protein
                        organism = synthetic construct
SEQUENCE: 457
MDETEAVGTH LDFLGADVKL QPTNIITVEV DAAAVIQQIR EIFQTMARHF NSTRVVRDEA       60
IKGIRDHFRA AVPTRNVVVI HTQHVHTLVG LEHTHLVLQT GIFKKVPVDI YVFKSGVFTN      120
LGDGGFINWA WGGFVDQVVG KRIHFRLPPG ALP                                  153

SEQ ID NO: 458          moltype = AA   length = 153
FEATURE                 Location/Qualifiers
REGION                  1..153
                        note = IPD103 variant
source                  1..153
                        mol_type = protein
                        organism = synthetic construct
SEQUENCE: 458
MDETEAVGTH LDFLGADVKL QPWNIITVEV DAAAVIQQIR EIFQTMARHF NSTRVVRDEA       60
IKGIRDHFRA AVPTRNVVVI HTQHVHTLVG LEHTHLVLQT GIFKKVPVDI YVFKSGVFTN      120
```

```
LGDGGFINWA WGGFVDQVVG KRIHFRLPPG ALP                                  153

SEQ ID NO: 459          moltype = AA  length = 153
FEATURE                 Location/Qualifiers
REGION                  1..153
                        note = IPD103 variant
source                  1..153
                        mol_type = protein
                        organism = synthetic construct
SEQUENCE: 459
MDETEAVGTH LDFLGADVKL QPYNIITVEV DAAAVIQQIR EIFQTMARHF NSTRVVRDEA      60
IKGIRDHFRA AVPTRNVVVI HTQHVHTLVG LEHTHLVLQT GIFKKVPVDI YVFKSGVFTN     120
LGDGGFINWA WGGFVDQVVG KRIHFRLPPG ALP                                  153

SEQ ID NO: 460          moltype = AA  length = 171
FEATURE                 Location/Qualifiers
REGION                  1..171
                        note = IPD103 variant
source                  1..171
                        mol_type = protein
                        organism = synthetic construct
SEQUENCE: 460
MADQAAAACE AEEEVETTMD ETEAVGTHLD FLGADVKLQP PNIITVEVDA AAVIQQIREI      60
FQTMARHFNS TRVVRDEAIK GIRDHFRAAV PTRNVVVIHT QHVHTLVGLE HTHLVLQTGI     120
FKKVPVDIYV FKSGVFTNLG DGGFINWAWG GFVDQVVGKR IHFRLPPGAL P              171

SEQ ID NO: 461          moltype = AA  length = 171
FEATURE                 Location/Qualifiers
REGION                  1..171
                        note = IPD103 variant
source                  1..171
                        mol_type = protein
                        organism = synthetic construct
SEQUENCE: 461
MADQAAAAVE AEEEVETTMD ETEAVGTHLD FLGADVKLQP PNIITVEVDA AAVIQQIREI      60
FQTMARHFNS TRVVRDEAIK GIRDHFRAAV PTRNVVVIHT QHVHTLVGLE HTHLVLQTGI     120
FKKVPVDIYV FKSGVFTNLG DGGFINWAWG GFVDQVVGKR IHFRLPPGAL P              171

SEQ ID NO: 462          moltype = AA  length = 171
FEATURE                 Location/Qualifiers
REGION                  1..171
                        note = IPD103 variant
source                  1..171
                        mol_type = protein
                        organism = synthetic construct
SEQUENCE: 462
MADQAAAADE AEEEVETTMD ETEAVGTHLD FLGADVKLQP TNIITVEVDA AAVIQQIREI      60
FQTMARHFNS TRVVRDEAIK GIRDHFRAAV PTRNVVVIHT QHVHTLVGLE HTHLVLQTGI     120
FKKVPVDIYV FKSGVFTNLG DGGFINWAWG GFVDQVVGKR IHFRLPPGAL P              171

SEQ ID NO: 463          moltype = AA  length = 171
FEATURE                 Location/Qualifiers
REGION                  1..171
                        note = IPD103 variant
source                  1..171
                        mol_type = protein
                        organism = synthetic construct
SEQUENCE: 463
MADQAAAAQE AEEEVETTMD ETEAVGTHLD FLGADVKLQP LNIITVEVDA AAVIQQIREI      60
FQTMARHFNS TRVVRDEAIK GIRDHFRAAV PTRNVVVIHT QHVHTLVGLE HTHLVLQTGI     120
FKKVPVDIYV FKSGVFTNLG DGGFINWAWG GFVDQVVGKR IHFRLPPGAL P              171

SEQ ID NO: 464          moltype = AA  length = 171
FEATURE                 Location/Qualifiers
REGION                  1..171
                        note = IPD103 variant
source                  1..171
                        mol_type = protein
                        organism = synthetic construct
SEQUENCE: 464
MADQAAAAGE AEEEVETTMD ETEAVGTHLD FLGADVKLQP LNIITVEVDA AAVIQQIREI      60
FQTMARHFNS TRVVRDEAIK GIRDHFRAAV PTRNVVVIHT QHVHTLVGLE HTHLVLQTGI     120
FKKVPVDIYV FKSGVFTNLG DGGFINWAWG GFVDQVVGKR IHFRLPPGAL P              171

SEQ ID NO: 465          moltype = AA  length = 172
FEATURE                 Location/Qualifiers
REGION                  1..172
                        note = IPD103 variant
source                  1..172
```

```
                          mol_type = protein
                          organism = synthetic construct
SEQUENCE: 465
MADKAAAAAR AAEEEVETTM DETEAVGTHL DFLGADVKLQ PWNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 466            moltype = AA  length = 172
FEATURE                   Location/Qualifiers
REGION                    1..172
                          note = IPD103 variant
source                    1..172
                          mol_type = protein
                          organism = synthetic construct
SEQUENCE: 466
MADKAAAAAA EAEEEVETTM DETEAVGTHL DFLGADVKLQ PTNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 467            moltype = AA  length = 172
FEATURE                   Location/Qualifiers
REGION                    1..172
                          note = IPD103 variant
source                    1..172
                          mol_type = protein
                          organism = synthetic construct
SEQUENCE: 467
MADKAAAAAM EAEEEVETTM DETEAVGTHL DFLGADVKLQ PTNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 468            moltype = AA  length = 172
FEATURE                   Location/Qualifiers
REGION                    1..172
                          note = IPD103 variant
source                    1..172
                          mol_type = protein
                          organism = synthetic construct
SEQUENCE: 468
MADKAAAAAS EAEEEVETTM DETEAVGTHL DFLGADVKLQ PLNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 469            moltype = AA  length = 172
FEATURE                   Location/Qualifiers
REGION                    1..172
                          note = IPD103 variant
source                    1..172
                          mol_type = protein
                          organism = synthetic construct
SEQUENCE: 469
MADKAAAAAA EAEEEVETTM DETEAVGTHL DFLGADVKLQ PWNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 470            moltype = AA  length = 172
FEATURE                   Location/Qualifiers
REGION                    1..172
                          note = IPD103 variant
source                    1..172
                          mol_type = protein
                          organism = synthetic construct
SEQUENCE: 470
MADKAAAAAM EAEEEVETTM DETEAVGTHL DFLGADVKLQ PWNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172

SEQ ID NO: 471            moltype = AA  length = 172
FEATURE                   Location/Qualifiers
REGION                    1..172
                          note = IPD103 variant
source                    1..172
                          mol_type = protein
                          organism = synthetic construct
SEQUENCE: 471
MADKAAAAAM EAEEEVETTM DETEAVGTHL DFLGADVKLQ PYNIITVEVD AAAVIQQIRE     60
IFQTMARHFN STRVVRDEAI KGIRDHFRAA VPTRNVVVIH TQHVHTLVGL EHTHLVLQTG    120
IFKKVPVDIY VFKSGVFTNL GDGGFINWAW GGFVDQVVGK RIHFRLPPGA LP            172
```

```
SEQ ID NO: 472              moltype = AA   length = 172
FEATURE                     Location/Qualifiers
REGION                      1..172
                            note = IPD103 variant
source                      1..172
                            mol_type = protein
                            organism = synthetic construct
SEQUENCE: 472
MADKAAAAAA EAEEEVETTM DETEAVGTHL DFLGADVKLQ PYNIITVEVD AAAVIQQIRE    60
IFQTMARHFN STRVVRDEAI KGIRDHFRAA VPTRNVVVIH TQHVHTLVGL EHTHLVLQTG   120
IFKKVPVDIY VFKSGVFTNL GDGGFINWAW GGFVDQVVGK RIHFRLPPGA LP           172

SEQ ID NO: 473              moltype = DNA   length = 40
FEATURE                     Location/Qualifiers
misc_feature                1..40
                            note = mutagenesis primer
source                      1..40
                            mol_type = other DNA
                            organism = synthetic construct
SEQUENCE: 473
agcatatggc ggacaaagca gcagcagcag ctagagaagc                          40

SEQ ID NO: 474              moltype = DNA   length = 36
FEATURE                     Location/Qualifiers
misc_feature                1..36
                            note = mutagenesis primer
source                      1..36
                            mol_type = other DNA
                            organism = synthetic construct
SEQUENCE: 474
cgactcgaga tgggtgccgg caggcaggca tattgc                              36

SEQ ID NO: 475              moltype = DNA   length = 37
FEATURE                     Location/Qualifiers
misc_feature                1..37
                            note = mutagenesis primer
source                      1..37
                            mol_type = other DNA
                            organism = synthetic construct
SEQUENCE: 475
agcatatggc ggaccaagca gcagcagcta gagaagc                             37

SEQ ID NO: 476              moltype = DNA   length = 25
FEATURE                     Location/Qualifiers
misc_feature                1..25
                            note = mutagenesis primer
source                      1..25
                            mol_type = other DNA
                            organism = synthetic construct
SEQUENCE: 476
aacatatggc cgaaccagca gcagc                                          25

SEQ ID NO: 477              moltype = DNA   length = 24
FEATURE                     Location/Qualifiers
misc_feature                1..24
                            note = mutagenesis primer
source                      1..24
                            mol_type = other DNA
                            organism = synthetic construct
SEQUENCE: 477
ttctcgagtc aagggagcgc ccca                                           24

SEQ ID NO: 478              moltype = DNA   length = 27
FEATURE                     Location/Qualifiers
misc_feature                1..27
                            note = mutagenesis primer
source                      1..27
                            mol_type = other DNA
                            organism = synthetic construct
SEQUENCE: 478
aacatatggc cgaccaagga gcagcag                                        27

SEQ ID NO: 479              moltype = DNA   length = 23
FEATURE                     Location/Qualifiers
misc_feature                1..23
                            note = mutagenesis primer
source                      1..23
                            mol_type = other DNA
                            organism = synthetic construct
```

```
SEQUENCE: 479
ttctcgagtc aagggagcgc ccc                                             23

SEQ ID NO: 480         moltype = DNA  length = 25
FEATURE                Location/Qualifiers
misc_feature           1..25
                       note = mutagenesis primer
source                 1..25
                       mol_type = other DNA
                       organism = synthetic construct
SEQUENCE: 480
aacatatggc cgaccaagct gcagc                                           25

SEQ ID NO: 481         moltype = DNA  length = 28
FEATURE                Location/Qualifiers
misc_feature           1..28
                       note = mutagenesis primer
source                 1..28
                       mol_type = other DNA
                       organism = synthetic construct
SEQUENCE: 481
aacatatgag agagcgagag cgagagcg                                        28

SEQ ID NO: 482         moltype = DNA  length = 25
FEATURE                Location/Qualifiers
misc_feature           1..25
                       note = mutagenesis primer
source                 1..25
                       mol_type = other DNA
                       organism = synthetic construct
SEQUENCE: 482
aacatatggc cgaaccagca gcagc                                           25

SEQ ID NO: 483         moltype = DNA  length = 24
FEATURE                Location/Qualifiers
misc_feature           1..24
                       note = mutagenesis primer
source                 1..24
                       mol_type = other DNA
                       organism = synthetic construct
SEQUENCE: 483
aacatatggc cgacaaagcg cctc                                            24

SEQ ID NO: 484         moltype = DNA  length = 24
FEATURE                Location/Qualifiers
misc_feature           1..24
                       note = mutagenesis primer
source                 1..24
                       mol_type = other DNA
                       organism = synthetic construct
SEQUENCE: 484
ttctcgagtc aagggagtgc cccg                                            24

SEQ ID NO: 485         moltype = DNA  length = 27
FEATURE                Location/Qualifiers
misc_feature           1..27
                       note = mutagenesis primer
source                 1..27
                       mol_type = other DNA
                       organism = synthetic construct
SEQUENCE: 485
aacatatggc cgaccaagta gcagcag                                         27

SEQ ID NO: 486         moltype = DNA  length = 25
FEATURE                Location/Qualifiers
misc_feature           1..25
                       note = mutagenesis primer
source                 1..25
                       mol_type = other DNA
                       organism = synthetic construct
SEQUENCE: 486
aacatatggc cgacccagca acagc                                           25

SEQ ID NO: 487         moltype = DNA  length = 33
FEATURE                Location/Qualifiers
misc_feature           1..33
                       note = mutagenesis primer
source                 1..33
                       mol_type = other DNA
```

```
                        organism = synthetic construct
SEQUENCE: 487
aacatatgca gagagagaga gagagagaga tgg                              33

SEQ ID NO: 488          moltype = DNA   length = 28
FEATURE                 Location/Qualifiers
misc_feature            1..28
                        note = mutagenesis primer
source                  1..28
                        mol_type = other DNA
                        organism = synthetic construct
SEQUENCE: 488
aacatatggc cgacaaagta gcagcagc                                    28

SEQ ID NO: 489          moltype = DNA   length = 23
FEATURE                 Location/Qualifiers
misc_feature            1..23
                        note = mutagenesis primer
source                  1..23
                        mol_type = other DNA
                        organism = synthetic construct
SEQUENCE: 489
ttctcgagtc aagggagtgc ccc                                         23

SEQ ID NO: 490          moltype = DNA   length = 28
FEATURE                 Location/Qualifiers
misc_feature            1..28
                        note = mutagenesis primer
source                  1..28
                        mol_type = other DNA
                        organism = synthetic construct
SEQUENCE: 490
aacatatgag agagcgagag cgagagcg                                    28

SEQ ID NO: 491          moltype = DNA   length = 28
FEATURE                 Location/Qualifiers
misc_feature            1..28
                        note = mutagenesis primer
source                  1..28
                        mol_type = other DNA
                        organism = synthetic construct
SEQUENCE: 491
aacatatggc cgatgacaaa gtagcaag                                    28

SEQ ID NO: 492          moltype = DNA   length = 22
FEATURE                 Location/Qualifiers
misc_feature            1..22
                        note = mutagenesis primer
source                  1..22
                        mol_type = other DNA
                        organism = synthetic construct
SEQUENCE: 492
ttctcgagtc aagggagggc cc                                          22

SEQ ID NO: 493          moltype = DNA   length = 27
FEATURE                 Location/Qualifiers
misc_feature            1..27
                        note = mutagenesis primer
source                  1..27
                        mol_type = other DNA
                        organism = synthetic construct
SEQUENCE: 493
aacatatggc cgatgaggta gctggtc                                     27

SEQ ID NO: 494          moltype = DNA   length = 21
FEATURE                 Location/Qualifiers
misc_feature            1..21
                        note = mutagenesis primer
source                  1..21
                        mol_type = other DNA
                        organism = synthetic construct
SEQUENCE: 494
aacatatgga cgccgctgcc g                                           21

SEQ ID NO: 495          moltype = DNA   length = 22
FEATURE                 Location/Qualifiers
misc_feature            1..22
                        note = mutagenesis primer
source                  1..22
```

```
                              mol_type = other DNA
                              organism = synthetic construct
SEQUENCE: 495
ttctcgagtc aagggagcgc cc                                             22

SEQ ID NO: 496            moltype = DNA   length = 516
FEATURE                   Location/Qualifiers
misc_feature              1..516
                          note = IPD103 variant
source                    1..516
                              mol_type = other DNA
                              organism = synthetic construct
SEQUENCE: 496
atggcggacg aagtagcagg tcaccatggt ccagcatgtg aagaagagga ggaggaaatg   60
ctgatggacg agactgaggc ggtgggggtg cacgcgatcg acggtctgcc ggtgcaaaac  120
cgcagcatca tcaccgtgga ggtggacgcc gctgccgtaa tccaacagat cagagagatc  180
ttcgcgtcaa tgatcaaaca ctacaactct acgagggtgg tgcgggatga agccatcaag  240
agcattcgag accacttcag gctcgccgtc ccgactcgca acgtggtggt cattcacact  300
cagcacgttc acacactgga cgccgtggag tcctcccacc tcgtcttgcg gaccggcctg  360
ttcaaaaagg tccctgtcga catctttgtc ttcaagtccg gcgtcttcac caacctggga  420
gacgaggctc tcatcaactg ggcatggggt ggctacggcg tcaaccacac cgccaagcgt  480
gtcgtcttca gccggccccc cggggcgctc ccttga                            516

SEQ ID NO: 497            moltype = DNA   length = 495
FEATURE                   Location/Qualifiers
misc_feature              1..495
                          note = Mutagenesis assembly block
misc_feature              132..133
                          note = n is a, c, g, or t
misc_feature              134
                          note = k is g or t
source                    1..495
                              mol_type = other DNA
                              organism = synthetic construct
SEQUENCE: 497
gcagccatat ggcggacaaa gcagcagcag cagctagaga agctgaagaa gaggtggaga   60
cgacgatgga cgagactgag gcggtgggga cgcacctgga cttcttgggc gcggacgtga  120
agttgcaacc cnnkaacatc atcaccgtgg aggtggacgc ggctgccgta atccaacaga  180
tcagagagat cttccagaca atggcgcgtc acttcaactc tacgagggtg gtgcgggatg  240
aagccatcaa gggcattcga gaccacttca gggccgccgt cccgactcgc aacgtggtgg  300
tcattcacac tcagcacgtt cacacactgg tgggcttgga gcacacccac ctcgtcttgc  360
agaccggcat cttcaaaaag gtccccgtcg acatctatgt cttcaagtcc ggcgtcttca  420
ccaaccttgg agacggaggc ttcatcaact gggcatgggg tggcttcgtc gaccaggtcg  480
tcggcaagcg tatcc                                                   495

SEQ ID NO: 498            moltype = DNA   length = 30
FEATURE                   Location/Qualifiers
misc_feature              1..30
                          note = mutagenesis primer
source                    1..30
                              mol_type = other DNA
                              organism = synthetic construct
SEQUENCE: 498
ctgctgctgc tttgtccgcc atatggctgc                                    30

SEQ ID NO: 499            moltype = DNA   length = 26
FEATURE                   Location/Qualifiers
misc_feature              1..26
                          note = mutagenesis primer
source                    1..26
                              mol_type = other DNA
                              organism = synthetic construct
SEQUENCE: 499
cgaccaggtc gtcggcaagc gtatcc                                        26

SEQ ID NO: 500            moltype = DNA   length = 51
FEATURE                   Location/Qualifiers
misc_feature              1..51
                          note = mutagensis primer
misc_feature              33..34
                          note = n is a, c, g, or t
misc_feature              35
                          note = k is g or t
source                    1..51
                              mol_type = other DNA
                              organism = synthetic construct
SEQUENCE: 500
agcatatggc ggacaaagca gcagcagcag ctnnkgaagc tgaagaagag g             51
```

| | | |
|---|---|---|
| SEQ ID NO: 501 | moltype = DNA  length = 32 | |
| FEATURE | Location/Qualifiers | |
| misc_feature | 1..32 | |
| | note = mutagensis primer | |
| source | 1..32 | |
| | mol_type = other DNA | |
| | organism = synthetic construct | |
| SEQUENCE: 501 | | |
| agcatatgga cgagactgag gcggtgggga cg | | 32 |
| | | |
| SEQ ID NO: 502 | moltype = DNA  length = 48 | |
| FEATURE | Location/Qualifiers | |
| misc_feature | 1..48 | |
| | note = mutagensis primer | |
| misc_feature | 30..31 | |
| | note = n is a, c, g, or t | |
| misc_feature | 32 | |
| | note = k is g or t | |
| source | 1..48 | |
| | mol_type = other DNA | |
| | organism = synthetic construct | |
| SEQUENCE: 502 | | |
| agcatatggc ggaccaagca gcagcagctn nkgaagctga agaagagg | | 48 |
| | | |
| SEQ ID NO: 503 | moltype = DNA  length = 51 | |
| FEATURE | Location/Qualifiers | |
| misc_feature | 1..51 | |
| | note = mutagensis primer | |
| source | 1..51 | |
| | mol_type = other DNA | |
| | organism = synthetic construct | |
| SEQUENCE: 503 | | |
| agcatatggc ggacaaagca gcagcagcag ctgctgaagc tgaagaagag g | | 51 |
| | | |
| SEQ ID NO: 504 | moltype = DNA  length = 51 | |
| FEATURE | Location/Qualifiers | |
| misc_feature | 1..51 | |
| | note = mutagensis primer | |
| source | 1..51 | |
| | mol_type = other DNA | |
| | organism = synthetic construct | |
| SEQUENCE: 504 | | |
| agcatatggc ggacaaagca gcagcagcag ctatggaagc tgaagaagag g | | 51 |
| | | |
| SEQ ID NO: 505 | moltype = DNA  length = 51 | |
| FEATURE | Location/Qualifiers | |
| misc_feature | 1..51 | |
| | note = mutagensis primer | |
| source | 1..51 | |
| | mol_type = other DNA | |
| | organism = synthetic construct | |
| SEQUENCE: 505 | | |
| agcatatggc ggacaaagca gcagcagcag ctagtgaagc tgaagaagag g | | 51 |
| | | |
| SEQ ID NO: 506 | moltype = DNA  length = 576 | |
| FEATURE | Location/Qualifiers | |
| misc_feature | 1..576 | |
| | note = IPD103 his-tagged | |
| source | 1..576 | |
| | mol_type = other DNA | |
| | organism = synthetic construct | |
| SEQUENCE: 506 | | |
| atgggcagca gccatcatca tcatcatcac agcagcggcc tggtgccgcg cggcagccat | | 60 |
| atggcggacc aagcagcagc agctagagaa gctgaagaag aggtggagac gacgatggac | | 120 |
| gagactgagg cggtggggac gcacctggac ttccttgggcg cggacgtgaa gttgcaaccc | | 180 |
| cgcaacatca tcaccgtgga ggtggacgcc gctgccgtaa tccaacagat cagagagatc | | 240 |
| ttccagacaa tggcgcgtca cttcaactct acgagggtgg tgcggatga agccatcaag | | 300 |
| ggcattcgag accacttcag gccgccgtc ccgactcgca acgtggtggt cattcacact | | 360 |
| cagcacgttc acacactggt gggcttgag cacacccacc tcgtcttgca gaccggcatc | | 420 |
| ttcaaaaagg tccccgtcga catctatgtc ttcaagtccg gcgtcttcac caaccttgga | | 480 |
| gacgaggct tcatcaactg gcatgggt ggcttcgtcg accaggtcgt cggcaagcgt | | 540 |
| atccacttcc gcttgccccc cggggcgctc ccttga | | 576 |
| | | |
| SEQ ID NO: 507 | moltype = AA  length = 191 | |
| FEATURE | Location/Qualifiers | |
| REGION | 1..191 | |
| | note = IPD103 his-tagged | |
| source | 1..191 | |
| | mol_type = protein | |

```
                    organism = synthetic construct
SEQUENCE: 507
MGSSHHHHHH SSGLVPRGSH MADQAAAARE AEEEVETTMD ETEAVGTHLD FLGADVKLQP    60
RNIITVEVDA AAVIQQIREI FQTMARHFNS TRVVRDEAIK GIRDHFRAAV PTRNVVVIHT   120
QHVHTLVGLE HTHLVLQTGI FKKVPVDIYV FKSGVFTNLG DGGFINWAWG GFVDQVVGKR   180
IHFRLPPGAL P                                                       191

SEQ ID NO: 508          moltype = AA  length = 5
FEATURE                 Location/Qualifiers
REGION                  1..5
                        note = fusion linker
source                  1..5
                        mol_type = protein
                        organism = synthetic construct
SEQUENCE: 508
EEKKN                                                                5
```

That which is claimed is:

1. A recombinant insecticidal polypeptide comprising an amino acid sequence having at least 95% sequence identity to SEQ ID NO: 345, wherein the insecticidal polypeptide is joined to a heterologous signal sequence or a transit sequence.

2. A composition comprising at least one recombinant insecticidal polypeptide of claim 1.

3. A recombinant polynucleotide encoding an insecticidal polypeptide comprising an amino acid sequence having at least 95% sequence identity to SEQ ID NO: 345, wherein the polynucleotide is operably linked to a heterologous regulatory element.

4. The recombinant polynucleotide of claim 3, wherein the polynucleotide has codons optimized for expression in an agriculturally important crop.

5. A DNA construct comprising the recombinant polynucleotide of claim 3.

6. A transgenic plant comprising the polynucleotide of claim 3.

7. A transgenic plant comprising the DNA construct of claim 5.

8. A method of inhibiting growth or killing an insect pest or pest population, comprising contacting the insect pest with the insecticidal polypeptide of claim 1.

9. A method of inhibiting growth or killing an insect pest or pest population comprising expressing in a plant the polynucleotide of claim 4.

10. A method for controlling pest infestation comprising providing in the diet of the pest the transgenic plant of claim 7 or a part thereof.

11. A method for improving the yield of a crop comprising growing the transgenic plant of claim 7, wherein the yield of the crop is increased in the presence of an insect pest relative to the crop not comprising said transgenic plant.

12. The method of claim 8, wherein the insect pest or pest population is resistant to at least one Cry insecticidal protein.

* * * * *